US007846455B2

(12) United States Patent
Collins et al.

(10) Patent No.: US 7,846,455 B2
(45) Date of Patent: *Dec. 7, 2010

(54) ATTENUATED CHIMERIC RESPIRATORY SYNCYTIAL VIRUS

(75) Inventors: Peter L. Collins, Rockville, MD (US); Brian R. Murphy, Bethesda, MD (US); Stephen S. Whitehead, Gaithersburg, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 453 days.

This patent is subject to a terminal disclaimer.

(21) Appl. No.: 10/722,000

(22) Filed: Nov. 25, 2003

(65) Prior Publication Data

US 2005/0100557 A1    May 12, 2005

Related U.S. Application Data

(63) Continuation of application No. 09/291,894, filed on Apr. 13, 1999, now Pat. No. 6,688,367, which is a continuation-in-part of application No. 08/892,403, filed on Jul. 15, 1997, now Pat. No. 5,993,824.

(60) Provisional application No. 60/047,634, filed on May 23, 1997, provisional application No. 60/046,141, filed on May 9, 1997, now abandoned, provisional application No. 60/021,773, filed on Jul. 15, 1996, now abandoned.

(51) Int. Cl.
| | | |
|---|---|---|
| *A61K 39/155* | (2006.01) | |
| *A61K 39/12* | (2006.01) | |
| *C12N 7/00* | (2006.01) | |
| *C12N 7/01* | (2006.01) | |
| *C12N 7/04* | (2006.01) | |

(52) U.S. Cl. .............. 424/211.1; 424/199.1; 424/204.1; 435/235.1; 435/236; 435/239

(58) Field of Classification Search ...................... None
See application file for complete search history.

(56) References Cited

U.S. PATENT DOCUMENTS

| | | | | |
|---|---|---|---|---|
| 5,716,821 | A | | 2/1998 | Wertz et al. |
| 5,789,229 | A | * | 8/1998 | Wertz et al. ............... 435/235.1 |
| 5,840,520 | A | * | 11/1998 | Clarke et al. ............... 435/69.1 |
| 5,869,036 | A | | 2/1999 | Belshe et al. |
| 5,882,651 | A | * | 3/1999 | Murphy et al. ............ 424/211.1 |
| 5,932,222 | A | * | 8/1999 | Randolph et al. ......... 424/211.1 |
| 6,264,957 | B1 | | 7/2001 | Collins |
| 6,689,367 | B1 | * | 2/2004 | Collins et al. ............. 424/211.1 |
| 6,699,476 | B1 | * | 3/2004 | Collins et al. ............. 424/199.1 |
| 6,713,066 | B1 | * | 3/2004 | Collins et al. ............. 424/199.1 |

FOREIGN PATENT DOCUMENTS

| | | |
|---|---|---|
| EP | 0 440 219 A1 | 8/1991 |
| EP | 0 702 085 A1 | 3/1996 |
| WO | WO-93/21310 | 10/1993 |
| WO | WO-97/06270 | 2/1997 |
| WO | WO-97/12032 | 4/1997 |
| WO | WO-97/20468 | 6/1997 |
| WO | WO-98/02530 | 1/1998 |
| WO | WO-98/43668 | 10/1998 |
| WO | WO-99/15631 | 4/1999 |

OTHER PUBLICATIONS

Collins et al., "Production of Infectious Human Respiratory Syncytial Virus from Cloned cDNA Confirms an Essential Role for the Transcription Elongation Factor from the 5' Proximal Open Reading Frame of the M2 mRNA in Gene Expression and Provides a Capability for Vaccine Development," PNAS, vol. 92, pp. 11563-11567 (Dec. 1995).*

Firestone et al., "Nucleotide Sequence Analysis of the Respiratory Syncytial Virus Subgroup A Cold-Passaged (cp) Temperature Sensitive (ts)cpts-248/404 Live Attenuated Virus Vaccine Candidate," Virology, vol. 225 No. 2, pp. 419-422 (Nov. 1996).*

Whitehead et al., "Addition of a Missense Mutation Present in the L Gene of Respiratory Syncytial Virus (RSV) cpts530/1030 to RSV Vaccine Candidate cpts248/404 Increases Its Attenuation and Temperature Sensitivity," Journal of Virology, vol. 73 No. 2, pp. 871-877 (Feb. 1999).*

Baron et al., "Rescue of Rinderpest Virus from Cloned cDNA," J. Virol. 71:1265-1271, 1997.

(Continued)

*Primary Examiner*—Zachariah Lucas
(74) *Attorney, Agent, or Firm*—Woodcock Washburn LLP

(57) ABSTRACT

Chimeric respiratory syncytial virus (RSV) and vaccine compositions thereof are produced by introducing one or more heterologous gene(s) or gene segment(s) from one RSV subgroup or strain into a recipient RSV backround of a different subgroup or strain. The resulting chimeric RSV virus or subviral particle is infectious and attenuated, preferably by introduction of selected mutations specifying attenuated phenotypes into a chimeric genome or antigenome to yield, for example, temperature sensitive (ts) and/or cold adapted (ca) vaccine strains. Alternatively, chimeric RSV and vaccine compositions thereof incorporate other mutations specifying desired structural and/or phenotypic characteristics in an infectious chimeric RSV. Such chimeric RSV incorporate desired mutations specified by insertion, deletion, substitution or rearrangement of one or more selected nucleotide sequence(s), gene(s), or gene segment(s) in a chimeric RSV clone. This provides a method for development of novel vaccines against diverse RSV strains by using a common attenuated backbone as a vector to express protective antigens of heterologous strains. The immune system of an individual is stimulated to induce protection against natural RSV infection, preferably in a multivalent manner to achieve protection against multiple RSV strains and/or subgroups.

11 Claims, 24 Drawing Sheets

OTHER PUBLICATIONS

Buchholz et al., "Generation of Bovine Respiratory Syncytial Virus (BRSV) from cDNA: BRSV NS2 Is Not Essential for Virus Replication in Tissue Culture, and the Human RSV Leader Region Acts as a Functional BRSV Genome Promoter," J. Virol. 73:251-259, 1999.

Bukreyev, et al., "Recovery of Infectious Respiratory Syncytial Virus Expressing an Additional, Foreign Gene," J. Virol. 70:6634-41, 1996.

Bukreyev, et al., "Interferon Y Expressed by a Recombinant Respiratory Syncytial Virus Attenuates Virus Replication in Mice Without Compromising Immunogenicity," Proc. Nat. Acad. Sci. USA 96:2367-2372, 1999.

Collins et al., "Rescue of Synthetic Analogs of Respiratory Syncytial Virus Genomic RNA and Effect of Truncations and Mutations on the Expression of a Foreign Reporter Gene," Proc. Natl. Acad. Sci. USA, 88:9663-9667, 1991.

Collins et al., "Rescue of a 7502-Nucleotide (49.3% of Full Length) Synthetic Analog of Respiratory Syncytial Virus Genomic RNA," Virology 195:252-256, 1993.

Connors et al., "A Cold-Passaged, Attenuated Strain of Human Respiratory Syncytial Virus Contains Mutations in the F and L Genes," Virology 208:478-484, 1995.

Conzelmann et al., "Rescue of Synthetic Genomic RNA Analogs of Rabies Virus by Plasmid-Encoded Proteins," J. Virol, 68:713-719, 1994.

Conzelmann, "Genetic Manipulation of Non-Segmented Negative-strand RNA Viruses," J. Gen. Virol. 77:381-389, 1996.

Crowe, et al., "A Further Attenuated Derivative of a Cold-Passaged Temperature-Sensitive Mutant of Human Respiratory Syncytial Virus Retains Immunogenicity and Protective Efficacy Against Wild-Type challenge in Seronegative Chimpanzees," Vaccine 12:893-790, 1994.

Crowe, et al., "Acquisition of the *ts* Phenotype by a Chemically Mutagenized Cold-Passaged Human Respiratory Syncytial Virus Vaccine Candidate Results from the Acquisition of a Single Mutation in the Polymerase (L) Gene," Virus Genes 13:269-273, 1996.

Dimock, et al., "Rescue of Synthetic Analogs of Genomic RNA and Replicative-Intermediate RNA of Human Parainfluenza Virus Type 3," J. Virol, 67:2772-2778, 1993.

Durbin, et al., "Minimum Protein Requirements for Transcription and RNA Replication of a Minigenome of Human Parainfluenza Virus type 3 and Evaluation of the Rule of Six," Virology 234:74-83, 1997.

Durbin et al., "Recovery of Infectious Human Parainfluenza virus type 3 from cDNA," Virology 235:323-332, 1997.

Grosfeld et al., "RNA Replication by Respiratory Syncytial Virus (RSV) Is Directed by the N, P, and L Proteins; Transcription Also Occurs under These Conditions but Required RSV Superinfection for Efficient Synthesis of Full-Length MRNA," J. Viorol. 69: 5677-5686, 1995.

He et al., "Recovery of Infectious SV5 from Cloned DNA and Expression of a foreign Gene," Virology 237:249-260, 1997.

Hoffman et al., "An Infectious Clone of Human Parainfluenza virus Type 3," J. Virol. 71:4272-4277, 1997.

Jin et al., "Recombinant Human Respiratory Syncytial Virus (RSV) from cDNA and Construction of Subgroup A and B Chimeric RSV," Virology 251:206-214, 1998.

Juhasz et al., "The Temperature-Sensitive (*ts*) Phenotype of a Cold-Passaged (*cp*) Live Attenuated Respiratory Syncytial Virus Vaccine Candidate, Designated *cpts*530, Results from a Single Amino Acid Substitution in the L Protein," J. Virol. 71:5814-5819, 1997.

Kato et al., "Initiation of Sendai Virus Multiplication From Transfected cDNA or RNA with Negative or Positive Sense," Genes to Cells 1:569-579, 1996.

Kuo at al., "Effect of Mutations in the Gene-Start and Gene-End Sequence Motifs on Transcription of Monocistronic and Dicistronic Minigenomes of Respiratory Syncytial Virus," J. Virol. 70:6892-6901, 1996.

Lawson et al., "Recombinant Vesicular Stomatitis Viruses from DNA," Proc. Natl. Acad. Sci. USA 92:4477-4481, 1995.

McIntosh et al., "Respiratory syncytial Virus," in virology, pp. 1046 and 1047, Fields et al., eds., 2nd ed., Raven Press, Ltd, New York, 1990.

Mink, et al., "Nucleotide Sequences of the e' Leader and 5' Trailer Regions of Human Respiratory Syncytial Virus Genomic RNA," Virology 185:615-624, 1991.

Murphy et al., "Current Approaches to the Development of Vaccines Effective Against Parainfluenza and Respiratory Syncytial Viruses," Virus Res. 11:1-15, 1988.

Palese et al., "Negative-Strand RNA Viruses: Genetic Engineering and Applications," Proc. Natl. Acad. Sci. USA 93:11354-11358, 1996.

Pastey et al., "Structure and Sequence Comparison of Bovine Respiratory Syncytial Virus Fusion Protein," Virus. Res. 29:195-202, 1993.

Pastey et al., "Nucleotide Sequence Analysis of the Non-Structural NS1(1C) and NS2 (1B) Protein Genes of Bovine Respiratory Syncytial Virus." J. of Gen. Virol. 76:193-197, 1995.

Peeters et al., "Rescue of Newcastle Disease Virus from Cloned cDNA: Evidence that Cleavability of the Fusion Protein is a Major Determinant for Virulence," J. Virol. 73:5001-5009, 1999.

Radecke et al., "Rescue of Measles Viruses from Cloned DNA," EMBO J. 14:5773-5784, 1995.

Roberts et al., "Recovery of Negative-Strand RNA Viruses from Plasmid DNAs: A Positive Approach Revitalizes a Negative Field," Virology 247-1-6, 1998.

Sakai et al., "Accommodation of Foreign Genes Into the Sendai Virus Genome: Sizes of Inserted Genes and Viral Replication," FEBS Letters 456:221-226, 1999.

Schneider et al., "Recombinant Measles Viruses defective for RNA Editing and V. Protein Synthesis Are Viable in Cultured Cells," Virology 277:314-322, 1997.

Schnell et al., "Infectious Rabies Viruses from Cloned cDNA," EMBO J. 13:4195-4203, 1994.

Skiadopoulos et al., "Identification of Mutations Contributing to the Temperature-Sensitive, Cold-Adapted, and Attenuation Phenotypes of the Live-Attenuated Cold-Passage 45 (*cp*45) Human Parainfluenza Virus 3 Candidate Vaccine," J. Virol, 73:1374-1381, 1999.

Tao et al., "Recovery of a Fully Viable Chimeric Human Parainfluenza Virus (PIV) Type 3 in Which the Hemagglutinin-Neuraminidase and Fusion Glycoproteins Have Been Replaced by Those of PIV Type 1," J. Virol. 72:2955-2961, 1998.

Tao et al., "A Live Attenuated Recombinant Chimeric Parainfluenza Virus (PIV) Candidate Vaccine Containing the Hemagglutinin-Neuraminidase and Fusion Glycoproteins of PIV1 and the Remaining Proteins from PIV3 Induces Resistance to PIV1 Even in Animals Immune to PIV3" Vaccine 17:1101-1108, 1999.

Wathen et al., "Characterization of a Novel Human Respiratory Syncytial Virus Chimeric FG Glycoprotein Expressed Using a Baculovirus Vector," J. Gen Virol. 70:2625-2635, 1989.

Whelan et al., "Efficient Recovery of Infectious Vesicular Stomatitis Virus Entirely From cDNA Clones," Proc. Natl. Acad. Sci. USA 92:8388-7392,1995.

Whitehead et al., "A Single Nucleotide Substitution inn the Transcription Start Signal of the M2 Gene of Respiratory Syncytial Virus Vaccine Candidate *cpts*243/404 is the Major Determinant of the Temperature-Sensitive and Attenuation Phenotypes," Virology 247:232-239, 1998a.

Whitehead et al., "Recombinant Respiratory Syncytial Virus (RSV) Bearing a Set of Mutations from cold-Passaged RSV is Attenuated in Chimpanzees," J. Virol. 72:4467-4471, 1998b.

Whitehead et al., "Recombinant Respiratory Syncytial Virus Bearing a Deletion of Either the NS2 or SH Gene is Attenuated in Chimpanzees," J. Virol. 73:3438-3442, 1999.

* cited by examiner

FIG. 1

$y = 0.94254 + 0.79703X \quad R^2 = 0.630$

Best fit curve

FIG. 9B
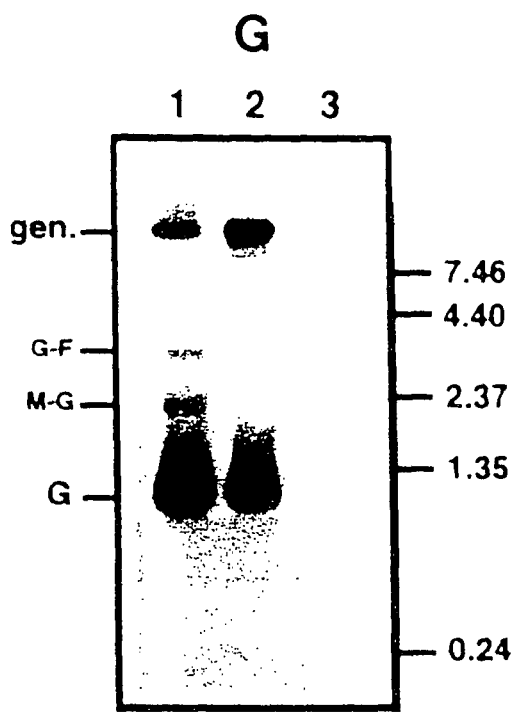
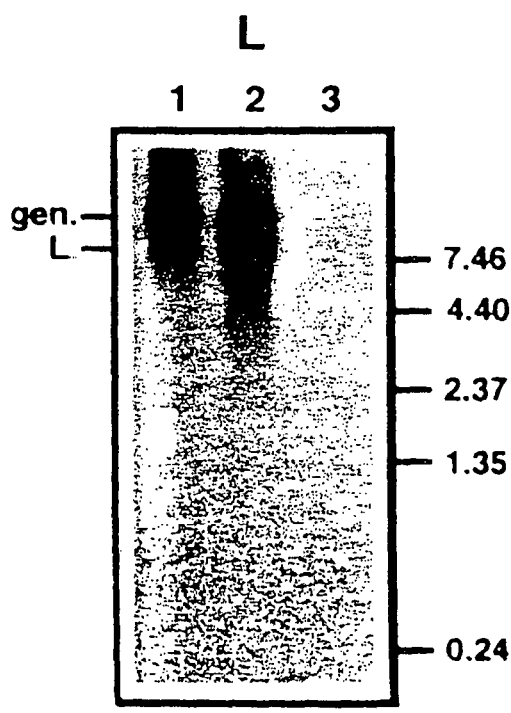

The SH-minus mutant has a steeper gradient of polar transcription

| Relative mRNA abundance: SH-minus/wild type | | | | |
|---|---|---|---|---|
| M | G | F | M2 | L |
| 1.1 | 1.3 | 0.61 | 0.32 | 0.17 |

```
Positions of genes in 3'-5' map 5  6  7      10
       WT:   3'-M-SH-G-F-M2-L 5     6       9
SH-minus:    3'-M----G-F-M2-L
```

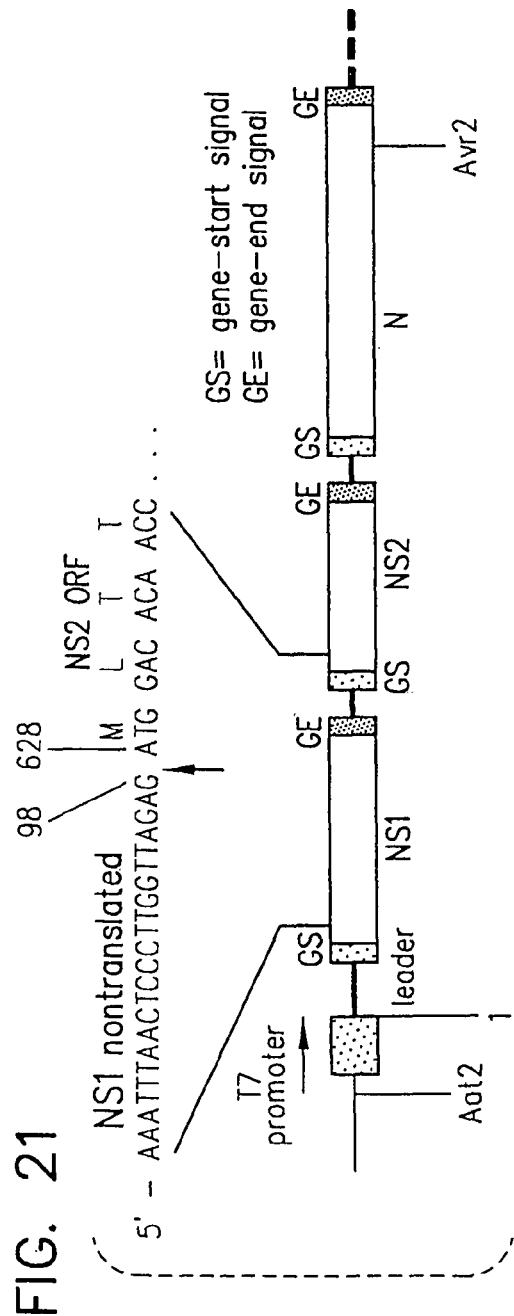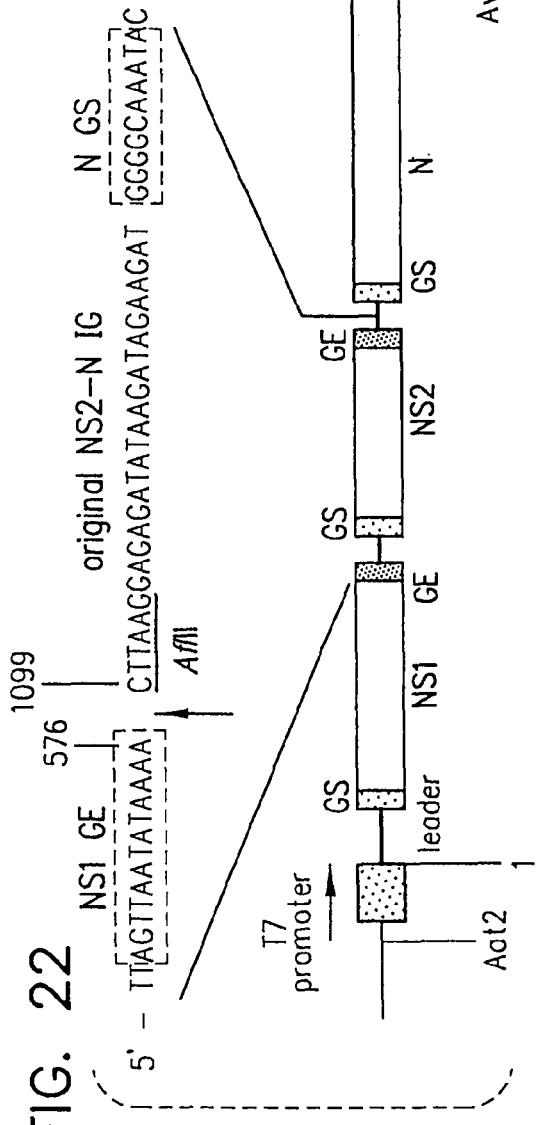

Fig. 25A

G and F genes of B1
virus of subgroup B

```
           G     F
          ┌──┬─────┐
          │  │     │
         PacI     SphI
NS1 NS2 N  P  M SH  G    F    M2        L
3'─▯─▯─▯─▯─▯─▯─▯─▯──▯────▯────▯─────────────────────5'
``` genome of RSV A2 virus of subgroup A

Fig. 25B

```
                       4630
              SH GE     |    SH-G IG
...actataaagt agttaattaaaaa tTAACATAATGATGAATTAT...
                PacI
```

Fig. 25C

```
                              7559
              F GE             |   F-M2 IG
...CTTAACTCAT AGTTACATAAAAA CCTCAAgcatgccagattaacttaccatctg...
                                    SphI
```

Fig. 27

Replication of chimeric recombinant AB RSVs in seronegative juvenile chimpanzees

Nasopharyngeal swab titer $\log_{10}$ pfu/ml

▲—▲ rAB (4 animals)
■---■ rABcp248/404/1030 (3 animals)

Tracheal lavage titer $\log_{10}$ pfu/ml

ATTENUATED CHIMERIC RESPIRATORY SYNCYTIAL VIRUS

RELATED APPLICATIONS

This The present application is a continuation of the prior application Ser. No. 09/291,894, filed Apr. 13, 1999, and issued Feb. 10, 2004 as U.S. Pat. No. 6,688,367, the benefit of the filing date of which is hereby claimed under 35 USC 120, which in turn is a continuation-in-part of U.S. patent application Ser. No. 08/892,403 filed Jul. 15, 1997 and issued Jul. 1, 2003 as U.S. Pat. 5,993,824, which in turn claims priority under 35 USC 119(e) of U.S. Provisional Application Nos. 60/047,634 filed May 23, 1997 and now abandoned, 60/046,141 filed May 9, 1997 and now abandoned, and 60/021,773 filed Jul. 15, 1996 and now abandoned, each of which is incorporated herein by reference.

BACKGROUND OF THE INVENTION

Human respiratory syncytial virus (RSV) outranks all other microbial pathogens as a cause of pneumonia and bronchiolitis in infants under one year of age. Virtually all children are infected by two years of age, and reinfection occurs with appreciable frequency in older children and young adults (Chanock et al., in *Viral Infections of Humans,* 3rd ed., A. S. Evans, ed., Plenum Press, N.Y. (1989). RSV is responsible for more than one in five pediatric hospital admissions due to respiratory tract disease, and causes an estimated 91,000 hospitalizations and 4,500 deaths yearly in the United States alone. Although most healthy adults do not have serious disease due to RSV infection, elderly patients and immunocompromised individuals often suffer severe and possibly life-threatening infections from this pathogen.

Despite decades of investigation to develop effective vaccine agents against RSV, no safe and effective vaccine has yet been achieved to prevent the severe morbidity and significant mortality associated with RSV infection. Failure to develop successful vaccines relates in part to the fact that small infants have diminished serum and secretory antibody responses to RSV antigens. Thus, these individuals suffer more severe infections from RSV, whereas cumulative immunity appears to protect older children and adults against more serious impacts of the virus. One antiviral compound, ribavarin, has shown promise in the treatment of severely infected infants, although there is no indication that it shortens the duration of hospitalization or diminishes the infant's need for supportive therapy.

The mechanisms of immunity in RSV infection have recently come into focus. Secretory antibodies appear to be most important in protecting the upper respiratory tract, whereas high levels of serum antibodies are thought to have a major role in resistance to RSV infection in the lower respiratory tract. Purified human immunoglobulin containing a high titer of neutralizing antibodies to RSV may prove useful in some instances of immunotherapeutic approaches for serious lower respiratory tract disease in infants and young children. Immune globulin preparations, however, suffer from several disadvantages, such as the possibility of transmitting blood-borne viruses and difficulty and expense in preparation and storage.

RSV-specific cytotoxic T cells, another effector arm of induced immunity, are also important in resolving an RSV infection. However, while this latter effector can be augmented by prior immunization to yield increased resistance to virus challenge, the effect is short-lived. The F and G surface glycoproteins are the two major protective antigens of RSV, and are the only two RSV proteins which have been shown to induce RSV neutralizing antibodies and long term resistance to challenge (Collins et al., *Fields Virology,* Fields et al. eds., 2:1313-1352. Lippincott-Raven, Philadelphia. (1996); Connors et al., *J. Virol.* 65(3):1634-7 (1991)). The third RSV surface protein, SH, did not induce RSV-neutralizing antibodies or significant resistance to RSV challenge.

One obstacle to development of live RSV vaccines is the difficulty in achieving an appropriate balance between attenuation and immunogenicity. Genetic stability of attenuated viruses also can be a problem. Vaccine development also is impeded by the relatively poor growth of RSV in cell culture and the instability of the virus particle. Another feature of RSV infection is that the immunity which is induced is not fully protective against subsequent infection. A number of factors probably contribute to this, including the relative inefficiency of the immune system in restricting virus infection on the luminal surface of the respiratory tract, the short-lived nature of local mucosal immunity, rapid and extensive virus replication, reduced immune responses in the young due to immunological immaturity, immunosuppression by transplacentally derived maternal serum antibodies, and certain features of the virus such as a high degree of glycosylation of the G protein. Also, as will be described below, RSV exists as two antigenic subgroups A and B, and immunity against one subgroup is of reduced effectiveness against the other.

Although RSV can reinfect multiple times during life, reinfections usually are reduced in severity due to protective immunity induced by prior infection, and thus immunoprophylaxis is feasible. A live-attenuated RSV vaccine would be administered intranasally to initiate a mild immunizing infection. This has the advantage of simplicity and safety compared to a parenteral route. It also provides direct stimulation of local respiratory tract immunity, which plays a major role in resistance to RSV. It also abrogates the immunosuppressive effects of RSV-specific maternally-derived serum antibodies, which typically are found in the very young. Also, while the parenteral administration of RSV antigens can sometimes be associated with immunopathologic complications (Murphy et al., *Vaccine* 8(5):497-502 (1990)), this has never been observed with a live virus.

Formalin-inactivated virus vaccine was tested against RSV in the mid-1960s, but failed to protect against RSV infection or disease, and in fact exacerbated symptoms during subsequent infection by the virus. (Kim et al., *Am. J. Epidemiol.,* 89:422-434 (1969), Chin et al., *Am J. Epidemiol.,* 89:449-463 (1969); Kapikian et al., *Am. J. Epidemiol.,* 89:405-421 (1969)).

More recently, vaccine development for RSV has focused on attenuated RSV mutants. Friedewald et al., *J. Amer. Med. Assoc.* 204:690-694 (1968) reported a cold passaged mutant of RSV (cpRSV) which appeared to be sufficiently attenuated to be a candidate vaccine. This mutant exhibited a slight increased efficiency of growth at 26° C. compared to its wild-type (wt) parental virus, but its replication was neither temperature sensitive nor significantly cold-adapted. The cold-passaged mutant, however, was attenuated for adults. Although satisfactorily attenuated and immunogenic for infants and children who had been previously infected with RSV (i.e., seropositive individuals), the cpRSV mutant retained a low level virulence for the upper respiratory tract of seronegative infants.

Similarly, Gharpure et al., *J. Virol.* 3:414-421 (1969) reported the isolation of temperature sensitive RSV (tsRSV) mutants which also were promising vaccine candidates. One mutant, ts-1, was evaluated extensively in the laboratory and in volunteers. The mutant produced asymptomatic infection in adult volunteers and conferred resistance to challenge with wild-type virus 45 days after immunization. Again, while seropositive infants and children underwent asymptomatic infection, seronegative infants developed signs of rhinitis and other mild symptoms. Furthermore, instability of the ts phenotype was detected, although virus exhibiting a partial or complete loss of temperature sensitivity represented a small proportion of virus recoverable from vaccinees, and was not associated with signs of disease other than mild rhinitis.

These and other studies revealed that certain cold-passaged and temperature sensitive RSV strains were underattenuated and caused mild symptoms of disease in some vaccinees, particularly seronegative infants, while others were overattenuated and failed to replicate sufficiently to elicit a protective immune response, (Wright et al., *Infect. Immun.*, 37:397-400 (1982)). Moreover, genetic instability of candidate vaccine mutants has resulted in loss of their temperature-sensitive phenotype, further hindering development of effective RSV vaccines. See generally, Hodes et al., *Proc. Soc. Exp. Biol. Med.* 145:1158-1164 (1974), McIntosh et al., *Pediatr. Res.* 8:689-696 (1974), and Belshe et al., *J. Med. Virol.*, 3:101-110 (1978).

Abandoning the approach of creating suitably attenuated RSV strains through undefined biological methods such as cold-passaging, investigators tested subunit vaccine candidates using purified RSV envelope glycoproteins. The glycoproteins induced resistance to RS virus infection in the lungs of cotton rats, Walsh et al., *J. Infect. Dis.* 155:1198-1204 (1987), but the antibodies had very weak neutralizing activity and immunization of rodents with purified subunit vaccine led to disease potentiation (Murphy et al., *Vaccine* 8:497-502 (1990)).

Vaccinia virus recombinant-based vaccines which express the F or G envelope glycoprotein have also been explored. These recombinants express RSV glycoproteins which are indistinguishable from the authentic viral counterpart, and rodents infected intradermally with vaccinia-RSV F and G recombinants developed high levels of specific antibodies that neutralized viral infectivity. Indeed, infection of cotton rats with vaccinia-F recombinants stimulated almost complete resistance to replication of RSV in the lower respiratory tract and significant resistance in the upper tract. Olmsted et al., *Proc. Natl. Acad. Sci. USA* 83:7462-7466 (1986). However, immunization of chimpanzees with vaccinia-F and -G recombinant provided almost no protection against RSV challenge in the upper respiratory tract (Collins et al., *Vaccine* 8:164-168 (1990)) and inconsistent protection in the lower respiratory tract (Crowe et al., *Vaccine* 11:1395-1404 (1993)).

The unfulfilled promises of attenuated RSV strains, subunit vaccines, and other strategies for RSV vaccine development underscores a need for new methods to develop novel RSV vaccines, particularly methods for manipulating recombinant RSV to incorporate genetic changes to yield new phenotypic properties in viable, attenuated RSV recombinants. However, manipulation of the genomic RNA of RSV and other negative-sense RNA viruses has heretofore proven difficult. Major obstacles in this regard include non-infectivity of naked genomic RNA of these viruses, poor viral growth in tissue culture, lengthy replication cycles, virion instability, a complex genome, and a refractory organization of gene products.

Recombinant DNA technology has made it possible to recover infectious negative-stranded RNA viruses from cDNA, to genetically manipulate viral clones to construct novel vaccine candidates, and to rapidly evaluate their level of attenuation and phenotypic stability (for reviews, see Conzelmann, *J. Gen. Virol.* 77:381-89 (1996); Palese et al., *Proc. Natl. Acad. Sci. U.S.A.* 93:11354-58, (1996)). In this context, recombinant rescue has been reported for infectious respiratory syncytial virus (RSV), parainfluenza virus (PIV), rabies virus (RaV), vesicular stomatitis virus (VSV), measles virus (MeV), and Sendai virus (SeV) from cDNA-encoded antigenomic RNA in the presence of essential viral proteins (see, e.g., Garcin et al., *EMBO J.* 14:6087-6094 (1995); Lawson et al., *Proc. Natl. Acad. Sci. U.S.A.* 92:4477-81 (1995); Radecke et al., *EMBO J.* 14:5773-5784 (1995); Schnell et al., *EMBO J.* 13:4195-203 (1994); Whelan et al., *Proc. Natl. Acad. Sci. U.S.A.* 92:8388-92 (1995); Hoffman et al., *J. Virol.* 71:4272-4277 (1997); Kato et al., *Genes to Cells* 1:569-579 (1996), Roberts et al., *Virology* 247(1), 1-6 (1998); Baron et al., *J. Virol.* 71:1265-1271 (1997); International Publication No. WO 97/06270; Collins et al., *Proc. Natl. Acad. Sci. USA* 92:11563-11567 (1995); Durbin et al., *Virology* 235:323-332 (1997); U.S. patent application Ser. No. 08/892,403, filed Jul. 15, 1997 (corresponding to published International Application No. WO 98/02530 and priority U.S. Provisional Application Nos. 60/047,634, filed May 23, 1997, 60/046,141, filed May 9, 1997, and 60/021,773, filed Jul. 15, 1996); Juhasz et al., *J. Virol.* 71(8):5814-5819 (1997); He et al. *Virology* 237: 249-260 (1997); Baron et al. *J. Virol.* 71:1265-1271 (1997); Whitehead et al., *Virology* 247(2):232-9 (1998a); Whitehead et al., *J. Virol.* 72(5):4467-4471 (1998b); Jin et al. *Virology* 251:206-214 (1998); Bucholz et al. *J. Virol.* 73:251-259 (1999); and Whitehead et al., *J. Virol.* 73:(4)3438-3442 (1999), each incorporated herein by reference).

Among the remaining challenges to RSV vaccine development is the difficulty of achieving vaccine candidates that are effective against a broad range of existing and emergent strains and subgroups of RSV. In particular, it will be useful to provide a RSV subgroup B-specific vaccine virus, as well as multivalent vaccines to provide protection against both RSV A and RSV B subgroups. In this context, recent research has focused on development of chimeric viruses to carry antigenic determinants between viral strains. For example, the HN and F glycoproteins of human parainfluenza virus type 3 (PIV3) have been replaced by those of human parainfluenza virus type 1 (HPIV1), and the resulting chimeric virus grew in cell culture and in experimental animals with an efficiency similar to its wild-type parents (Tao et al., *J. Virol.* 72(4): 2955-61 (1998), incorporated herein by reference. Also reported is a chimeric measles virus where the H and F glycoproteins were replaced with the G glycoprotein of vesicular stomatitis virus, which was inserted with or without replacement of the cytoplasmic and transmembrane region of G with that of measles virus F (Spielhofer et al., *J. Virol.* 72(3): 2150-9 (1998)). This yielded a chimeric virus that was reportedly 50-fold reduced in growth. In a third example, Jin et al., *Virology* 251(1):206-14 (1998) report a subgroup A virus which expresses the G protein of a subgroup B RSV as an additional gene (Jin et al., *Virology* 251(1):206-14 (1998)). However, since the F protein also exhibits significant subgroup-specificity, it would be preferable to express both subgroup B glycoproteins in a subgroup B-specific vaccine. In addition, production of a chimeric A-B virus will not produce a viable vaccine candidate without further modifications to achieve proper attenuation and virulence.

Accordingly, an urgent need remains in the art for tools and methods to engineer safe and effective vaccines to alleviate the serious health problems attributable to RSV, particularly that will be effective against multiple existing and emergent

SUMMARY OF THE INVENTION

The present invention provides chimeric, recombinant respiratory syncytial virus (RSV) that are infectious and elicit a propylactic or therapeutic immune response in humans or other mammals. In related aspects, the invention provides novel methods and compositions for designing and producing attenuated, chimeric RSV suitable for vaccine use. Included within these aspects of the invention are novel, isolated polynucleotide molecules and vectors incorporating such molecules that comprise a chimeric RSV genome or antigenome including a partial or complete RSV genome or antigenome of one RSV strain or subgroup virus combined with one or more heterologous gene(s) or gene segment(s) of a different RSV strain or subgroup virus. Also provided within the invention are methods and compositions incorporating chimeric, recombinant RSV for prophylaxis and treatment of RSV infection.

Chimeric RSV of the invention are recombinantly engineered to incorporate nucleotide sequences from more than one RSV strain or subgroup to produce an infectious, chimeric virus or subviral particle. In this manner, candidate vaccine viruses are recombinantly engineered to elicit an immune response against RSV in a mammalian host susceptible to RSV infection, including humans and non-human primates. Chimeric RSV according to the invention may elicit an immune response to a specific RSV subgroup or strain, or a polyspecific response against multiple RSV subgroups or strains.

Exemplary chimeric RSV of the invention incorporate a chimeric RSV genome or antigenome, as well as a major nucleocapsid (N) protein, a nucleocapsid phosphoprotein (P), a large polymerase protein (L), and a RNA polymerase elongation factor. Additional RSV proteins may be included in various combinations to provide a range of infectious subviral particles as well as complete viral particles.

Chimeric RSV of the invention include a partial or complete RSV genome or antigenome from one RSV strain or subgroup virus combined with one or more heterologous gene(s) or gene segment(s) of a different RSV strain or subgroup virus to form the chimeric RSV genome or antigenome. In preferred aspects of the invention, chimeric RSV incorporate a partial or complete human RSV genome or antigenome of one RSV subgroup or strain combined with one or more heterologous gene(s) or gene segment(s) from a different human RSV subgroup or strain. For example, a chimeric RSV may incorporate a chimeric genome or antigenome comprised of a partial or complete human RSV A subgroup genome or antigenome combined with one or more heterologous gene(s) or gene segment(s) from a human RSV B subgroup virus.

Heterologous genes or gene segments from one RSV strain or subgroup represent "donor" genes or polynucleotides that are combined with, or substituted within, a "recipient" genome or antigenome. The recipient genome or antigenome typically acts as a "backbone" or vector to import heterologous genes or gene segments to yield a chimeric RSV exhibiting novel phenotypic characteristics. For example, addition or substitution of heterologous genes or gene segments within a selected recipient RSV strain may result in attenuation, growth changes, altered immunogenicity, or other desired phenotypic changes as compared with a corresponding phenotype(s) of the unmodified recipient and/or donor. Genes and gene segments that may be selected for use as heterologous inserts or additions within the invention include genes or gene segments encoding a NS1, NS2, N, P, M, SH, M2(ORF1), M2(ORF2), L, F or G protein or portion thereof.

In preferred embodiments of the invention, chimeric RSV incorporates one or more heterologous gene(s) that encode an RSV F, G or SH glycoprotein. Alternatively, the chimeric RSV may incorporate a gene segment encoding a cytoplasmic domain, transmembrane domain, ectodomain or immunogenic epitope of a RSV F, G or SH glycoprotein. These immunogenic proteins, domains and epitopes are particularly useful within chimeric RSV because they can generate novel immune responses in an immunized host.

For example, addition or substitution of one or more immunogenic gene(s) or gene segment(s) from one donor RSV subgroup or strain within a recipient genome or antigenome of a different RSV subgroup or strain can generate an immune response directed against the donor subgroup or strain or against both the donor and recipient subgroup or strain. In one exemplary embodiment, one or more human RSV subgroup B glycoprotein genes F, G and SH or a cytoplasmic domain, transmembrane domain, ectodomain or immunogenic epitope thereof, is added to, or substituted within, an RSV A genome or antigenome.

In additional aspects of the invention, attenuated, chimeric RSV are produced in which the chimeric genome or antigenome is further modified by introducing one or more attenuating point mutations specifying an attenuating phenotype. These point mutations may be generated de novo and tested for attenuating effects according to a rational design mutagenesis strategy. Alternatively, the attenuating point mutations are identified in biologically derived mutant RSV and thereafter incorporated into a chimeric RSV of the invention.

Preferably, chimeric RSV of the invention are attenuated by incorporation of at least one, and more preferably two or more, attenuating point mutations identified from a panel of known, biologically derived mutant RSV strains. Preferred mutant RSV strains described herein are cold passaged (cp) and/or temperature sensitive (ts) mutants, for example the mutants designated "cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579)" (each deposited under the terms of the Budapest Treaty with the American Type Culture Collection (ATCC) of 10801 University Boulevard, Manassas, Va. 20110-2209, U.S.A., and granted the above identified accession numbers). From this exemplary panel of biologically derived mutants, a large "menu" of attenuating mutations are provided which can each be combined with any other mutation(s) within the panel for calibrating the level of attenuation in the recombinant, chimeric RSV for vaccine use. Additional mutations may be derived from RSV having non-ts and non-cp attenuating mutations as identified, e.g., in small plaque (sp), cold-adapted (ca) or host-range restricted (hr) mutant strains.

In yet additional aspects of the invention, chimeric RSV, with or without attenuating point mutations, are mutated by a non-point nucleotide modification to produce desired phenotypic, structural, or functional changes. Typically, the selected nucleotide modification will specify a phenotypic change, for example a change in growth characteristics, attenuation, temperature-sensitivity, cold-adaptation, plaque size, host range restriction, or immunogenicity. Structural or functional changes include introduction or ablation of restriction sites into RSV encoding cDNAs for ease of manipulation and identification.

In preferred embodiments, an SH, NS1, NS2 or G gene is modified in the chimeric RSV, e.g., by deletion of the gene or ablation of its expression. Alternatively, the nucleotide modification can include a deletion, insertion, addition or rearrangement of a cis-acting regulatory sequence for a selected RSV gene.

In one example, a cis-acting regulatory sequence of one RSV gene is changed to correspond to a heterologous regulatory sequence, which may be a counterpart cis-acting regulatory sequence of the same gene in a different RSV or a cis-acting regulatory sequence of a different RSV gene. For example, a gene end signal may be modified by conversion or substitution to a gene end signal of a different gene in the same RSV strain.

In a separate embodiment, the nucleotide modification may comprise an insertion, deletion, substitution, or rearrangement of a translational start site within the chimeric genome or antigenome, e.g., to ablate an alternative translational start site for a selected form of a protein. In one example, the translational start site for a secreted form of the RSV G protein is ablated to modify expression of this form of the G protein and thereby produce desired in vivo effects.

Yet additional modifications may be made to the chimeric RSV genome or antigenome according to the invention, including modifications that introduce into the chimeric genome or antigenome a non-RSV molecule such as cytokine, a T-helper epitope, a restriction site marker, or a protein of a microbial pathogen capable of eliciting a protective immune response against the pathogen in a mammalian host. In one such embodiment, chimeric RSV are constructed that incorporate a gene or gene segment from a parainfluenza virus (PIV), for example a PIV HN or F glycoprotein or an immunogenic domain or epitope thereof.

Chimeric RSV designed and selected for vaccine use often have at least two and sometimes three or more attenuating mutations to achieve a satisfactory level of attenuation for broad clinical use. In one embodiment, at least one attenuating mutation occurs in the RSV polymerase gene (either in the donor or recipient gene) and involves one or more nucleotide substitution(s) specifying an amino acid change in the polymerase protein specifying an attenuation phenotype which may or may not involve a temperature-sensitive (ts) phenotype. Exemplary chimeric RSV in this context incorporate one or more nucleotide substitutions in the large polymerase gene L resulting in an amino acid change at amino acid $Phe_{521}$, $Gln_{831}$, $Met_{1169}$, or $Tyr_{1321}$, as exemplified by the changes, Leu for $Phe_{521}$, Leu for $Gln_{831}$, Val for $Met_{1169}$, and Asn for $Tyr_{1321}$. Other alternative amino acid assignments at this position can of course be made to yield a similar effect as the identified, mutant substitution. In this context, it is preferable to modify the chimeric genome or antigenome to encode an alteration at the subject site of mutation that corresponds conservatively to the alteration identified in the mutant virus. For example, if an amino acid substitution marks a site of mutation in the mutant virus compared to the corresponding wild-type sequence, then a similar substitution should be engineered at the corresponding residue(s) in the recombinant virus. Preferably the substitution will involve an identical or conservative amino acid to the substitute residue present in the mutant viral protein. However, it is also possible to alter the native amino acid residue at the site of mutation non-conservatively with respect to the substitute residue in the mutant protein (e.g., by using any other amino acid to disrupt or impair the identity and functio of the wild-type residue). In the case of mutations marked by deletions or insertions, these can be introduced as corresponding deletions or insertions into the recombinant virus, however the particular size and amino acid sequence of the deleted or inserted protein fragment can vary. Chimeric RSV of the invention may incorporate a ts mutation in any additional RSV gene besides L, e.g., in the M2 gene.

Preferably, two or more nucleotide changes are incorporated in a codon specifying an attenuating mutation, e.g., in a codon specifying a ts mutation, thereby decreasing the likelihood of reversion from an attenuated phenotype.

Attenuating mutations may be selected in coding portions of a donor or recipient RSV gene or in non-coding regions such as a cis-regulatory sequence. Exemplary non-coding mutations include single or multiple base changes in a gene start sequence, as exemplified by a single or multiple base substitution in the M2 gene start sequence at nucleotide 7605 (nucleotide 7606 in recombinant sequence).

In another aspect of the invention, compositions (e.g., isolated polynucleotides and vectors incorporating an RSV-encoding cDNA) and methods are provided for producing an isolated infectious chimeric RSV. Using these compositions and methods, infectious chimeric RSV are generated from a chimeric RSV genome or antigenome, a nucleocapsid (N) protein, a nucleocapsid phosphoprotein (P), a large (L) polymerase protein, and an RNA polymerase elongation factor. In related aspects of the invention, compositions and methods are provided for introducing the aforementioned structural and phenotypic changes into a recombinant chimeric RSV to yield infectious, attenuated vaccine viruses.

In one embodiment, an expression vector is provided which comprises an isolated polynucleotide molecule encoding a chimeric RSV genome or antigenome. Also provided is the same or different expression vector comprising one or more isolated polynucleotide molecules encoding N, P, L and RNA polymerase elongation factor proteins. The vector(s) is/are preferably expressed or coexpressed in a cell or cell-free lysate, thereby producing an infectious chimeric RSV particle or subviral particle.

The RSV genome or antigenome and the N, P, L and RNA polymerase elongation factor (preferably the product of the M2(ORF1) of RSV) proteins can be coexpressed by the same or different expression vectors. In some instances the N, P, L and RNA polymerase elongation factor proteins are each encoded on different expression vectors. The polynucleotide molecule encoding the chimeric RSV genome or antigenome can be a chimera of different human RSV subgroups or strains, for example a polynucleotide containing sequences from a subgroup A RSV operably joined with sequences from a subgroup B RSV. Alternatively, the chimeric genome or antigenome can be a chimera of human and non-human (e.g., bovine or murine) RSV sequences. In yet another alternative aspect of the invention, the chimeric genome or antigenome can be a chimera of RSV and non-RSV sequences, for example a polynucleotide containing sequences from a human RSV operably joined with PIV sequences. The chimeric genome or antigenome can be further modified by insertion, rearrangement, deletion or substitution of one or more nucleotides, including point mutations, site-specific nucleotide changes, and changes involving entire genes or gene segments introduced within a heterologous donor gene or gene segment or the recipient, background genome or antigenome. These alterations typically specify one or more phenotypic change(s) in the resulting recombinant RSV, such as a phenotypic change that results in attenuation, temperature-sensitivity, cold-adaptation, small plaque size, host range restriction, alteration in gene expression, or a change in an immunogenic epitope.

The above methods and compositions for producing chimeric RSV yield infectious viral or subviral particles, or derivatives thereof. An infectious virus is comparable to the authentic RSV virus particle and is infectious as is. It can directly infect fresh cells. An infectious subviral particle typically is a subcomponent of the virus particle which can initiate an infection under appropriate conditions. For example, a nucleocapsid containing the genomic or antigenomic RNA and the N, P, L and M2(ORF1) proteins is an example of a subviral particle which can initiate an infection if introduced into the cytoplasm of cells. Subviral particles provided within the invention include, inter alia, viral particles which lack one or more protein(s), protein segment(s), or other viral component(s) not essential for infectivity.

Infectious chimeric RSV according to the invention can incorporate heterologous, coding or non-coding nucleotide sequences from any RSV or RSV-like virus, e.g., human, bovine, murine (pneumonia virus of mice), or avian (turkey rhinotracheitis virus) RSV, or from another enveloped virus, e.g., parainfluenza virus (PIV). In exemplary aspects, the recombinant RSV comprises a chimera of a human RSV genomic or antigenomic sequence recombinantly joined with one or more heterologous RSV sequence(s). Exemplary heterologous sequences include RSV sequences from one human RSV strain combined with sequences from a different human RSV strain. For example, chimeric RSV of the invention may incorporate sequences from two or more wild-type or mutant RSV strains, for example mutant strains selected from cpts RSV 248, cpts 248/404, cpts 248/955, cpts RSV 530, cpts 530/1009, or cpts 530/1030). Alternatively, chimeric RSV may incorporate sequences from two or more, wild-type or mutant RSV subgroups, for example a combination of RSV subgroup A and subgroup B sequences. In yet additional aspects, one or more human RSV coding or non-coding polynucleotides are substituted with a counterpart sequence from bovine or murine RSV, alone or in combination with one or more selected attenuating point mutations, e.g., cp and/or ts mutations, to yield novel attenuated vaccine strains. In one embodiment, a chimeric bovine-human RSV incorporates a substitution of the human RSV NP gene or gene segment with a counterpart bovine NP gene or gene segment, which chimera can optionally be constructed to incorporate a SH gene deletion, one or more cp or ts point mutations, or various combinations of these and other mutations disclosed herein.

In one embodiment of the invention, isolated polynucleotides, expression vectors, and methods for producing chimeric RSV are provided wherein the genome or antigenome is recombinantly altered compared to either the donor or recipient sequence. In particular, mutations are incorporated within a chimeric RSV genome or antigenome based on their ability to alter the structure and/or function of a chimeric RSV clone, e.g., by altering the structure, expression and or function of a selected protein encoded or a cis-acting RNA sequence thereby yielding a desired phenotypic change. Desired phenotypic changes include, e.g., changes in viral growth in culture, temperature sensitivity, plaque size, attenuation, and immunogenicity.

In one aspect of the invention, isolated polynucleotides and expression vectors are provided which comprise a chimeric RSV genome or antigenome having at least one attenuating point mutation adopted from a biologically derived mutant RSV. In one such embodiment, at least one point mutation is present in the polymerase gene L involving a nucleotide substitution that specifies a ts phenotype., Exemplary RSV clones and vectors incorporate a nucleotide substitution that results in an amino acid change in the polymerase gene at $Phe_{521}$, $Gln_{831}$, $Met_{1169}$, or $Tyr_{1321}$. Preferably, two or three mutations are incorporated in a codon specifying the attenuating mutation in order to increase the level of genetic stability. Other exemplary RSVs incorporate at least two attenuating ts mutations.

Mutations incorporated within chimeric cDNAs, vectors and viral particles of the invention can be introduced individually or in combination into a full-length RSV cDNA and the phenotypes of rescued virus containing the introduced mutations can be readily determined. In exemplary embodiments, amino acid changes displayed by attenuated, biologically-derived viruses versus a wild-type RSV, for example changes exhibited by cpRSV or tsRSV, are incorporated in combination within recombinant RSV to yield a desired level of attenuation.

The present invention also provides chimeric RSV clones, vectors and particles incorporating multiple, phenotype-specific mutations introduced in selected combinations into the chimeric genome or antigenome to produce an attenuated, infectious virus or subviral particle. This process, coupled with routine phenotypic evaluation, provides chimeric RSV having such desired characteristics as attenuation, temperature sensitivity, altered immunogenicity, cold-adaptation, small plaque size, host range restriction, etc. Mutations thus identified are compiled into a "menu" and introduced in various combinations to calibrate a vaccine virus to a selected level of attenuation, immunogenicity and stability.

In preferred embodiments, the invention provides for supplementation of one or more mutations adopted from biologically derived RSV, e.g., cp and ts mutations, with additional types of mutations involving the same or different genes. Target genes for mutation in this context include the attachment (G) protein, fusion (F) protein, small hydrophobic (SH), RNA binding protein (N), phosphoprotein (P), the large polymerase protein (L), the transcription elongation factor (M2), M2 ORF2, the matrix (M) protein, and two nonstructural proteins, NS1 and NS2. Each of these proteins can be selectively deleted, substituted or rearranged, in whole or in part, alone or in combination with other desired modifications, to achieve novel chimeric RSV recombinants.

In one aspect, the SH gene is deleted in the donor or recipient context to yield a chimeric RSV having novel phenotypic characteristics, including enhanced growth in vitro and/or attenuation in vivo. In a related aspect, this gene deletion, or another selected, non-essential gene or gene segment deletion, such as a NS1 or NS2 gene deletion is combined in a chimeric RSV with one or more separate mutations specifying an attenuated phenotype, e.g., a point mutation adopted directly (or in modified form, e.g., by introducing multiple nucleotide changes in a codon specifying the mutation) from a biologically derived attenuated RSV mutant.

For example, the SH gene or NS2 gene may be deleted in combination with one or more cp and/or ts mutations adopted from cpts248/404, cpts530/1009, cpts530/1030, or another selected mutant RSV strain, to yield a chimeric RSV having increased yield of virus, enhanced attenuation, and genetic resistance to reversion from an attenuated phenotype, due to the combined effects of the different mutations.

In addition, a variety of other genetic alterations can be produced in a chimeric RSV genome or antigenome, alone or together with one or more attenuating point mutations adopted from a biologically derived mutant RSV. For example, genes or gene segments from non-RSV sources may be inserted in whole or in part. Alternatively, the order of genes can be changed, gene overlap removed, or a RSV genome promoter replaced with its antigenomic counterpart. Different or additional modifications in the chimeric genome or antigenome can be made to facilitate manipulations, such as the insertion of unique restriction sites in various intergenic regions (e.g., a unique StuI site between the G and F genes) or elsewhere. Nontranslated gene sequences can be removed to increase capacity for inserting foreign sequences.

Alternatively, polynucleotide molecules or vectors encoding the chimeric RSV genome or antigenome can be modified to encode non-RSV sequences, e.g., a cytokine, a T-helper epitope, a restriction site marker, or a protein of a microbial pathogen (e.g., virus, bacterium or fungus) capable of eliciting a protective immune response in an intended host.

In other embodiments the invention provides a cell or cell-free lysate containing an expression vector which comprises an isolated polynucleotide molecule encoding a chimeric RSV genome or antigenome as described above, and an expression vector (the same or different vector) which comprises one or more isolated polynucleotide molecules encoding the N, P, L and RNA polymerase elongation factor proteins of RSV. Upon expression the genome or antigenome and N, P, L, and RNA polymerase elongation factor proteins combine to produce an infectious RSV viral or subviral particle.

Attenuated chimeric RSV of the invention is capable of eliciting a protective immune response in an infected human host, yet is sufficiently attenuated so as to not cause unacceptable symptoms of severe respiratory disease in the immunized host. The attenuated chimeric virus or subviral particle may be present in a cell culture supernatant, isolated from the culture, or partially or completely purified. The virus may also be lyophilized, and can be combined with a variety of other components for storage or delivery to a host, as desired.

The invention further provides novel vaccines comprising a physiologically acceptable carrier and/or adjuvant and an isolated attenuated chimeric RSV as described above. In one embodiment, the vaccine is comprised of chimeric RSV having at least one, and preferably two or more attenuating mutations or other nucleotide modifications as described above. The vaccine can be formulated in a dose of $10^3$ to $10^6$ PFU of attenuated virus. The vaccine may comprise attenuated chimeric virus that elicits an immune response against a single RSV strain or antigenic subgroup, e.g. A or B, or against multiple RSV strains or subgroups. In this regard, chimeric RSV of the invention can individually elicit a monospecific immune response or a polyspecific immune response against multiple RSV strains or subgroups. Chimeric RSV can be combined in vaccine formulations with other chimeric RSV or non-chimeric RSV having different immunogenic characteristics for more effective protection against one or multiple RSV strains or subgroups.

In related aspects, the invention provides a method for stimulating the immune system of an individual to elicit an immune response against one or more strains or subgroups of RSV in a mammalian subject. The method comprises administering a formulation of an immunologically sufficient amount of an attenuated, chimeric RSV as described above in a physiologically acceptable carrier and/or adjuvant. In one embodiment, the immunogenic composition is a vaccine comprised of chimeric RSV having at least one, and preferably two or more attenuating mutations or other nucleotide modifications as described above. The vaccine can be formulated in a dose of $10^3$ to $10^6$ PFU of attenuated virus. The vaccine may comprise attenuated chimeric virus that elicits an immune response against a single RSV strain or antigenic subgroup, e.g. A or B, or against multiple RSV strains or subgroups. In this context, the chimeric RSV can elicit a monospecific immune response or a polyspecific immune response against multiple RSV strains or subgroups. Alternatively, chimeric RSV having different immunogenic characteristics can be combined in a vaccine mixture or administered separately in a coordinated treatment protocol to elicit more effective protection against one RSV strain, or against multiple RSV strains or subgroups.

BRIEF DESCRIPTION OF THE DRAWINGS

FIG. 1 is a graph demonstrating the substantially complete correlation between the replication of a series of subgroup A respiratory syncytial viruses in the lungs of mice with their replication in the chimpanzee.

FIG. 2 shows the structures of the cDNA and the encoded antigenome RNA (not to scale). For the purposes of the present Figures, and in all subsequent Examples hereinbelow, the specific cDNAs and viruses used were of strain A2 of subgroup A RSV. The diagram of the antigenome includes the following features: the 5'-terminal nonviral G triplet contributed by the T7 promoter, the four sequence markers at positions 1099 (which adds one nt to the length), 1139, 5611, and 7559 (numbering referring to the first base of the new restriction site), the ribozyme and tandem T7 terminators, and the single nonviral 3'-phosphorylated U residue contributed to the 3' end by ribozyme cleavage (the site of cleavage is indicated with an arrow). Note that the nonviral 5'-GGG and 3'-U residues are not included in length values given here and thereafter for the antigenome. However, the nucleotide insertion at position 1099 is included, and thus the numbering for cDNA-derived antigenome is one nucleotide greater downstream of this position than for biologically derived antigenome. The 5' to 3' positive-sense sequence of D46 (the genome itself being negative-sense) is depicted in SEQ ID NO: 1, where the nucleotide at position four can be either C or G. Also note that the sequence positions assigned to restriction sites in this Figure and throughout are intended as a descriptive guide and do not alone define all of the nucleotides involved. The length values assigned to restriction fragments here and throughout also are descriptive, since length assignments may vary based on such factors as sticky ends left following digestion. Cloned cDNA segments representing in aggregate the complete antigenome are also shown. The box illustrates the removal of the BamHI site from the plasmid vector, a modification that facilitated assembly: the naturally occurring BamHI-SalI fragment (the BamHI site is shown in the top line in positive sense, underlined) was replaced with a PCR-generated BglII-SalI fragment (the BglII site is shown in the bottom line, underlined; its 4-nt sticky end, shown in italics, is compatible with that of BamHI). This resulted in a single nt change (middle line, underlined) which was silent at the amino acid level. FIG. 3 shows the sequence markers contained in the cDNA-encoded antigenome RNA, where sequences are positive sense and numbered relative to the first nt of the leader region complement as 1; identities between strains A2 and 18537, representing RSV subgroups A and B, respectively, are indicated with dots; sequences representing restriction sites in the cDNA are underlined; gene-start (GS) and gene-end (GE) transcription signals are boxed; the initiation codon of the N translational open reading frame at position 1141 is italicized, and the restriction sites are shown underneath each sequence. In the top sequence (SEQ ID NO. 22), a single C residue was inserted at position 1099 to create an AflII site in the NS2-N intergenic region, and the AG at positions 1139 and 1140 immediately upstream of the N translational open reading frame were replaced with CC to create a new NcoI site. In the middle sequence (SEQ ID NO. 23), substitution of G and U at positions 5612 and 5616, respectively, created a new StuI site in the G-F intergenic region. In the bottom sequence (SEQ ID NO. 24), a C replacement at position 7560 created a new SphI site in the F-M2intergenic region.

Figure 4A:
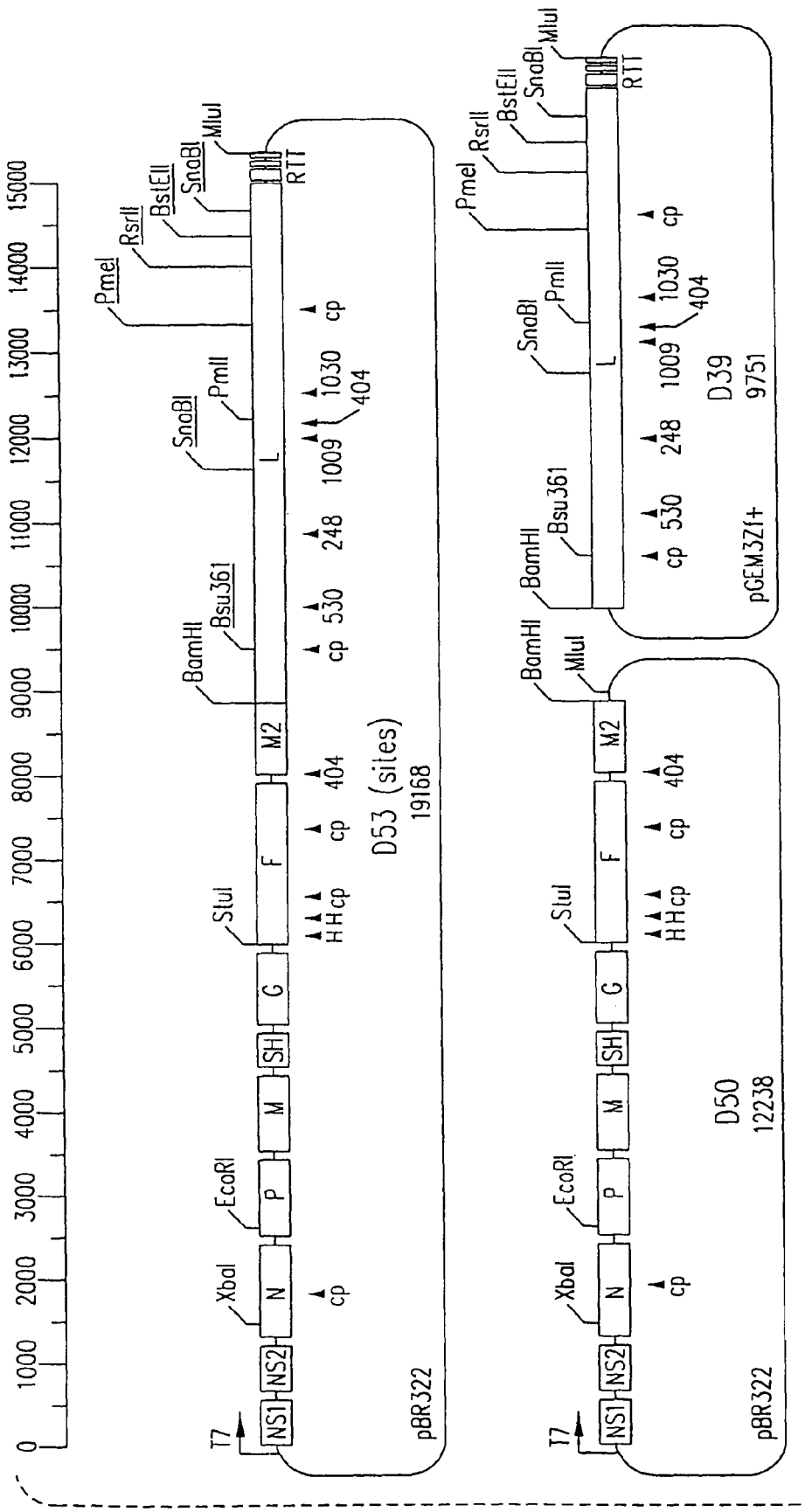
Figure 4B:
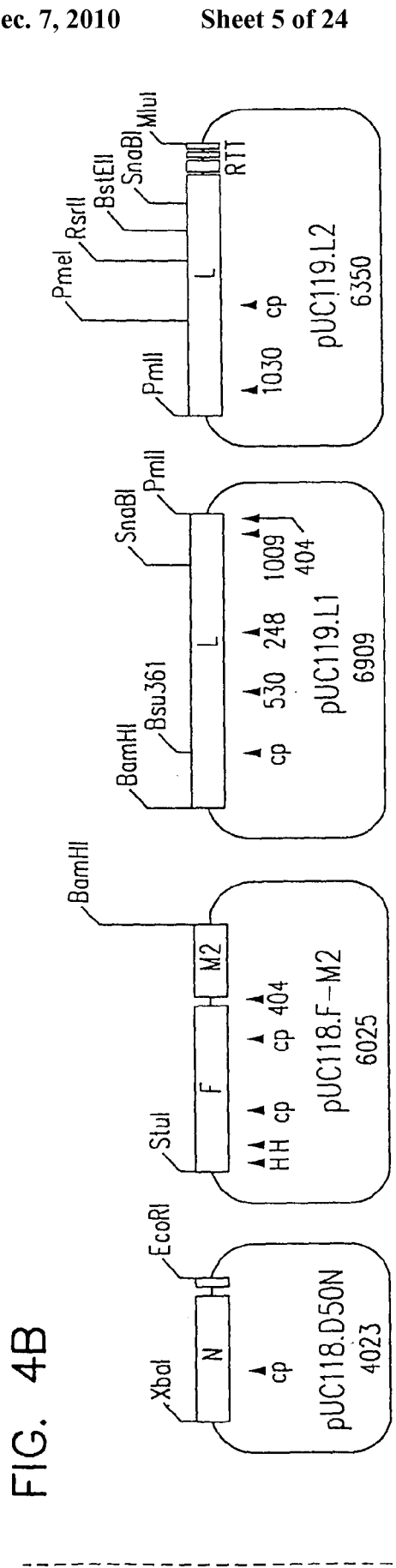

FIG. 4 illustrates structures of cDNAs (approximately to scale) involved in the insertion of mutations, assembly of complete antigenome constructs, and recovery of recombinant virus. Four types of mutations were inserted into the pUC118- or pUC119-borne cDNA subclones shown in the bottom row, namely six silent restriction sites in the L gene (underlined over the D53 diagram on the top), two HEK changes in the F gene (H), five cp changes (cp), and the mutations specific to the various biological mutagenesis steps: 248, 404, 530, 1009, and 1030 (as indicated). The mutagenized subclones were inserted into the D50 (representing the RSV antigenome from the leader to the beginning of the M2-L overlap with the T7 promoter immediately upstream of the leader) or D39 (representing the RSV antigenome from the M2-L overlap to the trailer with the ribozyme and T7 terminators immediately downstream of the trailer) intermediate plasmids shown in the middle row. The appropriate D50 and D39 were assembled into full-length D53 antigenome cDNA as shown on the top row (RTT indicates the location of the hammer-head ribozyme followed by two T7 transcription terminators).

Figure 5:
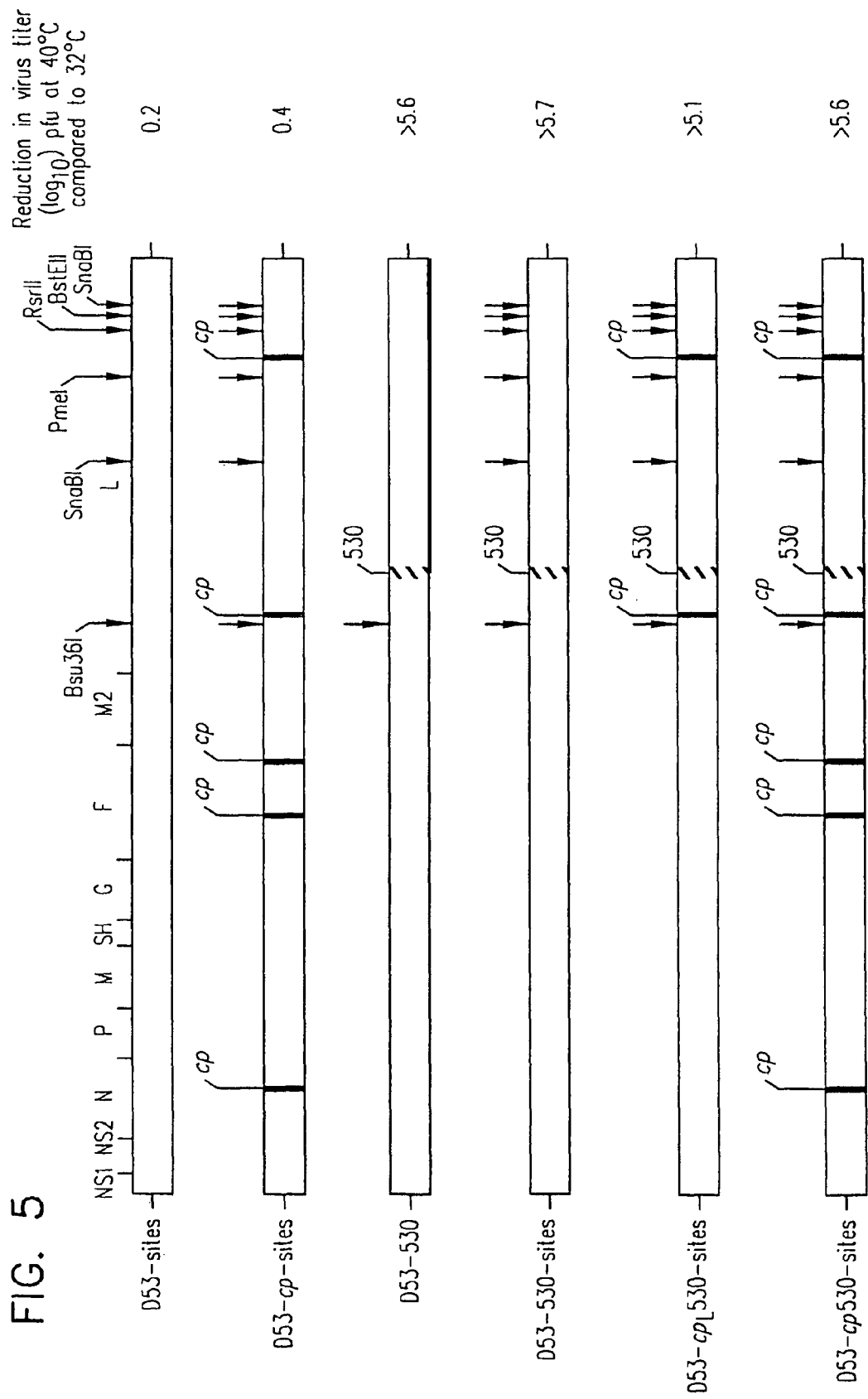

FIG. 5 provides maps of six mutant antigenome cDNAs which were used to recover recombinant RSV. The ts phenotypes of the recombinants are summarized on the right of the figure.

Figure 6:
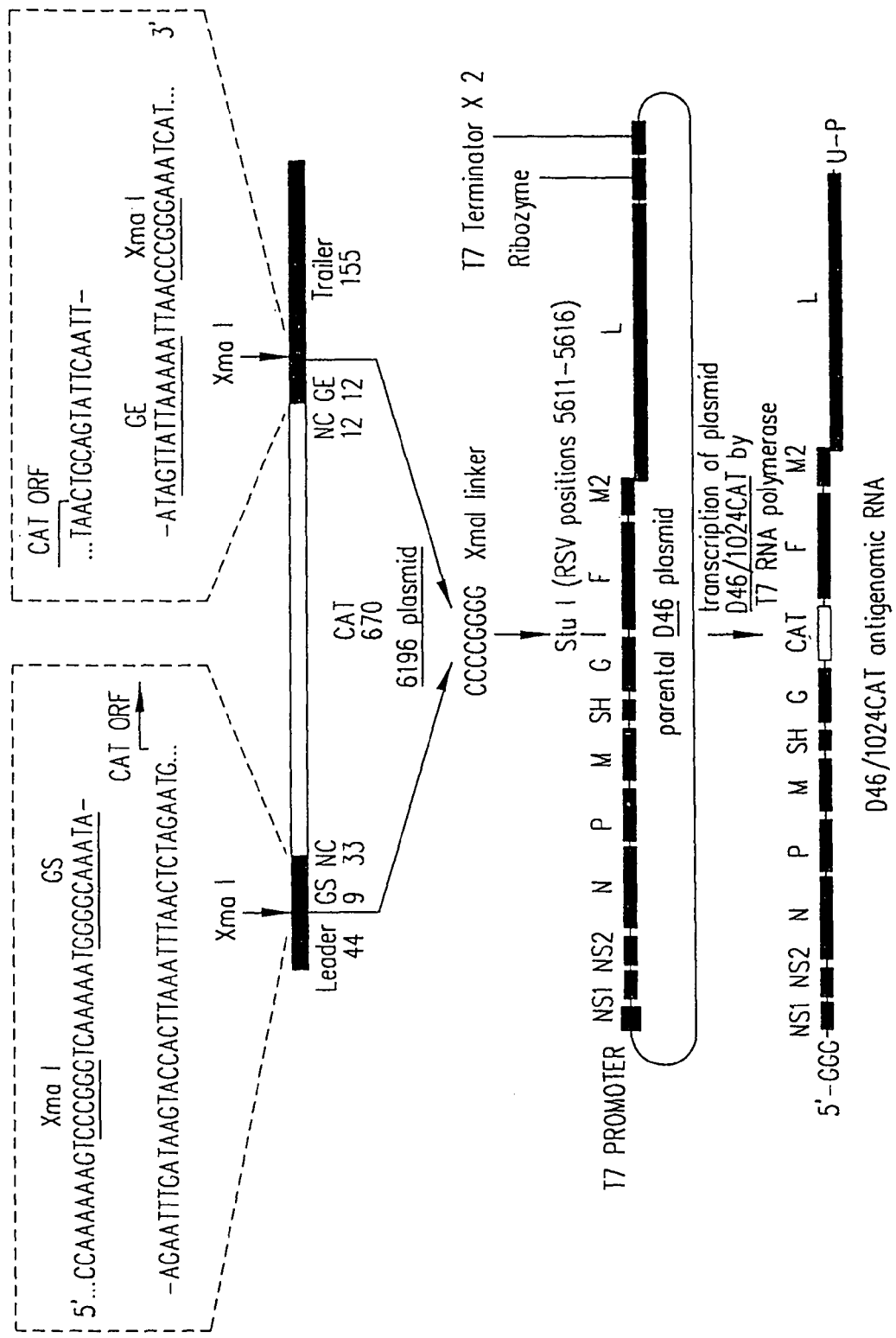

FIG. 6 shows construction of D46/1024CAT cDNA encoding an RSV antigenome containing the CAT ORF flanked by RSV transcription signals (not to scale, RSV-specific segments are shown as filled boxes and CAT sequence as an open box). The source of the CAT gene transcription cassette was RSV-CAT minigenome cDNA 6196(diagram at top). The RSV-CAT minigenome contains the leader region, GS and GE signals, noncoding (NC) RSV gene sequences, and the CAT ORF, with XmaI restriction endonuclease sites preceding the GS signal and following the GE signal (5' and 3' sequences are shown, SEQ ID NOs. 25 and 26, respectively). The nucleotide lengths of these elements are indicated, and the sequences (positive-sense) surrounding the XmaI sites are shown above the diagram. A 8-nucleotide XmaI linker was inserted into StuI site of the parental plasmid D46 to construct the plasmid D46/1024. D46 is the complete antigenome cDNA and is equivalent to D53; the difference in nomenclature is to denote that these represent two different preparations. The Xma-XmaI fragment of the plasmid 6196 was inserted into the plasmid D46/1024 to construct the plasmid D46/1024CAT. The RNA encoded by the D46cDNA is shown at the bottom, including the three 5'-terminal nonviral G residues contributed by the T7 promoter and the 3'-terminal phosphorylated U residue contributed by cleavage of the hammerhead ribozyme; the nucleotide lengths given for the antigenome do not include these nonviral nucleotides. The L gene is drawn offset to indicate the gene overlap.

Figure 7A:
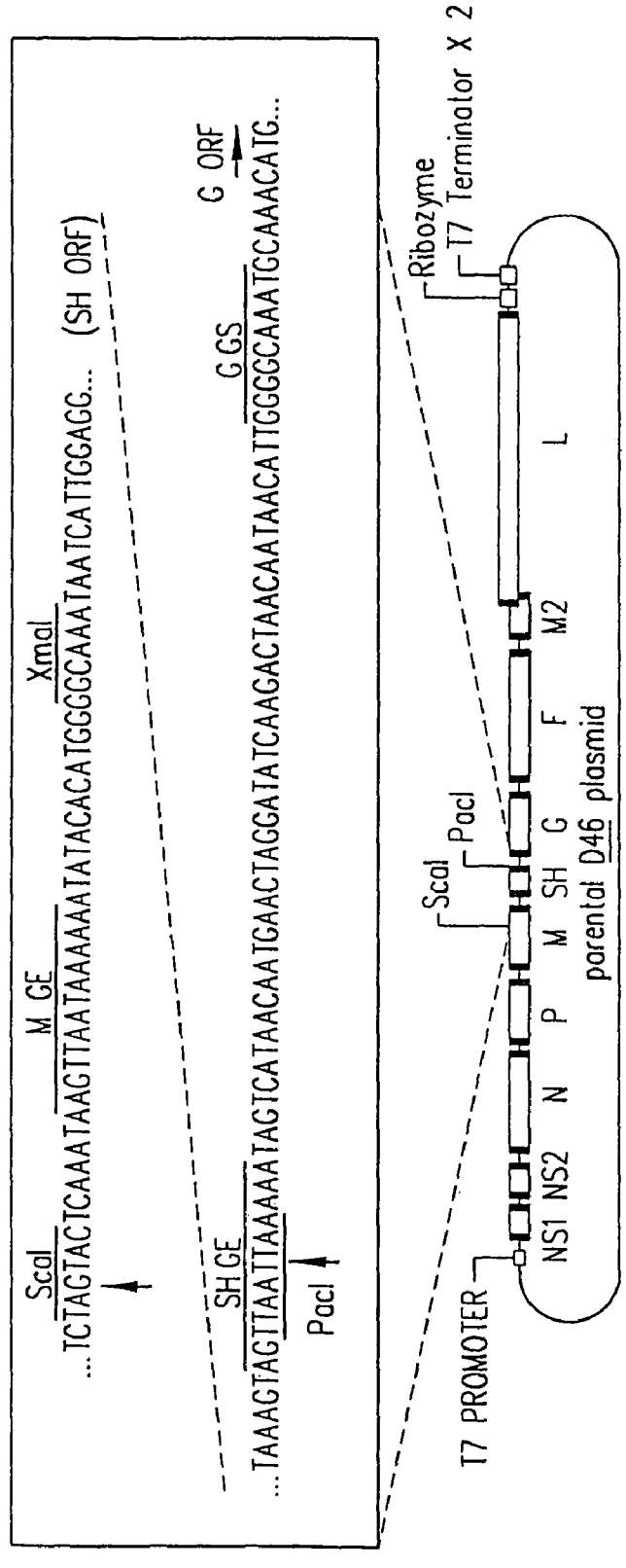
Figure 7B:
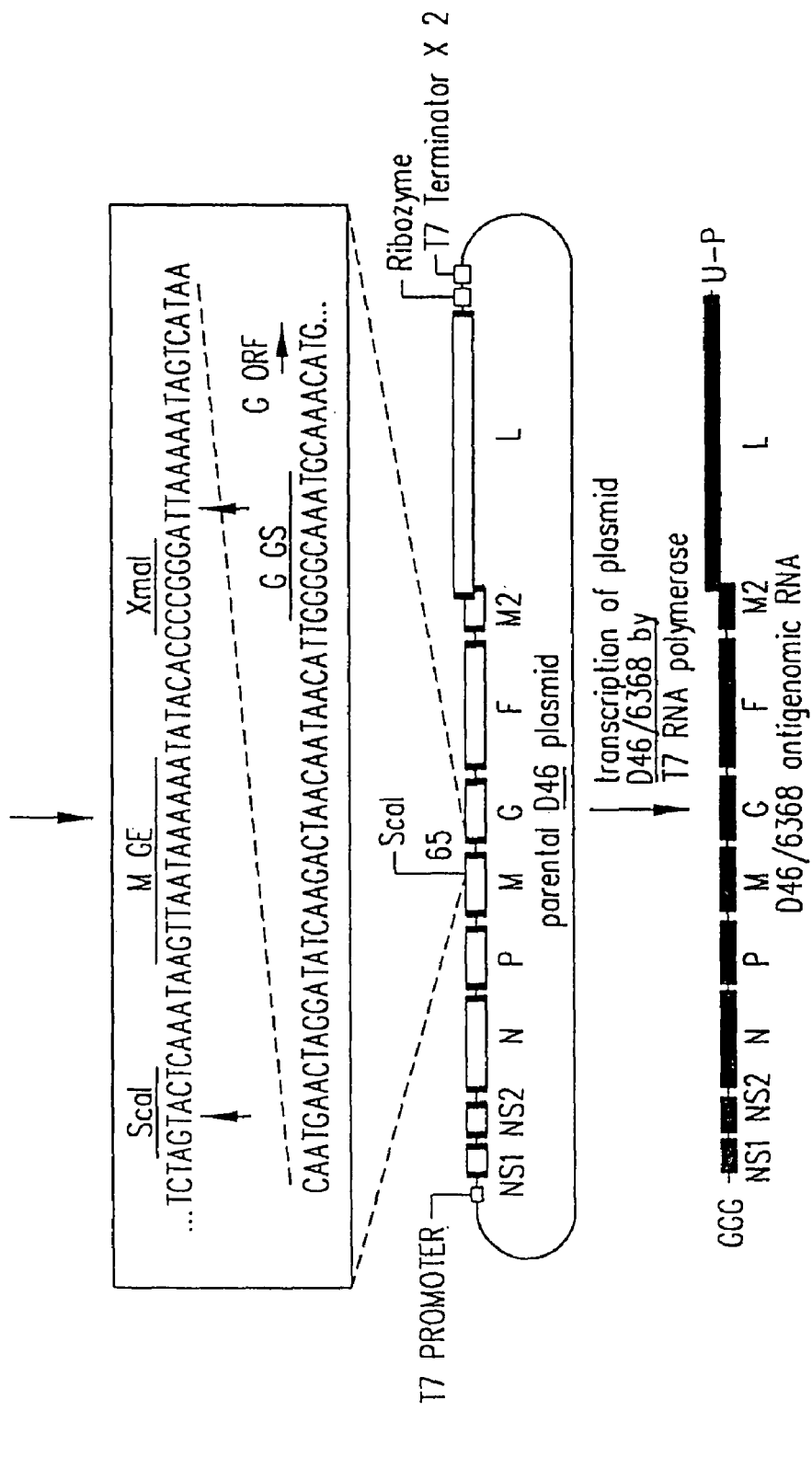

FIG. 7 is a diagram (not to scale) of the parental wild-type D46 plasmid encoding an RSV antigenome (top), and the D46/6368 derivative in which the SH gene has been deleted (bottom). The RSV genes are shown as open rectangles with the GS and GE transcription signals shown as filled boxes on the upstream and downstream ends, respectively. The T7 phage promoter (left) and hammerhead ribozyme and T7 terminators used to generate the 3' end of the RNA transcript (right) are shown as small open boxes. The ScaI and PacI fragment of D46 was replaced with a short synthetic fragment, resulting in D46/6368. The sequence flanking the SH gene in D46, and the sequence of the engineered region in D46/6368, are each shown framed in a box over the respective plasmid map (the top and bottom lines of nucleotides represent sequences 4183-4240 and 4611-4691 of SEQ ID NO: 1, respectively). The sequence of the ScaI-PacI fragment in D46, and its replacement in D46/6368, are shown in bold and demarcated with arrows facing upward. The M GE, SH GS, SH GE and G GS sites are indicated with overlining. The new M-G intergenic region in D46/6368 is labeled 65 in the diagram at the bottom to indicate its nucleotide length. The positive-sense T7 transcript of the SH-minus D46/6368 construct is illustrated at the bottom; the three 5'-terminal nonviral G residues contributed by the T7 promoter and the 3'-terminal U residue are shown (Collins, et al. Proc. Natl. Acad. Sci. USA 92:11563-11567 (1995), incorporated herein by reference). These nonviral nucleotides are not included in length measurements.

Figure 8:
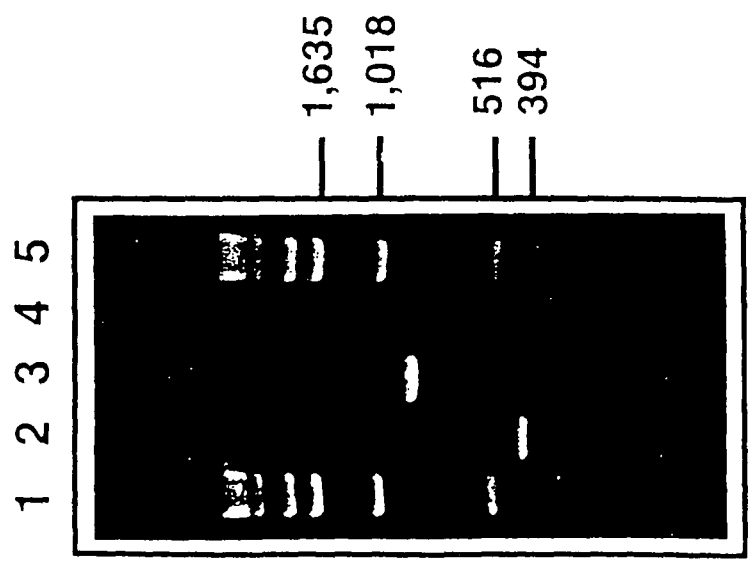

FIG. 8 provides results of RT-PCR analysis of total intracellular RNA from cells infected with the D46 wild-type or D46/6368 SH-minus virus to confirm the deletion in the SH locus. RT was performed with a positive-sense primer that anneals upstream of the SH gene, and the PCR employed in addition a negative-sense primer that anneals downstream of the SH gene. Lanes: (1 and 5) markers consisting of the 1 Kb DNA ladder (Life Technologies, Gaithersburg, Md.); (2) D46/6368 RNA subjected to RT-PCR; (3) D46 RNA subjected to RT-PCR; (4) D46/6368 RNA subjected to PCR alone. PCR products were electrophoresed on a 2.5% agarose gel and stained with ethidium bromide. Nucleotides lengths of some marker DNA fragments are shown to the right.

Figure 9A:
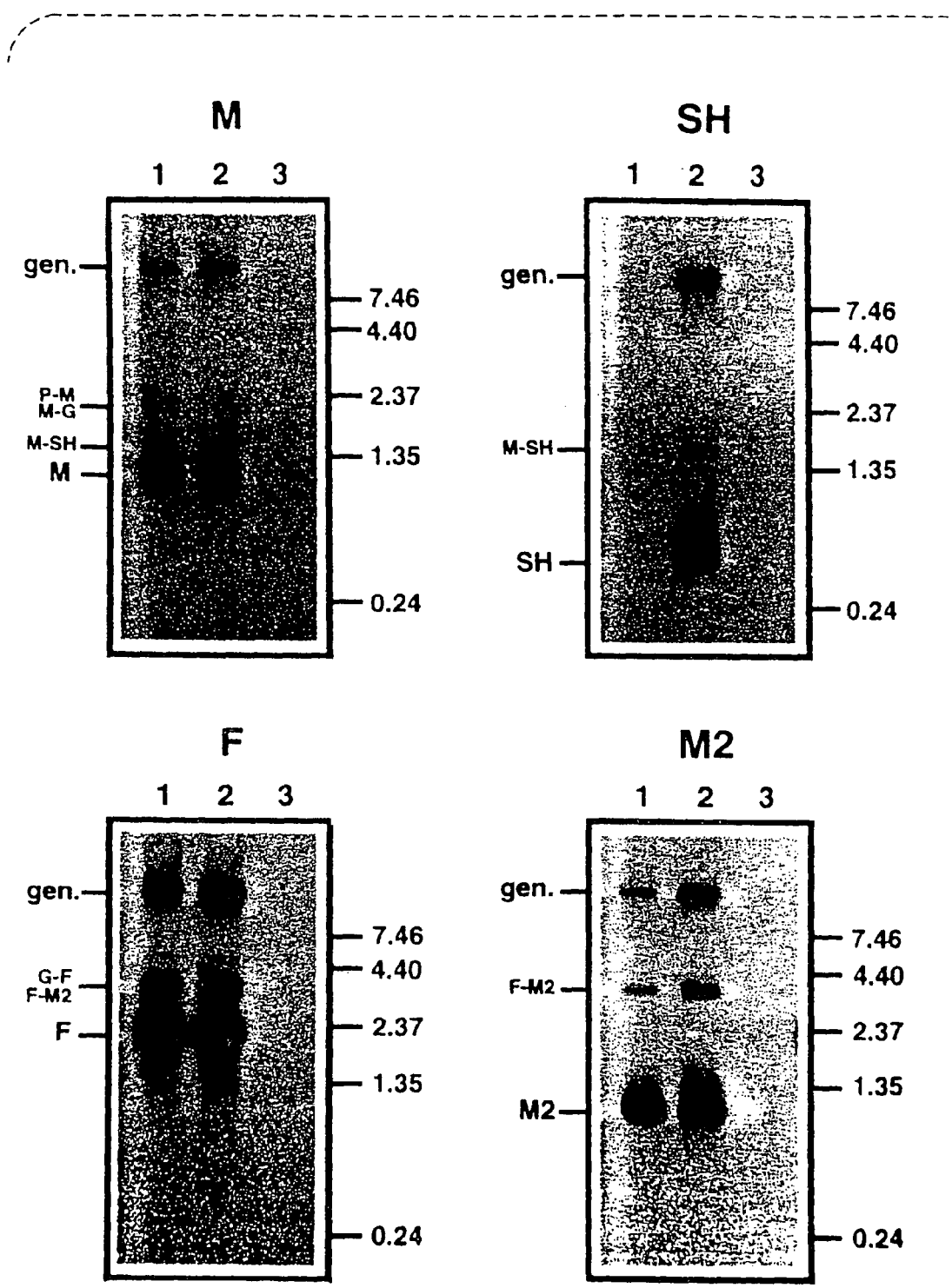

FIG. 9 shows Northern blot hybridization of RNAs encoded by the D46 wild-type and D46/6368 SH-minus virus. Total intracellular RNA was isolated from infected cells and subjected to oligo(dT) chromatography without a prior denaturation step, conditions under which the selected RNA also includes genomic RNA due to sandwich hybridization. RNAs were electrophoresed on formaldehyde-agarose gels and blotted onto nitrocellulose membrane. Replicate blots were hybridized individually with [$^{32}$P]-labeled DNA probes of the M, SH, G, F, M2, or L genes, as indicated. Lanes: (1) D46/6368 RNA; (2) D46 RNA; (3) uninfected HEp-2 cell RNA. Positions of the genomic RNA (gen.), mRNAs (large letters) and read-through transcripts (small letters) are shown on the left. The positions of the read-through transcripts P-M and M-G (M probe) coincide, as well as the positions of G-F and F-M2 transcripts (F probe). The positions of the 0.24-9.5 kb RNA ladder molecular weight markers (Life Technologies), which was run in parallel and visualized by hybridization with [$^{32}$P]-labeled DNA of phage lambda, are shown on the right.

Figure 10:
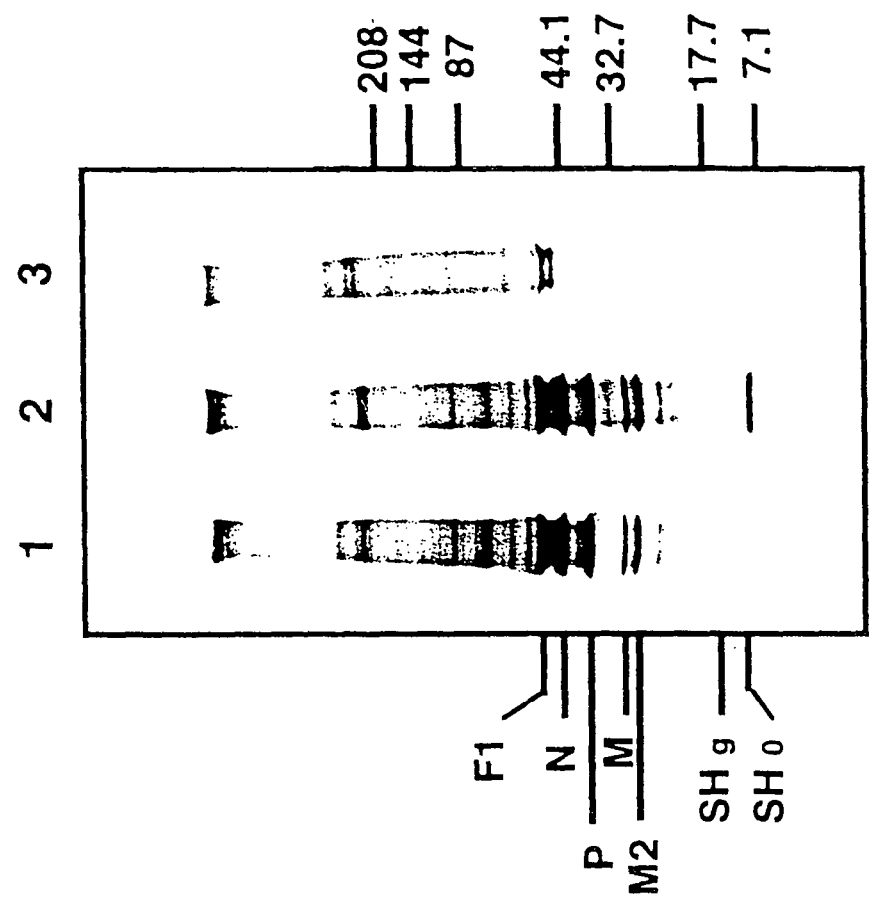

FIG. 10 shows SDS-PAGE of [$^{35}$S]-labeled RSV proteins synthesized in HEp-2 cells infected with the D46 wild-type or D46/6368 SH-minus virus. Proteins were subjected to immunoprecipitation with antiserum raised against purified virions and analyzed by electrophoresis in pre-cast gradient 4%-20% Tris-glycine gels (Novex, San Diego, Calif.). Positions of viral proteins are indicated to the left; positions and molecular masses (in kilodaltons) of marker proteins (Kaleidoscope Prestained Standards, Bio-Rad, Richmond, Calif.), are shown to the right.

Figure 11:
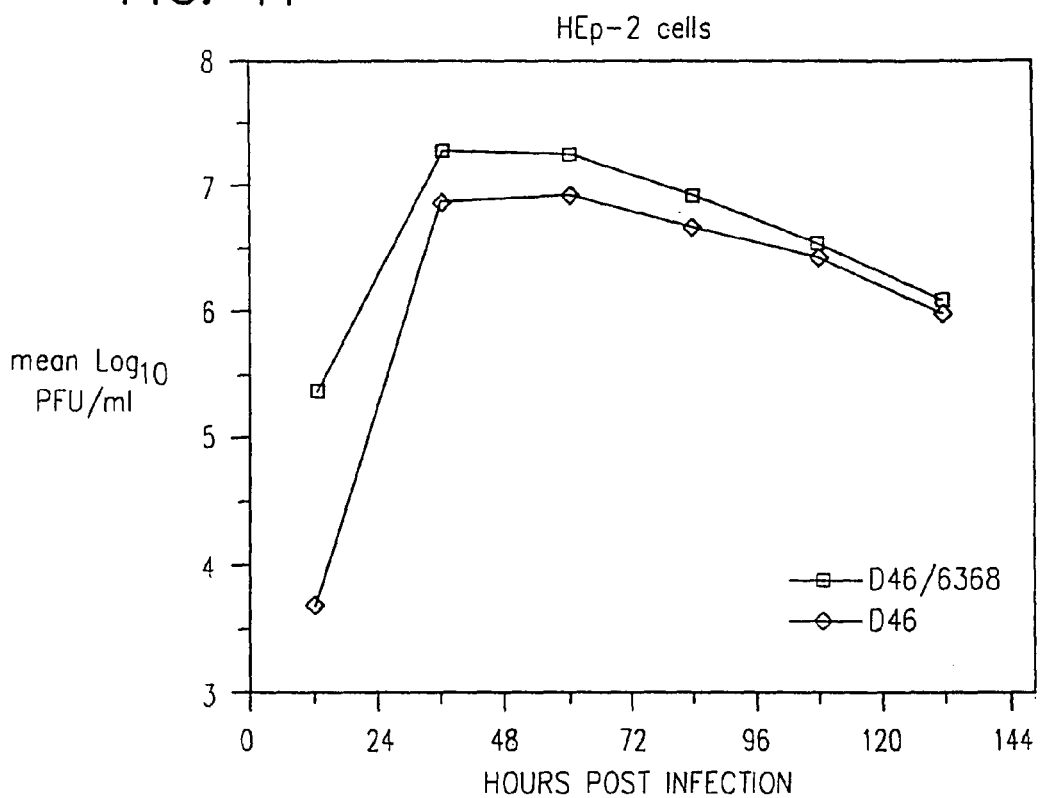
Figure 12:
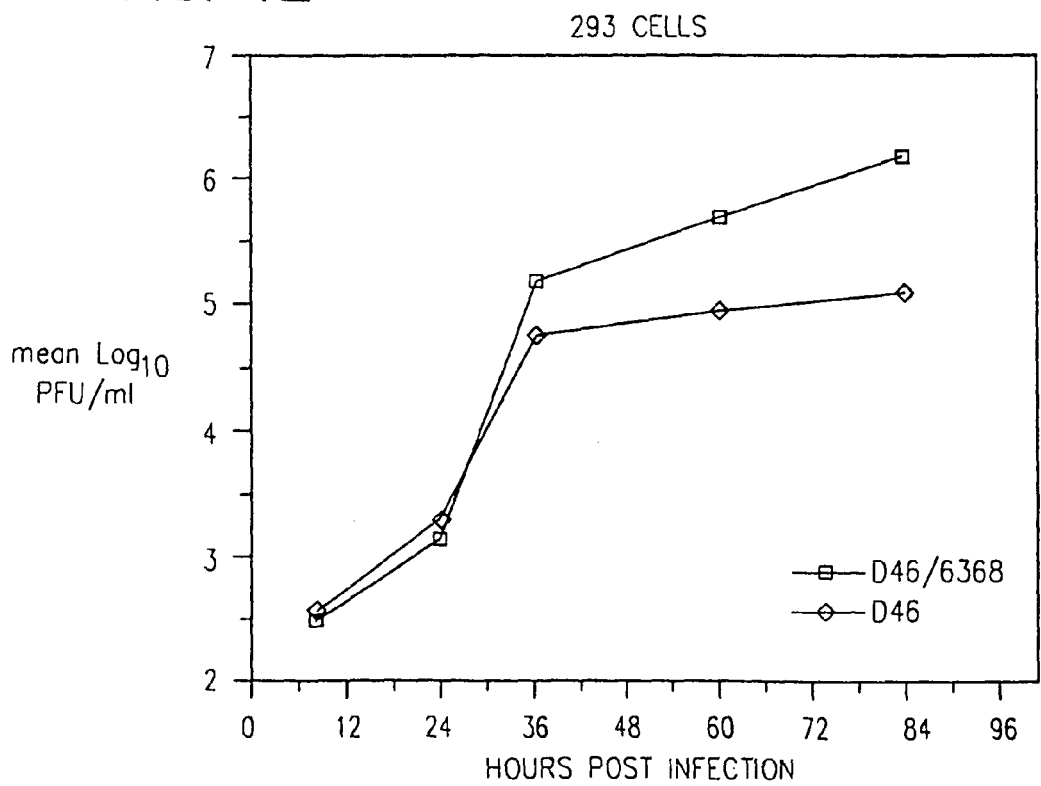
Figure 13:
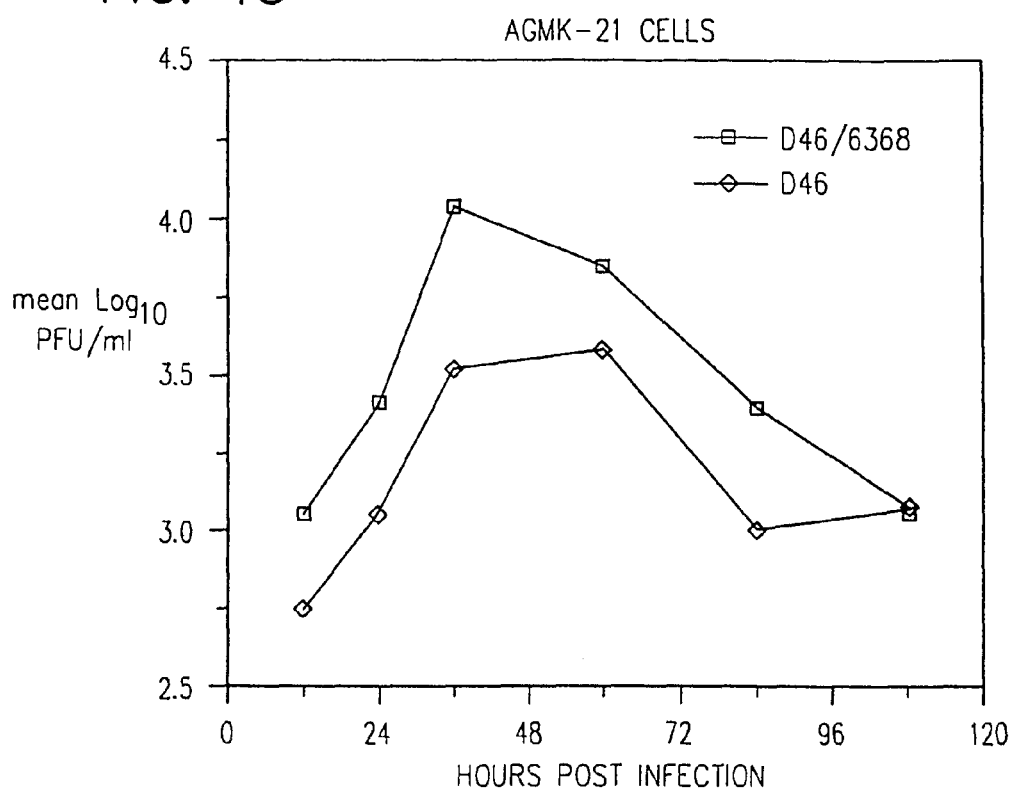

FIGS. 11-13 provide growth curves for D46 wild-type and D46/6368 SH-minus viruses in HEp-2 cells (FIG. 11), 293 cells (FIG. 12), and AGMK-21 cells (FIG. 13). Triplicate cell monolayers in 25-cm$^2$ culture flasks were infected with 2

PFU per cell of either virus, and incubated at 37° C. Aliquots were taken at indicated time points, stored at −70° C., and titrated in parallel by plaque assay with antibody staining. Each point shown is the average titer of three infected cell monolayers.

Figure 14:
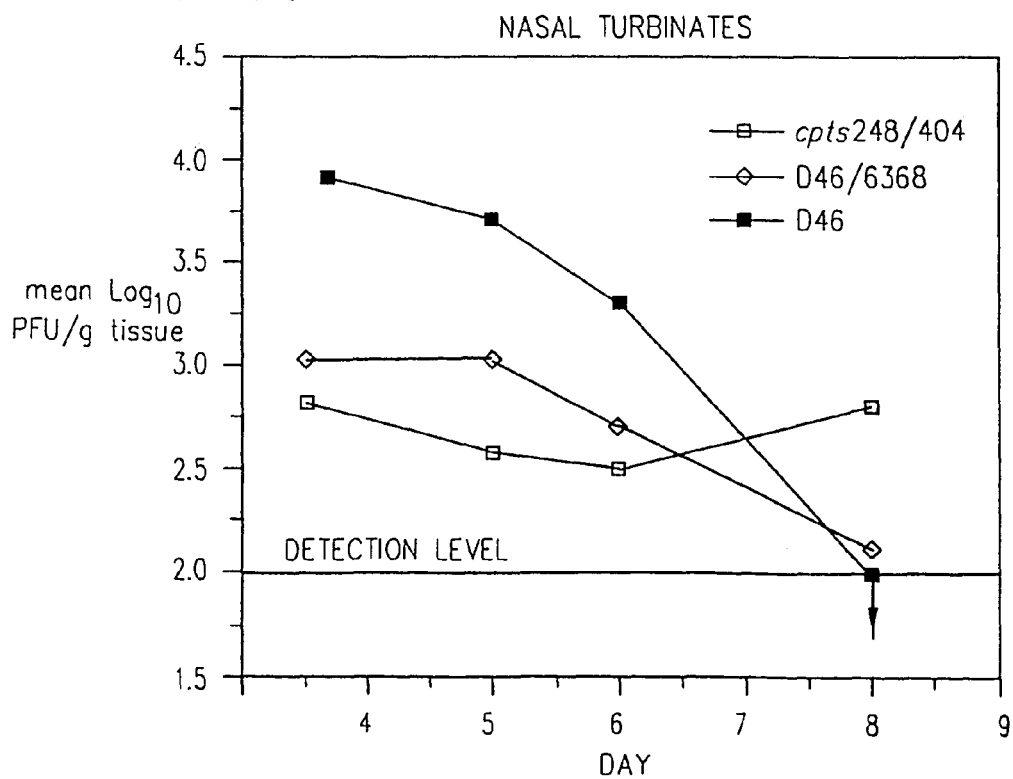
Figures 15, 16:
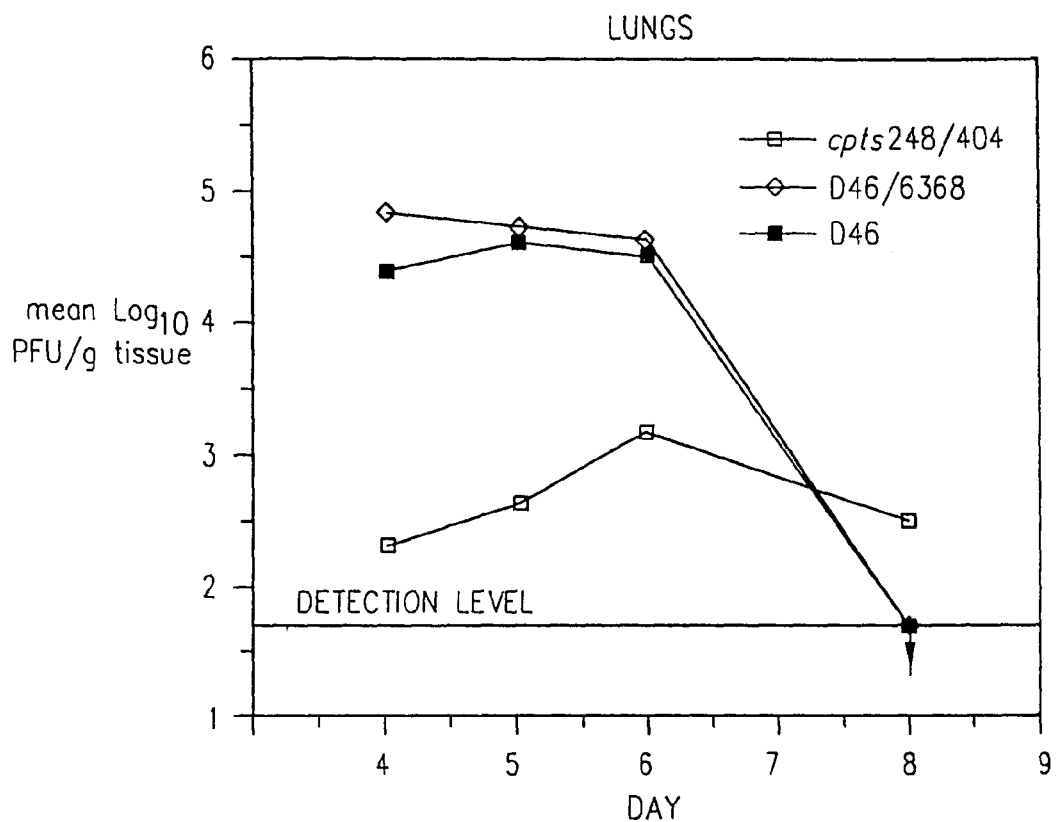

FIGS. 14 and 15 show kinetics of virus replication in the upper (FIG. 14) and lower (FIG. 15) respiratory tract of mice inoculated intranasally with the D46 wild-type virus, D46/6368 SH-minus virus, or the biologically-derived cpts248/404 virus. Mice in groups of 24 were inoculated intranasally with $10^6$ PFU of the indicated virus. Six mice from each group were sacrificed on the indicated day and the nasal turbinates and lung tissues were removed and homogenized, and levels of infectious virus were determined by plaque assay on individual specimens and mean $\log_{10}$ titers were determined.

FIG. 16 shows a comparison of the transcription products and gene order of SH-minus virus compared to its wild-type counterpart. The upper panel summarizes an analysis of the amounts of certain mRNAs produced by the SH-minus virus compared with the wild-type parent recombinant virus. Intracellular mRNAs were isolated from cells infected with the SH-minus or wild-type virus and analyzed by Northern blot hybridization with gene-specific probes. The amount of hybridized radioactivity was quantitated, and the relative abundance of each individual mRNA produced by the SH-minus virus versus its wild-type parent is shown. The lower panel shows the gene order of the wild-type virus from the M gene (position 5 in the gene order) to the L gene (position 10). This is compared to that of the SH-minus virus, in which the positions in the gene order of the G, F, M2 and L genes are altered due to deletion of the SH gene.

Figure 17:
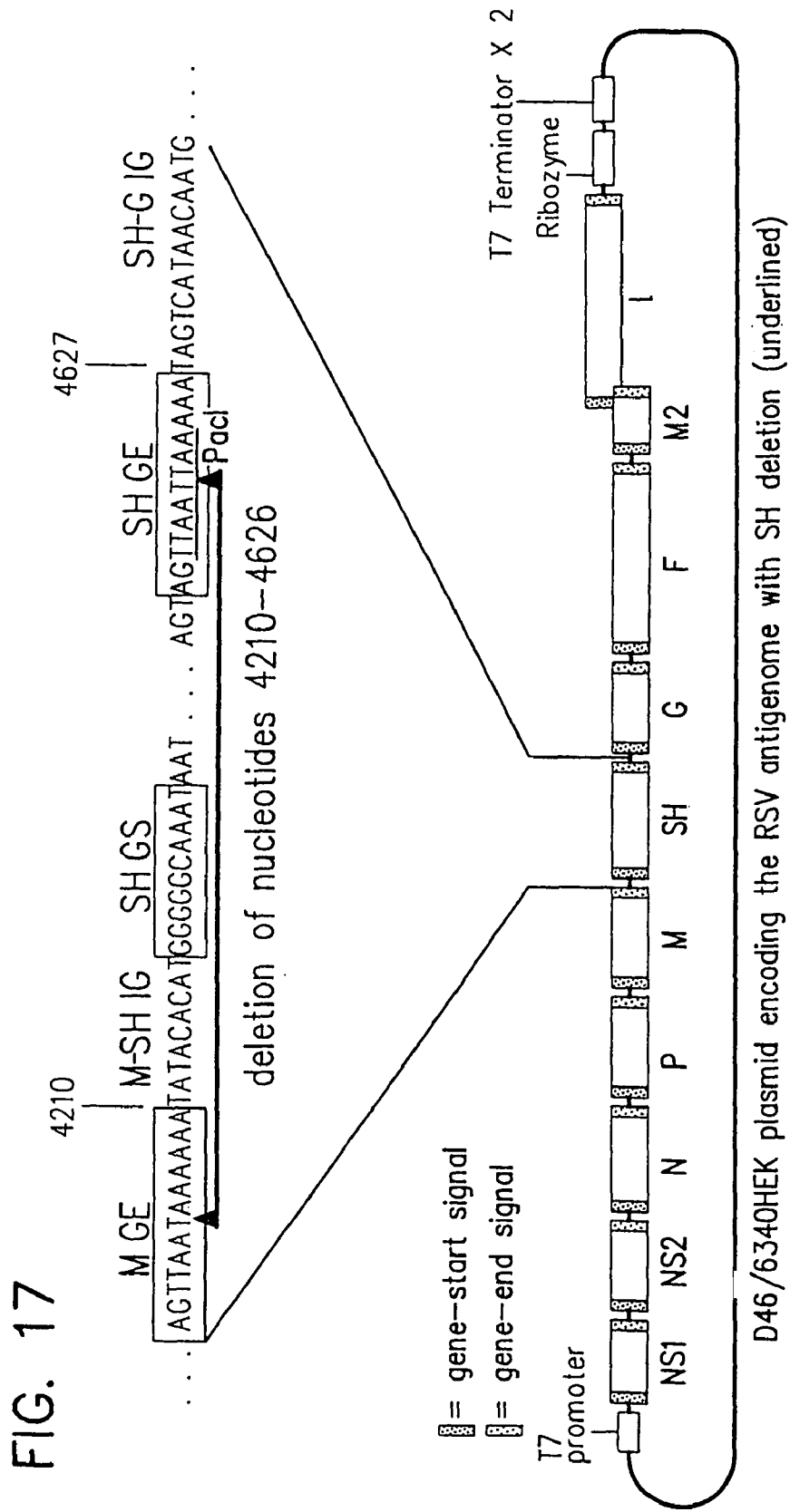

FIG. 17 depicts the D46 antigenome plasmid which was modified by deletion of the SH gene in such a way as to not insert any heterologous sequence into the recombinant virus. The sequence flanking the SH gene depicted at the top. The MGE, M-SH intergenic (IG), SH GS, SH GE and SH-G IG sequences are shown. The area which was removed by the deletion is underlined, with the deletion points indicated with upward pointing triangles. The described nucleotide segment consists of sequences 4198-4643 of SEQ ID NO: 1. The antigenome resulting from this deletion is D46/6340.

Figure 18:
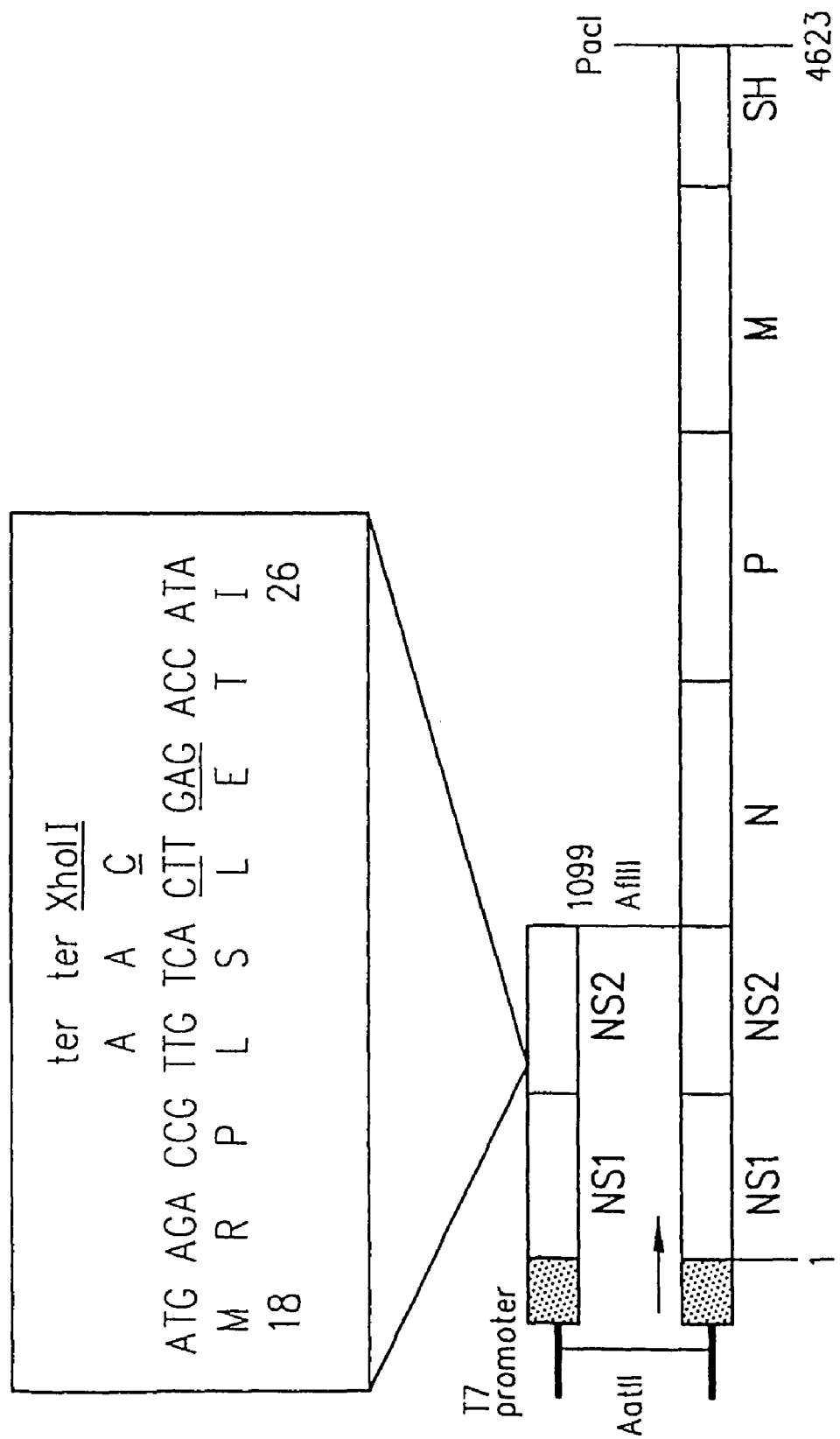

FIG. 18 depicts the introduction of tandem translation stop codons into the translational open reading frame (ORF) encoding the NS2 protein. Plasmid D13 contains the left end of the antigenome cDNA, including the T7 promoter (shaded box), the leader region, and the NS1, NS2, N, P, M and SH genes. Only the cDNA insert of D13 is shown. The AatII-AflII fragment containing the T7 promoter and NS1 and NS2 genes was subcloned into a pGem vector, and site-directed mutagenesis was used to modify the NS2 ORF in the region illustrated by the sequence. The wild-type sequence of codons 18 to 26 (SEQ ID NO: 27) is shown (the encoded amino acids are indicated below(SEQ ID NO: 28)), and the three nucleotides above are the three substitutions which were made to introduce two termination codons (ter) and an XhaI site (underlined) as a marker. The resulting cDNA and subsequent recovered virus are referred to as NS2-knockout (KO).

Figure 19:
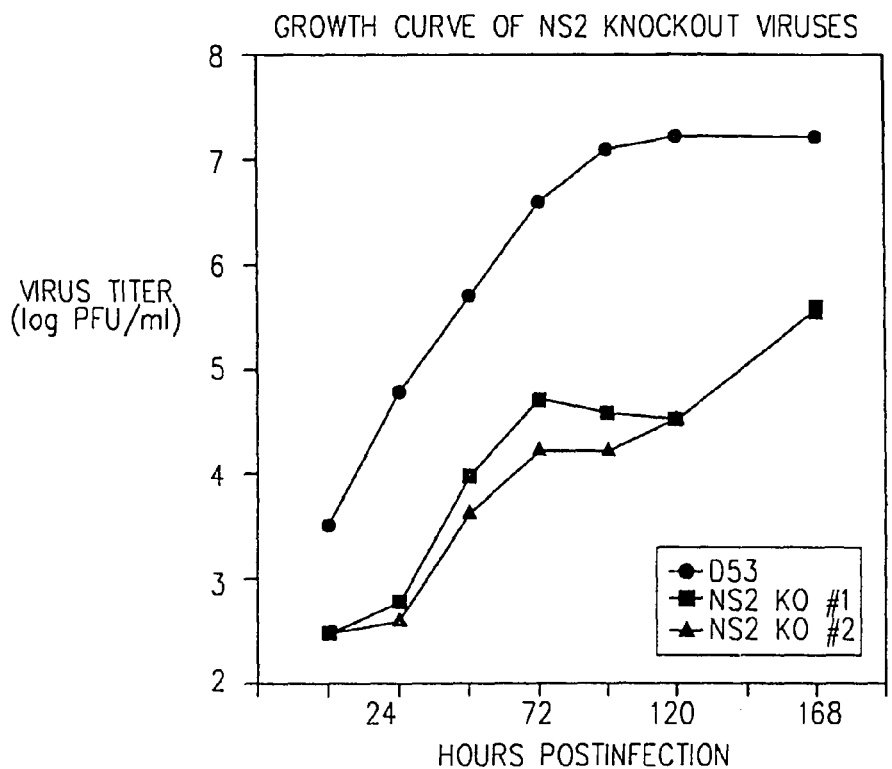

FIG. 19 compares production of infectious virus by wild-type RSV (D53) versus NS2-knockout RSV in HEp-2 cells. Triplicate monolayers were infected with either virus at an input moi of three pfu/cell, and samples were taken at the indicated intervals and quantitated by plaque assay and immunostaining.

Figure 20:
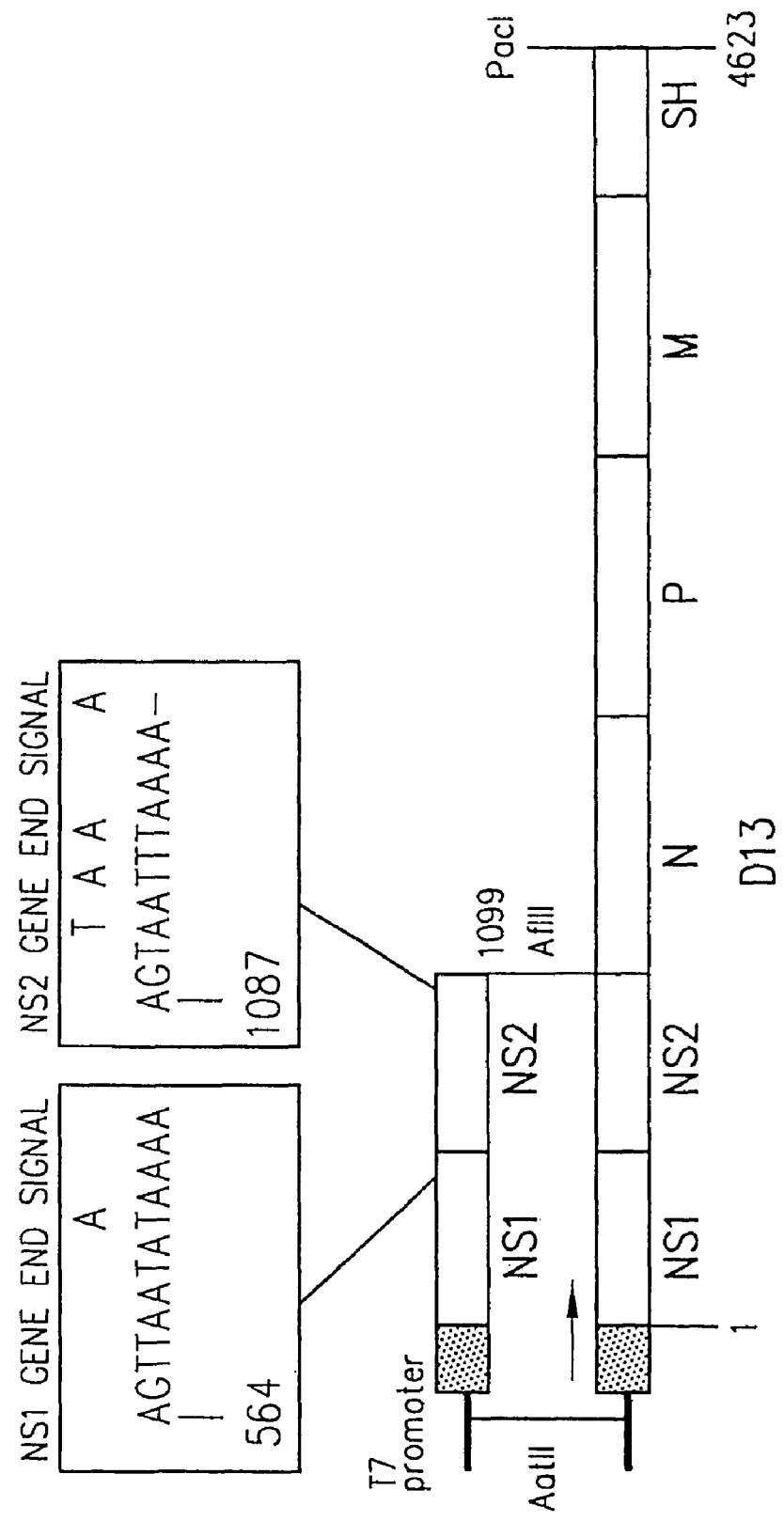

FIG. 20 depicts alteration of gene-end (GE) signals of the NS1 and NS2 genes. The cDNA insert of plasmid D13, representing the left hand end of the antigenome cDNA from the T7 promoter (shaded) to the PacI site at position 4623, is shown. The AatI-AflII fragment containing the T7 promoter and the NS1 and NS2 genes was subcloned into a pGem vector. It was modified by site-directed mutagenesis simultaneously at two sites, namely the NS1 and NS2 GE signals were each modified to be identical to that found in nature for the N gene. The sequences of the wild-type NS1 (SEQ ID NO: 29) and NS2 (SEQ ID NO: 30) GE signals are shown (and identified by sequence position relative to the complete antigenome sequence of SEQ ID NO: 1), and the nucleotide substitutions are shown above the line (SEQ ID NOs: 31 and 32, respectively). The dash in the wildtype sequence of the NS2 GE signal indicates that the mutation increased the length of the GE signal by one nucleotide.

FIG. 21 depicts the deletion of the polynucleotide sequence encoding the NS1 protein. The left hand part of the D13 cDNA is shown at the bottom: D13 contains the left hand part of the antigenome cDNA, from the leader to the end of the SH gene, with the T7promoter immediately upstream of the leader. The sequence on either side of the deletion point (upward arrow) is shown on top; nucleotide numbering corresponds to that of SEQ ID NO:1. The deletion spans from immediately before the translational start site of the NS1 ORF to immediately before that of the NS2 ORF. Thus, it has the effect of fusing the NS1 GS and upstream noncoding region to the N52 ORF. This precludes the disruption of any cis-acting sequence elements which might extend into the NS1 gene due to its leader-proximal location.

FIG. 22 depicts the deletion of the polynucleotide sequence encoding the NS2mRNA. As described above, the left hand part of the D13 cDNA is shown along with the sequence on either side of the deletion point (upward arrow); nucleotide numbering corresponds to that of SEQ ID NO:1. The deletion spans from immediately downstream of the NS1 gene to immediately downstream of the NS2 gene. Thus, the sequence encoding the NS2 mRNA has been deleted in its entirety, but no other sequence has been disrupted. The resulting cDNA and subsequent recovered recombinant virus are referred to as ΔNS2.

Figure 23:
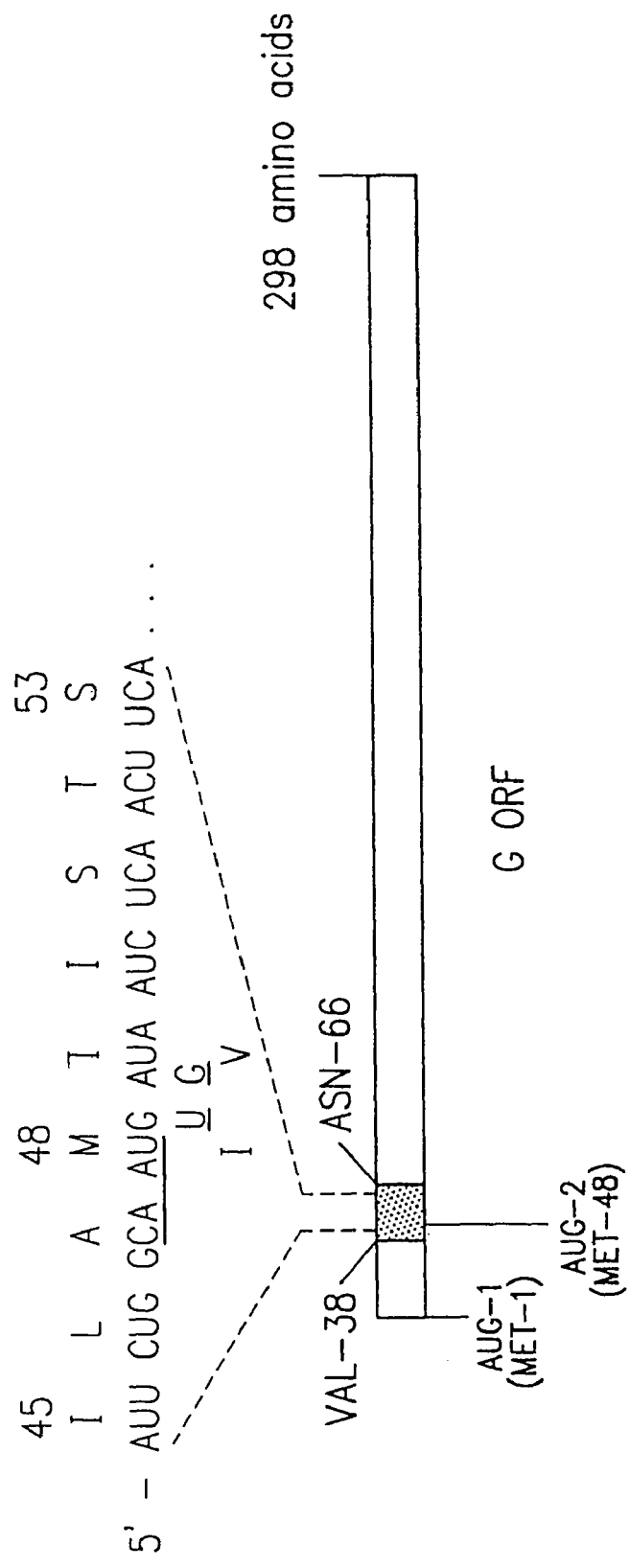

FIG. 23 depicts the ablation of the translational start site for the secreted form of the G protein. The 298-amino acid G protein is shown as an open rectangle with the signal-anchor sequence filled in. The amino acid sequence for positions 45 to 53 (SEQ ID NO: 33) is shown overhead to illustrate two nucleotide substitutions (SEQ ID NO: 34) which change amino acid 48 from methionine to isoleucine and amino acid 49 from isoleucine to valine. The former mutation eliminates the translational start site for the secreted form. The two mutations also create an MfeI site, which provides a convenient method for detecting the mutation. The resulting cDNA and subsequent recovered virus are referred to as M48I (methionine-48 to isoleucine-48).

Figure 24:
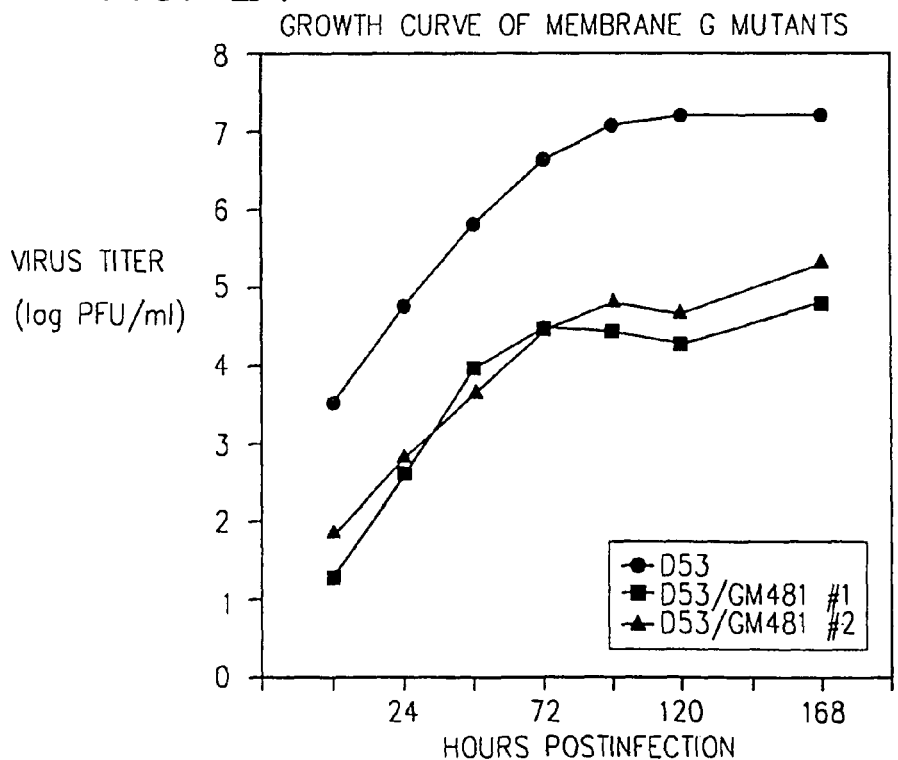

FIG. 24 shows the results of a comparison of production of infectious virus by wild-type RSV (D53) versus that of two isolates of recovered D53/M481 membrane G mutant virus.

FIG. 25A shows the negative-sense genomic RNA of RSV strain A2 (antigenic subgroup A) and illustrates replacement of the F and G genes with their counterparts of strain B1 (antigenic subgroup B). Each rectangle represents a gene encoding a single mRNA, and the grey and filled boxes at the left and right ends of each rectangle represent gene-start (GS) and gene-end (GE) transcription signals, respectively. The thin lines at each end of the genome represent the leader (left end) and trailer (right end) extragenic regions, and the thin lines between rectangles represent intergenic regions. The gene replacement is done at the level of an antigenome cDNA using PacI and SphI sites which precede the G gene and follow the F gene, respectively. The L gene is drawn offset to illustrate that it overlaps with the upstream M2 gene, a detail which is not immediately germane to this example.

FIGS. 25B and 25C illustrate the sequence (positive-sense) in the chimeric rAB virus, namely recombinant RSV strain A2 in which the F and G glycoprotein genes were replaced with those of strain B1. The sequence shown contains part of the SH-G (Part B, SEQ ID NO: 35) and F-M2 (Part C, SEQ ID NO: 36) junction. Sequence derived from the strain A2 backbone is shown in lower case, and that from the strain B1 donor is in upper case. The last A2-specific nucleotide at the junction between the A2 and B1 sequence is numbered according to the unmodified recombinant A2 genomic sequence. The SH gene-end (GE) and F GE signals are boxed. The PacI and SphI recognition sites are italicized. IG: intergenic region.

Figure 26:
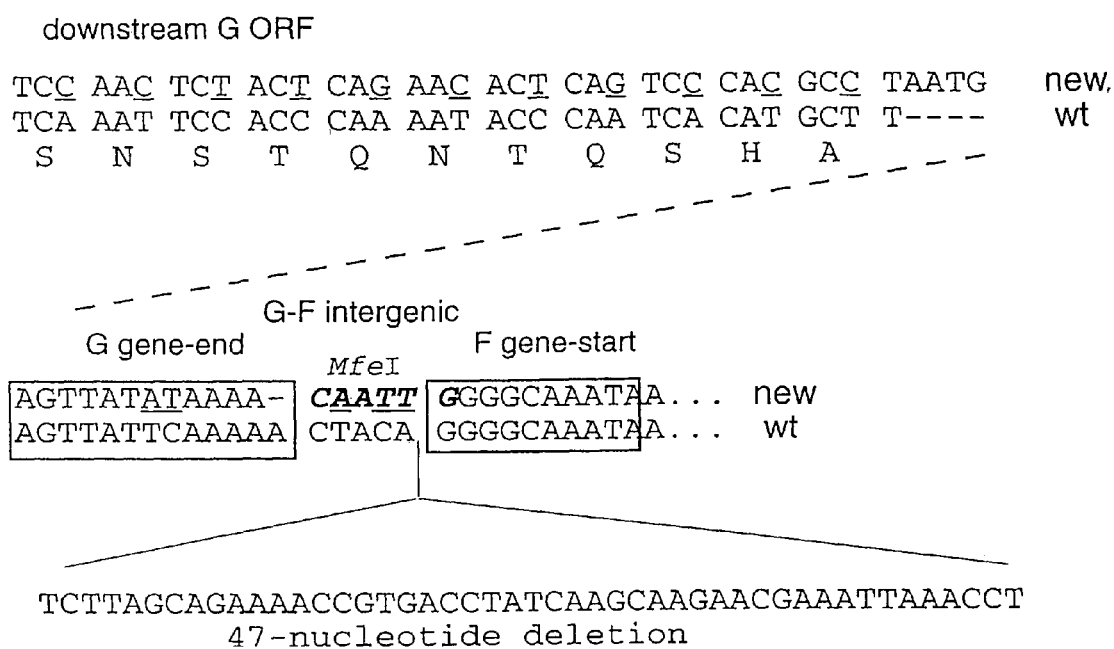

FIG. 26 illustrates modification the cDNA of the strain B1 G and F genes in order to improve stability during growth in E. coli. Two positive-sense sequences are shown: the upper one (labeled "new") is the modified B1 sequence (SEQ ID NO: 37), and the lower ("wt") is the wild-type B1 sequence (nucleotides 5554-5663 of SEQ ID NO: 2). The sequence shown includes the downstream end of the G translational open reading frame (ORF), its encoded amino acids (shown as the single letter code below the sequence, SEQ ID NO: 38), the G GE signal (boxed), the G-F intergenic region, and the F gene-start (GS) signal (boxed). Underlined positions in the new sequence represent substitutions; dashes in the new sequence represent deletions; dashes in the wt sequence indicate an insertion in the new sequence. An MfeI site created in the new sequence is in bold italics. A 47-nucleotide sequence from the G-F intergenic region which was deleted in creating the new sequence is indicated.

FIG. 27 illustrates replication of the chimeric recombinant AB wt RSV and ABcp248/404/1030 derivative in the upper (top panel; nasopharyngeal swab) and lower (lower panel; tracheal lavage) respiratory tract of seronegative chimpanzees. This is based on data from Table 46. The light horizontal dotted line in each graph is the lower limit of detectability. Bars indicate Standard Error.

DESCRIPTION OF THE SPECIFIC EMBODIMENTS

The present invention provides infectious, chimeric respiratory syncytial virus (RSV) that are attenuated and capable of eliciting a propylactic or therapeutic immune response in mammalian patients susceptible to RSV infection. Also provided within the invention are novel methods and compositions for designing and producing attenuated, chimeric RSV, as well as methods and compositions for prophylaxis and treatment of RSV infection.

Chimeric RSV of the invention are recombinantly engineered to incorporate nucleotide sequences from more than one RSV strain or subgroup to produce an infectious, chimeric virus or subviral particle. In this manner, candidate vaccine virus are recombinantly engineered to elicit an immune response against RSV in a mammalian host, including humans and non-human primates. Chimeric RSV according to the invention may elicit an immune response to a specific RSV subgroup or strain, or they may elicit a polyspecific response against multiple RSV subgroups or strains.

In exemplary embodiments of the invention, heterologous genes, gene segments, or single or multiple nucleotides of one RSV are added to a partial or complete RSV genome or antigenome or substituted therein by counterpart sequence(s) from a heterologous RSV to produce a chimeric RSV genome or antigenome. The chimeric RSV of the invention thus includes a partial or complete "recipient" RSV genome or antigenome from one RSV strain or subgroup virus combined with an additional or replacement "donor" gene or gene segment of a different RSV strain or subgroup virus.

In preferred aspects of the invention, chimeric RSV incorporate a partial or complete human RSV genome or antigenome of one RSV subgroup or strain combined with a heterologous gene or gene segment from a different human RSV subgroup or strain. For example, preferred chimeric RSV incorporate a chimeric genome or antigenome comprised of a partial or complete human RSV A or B subgroup genome or antigenome combined with a heterologous gene or gene segment from a different human RSV A or B subgroup virus.

Heterologous donor genes or gene segments from one RSV strain or subgroup are combined with or substituted within a recipient genome or antigenome that serves as a backbone for insertion or addition of the donor gene or gene segment. Thus, the recipient genome or antigenome acts as a vector to import and express heterologous genes or gene segments to yield chimeric RSV that exhibit novel structural and/or phenotypic characteristics. Preferably, addition or substitution of a heterologous gene or gene segment within a selected recipient RSV strain yields novel phenotypic effects, for example attenuation, growth changes, altered immunogenicity, or other desired phenotypic changes, as compared with corresponding phenotypes of the unmodified recipient and/or donor.

Genes and gene segments that are useful as heterologous inserts or additions within a chimeric RSV genome or antigenome include genes or gene segments encoding a NS1, NS2, N, P, M, SH, M2(ORF1), M2(ORF2), L, F or G protein or a portion thereof. In preferred embodiments invention, chimeric RSV incorporate a heterologous gene encoding a RSV F, G or SH glycoprotein. Alternatively, the chimeric RSV may incorporate a gene segment encoding only a portion of a selected protein, for example a cytoplasmic domain, transmembrane domain, ectodomain or immunogenic epitope of a RSV F, G or SH glycoprotein.

In other embodiments, chimeric RSV useful in a vaccine formulation can be conveniently modified to accommodate antigenic drift in circulating virus. Typically the modification will be in the G and/or F proteins. An entire G or F gene, or a gene segment encoding a particular immunogenic region thereof, from one RSV strain is incorporated into a chimeric RSV genome or antigenome cDNA by replacement of a corresponding region in a recipient clone of a different RSV strain or subgroup, or by adding one or more copies of the gene, such that several antigenic forms are represented. Progeny virus produced from the modified RSV clone can then be used in vaccination protocols against emerging RSV strains.

Thus, the introduction of heterologous immunogenic proteins, domains and epitopes to produce chimeric RSV is particularly useful to generate novel immune responses in an immunized host. Addition or substitution of an immunogenic gene or gene segment from one, donor RSV subgroup or strain within a recipient genome or antigenome of a different RSV subgroup or strain can generate an immune response directed against the donor subgroup or strain, the recipient subgroup or strain, or against both the donor and recipient subgroup or strain. To achieve this purpose, chimeric RSV may also be constructed that express a chimeric protein, e.g., an immunogenic protein having a cytoplasmic tail and/or transmembrane domain specific to one RSV strain or subgroup fused to an ectodomain of a different RSV. Other exemplary recombinants of this type may express duplicate protein regions, such as duplicate immunogenic regions.

Although it is often useful to add or substitute entire genes (including cis-acting elements and coding regions) within a chimeric genome or antigenome, it is also useful to transfer only a portion of a donor gene of interest. Quite commonly, non-coding nucleotides such as cis-acting regulatory elements and intergenic sequences need not be transferred with the donor gene coding region. In addition, a variety of gene segments provide useful donor polynucleotides for inclusion within a chimeric genome or antigenome to express chimeric RSV having novel and useful properties. Thus, heterologous gene segments may beneficially encode a cytoplasmic tail, transmembrane domain or ectodomain, an epitopic site or region, a binding site or region, an active site or region containing an active site, etc., of a selected protein from one RSV. These and other gene segments can be added or substituted for a counterpart gene segment in another RSV to yield novel chimeric recombinants, for example recombinants expressing a chimeric protein having a cytoplasmic tail and/or transmembrane domain of one RSV fused to an ectodomain of another RSV. Useful genome segments in this regard range from about 15-35 nucleotides in the case of gene segments encoding small functional domains of proteins, e.g., epitopic sites, to about 50, 75, 100, 200-500, and 500-1,500 or more nucleotides for gene segments encoding larger domains or protein regions.

To construct chimeric RSV, heterologous genes may be added or substituted in whole or in part to a background genome or antigenome to form a chimeric genome or antigenome. In the case of chimeras generated by substitution, a selected protein or protein region (e.g., a cytoplasmic tail, transmembrane domain or ectodomain, an epitopic site or region, a binding site or region, an active site or region containing an active site, etc.) from one RSV is substituted for a counterpart gene or gene segment in a different RSV genome or antigenome to yield novel recombinants having desired phenotypic changes compared to wild-type or parent RSV strains. As used herein, "counterpart" genes, gene segments, proteins or protein regions two counterpart polynucleotides from a heterologous source, including different genes in a single RSV strain, or different variants of the same gene, including species and allelic variants among different RSV subgroups or strains.

Counterpart genes and gene segments share at least moderate structural similarity. For example counterpart gene segments may encode a common structural domain of a protein of interest, such as a cytoplasmic domain, transmembrane domain, ectodomain, binding site or region, epitopic site or region, etc. Typically, they will share a common biological function as well. For example, protein domains encoded by counterpart gene segments may providing a common membrane spanning function, a specific binding activity, an immunological recognition site, etc. Typically, a desired biological activity shared between the products of counterpart genes and gene segments will be substantially similar in quantitative terms, i.e., they will not differ by more than 30%, preferably by no more than 20%, more preferably by no more than 5-10%.

Counterpart genes and gene segments for use within the invention embrace an assemblage of alternate species having a range of size and sequence variation. However, selection of counterpart genes and gene segments relies on substantial sequence identity between the subject counterparts. In this context, a selected polynucleotide "reference sequence" is defined as a sequence or portion thereof present in either the donor or recipient genome or antigenome. This reference sequence is used as a defined sequence to provide a rationale basis for a sequence comparison. For example, the reference sequence may be a defined a segment of a cDNA or gene, or a complete cDNA or gene sequence.

Generally, a reference sequence for use in defining counterpart genes and gene segments is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988) (each of which is incorporated by reference), by computerized implementations of these algorithms (GAP, BESTFIT, FASTA, and TFASTA in the Wisconsin Genetics Software Package Release 7.0, Genetics Computer Group, 575 Science Dr., Madison, Wis., incorporated herein by reference), or by inspection, and the best alignment (i.e., resulting in the highest percentage of sequence similarity over the comparison window) generated by the various methods is selected.

The term "sequence identity" as used herein means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

In addition to these polynucleotide sequence relationships, proteins and protein regions encoded by chimeric RSV of the invention are also typically selected to have conservative relationships, i.e., to have substantial sequence identity or sequence similarity, with selected reference polypeptides. As applied to polypeptides, the term "sequence identity" means peptides share identical amino acids at corresponding positions. The term "sequence similarity" means peptides have identical or similar amino acids (i.e., conservative substitutions) at corresponding positions. The term "substantial sequence identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). The term "substantial similarity" means that two peptide sequences share corresponding percentages of sequence similarity.

Preferably, residue positions which are not identical differ by conservative amino acid substitutions. Conservative amino acid substitutions refer to the interchangeability of residues having similar side chains. For example, a conservative group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other amino and imino acids (e.g., 4-hydroxyproline). Moreover, amino acids may be modified by glycosylation, phosphorylation and the like.

The invention disclosed herein describes cDNA-based methods that are useful to construct a large panel of recombinant, chimeric RSV viruses and subviral particles. These recombinant constructs offer improved characteristics of attenuation and immunogenicity for use as vaccine agents. Among desired phenotypic changes in this context are resistance to reversion from an attenuated phenotype, improvements in attenuation in culture or in a selected host environment, immunogenic characteristics (e.g., as determined by enhancement, or diminution, of an elicited immune response), upregulation or downregulation of transcription and/or translation of selected viral products, etc.

In one preferred aspect of the invention, attenuated, chimeric RSV are produced in which the chimeric genome or antigenome is further modified by introducing one or more attenuating point mutations that specifies an attenuating phenotype. These point mutations may be generated de novo and tested for attenuating effects according to a rational design mutagenesis strategy. Alternatively, the attenuating point mutations are identified in biologically derived mutant RSV and thereafter incorporated into a chimeric RSV of the invention.

Attenuating point mutations in biologically derived RSV for incorporation within a chimeric vaccine strain may occur naturally or may be introduced into wild-type RSV strains by well known mutagenesis procedures. For example, incompletely attenuated parental RSV strains can be produced by chemical mutagenesis during virus growth in cell cultures to which a chemical mutagen has been added, by selection of virus that has been subjected to passage at suboptimal temperatures in order to introduce growth restriction mutations, or by selection of a mutagenized virus that produces small plaques (sp) in cell culture, as generally described herein and in U.S. Ser. No. 08/327,263, incorporated herein by reference.

By "biologically derived RSV" is meant any RSV not produced by recombinant means. Thus, biologically derived RSV include naturally occurring RSV of all subgroups and strains, including, e.g., naturally occurring RSV having a wild-type genomic sequence and RSV having genomic variations from a reference wild-type RSV sequence, e.g., RSV having a mutation specifying an attenuated phenotype. Likewise, biologically derived RSV include RSV mutants derived from a parental RSV strain by, inter alia, artificial mutagenesis and selection procedures.

To produce a satisfactorily attenuated RSV from biologically derived strains, mutations are preferably introduced into a parental strain which has been incompletely or partially attenuated, such as the well known ts-1 or ts-1NG or cpRSV mutants of the A2 strain of RSV subgroup A, or derivatives or subclones thereof. Using these and other partially attenuated strains additional mutation(s) can be generated that further attenuate the strain, e.g., to a desired level of restricted replication in a mammalian host, while retaining sufficient immunogenicity to confer protection in vaccinees.

Partially attenuated mutants of the subgroup A or B virus can be produced by well known methods of biologically cloning wild-type virus in an acceptable cell substrate and developing, e.g., cold-passaged mutants thereof, subjecting the virus to chemical mutagenesis to produce ts mutants, or selecting small plaque or similar phenotypic mutants (see, e.g., Murphy et al., International Publication WO 93/21310, incorporated herein by reference). For virus of subgroup B, an exemplary, partially attenuated parental virus is cp 23, which is a mutant of the B1 strain of subgroup B.

Various known selection techniques may be combined to produce partially attenuated mutants from non-attenuated subgroup A or B strains which are useful for further derivatization as described herein. Further, mutations specifying attenuated phenotypes may be introduced individually or in combination in incompletely attenuated subgroup A or B virus to produce vaccine virus having multiple, defined attenuating mutations that confer a desired level of attenuation and immunogenicity in vaccinees.

As noted above, production of a sufficiently attenuated biologically derived RSV mutant can be accomplished by several known methods. On such procedure involves subjecting a partially attenuated virus to passage in cell culture at progressively lower, attenuating temperatures. For example, whereas wild-type virus is typically cultivated at about 34-37° C., the partially attenuated mutants are produced by passage in cell cultures (e.g., primary bovine kidney cells) at suboptimal temperatures, e.g., 20-26° C. Thus, the cp mutant or other partially attenuated strain, e.g., ts-1 or spRSV, is adapted to efficient growth at a lower temperature by passage in MRC-5 or Vero cells, down to a temperature of about 20-24° C., preferably 20-22° C. This selection of mutant RSV during cold-passage substantially eliminates any residual virulence in the derivative strains as compared to the partially attenuated parent.

Alternatively, specific mutations can be introduced into biologically derived RSV by subjecting a partially attenuated parent virus to chemical mutagenesis, e.g., to introduce ts mutations or, in the case of viruses which are already ts, additional ts mutations sufficient to confer increased attenuation and/or stability of the ts phenotype on the attenuated derivative. Means for the introduction of ts mutations into RS virus include replication of the virus in the presence of a mutagen such as 5-fluorouridine or 5-fluorouracil in a concentration of about $10^{-3}$ to $10^{-5}$ M, preferably about $10^{-4}$ M, exposure of virus to nitrosoguanidine at a concentration of about 100 μg/ml, according to the general procedure described in, e.g., Gharpure et al., *J. Virol.* 3:414-421 (1969) and Richardson et al., *J. Med. Virol.* 3:91-100 (1978), or genetic introduction of specific ts mutations. Other chemical mutagens can also be used. Attenuation can result from a ts mutation in almost any RSV gene, although a particularly amenable target for this purpose has been found to be the polymerase (L) gene.

The level of temperature sensitivity of replication in exemplary attenuated RSV for use within the invention is determined by comparing its replication at a permissive temperature with that at several restrictive temperatures. The lowest temperature at which the replication of the virus is reduced 100-fold or more in comparison with its replication at the permissive temperature is termed the shutoff temperature. In experimental animals and humans, both the replication and virulence of RSV correlate with the mutant's shutoff temperature. Replication of mutants with a shutoff temperature of 39° C. is moderately restricted, whereas mutants with a shutoff of 38° C. replicate less well and symptoms of illness are mainly restricted to the upper respiratory tract. A virus with a shutoff temperature of 35 to 37° C. will typically be fully attenuated in humans. Thus, attenuated biologically derived mutant and chimeric RSV of the invention which are ts will have a shutoff temperature in the range of about 35 to 39° C., and preferably from 35 to 38° C. The addition of a ts mutation into a partially attenuated strain produces multiply attenuated virus useful within vaccine compositions of the invention.

A number of attenuated RSV strains as candidate vaccines for intranasal administration have been developed using multiple rounds of chemical mutagenesis to introduce multiple mutations into a virus which had already been attenuated during cold-passage (e.g., Connors et al., *Virology* 208: 478-484 (1995); Crowe et al., *Vaccine* 12: 691-699 (1994); and Crowe et al., *Vaccine* 12: 783-790 (1994), incorporated herein by reference). Evaluation in rodents, chimpanzees, adults and infants indicate that certain of these candidate vaccine strains are relatively stable genetically, are highly immunogenic, and may be satisfactorily attenuated. Nucleotide sequence analysis of some of these attenuated viruses, as exemplified hereinbelow, indicates that each level of increased attenuation is associated with specific nucleotide and amino acid substitutions. The present invention provides the ability to distinguish between silent incidental mutations versus those responsible for phenotype differences by introducing the mutations, separately and in various combinations, into the genome or antigenome of infectious RSV clones. This process coupled with evaluation of phenotype characteristics of parental and derivative virus identifies mutations responsible for such desired characteristics as attenuation, temperature sensitivity, cold-adaptation, small plaque size, host range restriction, etc.

Mutations thus identified are compiled into a "menu" and are then introduced as desired, singly or in combination, to calibrate a chimeric vaccine virus to an appropriate level of attenuation, immunogenicity, genetic resistance to reversion from an attenuated phenotype, etc., as desired. Preferably, chimeric RSV of the invention are attenuated by incorporation of at least one, and more preferably two or more, attenuating point mutations identified from such a menu, which may be defined as a group of known mutations within a panel of biologically derived mutant RSV strains. Preferred panels of mutant RSV strains described herein are cold passaged (cp) and/or temperature sensitive (ts) mutants, for example a panel comprised of RSV mutants designated "cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579)" (each deposited under the terms of the Budapest Treaty with the American Type Culture Collection (ATCC) of 10801 University Boulevard, Manassas, Va. 20110-2209, U.S.A., and granted the above identified accession numbers).

From this exemplary panel of biologically derived mutants, a large menu of attenuating mutations are provided which can each be combined with any other mutation(s) within the panel for calibrating the level of attenuation in a recombinant, chimeric RSV for vaccine use. Additional mutations may be derived from RSV having non-ts and non-cp attenuating mutations as identified, e.g., in small plaque (sp), cold-adapted (ca) or host-range restricted (hr) mutant strains. Attenuating mutations may be selected in coding portions of a donor or recipient RSV gene or in non-coding regions such as a cis-regulatory sequence. For example, attenuating mutations may include single or multiple base changes in a gene start sequence, as exemplified by a single or multiple base substitution in the M2 gene start sequence at nucleotide 7605.

Chimeric RSV designed and selected for vaccine use often have at least two and sometimes three or more attenuating mutations to achieve a satisfactory level of attenuation for broad clinical use. In one embodiment, at least one attenuating mutation occurs in the RSV polymerase gene (either in the donor or recipient gene) and involves a nucleotide substitution specifying an amino acid change in the polymerase protein specifying a temperature-sensitive (ts) phenotype. Exemplary chimeric RSV in this context incorporate one or more nucleotide substitutions in the large polymerase gene L resulting in an amino acid change at amino acid $Phe_{521}$, $Gln_{831}$, $Met_{1169}$, or $Tyr_{1321}$, as exemplified by the changes, Leu for $Phe_{521}$, Leu for $Gln_{831}$, Val for $Met_{1169}$, and Asn for $Tyr_{1321}$. Alternately or additionally, chimeric RSV of the invention may incorporate a ts mutation in a different RSV gene, e.g., in the M2 gene. Preferably, two or more nucleotide changes are incorporated in a codon specifying an attenuating mutation, e.g., in a codon specifying a ts mutation, thereby decreasing the likelihood of reversion from an attenuated phenotype.

In accordance with the methods of the invention, chimeric RSV can be readily constructed and characterized that incorporate at least one and up to a full complement of attenuating point mutations present within a panel of biologically derived mutant RSV strains. Thus, mutations can be assembled in any combination from a selected panel of mutants, for example, cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579). In this manner, attenuation of chimeric vaccine candidates can be finely calibrated for use in one or more classes of patients, including seronegative infants.

In more specific embodiments, chimeric RSV for vaccine use incorporate at least one and up to a full complement of attenuating mutations specifying a temperature-sensitive amino acid substitution at $Phe_{521}$, $Gln_{831}$, $Met_{1169}$ or $Tyr_{1321}$ in the RSV polymerase gene L, or a temperature-sensitive nucleotide substitution in the gene-start sequence of gene M2. Alternatively or additionally, chimeric RSV of claim may incorporate at least one and up to a full complement of mutations from cold-passaged attenuated RSV, for example one or more mutations specifying an amino acid substitution at $Val_{267}$ in the RSV N gene, $Glu_{218}$ or $Thr_{523}$ in the RSV F gene, $Cys_{319}$ or $His_{1690}$ in the RSV polymerase gene L.

In other detailed embodiments, the chimeric RSV of the invention features human RSV B subgroup glycoprotein genes F and G that are added or substituted within a human RSV A genome or antigenome to form a chimeric clone which is further modified to incorporate one or more attenuating point mutations adopted from biologically derived mutant RSV. In various examples, the chimeric RSV has both human RSV B subgroup glycoprotein genes F and G are substituted to replace counterpart F and G glycoprotein genes within an RSV A genome, which is further modified to incorporate attenuating point mutations selected from (i) a panel of mutations specifying temperature-sensitive amino acid substitutions $Gln_{831}$ to Leu, and $Tyr_{1321}$ to Asn in the RSV polymerase gene L; (ii) a temperature-sensitive nucleotide substitution in the gene-start sequence of gene M2; (iii) an attenuating panel of mutations adopted from cold-passaged RSV specifying amino acid substitutions $Val_{267}$ Ile in the RSV N gene, and $Cys_{319}$ to Tyr and $His_{1690}$ Tyr in the RSV polymerase gene L; or (iv) a deletion of the SH gene. Preferably, these and other examples of chimeric RSV incorporate at least two attenuating point mutations adopted from biologically derived mutant RSV, which may be derived from the same or different biologically derived mutant RSV strains. Also preferably, these exemplary mutants have one or more of their attenuating mutations stabilized by multiple nucleotide changes in a codon specifying the mutation.

In accordance with the foregoing description, the ability to produce infectious RSV from cDNA permits introduction of specific engineered changes within chimeric RSV. In particular, infectious, recombinant RSV are employed for identification of specific mutation(s) in biologically derived, attenuated RSV strains, for example mutations which specify ts, ca, att and other phenotypes. Desired mutations are thus identified and introduced into recombinant, chimeric RSV vaccine strains. The capability of producing virus from cDNA allows for routine incorporation of these mutations, individually or in various selected combinations, into a full-length cDNA clone, whereafter the phenotypes of rescued recombinant viruses containing the introduced mutations to be readily determined.

By identifying and incorporating specific, biologically derived mutations associated with desired phenotypes, e.g., a cp or ts phenotype, into infectious chimeric RSV clones, the invention provides for other, site-specific modifications at, or within close proximity to, the identified mutation. Whereas most attenuating mutations produced in biologically derived RSV are single nucleotide changes, other "site specific" mutations can also be incorporated by recombinant techniques into biologically derived or recombinant RSV. As used herein, site-specific mutations include insertions, substitutions, deletions or rearrangements of from 1 to 3, up to about 5-15 or more altered nucleotides (e.g., altered from a wild-type RSV sequence, from a sequence of a selected mutant RSV strain, or from a parent recombinant RSV clone subjected to mutagenesis). Such site-specific mutations may be incorporated at, or within the region of, a selected, biologically derived point mutation. Alternatively, the mutations can be introduced in various other contexts within an RSV clone, for example at or near a cis-acting regulatory sequence or nucleotide sequence encoding a protein active site, binding site, immunogenic epitope, etc. Site-specific RSV mutants typically retain a desired attenuating phenotype, but may exhibit substantially altered phenotypic characteristics unrelated to attenuation, e.g., enhanced or broadened immunogenicity, or improved growth. Further examples of desired, site-specific mutants include recombinant RSV designed to incorporate additional, stabilizing nucleotide mutations in a codon specifying an attenuating point mutation. Where possible, two or more nucleotide substitutions are introduced at codons that specify attenuating amino acid changes in a parent mutant or recombinant RSV clone, yielding a biologically derived or recombinant RSV having genetic resistance to reversion from an attenuated phenotype. In other embodiments, site-specific nucleotide substitutions, additions, deletions or rearrangements are introduced upstream (N-terminal direction) or downstream (C-terminal direction), e.g., from 1 to 3, 5-10 and up to 15 nucleotides or more 5' or 3', relative to a targeted nucleotide position, e.g., to construct or ablate an existing cis-acting regulatory element.

In addition to single and multiple point mutations and site-specific mutations, changes to chimeric RSV disclosed herein include deletions, insertions, substitutions or rearrangements of whole genes or gene segments. These mutations may alter small numbers of bases (e.g., from 15-30 bases, up to 35-50 bases or more), or large blocks of nucleotides (e.g., 50-100, 100-300, 300-500, 500-1,000 bases) in the donor or recipient genome or antigenome, depending upon the nature of the change (i.e., a small number of bases may be changed to insert or ablate an immunogenic epitope or change a small gene segment, whereas large block(s) of bases are involved when genes or large gene segments are added, substituted, deleted or rearranged.

In additional aspects, the invention provides for supplementation of mutations adopted into a chimeric RSV clone from biologically derived RSV, e.g., cp and ts mutations, with additional types of mutations involving the same or different genes in a further modified chimeric RSV clone. RSV encodes ten mRNAs and ten or eleven proteins. Three of these are transmembrane surface proteins, namely the attachment G protein, fusion F protein involved in penetration, and small hydrophobic SH protein. G and F are the major viral neutralization and protective antigens. Four additional proteins are associated with the viral nucleocapsid, namely the RNA binding protein N, the phosphoprotein P, the large polymerase protein L, and the transcription elongation factor M2 ORF1. The matrix M protein is part of the inner virion and probably mediates association between the nucleocapsid and the envelope. Finally, there are two nonstructural proteins, NS1 and NS2, of unknown function. These proteins can be selectively altered in terms of expression levels, or can be added deleted, substituted or rearranged, in whole or in part, alone or in combination, with other desired modifications, to yield a chimeric RSV exhibiting novel vaccine characteristics.

Thus, in addition to, or in combination with, attenuating mutations adopted from biologically derived RSV mutants, the present invention also provides a range of additional methods for attenuating chimeric RSV based on recombinant engineering of infectious RSV clones. In accordance with this aspect of the invention, a variety of alterations can be produced in an isolated polynucleotide sequence encoding the chimeric RSV genome or antigenome for incorporation into infectious clones. More specifically, to achieve desired structural and phenotypic changes in chimeric RSV, the invention allows for introduction of modifications which delete, substitute, introduce, or rearrange a selected nucleotide or plurality of nucleotides from a parent chimeric genome or antigenome, as well as mutations which delete, substitute, introduce or rearrange whole gene(s) or gene segment(s), within a chimeric RSV clone.

Desired modifications of infectious chimeric RSV are typically selected to specify a desired phenotypic change, e.g., a change in viral growth, temperature sensitivity, ability to elicit a host immune response, attenuation, etc. These changes can be brought about either in a donor or recipient genome or antigenome by, e.g., mutagenesis of a parent RSV clone to ablate, introduce or rearrange a specific gene(s) or gene region(s) (e.g., a gene segment that encodes a protein structural domain, such as a cytoplasmic, transmembrane or extracellular domain, an immunogenic epitope, binding region, active site, etc.). Genes of interest in this regard include all of the genes of the RSV genome: 3'-NS1-NS2-N-P-M-SH-G-F-M2-L-5', as well as heterologous genes from other RSV, other viruses and a variety of other non-RSV sources as indicated herein.

Also provided are modifications in a chimeric RSV which simply alter or ablate expression of a selected gene, e.g., by introducing a termination codon within a selected RSV coding sequence, changing the position of an RSV gene relative to an operably linked promoter, introducing an upstream start codon to alter rates of expression, modifying (e.g., by changing position, altering an existing sequence, or substituting an existing sequence with a heterologous sequence) GS and/or GE transcription signals to alter phenotype (e.g., growth, temperature restrictions on transcription, etc.), and various other deletions, substitutions, additions and rearrangements that specify quantitative or qualitative changes in viral replication, transcription of selected gene(s), or translation of selected protein(s).

The ability to analyze and incorporate other types of attenuating mutations into chimeric RSV for vaccine development extends to a broad assemblage of targeted changes in RSV clones. For example, deletion of the SH gene yields a recombinant RSV having novel phenotypic characteristics, including enhanced growth. In the present invention, an SH gene deletion (or any other selected, non-essential gene or gene segment deletion), is combined in a chimeric RSV with one or more additional mutations specifying an attenuated phenotype, e.g., one or more point mutation(s) adopted from a biologically derived attenuated RSV mutant. In exemplary embodiments, the SH gene or NS2 gene is deleted in combination with one or more cp and/or ts mutations adopted from cpts248/404, cpts530/1009, cpts530/1030, or another selected mutant RSV strain, to yield a recombinant RSV having increased yield of virus, enhanced attenuation, and resistance to phenotypic reversion, due to the combined effects of the different mutations.

In this regard, any RSV gene which is not essential for growth, for example the SH, N, P, NS1 and NS2 genes, can be ablated or otherwise modified in a chimeric RSV to yield desired effects on virulence, pathogenesis, immunogenicity and other phenotypic characters. For example, ablation by deletion of a non-essential gene such as SH results in enhanced viral growth in culture. Without wishing to be bound by theory, this effect is likely due in part to a reduced nucleotide length of the viral genome. In the case of one exemplary SH-minus clone, the modified viral genome is 14,825 nt long, 398 nucleotides less than wild-type. By engineering similar mutations that decrease genome size, e.g., in other coding or noncoding regions elsewhere in the RSV genome, such as in the P, M, F and M2 genes, the invention provides several readily obtainable methods and materials for improving chimeric RSV growth.

In addition, a variety of other genetic alterations can be produced in a RSV genome or antigenome for incorporation into infectious chimeric RSV, alone or together with one or more attenuating point mutations adopted from a biologically derived mutant RSV. Additional heterologous genes and gene segments (e.g. from different RSV genes, different RSV strains or types, or non-RSV sources) may be inserted in whole or in part, the order of genes changed, gene overlap removed, an RSV genome promoter replaced with its antigenome counterpart, portions of genes removed or substituted, and even entire genes deleted. Different or additional modifications in the sequence can be made to facilitate manipulations, such as the insertion of unique restriction sites in various intergenic regions or elsewhere. Nontranslated gene sequences can be removed to increase capacity for inserting foreign sequences.

Also provided within the invention are genetic modifications in a chimeric RSV which alter or ablate the expression of a selected gene or gene segment without removing the gene or gene segment from the chimeric RSV clone. For example, this can be achieved by introducing a termination codon within a selected coding sequence, changing the position of a gene or introducing an upstream start codon to alter its rate of expression, or changing GS and/or GE transcription signals to alter phenotype (e.g., growth, temperature restrictions on transcription, etc.).

Preferred mutations in this context include mutations directed toward cis-acting signals, which can be identified, e.g., by mutational analysis of RSV minigenomes. For example, insertional and deletional analysis of the leader and trailer and flanking sequences identified viral promoters and transcription signals and provided a series of mutations associated with varying degrees of reduction of RNA replication or transcription. Saturation mutagenesis (whereby each position in turn is modified to each of the nucleotide alternatives) of these cis-acting signals also has identified many mutations which reduced (or in one case increased) RNA replication or transcription. Any of these mutations can be inserted into a chimeric antigenome or genome as described herein.

Evaluation and manipulation of trans-acting proteins and cis-acting RNA sequences using the complete antigenome cDNA is assisted by the use of RSV minigenomes (see, e.g., Grosfeld et al., *J. Virol.* 69: 5677-5686 (1995), incorporated herein by reference), whose helper-dependent status is useful in the characterization of those mutants which are too inhibitory to be recovered in replication-independent infectious virus.

Other mutations within chimeric RSV of the present invention involve replacement of the 3' end of genome with its counterpart from antigenome, which is associated with changes in RNA replication and transcription. In addition, the intergenic regions (Collins et al., *Proc. Natl. Acad. Sci. USA* 83:4594-4598 (1986), incorporated herein by reference) can be shortened or lengthened or changed in sequence content, and the naturally-occurring gene overlap (Collins et al., *Proc. Natl. Acad. Sci. USA* 84:5134-5138 (1987), incorporated herein by reference) can be removed or changed to a different intergenic region by the methods described herein.

In one exemplary embodiment, the level of expression of specific RSV proteins, such as the protective F and G antigens, can be increased by substituting the natural sequences with ones which have been made synthetically and designed to be consistent with efficient translation. In this context, it has been shown that codon usage can be a major factor in the level of translation of mammalian viral proteins (Haas et al., *Current Biol.* 6:315-324 (1996)). Examination of the codon usage of the mRNAs encoding the F and G proteins of RSV, which are the major protective antigens, shows that the usage is consistent with poor expression. Thus, codon usage can be improved by the recombinant methods of the invention to achieve improved expression for selected genes.

In another exemplary embodiment, a sequence surrounding a translational start site (preferably including a nucleotide in the −3 position) of a selected RSV gene is modified, alone or in combination with introduction of an upstream start codon, to modulate chimeric RSV gene expression by specifying up- or down-regulation of translation.

Alternatively, or in combination with other RSV modifications disclosed herein, chimeric RSV gene expression can be modulated by altering a transcriptional GS signal of a selected gene(s) of the virus. In one exemplary embodiment, the GS signal of NS2 is modified to include a defined mutation (e.g., the 404(M2) mutation described hereinbelow) to superimpose a ts restriction on viral replication.

Yet additional chimeric RSV clones within the invention can incorporate modifications to a transcriptional GE signal. For example, RSV clones may be generated which have a substituted or mutated GE signal of the NS1 and NS2 genes for that of the N gene, resulting in decreased levels of readthrough mRNAs and increased expression of proteins from downstream genes. The resulting chimeric virus will exhibit increased growth kinetics and increased plaque size, providing but one example of alteration of RSV growth properties by modification of a cis-acting regulatory element in the RSV genome.

In another exemplary embodiment, expression of the G protein is increased by modification of the G mRNA. The G protein is expressed as both a membrane bound and a secreted form, the latter form being expressed by translational initiation at a start site within the G translational open reading frame. The secreted form can account for as much as one-half of the expressed G protein. Ablation of the internal start site (e.g., by sequence alteration, deletion, etc.), alone or together with altering the sequence context of the upstream start site yields desired changes in G protein expression. Ablation of the secreted form of G also will improve the quality of the host immune response to exemplary, chimeric RSV, because the soluble form of G is thought to act as a "decoy" to trap neutralizing antibodies. Also, soluble G protein has been implicated in enhanced immunopathology due to its preferential stimulation of a Th2-biased response.

In alternative embodiments, levels of chimeric RSV gene expression are modified at the level of transcription. In one aspect, the position of a selected gene in the RSV gene map can be changed to a more promoter-proximal or promotor-distal position, whereby the gene will be expressed more or less efficiently, respectively. According to this aspect, modulation of expression for specific genes can be achieved yielding reductions or increases of gene expression from two-fold, more typically four-fold, up to ten-fold or more compared to wild-type levels. In one example, the NS2 gene (second in order in the RSV gene map) is substituted in position for the SH gene (sixth in order), yielding a predicted decrease in expression of NS2. Increased expression of selected RSV genes due to positional changes can be achieved up to 10-fold, 30-fold, 50-fold, 100-fold or more, often attended by a commensurate decrease in expression levels for reciprocally, positionally substituted genes.

In other exemplary embodiments, the F and G genes are transpositioned singly or together to a more promoter-proximal or promoter-distal site within the chimeric RSV gene map to achieve higher or lower levels of gene expression, respectively. These and other transpositioning changes yield novel chimeric RSV clones having attenuated phenotypes, for example due to decreased expression of selected viral proteins involved in RNA replication.

In more detailed aspects of the invention, chimeric RSV is provided in which expression of a viral gene, for example the NS2 gene, is ablated at the translational level without deletion of the gene or of a segment thereof, by, e.g., introducing two tandem translational termination codons into a translational open reading frame (ORF). This yields viable virus in which a selected gene has been silenced at the level of translation, without deleting its gene. These forms of "knock-out" virus will exhibit reduced growth rates and small plaque sizes in tissue culture. Thus, the methods and compositions of the invention provide yet additional, novel types of attenuating mutations which ablate expression of a viral gene that is not one of the major viral protective antigens. In this context "knockout" virus phenotypes produced without deletion of a gene or gene segment can be alternatively produced by deletion mutagenesis, as described herein, to effectively preclude correcting mutations that may restore synthesis of a target protein.

Several other gene "knock-outs" for chimeric RSV can be made using alternate designs. For example, insertion of translation termination codons into ORFs, or disruption of the RNA editing sites, offer alternatives to silencing or attenuating the expression of selected genes. Methods for producing these and other knock-outs are well known in the art (as described, for example, in Kretzschmar et al., *Virology* 216: 309-316 (1996); Radecke et al., *Virology* 217:418-412 (1996); and Kato et al., *EMBO J.* 16:178-587 (1987); and Schneider et al., *Virology* 277:314-322 (1996), each incorporated herein by reference).

Infectious chimeric RSV clones of the invention can also be engineered according to the methods and compositions disclosed herein to enhance immunogenicity and induce a level of protection greater than that provided by infection with a wild-type RSV or a parent chimeric RSV. For example, an immunogenic epitope from a heterologous RSV strain or type, or from a non-RSV source such as PIV, can be added to a chimeric clone by appropriate nucleotide changes in the polynucleotide sequence encoding the chimeric genome or antigenome. Alternatively, chimeric RSV can be engineered to add or ablate (e.g., by amino acid insertion, substitution or deletion) immunogenic epitopes associated with desirable or undesirable immunological reactions.

Within the methods of the invention, additional genes or gene segments may be inserted into or proximate to the recipient RSV genome or antigenome. These genes may be under common control with recipient genes, or may be under the control of an independent set of transcription signals. Genes of interest include the RSV genes identified above, as well as non-RSV genes. Non-RSV genes of interest include those encoding cytokines (e.g., IL-2 through IL-15, especially IL-2, IL-6 and IL-12, etc.), gamma-interferon, and proteins rich in T helper cell epitopes. These additional proteins can be expressed either as a separate protein, or as a chimera engineered from a second copy of one of the RSV proteins, such as SH. This provides the ability to modify and improve the immune responses against RSV both quantitatively and qualitatively.

In exemplary embodiments of the invention, insertion of foreign genes or gene segments, and in some cases of non-coding nucleotide sequences, within a chimeric RSV genome results in a desired increase in genome length causing yet additional, desired phenotypic effects. Increased genome length results in attenuation of the resultant RSV, dependent in part upon the length of the insert. In addition, the expression of certain proteins, e.g. a cytokine, from a non-RSV gene inserted into chimeric RSV of the invention will result in attenuation of the virus due to the action of the protein. This has been described for IL-2 expressed in vaccinia virus (e.g. Flexner et al., *Nature* 33:-259-62 (1987)) and is also expected for gamma interferon.

Deletions, insertions, substitutions and other mutations involving changes of whole viral genes or gene segments within chimeric RSV of the invention yield highly stable vaccine candidates, which are particularly important in the case of immunosuppressed individuals. Many of these changes will result in attenuation of resultant vaccine strains, whereas others will specify different types of desired phenotypic changes. For example, certain viral genes are known which encode proteins that specifically interfere with host immunity (see, e.g., Kato et al., *EMBO. J.* 16:578-87 (1997), incorporated herein by reference). Ablation of such genes in chimeric vaccine viruses is expected to reduce virulence and pathogenesis and/or improve immunogenicity.

In alternative aspects of the invention, the infectious chimeric RSV produced from a cDNA-expressed genome or antigenome can be any of the RSV or RSV-like strains, e.g., human, bovine, murine, etc., or of any pneumovirus, e.g., pneumonia virus of mice or turkey rhinotracheitis virus. To engender a protective immune response, the RSV strain may be one which is endogenous to the subject being immunized, such as human RSV being used to immunize humans. The genome or antigenome of endogenous RSV can be modified, however, to express RSV genes or gene segments from a combination of different sources, e.g., a combination of genes or gene segments from different RSV species, subgroups, or strains, or from an RSV and another respiratory pathogen such as PIV.

In certain embodiments of the invention, chimeric RSV are provided wherein genes or gene segments within a human RSV are replaced with counterpart heterologous genes or gene segments from a non-human RSV, e.g., a bovine or murine RSV. Alternatively, chimeric RSV may incorporate genes or gene segments from a human RSV in a non-human RSV recipient or background clone, e.g., a bovine or murine RSV clone. Substitutions, deletions, and additions of RSV genes or gene segments in this context can include part or all of one or more of the NS1, NS2, N, P, M, SH, M2(ORF1), M2(ORF2) and L genes, or non-immunogenic parts of the G and F genes. Also, human and non-human RSV cis-acting sequences, such as promoter or transcription signals, can be replaced with, respectively, non-human or human counterpart sequences. Thus, methods are provided to generate live attenuated bovine RSV by inserting human attenuating genes or cis-acting sequences into a bovine RSV genome or antigenome background.

Chimeric human/non-human RSV bearing heterologous genes or cis-acting elements are selected for host range restriction and other desired phenotypes favorable for vaccine use. In exemplary embodiments, bovine RSV sequences are selected for introduction into human RSV based on known aspects of bovine RSV structure and function, as provided in, e.g., Pastey et al., *J. Gen. Viol.* 76:193-197 (1993); Pastey et al., *Virus Res.* 29:195-202 (1993); Zamora et al., *J. Gen. Virol.* 73:737-741 (1992); Mallipeddi et al., *J. Gen. Virol.* 74:2001-2004 (1993); Mallipeddi et al., *J. Gen. Virol.* 73:2441-2444 (1992); and Zamora et al., *Virus Res.* 24:115-121 (1992), each incorporated herein by reference, and in accordance with the teachings disclosed herein.

In other embodiments of the invention, mutations of interest for introduction within chimeric RSV are modeled after a tissue culture-adapted nonpathogenic strain of pneumonia virus of mice (the murine counterpart of human RSV) which lacks a cytoplasmic tail of the G protein (Randhawa et al., *Virology* 207:240-245 (1995)). Accordingly, in one aspect of the invention the cytoplasmic and/or transmembrane domains of one or more of the human RSV glycoproteins, F, G and SH, are added, deleted, modified, or substituted within a chimeric RSV using a heterologous counterpart sequence (e.g., a sequence from a cytoplasmic, or transmembrane domain of a F, G, or SH protein of murine pneumonia virus) to achieve a desired attenuation. As another example, a nucleotide sequence at or near the cleavage site of the F protein, or the putative attachment domain of the G protein, can be modified by point mutations, site-specific changes, or by alterations involving entire genes or gene segments to achieve novel effects on viral growth in tissue culture and/or infection and pathogenesis.

Thus, infectious chimeric RSV intended for administration to humans can be a human RSV that has been modified to contain genes from, e.g., a bovine or murine RSV or a PIV, such as for the purpose of attenuation. For example, by inserting a gene or gene segment from PIV, a bivalent vaccine to both PIV and RSV can be provided. Alternatively, a heterologous RSV species, subgroup or strain, or a distinct respiratory pathogen such as PIV, may be modified, e.g., to contain genes that encode epitopes or proteins which elicit protection against human RSV infection. For example, the human RSV glycoprotein genes can be substituted for the bovine glycoprotein genes such that the resulting chimeric RSV, which now bears the human RSV surface glycoproteins in a bovine background, would retain a restricted ability to replicate in a human host due to the remaining bovine genetic background, while eliciting a protective immune response in humans against human RSV strains.

In one embodiment of the invention, a chimeric bovine-human RSV incorporates a substitution of the human RSV NP gene or gene segment with a counterpart bovine NP gene or gene segment, which chimera can optionally be constructed to incorporate additional genetic changes, e.g., point mutations or gene deletions. For example, replacement of a human RSV coding sequence (e.g., of NS1, NS2, NP, etc.) or non-coding sequence (e.g., a promoter, gene-end, gene-start, intergenic or other cis-acting element) with a counterpart bovine or murine RSV sequence is expected to yield chimeric RSV having a variety of possible attenuating and other phenotypic effects. In particular, host range and other desired effects are expected to arise from a non-human RSV gene imported within a human RSV background, wherein the non-human gene does not function efficiently in a human cell, e.g., from incompatibility of the heterologous sequence or protein with a biologically interactive human RSV sequence or protein (i.e., a sequence or protein that ordinarily cooperates with the substituted sequence or protein for viral transcription, translation, assembly, etc.)

In more detailed aspects of the invention, chimeric RSV are employed as vectors for protective antigens of other pathogens, particularly respiratory tract pathogens such as parainfluenza virus (PIV). For example, chimeric RSV may be engineered which incorporate sequences that encode protective antigens from PIV to produce infectious, attenuated vaccine virus. The cloning of PIV cDNA and other disclosure is provided in United States Patent Application entitled PRODUCTION OF PARAINFLUENZA VIRUS VACCINES FROM CLONED NUCLEOTIDE SEQUENCES, filed May 22, 1998, Ser. No. 09/083,793 (corresponding to International Publication No. WO 98/53078) and its priority, provisional application filed May 23, 1997, Ser. No. 60/047,575, each incorporated herein by reference. This disclosure includes description of the following plasmids that may be employed to produce infectious PIV viral clones: p3/7(131) (ATCC 97990); p3/7(131)2G (ATCC 97889); and p218(131) (ATCC 97991); each deposited under the terms of the Budapest Treaty with the American Type Culture Collection (ATCC) of 10801 University Boulevard, Manassas, Va. 20110-2209, U.S.A., and granted the above identified accession numbers.

According to this aspect of the invention, a chimeric RSV is provided which comprises a chimera of a RSV genomic or antigenomic sequence and at least one PIV sequence, for example a polynucleotide containing sequences from both RSV and PIV1, PIV2, PIV3 or bovine PIV. For example, individual genes of RSV may be replaced with counterpart genes from human PIV, such as the HN and/or F glycoprotein genes of PIV1, PIV2, or PIV3. Alternatively, a selected, heterologous gene segment, such as a cytoplasmic tail, transmembrane domain or ectodomain of HN or F of HPIV1, HPIV2, or HPIV3 can be substituted for a counterpart gene segment in, e.g., the same gene in an RSV clone, within a different gene in the RSV clone, or into a non-coding sequence of the RSV genome or antigenome. In one embodiment, a gene segment from HN or F of HPIV3 is substituted for a counterpart gene segment in RSV type A, to yield constructs encoding chimeric proteins, e.g. fusion proteins having a cytoplasmic tail and/or transmembrane domain of RSV fused to an ectodomain of RSV to yield a novel attenuated virus, and/or a multivalent vaccine immunogenic against both PIV and RSV.

In addition to the above described modifications to recombinant RSV, different or additional modifications in RSV clones can be made to facilitate manipulations, such as the insertion of unique restriction sites in various intergenic regions (e.g., a unique StuI site between the G and F genes) or elsewhere. Nontranslated gene sequences can be removed to increase capacity for inserting foreign sequences.

In another aspect of the invention, compositions (e.g., isolated polynucleotides and vectors incorporating a chimeric RSV-encoding cDNA) are provided for producing an isolated infectious chimeric RSV. Using these compositions and methods, infectious chimeric RSV are generated from a chimeric RSV genome or antigenome, a nucleocapsid (N) protein, a nucleocapsid phosphoprotein (P), a large (L) polymerase protein, and an RNA polymerase elongation factor. In related aspects of the invention, compositions and methods are provided for introducing the aforementioned structural and phenotypic changes into a recombinant chimeric RSV to yield infectious, attenuated vaccine viruses.

Introduction of the foregoing defined mutations into an infectious, chimeric RSV clone can be achieved by a variety of well known methods. By "infectious clone" is meant cDNA or its product, synthetic or otherwise, which can be transcribed into genomic or antigenomic RNA capable of serving as template to produce the genome of an infectious virus or subviral particle. Thus, defined mutations can be introduced by conventional techniques (e.g., site-directed mutagenesis) into a cDNA copy of the genome or antigenome. The use of antigenome or genome cDNA subfragments to assemble a complete antigenome or genome cDNA as described herein has the advantage that each region can be manipulated separately (smaller cDNAs are easier to manipulate than large ones) and then readily assembled into a complete cDNA. Thus, the complete antigenome or genome cDNA, or any subfragment thereof, can be used as template for oligonucleotide-directed mutagenesis. This can be through the intermediate of a single-stranded phagemid form, such as using the Muta-gene® kit of Bio-Rad Laboratories (Richmond, Calif.) or a method using a double-stranded plasmid directly as template such as the Chameleon mutagenesis kit of Stratagene (La Jolla, Calif.), or by the polymerase chain reaction employing either an oligonucleotide primer or template which contains the mutation(s) of interest. A mutated subfragment can then be assembled into the complete antigenome or genome cDNA. A variety of other mutagenesis techniques are known and available for use in producing the mutations of interest in the RSV antigenome or genome cDNA. Mutations can vary from single nucleotide changes to replacement of large cDNA pieces containing one or more genes or genome regions.

Thus, in one illustrative embodiment mutations are introduced by using the Muta-gene phagemid in vitro mutagenesis kit available from Bio-Rad. In brief, cDNA encoding a portion of an RSV genome or antigenome is cloned into the plasmid pTZ18U, and used to transform CJ236 cells (Life Technologies). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome fragment is then amplified and the mutated piece is then reintroduced into the full-length genome or antigenome clone.

The ability to introduce defined mutations into infectious RSV has many applications, including the analyses of RSV molecular biology and pathogenesis. For example, the functions of the RSV proteins, including the NS1, NS2, SH, M2(ORF1) and M2(ORF2) proteins, can be investigated and manipulated by introducing mutations which ablate or reduce their level of expression, or which yield mutant protein. In one exemplary embodiment hereinbelow, recombinant RSV is constructed in which expression of a viral gene, namely the SH gene, is ablated by deletion of the mRNA coding sequence and flanking transcription signals. Surprisingly, not only could this virus be recovered, but it grew efficiently in tissue culture. In fact, its growth was substantially increased over that of the wild-type, based on both yield of infectious virus and on plaque size. This improved growth in tissue culture from the SH deletion and other RSV derivatives of the invention provides useful tools for developing RSV vaccines, which overcome the problem of RSV's poor yield in tissue culture that had complicated production of vaccine virus in other systems. These deletions are highly stable against genetic reversion, rendering the RSV clones derived therefrom particularly useful as vaccine agents.

The invention also provides methods for producing an infectious chimeric RSV from one or more isolated polynucleotides, e.g., one or more cDNAs. According to the present invention cDNA encoding a RSV genome or antigenome is constructed for intracellular or in vitro coexpression with the necessary viral proteins to form infectious RSV. By "RSV antigenome" is meant an isolated positive-sense polynucleotide molecule which serves as the template for the synthesis of progeny RSV genome. Preferably a cDNA is constructed which is a positive-sense version of the RSV genome, corresponding to the replicative intermediate RNA, or antigenome, so as to minimize the possibility of hybridizing with positive-sense transcripts of the complementing sequences that encode proteins necessary to generate a transcribing, replicating nucleocapsid, i.e., sequences that encode N, P, L and M2(ORF1) protein. In an RSV minigenome system, genome and antigenome were equally active in rescue, whether complemented by RSV or by plasmids, indicating that either genome or antigenome can be used and thus the choice can be made on methodologic or other grounds.

A native RSV genome typically comprises a negative-sense polynucleotide molecule which, through complementary viral mRNAs, encodes eleven species of viral proteins, i.e., the nonstructural species NS1 and NS2, N, P, matrix (M), small hydrophobic (SH), glycoprotein (G), fusion (F), M2(ORF1), M2(ORF2), and L, substantially as described in Mink et al., *Virology* 185:615-624 (1991), Stec et al., *Virology* 183:273-287 (1991), and Connors et al., *Virol.* 208:478-484 (1995), each incorporated herein by reference. For purposes of the present invention the genome or antigenome of the recombinant RSV of the invention need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule.

By recombinant RSV is meant a RSV or RSV-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in RSV gene expression, for example, a promoter, a structural or coding sequence which is transcribed into RSV RNA, and appropriate transcription initiation and termination sequences.

To produce infectious RSV from cDNA-expressed genome or antigenome, the genome or antigenome is coexpressed with those RSV proteins necessary to (i) produce a nucleocapsid capable of RNA replication, and (ii) render progeny nucleocapsids competent for both RNA replication and transcription. Transcription by the genome nucleocapsid provides the other RSV proteins and initiates a productive infection. Alternatively, additional RSV proteins needed for a productive infection can be supplied by coexpression.

An RSV antigenome may be constructed for use in the present invention by, e.g., assembling cloned cDNA segments, representing in aggregate the complete antigenome, by polymerase chain reaction (PCR; described in, e.g., U.S. Pat. Nos. 4,683,195 and 4,683,202, and *PCR Protocols: A Guide to Methods and Applications*, Innis et al., eds., Academic Press, San Diego (1990), incorporated herein by reference) of reverse-transcribed copies of RSV mRNA or genome RNA. For example, cDNAs containing the lefthand end of the antigenome, spanning from an appropriate promoter (e.g., T7 RNA polymerase promoter) and the leader region complement to the SH gene, are assembled in an appropriate expression vector, such as a plasmid (e.g., pBR322) or various available cosmid, phage, or DNA virus vectors. The vector may be modified by mutagenesis and/or insertion of synthetic polylinker containing unique restriction sites designed to facilitate assembly. For example, a plasmid vector described herein was derived from pBR322 by replacement of the PstI-EcoR1 fragment with a synthetic DNA containing convenient restriction enzyme sites. Use of pBR322 as a vector stabilized nucleotides 3716-3732 of the RSV sequence, which otherwise sustained nucleotide deletions or insertions, and propagation of the plasmid was in bacterial strain DH10B to avoid an artifactual duplication and insertion which otherwise occurred in the vicinity of nt 4499. For ease of preparation the G, F and M2 genes can be assembled in a separate vector, as can be the L and trailer sequences. The righthand end (e.g., L and trailer sequences) of the antigenome plasmid may contain additional sequences as desired, such as a flanking ribozyme and tandem T7 transcriptional terminators. The ribozyme can be hammerhead type (e.g., Grosfeld et al., *J. Virol.* 69:5677-5686 (1995)), which would yield a 3' end containing a single nonviral nucleotide, or can any of the other suitable ribozymes such as that of hepatitis delta virus (Perrotta et al., *Nature* 350:434-436 (1991)) which would yield a 3' end free of non-RSV nucleotides. A middle segment (e.g., G-to-M2 piece) is inserted into an appropriate restriction site of the leader-to-SH plasmid, which in turn is the recipient for the L-trailer-ribozyme-terminator piece, yielding a complete antigenome. In an illustrative example described herein, the leader end was constructed to abut the promoter for T7 RNA polymerase which included three transcribed G residues for optimal activity; transcription donates these three nonviral G's to the 5' end of the antigenome. These three nonviral G residues can be omitted to yield a 5' end free of nonviral nucleotides. To generate a nearly correct 3' end, the trailer end was constructed to be adjacent to a hammerhead ribozyme, which upon cleavage would donate a single 3'-phosphorylated U residue to the 3' end of the encoded RNA.

In certain embodiments of the invention, complementing sequences encoding proteins necessary to generate a transcribing, replicating RSV nucleocapsid are provided by one or more helper viruses. Such helper viruses can be wild-type or mutant. Preferably, the helper virus can be distinguished phenotypically from the virus encoded by the RSV cDNA. For example, it is desirable to provide monoclonal antibodies which react immunologically with the helper virus but not the virus encoded by the RSV cDNA. Such antibodies can be neutralizing antibodies. In some embodiments, the antibodies can be used in affinity chromatography to separate the helper virus from the recombinant virus. To aid the procurement of such antibodies, mutations can be introduced into the RSV cDNA to provide antigenic diversity from the helper virus, such as in the HN or F glycoprotein genes.

A variety of nucleotide insertions and deletions can be made in the RSV genome or antigenome to generate an attenuated, chimeric clone. The nucleotide length of the genome of wild-type human RSV (15,222 nucleotides) is a multiple of six, and members of the *Paramyxovirus* and *Morbillivirus* genera typically abide by a "rule of six," i.e., genomes (or minigenomes) replicate efficiently only when their nucleotide length is a multiple of six (thought to be a requirement for precise spacing of nucleotide residues relative to encapsidating NP protein). Alteration of RSV genome length by single residue increments had no effect on the efficiency of replication, and sequence analysis of several different minigenome mutants following passage showed that the length differences were maintained without compensatory changes. Thus, RSV lacks the strict requirement of genome length being a multiple of six, and nucleotide insertions and deletions can be made in the RSV genome or antigenome without defeating replication of the recombinant RSV of the present invention.

Alternative means to construct cDNA encoding an RSV genome or antigenome include by reverse transcription-PCR using improved PCR conditions (e.g., as described in Cheng et al., *Proc. Natl. Acad. Sci. USA* 91:5695-5699 (1994); Samal et al., J. Virol 70:5075-5082 (1996), each incorporated herein by reference) to reduce the number of subunit cDNA components to as few as one or two pieces. In other embodiments different promoters can be used (e.g., T3, SP6) or different ribozymes (e.g., that of hepatitis delta virus. Different DNA vectors (e.g., cosmids) can be used for propagation to better accommodate the large size genome or antigenome.

The N, P and L proteins, necessary for RNA replication, require an RNA polymerase elongation factor such as the M2(ORF1) protein for processive transcription. Thus M2(ORF1) or a substantially equivalent transcription elongation factor for negative strand RNA viruses is required for the production of infectious RSV and is a necessary component of functional nucleocapsids during productive infection.

The need for the M2(ORF1) protein is consistent with its role as a transcription elongation factor. The need for expression of the RNA polymerase elongation factor protein for negative strand RNA viruses is a feature of the present invention. M2(ORF1) can be supplied by expression of the complete M2-gene, either by the chimeric genome or antigenome or by coexpression therewith, although in this form the second ORF2 may also be expressed and have an inhibitory effect on RNA replication. Therefore, for production of infectious virus using the complete M2 gene the activities of the two ORFs should be balanced to permit sufficient expression of M(ORF1) to provide transcription elongation activity yet not so much of M(ORF2) to inhibit RNA replication. Alternatively, the ORF1 protein is provided from a cDNA engineered to lack ORF2 or which encodes a defective ORF2. Efficiency of virus production may also be improved by co-expression of additional viral protein genes, such as those encoding envelope constituents (i.e., SH, M, G, F proteins).

Isolated polynucleotides (e.g., cDNA) encoding the RSV genome or antigenome and, separately or in cis, the N, P, L and M2(ORF1) proteins, are inserted by transfection, electroporation, mechanical insertion, transduction or the like, into cells which are capable of supporting a productive RSV infection, e.g., HEp-2, FRhL-DBS2, MRC, and Vero cells. Transfection of isolated polynucleotide sequences may be introduced into cultured cells by, for example, calcium phosphate-mediated transfection (Wigler et al., *Cell* 14:725 (1978); Corsaro and Pearson, *Somatic Cell Genetics* 7:603 (1981); Graham and Van der Eb, *Virology* 52:456 (1973)), electroporation (Neumann et al., *EMBO J.* 1:841-845 (1982)), DEAE-dextran mediated transfection (Ausubel et al., (ed.) *Current Protocols in Molecular Biology*, John Wiley and Sons, Inc., NY (1987), cationic lipid-mediated transfection (Hawley-Nelson et al., *Focus* 15:73-79 (1993)) or a commercially available transfection regent, e.g., LipofectACE® (Life Technologies) (each of the foregoing references are incorporated herein by reference).

The N, P, L and M2(ORF1) proteins are encoded by one or more expression vectors which can be the same or separate from that which encodes the genome or antigenome, and various combinations thereof. Additional proteins may be included as desired, encoded by its own vector or by a vector encoding a N, P, L, or M2(ORF1) protein and/or the complete genome or antigenome. Expression of the genome or antigenome and proteins from transfected plasmids can be achieved, for example, by each cDNA being under the control of a promoter for T7 RNA polymerase, which in turn is supplied by infection, transfection or transduction with an expression system for the T7 RNA polymerase, e.g., a vaccinia virus MVA strain recombinant which expresses the T7 RNA polymerase (Wyatt et al., *Virology,* 210:202-205 (1995), incorporated herein by reference). The viral proteins, and/or T7 RNA polymerase, can also be provided from transformed mammalian cells, or by transfection of preformed mRNA or protein.

Alternatively, synthesis of antigenome or genome can be conducted in vitro (cell-free) in a combined transcription-translation reaction, followed by transfection into cells. Or, antigenome or genome RNA can be synthesized in vitro and transfected into cells expressing RSV proteins.

To select candidate chimeric vaccine viruses according to the invention, the criteria of viability, attenuation and immunogenicity are determined according to well known methods. Viruses which will be most desired in vaccines of the invention must maintain viability, have a stable attenuation phenotype, exhibit replication in an immunized host (albeit at lower levels), and effectively elicit production of an immune response in a vaccinee sufficient to confer protection against serious disease caused by subsequent infection from wild-type virus. Clearly, the heretofore known and reported RS virus mutants do not meet all of these criteria. Indeed, contrary to expectations based on the results reported for known attenuated RSV, viruses of the invention are not only viable and more attenuated then previous mutants, but are more stable genetically in vivo than those previously studied mutants—retaining the ability to stimulate a protective immune response and in some instances to expand the protection afforded by multiple modifications, e.g., induce protection against different viral strains or subgroups, or protection by a different immunologic basis, e.g., secretory versus serum immunoglobulins, cellular immunity, and the like. Prior to the invention, genetic instability of the ts phenotype following replication in vivo has been the rule for ts viruses (Murphy et al., *Infect. Immun.* 37:235-242 (1982)).

To propagate a RSV virus for vaccine use and other purposes, a number of cell lines which allow for RSV growth may be used. RSV grows in a variety of human and animal cells. Preferred cell lines for propagating attenuated RS virus for vaccine use include DBS-FRhL-2, MRC-5, and Vero cells. Highest virus yields are usually achieved with epithelial cell lines such as Vero cells. Cells are typically inoculated with virus at a multiplicity of infection ranging from about 0.001 to 1.0 or more, and are cultivated under conditions permissive for replication of the virus, e.g., at about 30-37° C. and for about 3-5 days, or as long as necessary for virus to reach an adequate titer. Virus is removed from cell culture and separated from cellular components, typically by well known clarification procedures, e.g., centrifugation, and may be further purified as desired using procedures well known to those skilled in the art.

Chimeric RSV which has been attenuated as described herein can be tested in various well known and generally accepted in vitro and in vivo models to confirm adequate attenuation, resistance to phenotypic reversion, and immunogenicity for vaccine use. In in vitro assays, the modified virus (e.g., a multiply attenuated, biologically derived or recombinant RSV) is tested for temperature sensitivity of virus replication, i.e. ts phenotype, and for the small plaque phenotype. Modified viruses are further tested in animal models of RSV infection. A variety of animal models have been described and are summarized in Meignier et al., eds., *Animal Models of Respiratory Syncytial Virus Infection*, Merieux Foundation Publication, (1991), which is incorporated herein by reference. A cotton rat model of RS infection is described in U.S. Pat. No. 4,800,078 and Prince et al., *Virus Res.* 3:193-206 (1985), which are incorporated herein by reference, and is considered predictive of attenuation and efficacy in humans and non-human primates. In addition, a primate model of RSV infection using the chimpanzee is predictive of attenuation and efficacy in humans, as is described in detail in Richardson et al., *J. Med. Virol.* 3:91-100 (1978); Wright et al., *Infect. Immun.* 37:397-400 (1982); Crowe et al., *Vaccine* 11:1395-1404 (1993), each incorporated herein by reference.

Figure 1:
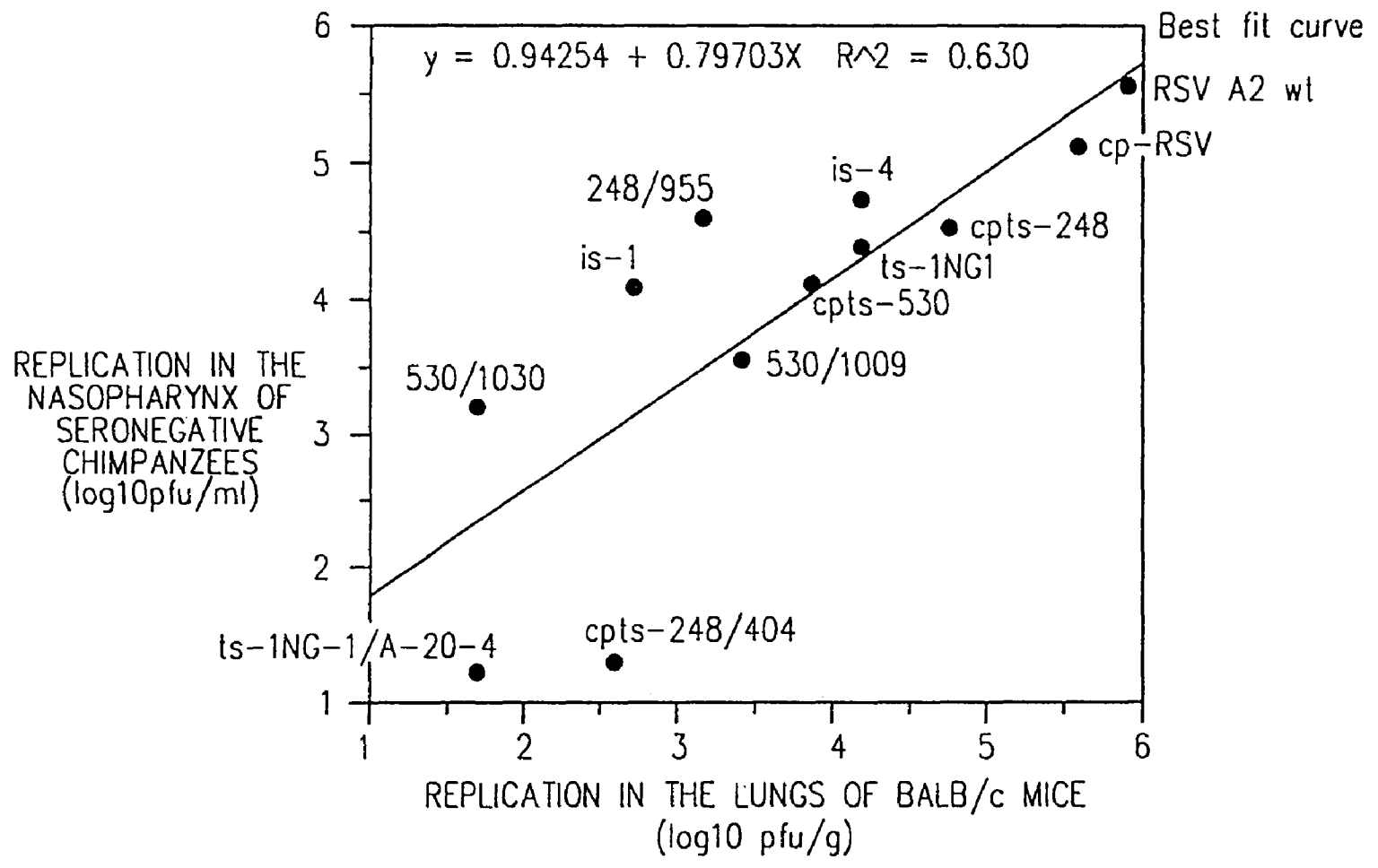

The interrelatedness of data derived from rodents and chimpanzees relating to the level of attenuation of RSV candidates can be demonstrated by reference to FIG. 1, which is a graph correlating the replication of a spectrum of respiratory syncytial subgroup A viruses in the lungs of mice with their replication in chimpanzees. The relative level of replication compared to that of wt RSV is substantially identical, allowing the mouse to serve as a model in which to initially characterize the level of attenuation of the vaccine RSV candidate. The mouse and cotton rat models are especially useful in those instances in which candidate RS viruses display inadequate growth in chimpanzees. The RSV subgroup B viruses are an example of the RS viruses which grow poorly in chimpanzees.

Moreover, the therapeutic effect of RSV neutralizing antibodies in infected cotton rats has been shown to be highly relevant to subsequent experience with immunotherapy of monkeys and humans infected with RSV. Indeed, the cotton rat appears to be a reliable experimental surrogate for the response of infected monkeys, chimpanzees and humans to immunotherapy with RSV neutralizing antibodies. For example, the amount of RSV neutralizing antibodies associated with a therapeutic effect in cotton rats as measured by the level of such antibodies in the serum of treated animals (i.e., serum RSV neutralization titer of 1:302 to 1:518) is in the same range as that demonstrated for monkeys (i.e., titer of 1:539) or human infants or small children (i.e., 1:877). A therapeutic effect in cotton rats was manifest by a one hundred fold or greater reduction in virus titer in the lung (Prince et al., *J. Virol.* 61:1851-1854) while in monkeys a therapeutic effect was observed to be a 50-fold reduction in pulmonary virus titer. (Hemming et al., *J. Infect. Dis.* 152:1083-1087 (1985)). Finally, a therapeutic effect in infants and young children who were hospitalized for serious RSV bronchiolitis or pneumonia was manifest by a significant increase in oxygenation in the treated group and a significant decrease in amount of RSV recoverable from the upper respiratory tract of treated patients. (Hemming et al., *Antimicrob. Agents Chemother.* 31:1882-1886 (1987)). Therefore, based on these studies, the cotton rat constitutes a relevant model for predicting success of chimeric RSV vaccines in infants and small children. Other rodents, including mice, will also be similarly useful because these animals are permissive for RSV replication and have a core temperature more like that of humans (Wright et al., *J. Infect. Dis.* 122:501-512 (1970) and Anderson et al., *J. Gen. Virol.* 71:(1990)).

In accordance with the foregoing description and based on the Examples below, the invention also provides isolated, infectious chimeric RSV compositions for vaccine use. The attenuated chimeric virus which is a component of a vaccine is in an isolated and typically purified form. By isolated is meant to refer to RSV which is in other than a native environment of a wild-type virus, such as the nasopharynx of an infected individual. More generally, isolated is meant to include the attenuated virus as a component of a cell culture or other artificial medium. For example, attenuated RSV of the invention may be produced by an infected cell culture, separated from the cell culture and added to a stabilizer which contains other non-naturally occurring RS viruses, such as those which are selected to be attenuated by means of resistance to neutralizing monoclonal antibodies to the F-protein.

Chimeric RSV vaccines of the invention contain as an active ingredient an immunogenically effective amount of RSV produced as described herein. Biologically derived or recombinant RSV can be used directly in vaccine formulations, or lyophilized. Lyophilized virus will typically be maintained at about 4° C. When ready for use the lyophilized virus is reconstituted in a stabilizing solution, e.g., saline or comprising SPG, $Mg^{++}$ and HEPES, with or without adjuvant, as further described below. The biologically derived or recombinantly modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, aluminum phosphate, aluminum hydroxide, or alum, which are materials well known in the art. Preferred adjuvants also include Stimulon™ QS-21 (Aquila Biopharmaceuticals, Inc., Farmingham, Mass.), MPL™ (3-O-deacylated monophosphoryl lipid A; RIBI ImmunoChem Research, Inc., Hamilton, Mont.), and interleukin-12 (Genetics Institute, Cambridge, Mass.).

Upon immunization with a chimeric RSV vaccine composition as described herein, via aerosol, droplet, oral, topical or other route, the immune system of the host responds to the vaccine by producing antibodies specific for one or more RSV virus proteins, e.g., F and/or G glycoproteins. As a result of the vaccination the host becomes at least partially or completely immune to RSV infection, or resistant to developing moderate or severe RSV disease, particularly of the lower respiratory tract.

Chimeric RSV vaccines of the invention may comprise attenuated chimeric virus that elicits an immune response against a single RSV strain or antigenic subgroup, e.g. A or B, or against multiple RSV strains or subgroups. In this context, the chimeric RSV can elicit a monospecific immune response or a polyspecific immune response against multiple RSV strains or subgroups. Alternatively, chimeric RSV having different immunogenic characteristics can be combined in a vaccine mixture or administered separately in a coordinated treatment protocol to elicit more effective protection against one RSV strain, or against multiple RSV strains or subgroups.

The host to which the vaccine is administered can be any mammal susceptible to infection by RSV or a closely related virus and capable of generating a protective immune response to antigens of the vaccinizing virus. Thus, suitable hosts include humans, non-human primates, bovine, equine, swine, ovine, caprine, lagamorph, rodents, etc. Accordingly, the invention provides methods for creating vaccines for a variety of human and veterinary uses.

The vaccine compositions containing the attenuated chimeric RSV of the invention are administered to a patient susceptible to or otherwise at risk of RS virus infection in an "immunogenically effective dose" which is sufficient to induce or enhance the individual's immune response capabilities against RSV. In the case of human subjects, the attenuated virus of the invention is administered according to well established human RSV vaccine protocols, as described in, e.g., Wright et al., *Infect Immun.* 37:397-400 (1982), Kim et al., *Pediatrics* 52:56-63 (1973), and Wright et al., *J. Pediatr.* 88:931-936 (1976), which are each incorporated herein by reference. Briefly, adults or children are inoculated intranasally via droplet with an immunogenically effective dose of RSV vaccine, typically in a volume of 0.5 ml of a physiologically acceptable diluent or carrier. This has the advantage of simplicity and safety compared to parenteral immunization with a non-replicating vaccine. It also provides direct stimulation of local respiratory tract immunity, which plays a major role in resistance to RSV. Further, this mode of vaccination effectively bypasses the immunosuppressive effects of RSV-specific maternally-derived serum antibodies, which typically are found in the very young. Also, while the parenteral administration of RSV antigens can sometimes be associated with immunopathologic complications, this has never been observed with a live virus.

In all subjects, the precise amount of chimeric RSV vaccine administered and the timing and repetition of administration will be determined based on the patient's state of health and weight, the mode of administration, the nature of the formulation, etc. Dosages will generally range from about $10^3$ to about $10^6$ plaque forming units (PFU) or more of virus per patient, more commonly from about $10^4$ to $10^5$ PFU virus per patient. In any event, the vaccine formulations should provide a quantity of attenuated RSV of the invention sufficient to effectively stimulate or induce an anti-RSV immune response, e.g., as can be determined by complement fixation, plaque neutralization, and/or enzyme-linked immunosorbent assay, among other methods. In this regard, individuals are also monitored for signs and symptoms of upper respiratory illness. As with administration to chimpanzees, the attenuated virus of the vaccine grows in the nasopharynx of vaccinees at levels approximately 10-fold or more lower than wild-type virus, or approximately 10-fold or more lower when compared to levels of incompletely attenuated RSV.

In neonates and infants, multiple administration may be required to elicit sufficient levels of immunity. Administration should begin within the first month of life, and at intervals throughout childhood, such as at two months, six months, one year and two years, as necessary to maintain sufficient levels of protection against native (wild-type) RSV infection. Similarly, adults who are particularly susceptible to repeated or serious RSV infection, such as, for example, health care workers, day care workers, family members of young children, the elderly, individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be indicated for administration to different recipient groups. For example, an engineered chimeric RSV strain expressing a cytokine or an additional protein rich in T cell epitopes may be particularly advantageous for adults rather than for infants. RSV vaccines produced in accordance with the present invention can be combined with viruses expressing antigens of another subgroup or strain of RSV to achieve protection against multiple RSV subgroups or strains. Alternatively, the vaccine virus may incorporate protective epitopes of multiple RSV strains or subgroups engineered into one RSV clone as described herein.

Typically when different vaccine viruses are used they will be administered in an admixture simultaneously, but they may also be administered separately. For example, as the F glycoproteins of the two RSV subgroups differ by only about 11% in amino acid sequence, this similarity is the basis for a cross-protective immune response as observed in animals immunized with RSV or F antigen and challenged with a heterologous strain. Thus, immunization with one strain may protect against different strains of the same or different subgroup.

The chimeric RSV vaccines of the invention elicit production of an immune response that is protective against serious lower respiratory tract disease, such as pneumonia and bronchiolitis when the individual is subsequently infected with wild-type RSV. While the naturally circulating virus is still capable of causing infection, particularly in the upper respiratory tract, there is a very greatly reduced possibility of rhinitis as a result of the vaccination and possible boosting of resistance by subsequent infection by wild-type virus. Following vaccination, there are detectable levels of host engendered serum and secretory antibodies which are capable of neutralizing homologous (of the same subgroup) wild-type virus in vitro and in vivo. In many instances the host antibodies will also neutralize wild-type virus of a different, nonvaccine subgroup.

Preferred chimeric RSV of the present invention exhibit a very substantial diminution of virulence when compared to wild-type virus that is circulating naturally in humans. The chimeric virus is sufficiently attenuated so that symptoms of infection will not occur in most immunized individuals. In some instances the attenuated virus may still be capable of dissemination to unvaccinated individuals. However, its virulence is sufficiently abrogated such that severe lower respiratory tract infections in the vaccinated or incidental host do not occur.

The level of attenuation of chimeric vaccine virus may be determined by, for example, quantifying the amount of virus present in the respiratory tract of an immunized host and comparing the amount to that produced by wild-type RSV or other attenuated RSV which have been evaluated as candidate vaccine strains. For example, the attenuated chimeric virus of the invention will have a greater degree of restriction of replication in the upper respiratory tract of a highly susceptible host, such as a chimpanzee, compared to the levels of replication of wild-type virus, e.g., 10- to 1000-fold less. Also, the level of replication of the attenuated RSV vaccine strain in the upper respiratory tract of the chimpanzee should be less than that of the RSV A2 ts-1 mutant, which was demonstrated previously to be incompletely attenuated in seronegative human infants. In order to further reduce the development of rhinorrhea, which is associated with the replication of virus in the upper respiratory tract, an ideal vaccine candidate virus should exhibit a restricted level of replication in both the upper and lower respiratory tract. However, the attenuated viruses of the invention must be sufficiently infectious and immunogenic in humans to confer protection in vaccinated individuals. Methods for determining levels of RS virus in the nasopharynx of an infected host are well known in the literature. Specimens are obtained by aspiration or washing out of nasopharyngeal secretions and virus quantified in tissue culture or other by laboratory procedure. See, for example, Belshe et al., *J. Med. Virology* 1:157-162 (1977), Friedewald et al., *J. Amer. Med. Assoc.* 204:690-694 (1968); Gharpure et al., *J. Virol.* 3:414-421 (1969); and Wright et al., *Arch. Ges. Virusforsch.* 41:238-247 (1973), each incorporated herein by reference. The virus can conveniently be measured in the nasopharynx of host animals, such as chimpanzees.

In some instances it may be desirable to combine the chimeric RSV vaccines of the invention with vaccines which induce protective responses to other agents, particularly other childhood viruses. For example, a chimeric RSV vaccine of the present invention can be administered simultaneously with parainfluenza virus vaccine, such as described in Clements et al., *J. Clin. Microbiol.* 29:1175-1182 (1991), which is incorporated herein by reference. In another aspect of the invention the chimeric RSV can be employed as a vector for protective antigens of other respiratory tract pathogens, such as parainfluenza, by incorporating the sequences encoding those protective antigens into the chimeric RSV genome or antigenome which is used to produce infectious chimeric RSV, as described herein.

In yet another aspect of the invention a chimeric RSV is employed as a vector for transient gene therapy of the respiratory tract. According to this embodiment the chimeric RSV genome or antigenome incorporates a sequence which is capable of encoding a gene product of interest. The gene product of interest is under control of the same or a different promoter from that which controls RSV expression. The infectious RSV produced by coexpressing the recombinant RSV genome or antigenome with the N, P, L and M2(ORF1) proteins and containing a sequence encoding the gene product of interest is administered to a patient.

Administration is typically by aerosol, nebulizer, or other topical application to the respiratory tract of the patient being treated. Chimeric RSV is administered in an amount sufficient to result in the expression of therapeutic or prophylactic levels of the desired gene product. Examples of representative gene products which are administered in this method include those which encode, for example, those particularly suitable for transient expression, e.g., interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl transferase, cytotoxins, tumor suppressor genes, antisense RNAs, and vaccine antigens.

The following examples are provided by way of illustration, not limitation.

EXAMPLE I

Isolation and Characterization of Mutagenized Derivatives of Cold-passaged RSV

This Example describes the chemical mutagenesis of incompletely attenuated host range-restricted cpRSV to produce derivative ts and sp mutations which are more highly attenuated and thus are preferred for use in RSV vaccine preparations.

A parent stock of cold-passaged RSV (cpRSV) was prepared. Flow Laboratories Lot 3131 virus, the cpRSV parent virus that is incompletely attenuated in humans, was passaged twice in MRC-5 cells at 25° C., terminally diluted twice in MRC-5 cells at 25° C., then passaged three times in MRC-5 to create cpRSV suspension for mutagenesis.

The cpRSV was mutagenized by growing the parent stock in MRC-5 cells at 32° C. in the presence of 5-fluorouracil in the medium at a concentration of $4 \times 10^{-4}$M. This concentration was demonstrated to be optimal in preliminary studies, as evidenced by a 100-fold decrease in virus titer on day 5 of growth in cell culture, compared to medium without 5-fluorouracil. The mutagenized stock was then analyzed by plaque assay on Vero cells that were maintained under an agar overlay, and after an appropriate interval of incubation, plaques were stained with neutral red dye. 854 plaques were picked and the progeny of each plaque were separately amplified by growth on fresh monolayers of Vero cells. The contents of each of the tissue cultures inoculated with the progeny of a single plaque of cpRSV-mutagenized virus were separately harvested when cytopathic effects on the Vero cells appeared maximal. Progeny virus that exhibited the temperature-sensitive (ts) or small-plaque (sp) phenotype was sought by titering these plaque pools on HEp-2 cells at 32° C. and 38° C. Any virus exhibiting a sp phenotype (plaque size that was reduced by 50% or more compared to parental virus at 32° C.) or a ts phenotype (100-fold or greater reduction in titer at restrictive temperature [37° to 40° C.] compared to 32° C.) was evaluated further. These strains were biologically cloned by serial plaque-purification on Vero cells three times, then amplified on Vero cells. The cloned strains were titered at 32°, 37°, 38°, 39° and 40° C. (in an efficiency of plaque formation (EOP) assay) to confirm their sp and ts phenotypes. Because titers of some cloned strains were relatively low even at the permissive temperature (32°), these viruses were passaged once in HEp-2 cells to create virus suspensions for in vitro analysis. The phenotypes of the progeny of the mutagenized cpRSV are presented on Table 1.

TABLE 1

The efficiency of plaque formation of nine derivatives of cold-passaged RSV (cpts or cpsp mutants) in HEp-2 cells at permissive and restrictive temperatures

| Virus | The titer of virus ($\log_{10}$pfu/ml) at the indicated temperature (° C.) | | | | | Shut-Off temperature (° C.)[1] | Small-plaques at 32 C. |
|---|---|---|---|---|---|---|---|
|  | 32 | 37 | 38 | 39 | 40 | | |
| A2 wild-type | 4.5 | 4.4 | 4.5 | 3.8 | 3.8 | >40 | no |
| cp-RSV | 6.0 | 5.8 | 5.8 | 6.2 | 5.4 | >40 | no |
| ts-1 | 5.7 | 4.5 | 2.7 | 2.4 | 1.7* | 38 | no |
| cpsp143 | 4.2* | 4.1* | 3.8* | 3.9* | 3.8* | >40 | yes |
| cpts368 | 6.7 | 6.3 | 6.1* | 5.8 | 2.0**** | 40 | no |
| cpts274 | 7.3 | 7.1 | 6.6 | 5.8* | 1.0** | 40 | no |
| cpts347 | 6.2 | 6.1 | 5.7* | 5.5 | <0.7** | 40 | no |
| cpts142 | 5.7 | 5.1 | 4.5* | 3.7** | <0.7 | 39 | no |
| cpts299 | 6.2 | 5.5 | 5.1* | 2.0** | <0.7 | 39 | no |
| cpts475 | 5.4 | 4.8* | 4.2 | <0.7** | <0.7 | 39 | no |
| cpts530 | 5.5 | 4.8* | 4.5* | <0.7 | <0.7 | 39 | no |
| cpts248 | 6.3 | 5.3 | <0.7** | <0.7 | <0.7 | 38 | no |

[1]Shut-off temperature is defined as the lowest restrictive temperature at which a 100-fold or greater reduction of plaque titer is observed (bold figures in table).
*Small-plaque phenotype (<50% wild-type plaque size)
**Pinpoint-plaque phenotype (<10% wild-type plaque size)

One of the mutant progeny had the small plaque phenotype, RSV cpsp143 (sp refers to the small plaque (sp) phenotype), and the remaining mutant progeny had the ts phenotype. The RSV cpts mutants exhibit a variation in ability to produce plaques in monolayer cultures in vitro over the temperature range 37° C. to 40° C., with cpts368 retaining the ability to produce plaques at 40° C., whereas the most temperature-sensitive (ts) virus, cpts248, failed to produce plaques at 38° C. Thus, several of the mutagenized cpRSV progeny exhibit a marked difference from their cpRSV parent virus with respect to temperature-sensitivity of plaque formation.

Replication and Genetic Stability Studies In Mice

The level of replication of the cpRSV derived mutants in the upper and lower respiratory tracts of BALB/c mice was studied next (Table 2). It was found that cpts530 and cpts248, two of the mutants exhibiting the greatest temperature sensitivity (see Table 1), were about 7- to 12-fold restricted in replication in the nasal turbinates of the mice (Table 2). However, none of the viruses was restricted in replication in the lungs compared to the cpRSV parent virus. This greater restriction of replication in the nasal turbinates than in the lungs is not characteristic of ts mutants, which generally are more restricted in replication in the warmer lower respiratory tract (Richman and Murphy, *Rev. Infect. Dis.* 1:413-433 (1979). The virus produced in the lungs and nasal turbinates retained the ts character of the input virus (data not presented). The present findings suggested that the combination of the ts mutations on the background of the mutations of the cp parent virus has resulted in cpRSV ts progeny with a higher level of stability of the ts phenotype after replication in vivo than had been seen with previously studied ts mutants.

To further explore the level of genetic stability of the ts phenotype of the cpRSV derived mutants, the efficiency of plaque formation of virus present in the lungs and nasal turbinates of nude mice was studied for two mutagenized cpRSV progeny that were among the most ts, namely cpts248 and cpts530. Nude mice were selected because they are immunocompromised due to congenital absence of functional T-cells, and a virus can replicate for a much longer period of time in these hosts. This longer period of replication favors the emergence of virus mutants with altered phenotype. The virus present on day 12 (NOTE: in normal mice, virus is no longer detectable at this time) was characterized and found to retain an unaltered ts phenotype (Table 3). As expected, the ts-1 mutant included in the test as a positive control exhibited an unstable ts phenotype in vivo. Thus, contrary to previous evaluation of ts mutant viruses in rodents, the results show that a high level of stability of the ts phenotype of the cpRSV derived mutants following prolonged replication in rodents was achieved, which represents a significant and heretofore unattained very desirable property in the viruses of the invention.

TABLE 2

Replication of cpts and cpsp- RSV mutants in BALB/c mice[1]

Virus titer at 32° C. (mean log $_{10}$pfu/g tissue from the tissues of 8 animals ± standard error)

| Animals infected with | Shutoff Temp. of virus (° C.) | Day 4 Nasal Turbinates | Day 4 Lungs | Day 5 Nasal Turbinates | Day 5 Lungs |
|---|---|---|---|---|---|
| A2 wild-type | >40 | 5.0 ± 0.16 | 5.8 ± 0.20 | 5.0 ± 0.11 | 5.8 ± 0.19 |
| cpRSV | >40 | 4.7 ± 0.07 | 5.3 ± 0.18 | 4.8 ± 0.16 | 5.3 ± 0.21 |
| ts-1 | 38 | 4.0 ± 0.19 | 4.7 ± 0.27 | 3.8 ± 0.33 | 4.9 ± 0.13 |
| cpsp143 | >40 | 4.5 ± 0.14 | 4.1 ± 0.37 | 4.4 ± 0.39 | 4.6 ± 0.39 |
| cpts368 | 40 | 4.8 ± 0.15 | 5.1 ± 0.35 | 4.7 ± 0.08 | 5.4 ± 0.23 |
| cpts274 | 40 | 4.2 ± 0.19 | 5.0 ± 0.15 | 4.2 ± 0.11 | 5.1 ± 0.55 |
| cpts347 | 40 | 4.4 ± 0.32 | 4.9 ± 0.40 | 4.5 ± 0.33 | 5.2 ± 0.35 |
| cpts142 | 39 | 4.1 ± 0.34 | 5.0 ± 0.19 | 4.3 ± 0.24 | 5.8 ± 0.40 |
| cpts299 | 39 | 3.9 ± 0.11 | 5.2 ± 0.15 | 3.9 ± 0.32 | 5.0 ± 0.29 |
| cpts475 | 39 | 4.0 ± 0.18 | 5.3 ± 0.25 | 4.1 ± 0.23 | 4.9 ± 0.42 |
| cpts530 | 39 | 3.9 ± 0.18 | 5.3 ± 0.15 | 3.9 ± 0.14 | 5.3 ± 0.19 |
| cpts248 | 38 | 3.9 ± 0.33 | 5.1 ± 0.29 | 4.2 ± 0.13 | 5.5 ± 0.35 |

[1]Mice were administered $10^{6.3}$ p.f.u. intranasally in a 0.1 ml inoculum on day 0, then sacrificed on day 4 or 5.

TABLE 3

The genetic stability of RSV cpts-248 and cpts-530 following prolonged replication in nude mice Efficiency of plaque formation at indicated temperature of virus present in nasal turbinates (n.t.) or lungs of nude mice sacrificed 12 days after virus administration[1]

| Animals infected with | Tissue harvest or input virus tested | Number of animals | 32° C. % animals with virus detectable | 32° C. Mean titer (log$_{10}$pfu per gram tissue or ml inoculum)[2] | 37° C. % animals with virus detectable | 37° C. % animals with virus with altered ts phenotype | 37° C. Mean titer (log$_{10}$pfu per gram tissue or ml inoculum)[2] |
|---|---|---|---|---|---|---|---|
| cpts-248 | n.t. | 19 | 100 | 3.8 ± 0.34 | 0 | 0 | <2.0 |
| " | lungs | " | 90 | 2.0 ± 0.29 | 0 | 0 | <1.7 |
| cpts-530 | n.t. | 20 | 100 | 3.0 ± 0.26 | 0 | 0 | <2.0 |
| " | lungs | " | 100 | 2.4 ± 0.29 | 0 | 0 | <1.7 |
| ts-1 | n.t. | 19 | 100 | 3.7 ± 0.23 | 74 | 74 | 2.7 ± 0.57 |
| " | lungs | " | 100 | 2.5 ± 0.30 | 74 | 74 | 1.8 ± 0.21 |
| Efficiency of plaque formation of input viruses | cpts-248 | — | — | 4.9 | — | — | <0.7 |
| | cpts-530 | — | — | 5.5 | — | — | 3.7* |
| | ts-1 | — | — | 6.1 | — | — | 3.3 |

TABLE 3-continued

The genetic stability of RSV cpts-248 and cpts-530 following prolonged replication in nude mice Efficiency of plaque formation at indicated temperature of virus present in nasal turbinates (n.t.) or lungs of nude mice sacrificed 12 days after virus administration[1]

| Animals infected with | Tissue harvest or input virus tested | 38° C. | | | 40° C. | | |
|---|---|---|---|---|---|---|---|
| | | % animals with virus detectable | % animals with virus with altered ts phenotype | Mean titer ($\log_{10}$pfu per gram tissue or ml inoculum)[2] | % animals with virus detectable | % animals with virus with altered ts phenotype | Mean titer ($\log_{10}$pfu per gram tissue or ml inoculum)[2] |
| cpts-248 | n.t. | 0 | 0 | <2.0 | 0 | 0 | <2.0 |
| " | lungs | 0 | 0 | <1.7 | 0 | 0 | <1.7 |
| cpts-530 | n.t. | 0 | 0 | <2.0 | 0 | 0 | <2.0 |
| " | lungs | 0 | 0 | <1.7 | 0 | 0 | <1.7 |
| ts-1 | n.t. | 63 | 63 | 2.4 ± 0.36 | 10 | 10 | 2.0 ± 0.13 |
| " | lungs | 35 | 32 | 1.8 ± 0.15 | 0 | 0 | <1.7 |
| Efficiency of plaque formation of input viruses | cpts-248 | — | | <0.7 | — | | <0.7 |
| | cpts-530 | — | | <0.7 | — | | <0.7 |
| | ts-1 | — | | 2.7 | — | | <0.7 |

[1]Plaque titers shown represent the mean $\log_{10}$pfu/gram tissue of 19 or 20 samples ± standard error.
[2]Each animal received $10^{6.3}$ p.f.u. intranasally in a 0.1 ml inoculum of the indicated virus on day 0.
*Small-plaque phenotype only.

In Chimpanzees

The level of attenuation of the cpRSV ts derivative was next evaluated in the seronegative chimpanzee, a host most closely related to humans. Trials in chimpanzees or owl monkeys are conducted according to the general protocol of Richardson et al., *J. Med. Virol.* 3:91-100 (1979); Crowe et al., *Vaccine* 11:1395-1404 (1993), which are incorporated herein by reference. One ml of suspension containing approximately $10^4$ plaque-forming units (PFU) of mutagenized, attenuated virus is given intranasally to each animal. An alternate procedure is to inoculate the RSV into both the upper and lower respiratory tract at a dose of $10^4$ PFU delivered to each site. Chimpanzees are sampled daily for 10 days, then every 3-4 days through day 20. The lower respiratory tract of chimpanzees can be sampled by tracheal lavage according to the protocol of Snyder et al., *J. Infec. Dis.* 154:370-371 (1986) and Crowe et al., *Vaccine* 11:1395-1404 (1993). Some animals are challenged 4 to 6 weeks later with the wild-type virus. Animals are evaluated for signs of respiratory disease each day that nasopharyngeal specimens are taken. Rhinorrhea is scored from 0 to 4+, with 2+ or greater being considered as evidence of significant upper respiratory disease.

Virus is isolated from nasal and throat swab specimens and tracheal lavage fluids by inoculation into RSV-sensitive HEp-2 cells as described above. Quantities of virus can also be determined directly by the plaque technique using HEp-2 cells as described in Schnitzer et al., *J. Virol.* 17:431-438 (1976), which is incorporated herein by reference. Specimens of serum are collected before administration of virus and at 3 to 4 weeks post-inoculation for determination of RSV neutralizing antibodies as described in Mills et al., *J. Immununol.* 107:123-130 (1970), which is incorporated herein by reference.

The most ts and attenuated of the cpRSV derivative (cpts248) was studied and compared to wild-type RSV and the cpRSV parent virus (Table 4). Replication of the cpRSV parent virus was slightly reduced in the nasopharynx compared to wild-type, there was a reduction in the amount of rhinorrhea compared to wild-type virus, and there was an approximate 600-fold reduction in virus replication in the lower respiratory tract compared to wild-type. Clearly, the cp virus was significantly restricted in replication in the lower respiratory tract of chimpanzees, a very desirable property not previously identified from prior evaluations of cpRSV in animals or humans. More significantly, the cpts 248 virus was 10-fold restricted in replication in the nasopharynx compared to wild-type, and this restriction was associated with a marked reduction of rhinorrhea. These findings indicated that the cpRSV derived mutant possesses two highly desirable properties for a live RSV vaccine, namely, evidence of attenuation in both the upper and the lower respiratory tracts of highly susceptible seronegative chimpanzees. The level of genetic stability of the virus present in the respiratory tract of chimpanzees immunized with cpts248 was evaluated next (Table 5). The virus present in the respiratory tract secretions retained the ts phenotype, and this was seen even with the virus from chimpanzee No. 3 on day 8 that was reduced 100-fold in titer at 40° C. and exhibited the small plaque phenotype at 40° C., indicating that its replication was still temperature-sensitive. This represents the most genetically stable ts mutant identified prior to the time of this test. The increased stability of the ts phenotype of the cpts248 and cpts530 viruses reflects an effect of the cp mutations on the genetic stability of the mutations that contribute to the ts phenotype in vivo. Thus, the ts mutations in the context of the mutations already present in the cp3131 parent virus appear to be more stable than would be expected in their absence. This important property has not been previously observed or reported. Infection of chimpanzees with the cpts 248 induced a high titer of serum neutralizing antibodies, as well as antibodies to the F and G glycoproteins (Table 6). Significantly, immunization with cpts248 protected the animals from wild-type RSV challenge (Table 7), indicating that this mutant functions as an effective vaccine virus in a host that is closely related to humans.

These above-presented findings indicate that the cpts248 virus has many properties desirable for a live RSV vaccine, including: 1) attenuation for the upper and lower respiratory tract; 2) increased genetic stability after replication in vivo, even after prolonged replication in immunosuppressed animals; 3) satisfactory immunogenicity; and 4) significant protective efficacy against challenge with wild-type RSV. The cpts530 virus shares with cpts248 similar temperature sensitivity of plaque formation, a similar degree of restriction of replication in the nasal turbinates of mice, and a high level of genetic stability in immunodeficient nude mice, whereby it also represents an RS virus vaccine strain.

TABLE 4

Replication of cpts-RSV 248, cp-RSV, or wild-type RSV A2 in the upper and lower respiratory tract of seronegative chimpanzees

| Animal Infected with indicated virus | Route of inoculation | Chimpanzee number | Virus recovery | | | | Rhinorrhea score | |
|---|---|---|---|---|---|---|---|---|
| | | | Nasopharynx | | Trachea | | | |
| | | | Duration[b] (days) | Peak titer ($\log_{10}$pfu/ml) | Duration[b] (days) | Peak titer ($\log_{10}$pfu/ml) | Mean[c] | Peak |
| cpts-248 | IN + IT | 1 | 10 | 4.6 | 8[d] | 5.4 | 0.2 | 1 |
| | IN + IT | 2 | 10 | 4.5 | 6 | 2.2 | 0.1 | 1 |
| | IN + IT | 3 | 9 | 4.7 | 10 | 2.1 | 0.1 | 1 |
| | IN + IT | 4 | 9 | 4.2 | 8[d] | 2.2 | 0.1 | 1 |
| | | | mean 9.5 | mean 4.5 | mean 8.0 | mean 3.0 | mean 0.1 | |
| cp-RSV | IN | 5 | 20 | 5.3 | 8[d] | 2.9 | 1.0 | 3 |
| | IN | 6 | 16 | 5.8 | 6[d] | 3.0 | 1.8 | 3 |
| | IN + IT | 7 | 13 | 4.3 | 6[d] | 3.0 | 0.6 | 1 |
| | IN + IT | 8 | 16 | 5.0 | 10[d] | 2.8 | 0.5 | 1 |
| | | | mean 16 | mean 5.1 | mean 7.5 | mean 2.9 | mean 1.0 | |
| A2 wild-type | IN | 9 | 9 | 5.1 | 13 | 5.4 | 1.0 | 1 |
| | IN | 10 | 9 | 6.0 | 8 | 6.0 | 1.7 | 4 |
| | IN + IT | 11 | 13 | 5.3 | 8 | 5.9 | 2.1 | 3 |
| | IN + IT | 12 | 9 | 5.4 | 8 | 5.6 | 1.0 | 3 |
| | | | mean 10 | mean 5.5 | mean 9.3 | mean 5.7 | mean 1.4 | |

[a]IN = Intranasal administration only, at a dose of $10^4$ p.f.u. in a 1.0 ml inoculum; IN + IT = Both intranasal and intratracheal administration, $10^4$ p.f.u. in a 1.0 ml inoculum at each site.
[b]Indicates last day post-infection on which virus was recovered.
[c]Mean rhinorrhea score represents the sum of daily scores for a period of eight days surrounding the peak day of virus shedding, divided by eight. Four is the highest score; zero is the lowest score.
[d]Virus isolated only on day indicated.

TABLE 5

Genetic stability of virus present in original nasopharyngeal (NP) swabs or tracheal lavage (TL) specimens obtained from animals experimentally infected with cptsRSV 248.

| Chimpanzee number | NP swab or TL specimen | Virus obtained on post-infection day | Titer of RSV at indicated temperature ($\log_{10}$pfu/ml) | | |
|---|---|---|---|---|---|
| | | | Titer at 32° C. | Titer at 39° C. | Titer at 40° C. |
| 1[a] | NP | 3 | 3.2 | <0.7 | NT |
| | " | 4 | 2.7 | <0.7 | NT |
| | " | 5 | 4.2 | <0.7 | NT |
| | " | 6 | 3.8 | <0.7 | NT |
| | " | 7 | 4.6 | <0.7 | NT |
| | " | 8 | 4.5 | <0.7 | NT |
| | " | 9 | 2.6 | <0.7 | NT |
| | " | 10 | 2.0 | <0.7 | NT |
| | TL | 6 | 5.4 | <0.7 | NT |
| | " | 8 | 2.7 | <0.7 | NT |
| 2[a] | NP | 3 | 3.2 | <0.7 | NT |
| | " | 4 | 3.7 | <0.7 | NT |
| | " | 5 | 4.5 | <0.7 | NT |
| | " | 6 | 4.1 | <0.7 | NT |
| | " | 7 | 3.3 | <0.7 | NT |
| | " | 8 | 4.2 | <0.7 | NT |
| | " | 9 | 2.8 | <0.7 | NT |
| | " | 10 | 1.6 | <0.7 | NT |
| | TL | 6 | 2.2 | <0.7 | NT |
| 3 | NP | 3 | 2.7 | <0.7 | <0.7 |
| | " | 4 | 3.4 | <0.7 | <0.7 |
| | " | 5 | 2.9 | <0.7 | <0.7 |
| | " | 6 | 3.3 | <0.7 | <0.7 |
| | " | 7 | 3.4 | 0.7[b] | <0.7 |
| | " | 8 | 4.7 | 3.5[b] | 2.0[c] |
| | " | 9 | 1.9 | <0.7 | <0.7 |
| | TL | 6 | 1.8 | <0.7 | <0.7 |
| | " | 8 | 1.9 | 1.2[b] | <0.7 |
| | " | 10 | 2.1 | 1.3[b] | <0.7 |
| 4 | NP | 3 | 3.2 | <0.7 | NT |
| | " | 4 | 2.7 | <0.7 | NT |
| | " | 5 | 3.4 | <0.7 | NT |
| | " | 6 | 3.3 | <0.7 | NT |
| | " | 7 | 4.2 | <0.7 | NT |
| | " | 8 | 3.5 | <0.7 | NT |
| | " | 9 | 2.1 | <0.7 | NT |
| | TL | 8 | 2.2 | <0.7 | NT |

NT = Not tested

[a]Isolates (once-passaged virus suspensions with average titer log $_{10}$pfu/ml of 4.0) were generated from these chimpanzees from each original virus-containing nasopharyngeal swab specimen or tracheal lavage specimen and tested for efficiency of plaque formation at 32°, 39° and 40° C. No isolate was able to form plaques at 39° C. Isolates from chimpanzees 3 and 4 were not tested in this manner.
[b]The percent titer at 39° C. versus that at 32° C.: NP swab day 7 = 0.2%, NP swab day 8 = 6T, TL day 8 - 20%, TL day 10 = 16%. All plaques were of small-plaque phenotype only; no wild-type size plaques seen.
[c]The percent titer at 40° C. versus that at 32° C. was 0.2%. All plaques were of pinpoint-plaque phenotype; wild-type size plaques were not detected.

TABLE 6

Serum antibody responses of chimpanzees infected with RSV cpts-248, cp-RSV, or RSV A2 wild-type

| Animals immunized with | No. of Chimpanzees | Serum antibody titers (reciprocal mean $\log_2$) | | | | | |
|---|---|---|---|---|---|---|---|
| | | Neutralizing | | ELISA-F | | ELISA-G | |
| | | Day 0 | Day 28 | Day 0 | Day 28 | Day 0 | Day 28 |
| cpts-248 | 4 | <3.3 | 10.7 | 7.3 | 15.3 | 6.3 | 9.8 |
| cp-RSV | 4 | <3.3 | 11.2 | 11.3 | 15.3 | 9.3 | 12.3 |
| RSVA2 wild-type | 4 | <3.3 | 11.2 | 8.3 | 15.3 | 7.3 | 10.3 |

TABLE 7

Immunization of chimpanzees with cpts-248 induces resistance to RSV A2 wild-type virus challenge on day 28

Response to challenge with $10^4$ p.f.u. wild-type virus administered on day 28

| Virus used to immunize animal | Chimpanzee number | Virus Recovery | | | | Rhinorrhea score | | Serum neutralizing antibody titer (reciprocal $\log_2$) on day indicated | |
|---|---|---|---|---|---|---|---|---|---|
| | | Nasopharynx | | Trachea | | | | | |
| | | Duration (days) | Peak titer ($\log_{10}$pfu/ml) | Duration (days) | Peak titer ($\log_{10}$pfu/ml) | Mean* | Peak | Day 28 | Day 42 or 56 |
| cpts-248 | 1 | 5 | 2.7 | 0 | <0.7 | 0 | 0 | 10.1 | 11.0 |
| | 2 | 9 | 1.8 | 0 | <0.7 | 0 | 0 | 10.3 | 14.5 |
| cp-RSV | 5 | 5 | 1.0 | 0 | <0.7 | 0 | 0 | 11.1 | 13.3 |
| | 6 | 8 | 0.7 | 0 | <0.7 | 0 | 0 | 11.4 | 12.9 |
| none | 9 | 9 | 5.1 | 13 | 5.4 | 1.0 | 1 | <3.3 | 12.4 |
| | 10 | 9 | 6.0 | 8 | 6.0 | 1.7 | 4 | <3.3 | 13.2 |
| | 11 | 13 | 5.3 | 8 | 5.9 | 2.1 | 3 | <3.3 | 11.6 |
| | 12 | 9 | 5.4 | 8 | 5.6 | 1.0 | 3 | <3.3 | 11.2 |

*Mean rhinorrhea score represents the sum of scores during the eight days of peak virus shedding divided by eight. Four is the highest score. A score of zero indicates no rhinorrhea detected on any day of the ten-day observation period.

Further Attenuations

Since RS virus produces more symptoms of lower respiratory tract disease in human infants than in the 1-2 year old chimpanzees used in these experimental studies, and recognizing that mutants which are satisfactorily attenuated for the chimpanzee may not be so for seronegative infants and children, the cpts248 and 530 derivatives, which possess the very uncharacteristic ts mutant properties of restricted replication and attenuation in the upper respiratory tract and a higher level of genetic stability, were further mutagenized.

Progeny viruses that exhibited a greater degree of temperature-sensitivity in vitro than cpts248 or that had the small plaque phenotype were selected for further study. Mutant derivatives of the cpts248 that possessed one or more additional ts mutations were produced by 5-fluorouracil mutagenesis (Table 8). Ts mutants that were more temperature-sensitive (ts) than the cpts248 parental strain were identified, and some of these had the small plaque (sp) phenotype. These cpts248 derivatives were administered to mice. cpts248/804, 248/955, 248/404, 248/26, 248/18, and 248/240 mutants were more restricted in replication in the upper and lower respiratory tract of the mouse than their cpts248 parental virus (Table 9). Thus, viable mutants of cpts248 which were more attenuated than their cpts248 parental virus were identified, and these derivatives of cpts248 exhibited a wide range of replicative efficiency in mice, with cpts248/26 being the most restricted. The ts phenotype of the virus present in nasal turbinates and lungs of the mice was almost identical to that of the input virus, indicating genetic stability. A highly attenuated derivative of cpts248, the cpts248/404 virus, was 1000-fold more restricted in replication in the nasopharynx compared to wild-type. The cpts248/404 mutant, possessing at least three attenuating mutations, was also highly restricted in replication in the upper and lower respiratory tracts of four seronegative chimpanzees and infection did not induce rhinorrhea (Table 10). Again, this virus exhibited a high degree of reduction in replication compared to wild-type, being 60,000-fold reduced in the nasopharynx and 100,000-fold in the lungs. Nonetheless, two chimpanzees which were subsequently challenged with RSV wild-type virus were highly resistant (Table 11).

Five small-plaque mutants of cpts248/404 were derived by chemical mutagenesis in a similar fashion to that described above. Suspensions of once-amplified plaque progeny were screened for the small-plaque (sp) phenotype by plaque titration at 32° C. on HEp-2 cells, and working suspensions of virus were prepared as described above.

Five of the plaque progeny of the mutagenized cpts248/404 virus exhibited a stable sp phenotype. The shut-off temperature of each mutant was 35° C. or less (Table 12), suggesting that each of these sp derivatives of the cpts248/404 virus also had acquired an additional ts mutation. Following intranasal inoculation of Balb/c mice with $10^{6.3}$ p.f.u. of a sp derivative of the cpts248/404, virus could not be detected in the nasal turbinates of mice inoculated with any of these sp derivatives. However, virus was detected in low titer in the lungs in one instance. These results indicate >300-fold restriction of replication in the nasal turbinates and >10,000-fold restriction in lungs compared with wild-type RSV.

Further ts derivatives of the cpts530 virus were also generated (Table 13). As with the cpts248 derivatives, the cpts-530 derivatives were more restricted in replication in mice than the cpts530 parental strain. One mutant, cpts-530/1009, was 30 times more restricted in replication in the nasal turbinates of mice. This cpts530 derivative, is also highly restricted in replication in the upper and lower respiratory tract of seronegative chimpanzees (Table 14). In the nasopharynx, cpts530 was 30-fold restricted in replication, while cpts530/1009 was 100-fold restricted compared to wild-type virus. Both of the cpts mutants were highly restricted (20,000 to 32,000-fold) in the lower respiratory tract compared with wild-type virus, even when the mutants were inoculated directly into the trachea. Also, chimpanzees previously infected with cpts530/1009, cpts530 or cpRSV exhibited significant restriction of virus replication in the nasopharynx and did not develop significant rhinorrhea following subsequent combined intranasal and intratracheal challenge with wild-type RSV (Table 15). In addition, chimpanzees previously infected with any of the mutants exhibited complete resistance in the lower respiratory tract to replication of wild-type challenge virus.

These results were completely unexpected based on experience gained during prior studies. For example, the results of an earlier study indicated that the in vivo properties of RSV ts mutants derived from a single cycle of 5-fluorouracil mutagenesis could not be predicted a priori. Moreover, although one of the first four ts mutants generated in this manner exhibited the same shut off temperature for plaque formation as the other mutants, it was overattenuated when tested in susceptible chimpanzees and susceptible infants and young children (Wright et al., *Infect Immun.* 37 (1):397-400 (1982). This indicated that the acquisition of the ts phenotype resulting in a 37-38° C. shut off temperature for plaque formation did not reliably yield a mutant with the desired level of attenuation for susceptible chimpanzees, infants and children. Indeed, the results of studies with heretofore known ts mutants completely fail to provide any basis for concluding that introduction of three independent mutations (or sets of mutations) into RSV by cold-passage followed by two successive cycles of chemical mutagenesis could yield viable mutants which retain infectivity for chimpanzees (and by extrapolation, young infants) and exhibit the desired level of attenuation, immunogenicity and protective efficacy required of a live virus vaccine to be used for prevention of RSV disease.

The above-presented results clearly demonstrate that certain ts derivatives of the cpRSV of the invention have a satisfactory level of infectivity and exhibit a significant degree of attenuation for mice and chimpanzees. These mutant derivatives are attenuated and appear highly stable genetically after replication in vivo. These mutants also induce significant resistance to RSV infection in chimpanzees. Thus, these derivatives of cpRSV represent virus strains suitable for use in a live RSV vaccine designed to prevent serious human RSV disease.

TABLE 8

The efficiency of plaque formation of ten mutants derived from RSV cpts248 by additional 5FU mutagenesis.

| Virus | The titer of virus ($log_{10}$pfu/ml) at the indicated temperature (° C.) | | | | | | | Shutoff temperature at 32 C. | Small-plaques |
|---|---|---|---|---|---|---|---|---|---|
| | 32 | 35 | 36 | 37 | 38 | 39 | 40 (° C.)[1] | | |
| A2 wild-type | 4.5 | 4.6 | 4.4 | 4.5 | 4.5 | 3.8 | 3.8 | >40 | no |
| cpRSV | 4.7 | 4.4 | 4.3 | 4.3 | 4.2 | 3.7 | 3.5 | >40 | no |
| ts-1 | 5.6 | 5.4 | 4.9 | 4.4 | 2.7 | 2.0 | <0.7 | 38 | no |
| cpts-248 | 3.4 | 3.0 | 2.6* | 1.7** | <0.7 | <0.7 | <0.7 | 38 | no |
| 248/1228 | 5.5* | 5.3* | 5.3 | <0.7** | <0.7 | <0.7 | <0.7 | 37 | yes |
| 248/1075 | 5.3* | 5.3* | 5.1 | <0.7** | <0.7 | <0.7 | <0.7 | 37 | yes |
| 248/965 | 4.5 | 4.2 | 4.2* | <0.7 | <0.7 | <0.7 | <0.7 | 37 | no |
| 248/967 | 4.4 | 3.7 | 3.6* | <0.7 | <0.7 | <0.7 | <0.7 | 37 | no |
| 248/804 | 4.9 | 4.5 | 4.0* | <0.7 | <0.7 | <0.7 | <0.7 | 37 | no |
| 248/955 | 4.8 | 3.7 | 2.8* | <0.7 | <0.7 | <0.7 | <0.7 | 36 | no |
| 248/404 | 3.6 | 2.9* | <0.7 | <0.7 | <0.7 | <0.7 | <0.7 | 36 | no |
| 248/26 | 3.1 | 2.9* | <0.7 | <0.7 | <0.7 | <0.7 | <0.7 | 36 | no |
| 248/18 | 4.0* | 4.0 | <0.7** | <0.7 | <0.7 | <0.7 | <0.7 | 36 | yes |
| 248/240 | 5.8* | 5.7 | <0.7** | <0.7 | <0.7 | <0.7 | <0.7 | 36 | yes |

[1]Shut-off temperature is defined as the lowest restrictive temperature at which a 100-fold or greater reduction of plaque titer in Hep-2 cells is observed (bold figures in table).
*Small-plaque phenotype (<50% wild-type plaque size).
**Pinpoint-plaque phenotype (<10% wild-type plaque size).

TABLE 9

Replication and genetic stability of ten mutants derived from RSV cpts-248 in Balb/c mice[1]

| Virus used to infect animal | Shutoff temperature of virus (° C.) | Virus titer [mean $log_{10}$pfu/g tissue of six animals ± standard error] | | | | | | | |
|---|---|---|---|---|---|---|---|---|---|
| | | Nasal turbinates | | | | Lungs | | | |
| | | 32° C. | 36° C. | 37° C. | 38° C. | 32° C. | 36° C. | 37° C. | 38° C. |
| A2 wild-type | >40 | 5.1 ± 0.15 | 5.2 ± 0.23 | 5.2 ± 0.14 | 5.2 ± 0.27 | 6.1 ± 0.14 | 5.8 ± 0.23 | 6.0 ± 0.12 | 5.9 ± 0.17 |
| cp-RSV | >40 | 4.9 ± 0.20 | 5.1 ± 0.16 | 4.9 ± 0.24 | 4.9 ± 0.22 | 6.0 ± 0.16 | 5.9 ± 0.23 | 5.6 ± 0.15 | 5.6 ± 0.13 |
| ts-1 | 38 | 3.9 ± 0.25 | 2.7 ± 0.27 | 2.4 ± 0.42 | 2.5 ± 0.29 | 4.1 ± 0.21 | 3.5 ± 0.23 | 2.6 ± 0.18 | 2.0 ± 0.23 |
| cpts-248 | 38 | 4.0 ± 0.16 | 2.5 ± 0.34 | <2.0 | <2.0 | 4.4 ± 0.37 | 1.8 ± 0.15 | <1.7 | <1.7 |
| 248/1228 | 37 | 4.1 ± 0.15 | 2.4 ± 0.48 | <2.0 | <2.0 | 2.0 ± 0.37 | <1.7 | <1.7 | <1.7 |
| 248/1075 | 37 | 4.2 ± 0.18 | 2.4 ± 0.40 | <2.0 | <2.0 | 5.5 ± 0.16 | 3.5 ± 0.18 | <1.7 | <1.7 |
| 248/965 | 37 | 3.8 ± 0.23 | <2.0 | <2.0 | <2.0 | 4.5 ± 0.21 | 3.4 ± 0.16 | <1.7 | <1.7 |
| 248/967 | 37 | 4.4 ± 0.20 | <2.0 | <2.0 | <2.0 | 5.4 ± 0.20 | 3.6 ± 0.19 | <1.7 | <1.7 |

TABLE 9-continued

Replication and genetic stability of ten mutants derived from RSV cpts-248 in Balb/c mice[1]

| Virus used to infect animal | Shutoff temperature of virus (° C.) | Virus titer [mean $\log_{10}$pfu/g tissue of six animals ± standard error] | | | | | | | |
|---|---|---|---|---|---|---|---|---|---|
| | | Nasal turbinates | | | | Lungs | | | |
| | | 32° C. | 36° C. | 37° C. | 38° C. | 32° C. | 36° C. | 37° C. | 38° C. |
| 248/804 | 37 | 2.9 ± 0.19 | <2.0 | <2.0 | <2.0 | 3.6 ± 0.19 | <1.7 | <1.7 | <1.7 |
| 248/955 | 36 | 3.2 ± 0.10 | <2.0 | <2.0 | <2.0 | 3.2 ± 0.22 | <1.7 | <1.7 | <1.7 |
| 248/404 | 36 | 2.1 ± 0.31[2] | <2.0 | <2.0 | <2.0 | 4.4 ± 0.12[2] | 1.8 ± 0.20 | <1.7 | <1.7 |
| 248/26 | 36 | <2.0 | <2.0 | <2.0 | <2.0 | 2.3 ± 0.20 | <1.7 | <1.7 | <1.7 |
| 248/18 | 36 | 2.9 ± 0.99 | <2.0 | <2.0 | <2.0 | 4.3 ± 0.23 | 1.8 ± 0.15 | <1.7 | <1.7 |
| 248/240 | 36 | 2.9 ± 0.82 | <2.0 | <2.0 | <2.0 | 3.9 ± 0.12 | <1.7 | <1.7 | <1.7 |

[1]Mice were administered $10^{6.3}$ p.f.u. intranasally under light anesthesia on day 0, then sacrificed by $CO_2$ asphyxiation on day 4.
[2]In a subsequent study, the level of replication of the cpts-248/404 virus was found to be 2.4 ± 0.24 and 2.6 ± 0.31 in the nasal turbinates and lungs, respectively.

TABLE 10

Replication of cpts-RSV 248/404, cpts-RSV 248/18, cpts-RSV 248, cp-RSV, or wild-type RSV A2 in the upper and lower respiratory tract of seronegative chimpanzees

| Animal infected with indicated virus | Route of inoculation | Chimpanzee number | Virus recovery | | | | | |
|---|---|---|---|---|---|---|---|---|
| | | | Nasopharynx | | Trachea | | Rhinorrhea scores | |
| | | | Duration[b] (days) | Peak titer ($\log_{10}$pfu/ml) | Duration[b] (days) | Peak titer ($\log_{10}$pfu/ml) | Mean[c] | Peak |
| cpts-248/404 | IN + IT | 13 | 0 | <0.7 | 0 | <0.7 | 0 | 0 |
| | IN + IT | 14 | 0 | <0.7 | 0 | <0.7 | 0 | 0 |
| | IN + IT | 15 | 8 | 1.9 | 0 | <0.7 | 0.3 | 2 |
| | IN + IT | 16 | 9 | 2.0 | 0 | <0.7 | 0.2 | 1 |
| | | | mean 4.3 | mean 1.3 | mean 0 | mean <0.7 | mean 0.1 | mean 0.8 |
| cpts-248# | IN + IT | 1 | 10 | 4.6 | 8[d] | 5.4 | 0.2 | 1 |
| | IN + IT | 2 | 10 | 4.5 | 6 | 2.2 | 0.1 | 1 |
| | IN + IT | 3 | 9 | 4.7 | 10 | 2.1 | 0.1 | 1 |
| | IN + IT | 4 | 9 | 4.2 | 8[d] | 2.2 | 0.1 | 1 |
| | | | mean 9.5 | mean 4.5 | mean 8.0 | mean 3.0 | mean 0.1 | mean 1.0 |
| cp-RSV# | IN | 5 | 20 | 5.3 | 8[d] | 2.9 | 1.0 | 3 |
| | IN | 6 | 16 | 5.8 | 6[d] | 3.0 | 1.8 | 3 |
| | IN + IT | 7 | 13 | 4.3 | 6[d] | 3.0 | 0.6 | 1 |
| | IN + IT | 8 | 16 | 5.0 | 10[d] | 2.8 | 0.5 | 1 |
| | | | mean 16 | mean 5.1 | mean 7.5 | mean 2.9 | mean 1.0 | mean 2.0 |
| A2 wild-type# | IN | 9 | 9 | 5.1 | 13 | 5.4 | 1.0 | 1 |
| | IN | 10 | 9 | 6.0 | 8 | 6.0 | 1.7 | 4 |
| | IN + IT | 11 | 13 | 5.3 | 8 | 5.9 | 2.1 | 3 |
| | IN + IT | 12 | 9 | 5.4 | 8 | 5.6 | 1.0 | 3 |
| | | | mean 10 | mean 5.5 | mean 9.3 | mean 5.7 | mean 1.4 | mean 2.8 |

[a]IN intranasal administration only; IN + IT = Both intranasal and intratracheal administration.
[b]Indicates last day post-infection on which virus was recovered.
[c]Mean rhinorrhea score represents the sum of daily scores for a period of eight days surrounding the peak day of virus shedding, divided by eight. Four is the highest score; zero is the lowest score.
[d]Virus isolated only on day indicated.
These are the same animals included in Tables 4 and 7.

TABLE 11

Immunization of chimpanzees with cpts-248/404 induces resistance to RSV A2 wild-type virus challenge on day 28

| Virus used to immunize animal | Chimpanzee number | Virus Recovery | | | | | | Serum neutralizing antibody titer | |
|---|---|---|---|---|---|---|---|---|---|
| | | Nasopharynx | | Tracheal lavage | | Rhinorrhea scores | | [reciprocal $\log_2$] on day indicated[b] | |
| | | Duration [days] | Peak titer [$\log_{10}$pfu/ml] | Duration [days] | Peak titer [$\log_{10}$pfu/ml] | Mean[a] | Peak | Day 28 | Day 49 or 56 |
| cpts-248/404 | 13 | 0 | <0.7 | 0 | <0.7 | 0 | 0 | 7.9 | 9.0 |
| | 14 | 8 | 3.4 | 0 | <0.7 | 0 | 0 | 7.0 | 12.5 |
| | | mean 4.0 | mean 2.0 | mean 0 | mean <0.7 | mean 0 | mean 0 | mean 7.5 | mean 10.8 |

TABLE 11-continued

Immunization of chimpanzees with cpts-248/404 induces resistance to RSV A2 wild-type virus challenge on day 28

| Virus used to immunize animal | Chimpanzee number | Virus Recovery | | | | Rhinorrhea scores | | Serum neutralizing antibody titer [reciprocal $\log_2$] on day indicated[b] | |
|---|---|---|---|---|---|---|---|---|---|
| | | Nasopharynx | | Tracheal lavage | | | | | |
| | | Duration [days] | Peak titer [$\log_{10}$pfu/ml] | Duration [days] | Peak titer [$\log_{10}$pfu/ml] | Mean[a] | Peak | Day 28 | Day 49 or 56 |
| cpts-248# | 1 | 5 | 2.7 | 0 | <0.7 | 0 | 0 | 11.5 | 13.0 |
| | 2 | 9 | 1.8 | 0 | <0.7 | 0 | 0 | 12.7 | 14.5 |
| | | mean 7.0 | mean 2.3 | mean 0 | mean <0.7 | mean 0 | mean 0 | mean 12.1 | mean 13.8 |
| cp-RSV# | 5 | 5 | 1.0 | 0 | <0.7 | 0 | 0 | 12.2 | 11.1 |
| | 6 | 8 | 0.7 | 0 | <0.7 | 0 | 0 | 11.9 | 9.9 |
| | | mean 6.5 | mean 0.9 | mean 0 | mean 0.7 | mean 0 | mean 0 | mean 12.1 | mean 10.5 |
| None | 9 | 9 | 5.1 | 13 | 5.4 | 1.0 | 1 | <3.3 | 11.0 |
| | 10 | 9 | 6.0 | 8 | 6.0 | 1.7 | 4 | <3.3 | 9.8 |
| | 11 | 13 | 5.3 | 8 | 5.9 | 2.1 | 3 | <3.3 | 9.4 |
| | 12 | 9 | 5.4 | 8 | 5.6 | 1.0 | 3 | <3.3 | 14.5 |
| | | mean 10 | mean 5.5 | mean 9.2 | mean 5.7 | mean 1.4 | mean 2.8 | mean <3.3 | mean 11.2 |

[a]Mean rhinorrhea score represents the sum of scores during the eight days of peak virus shedding divided by eight. Four is the highest score. A score of zero indicates no rhinorrhea detected on any day of the ten-day observation period.
These are the same animals included in Tables 4, 7 and 10.
[b]Serum neutralizing titers in this table, including those from animals previously described, were determined simultaneously in one assay.

TABLE 12

The efficiency of plaque formation and replication of Balb/c mice of five small-plaque derivatives of RSV cpts-248/404.

Efficiency of plaque formation tested in HEp-2 cells at permissive and restrictive temperatures

| Virus | The titer of virus [$\log_{10}$pfu/ml] at the indicated temperature [° C.] | | | | | | | Shut-off temp [° C.][1] | Small-plaques at 32° C. | Replication in Balb/c mice[2] | |
|---|---|---|---|---|---|---|---|---|---|---|---|
| | 32 | 35 | 36 | 37 | 38 | 39 | 40 | | | Nasal turbinates[3] | Lungs[3] |
| A2 wild-type | 6.0 | 6.1 | 6.0 | 5.8 | 5.9 | 5.4 | 5.4 | >40 | no | 4.5 ± 0.34 | 5.6 ± 0.13 |
| cp-RSV | 6.2 | 6.2 | 6.0 | 5.9 | 5.6 | 5.4 | 5.4 | >40 | no | 4.5 ± 0.10 | 5.3 ± 0.20 |
| cpts-248 | 7.5 | 7.3 | 6.2** | 5.3** | <0.7 | <0.7 | <0.7 | 37 | no | 3.3 ± 0.35 | 4.8 ± 0.14 |
| 248/404 | 5.5 | 3.6** | <0.7 | <0.7 | <0.7 | <0.7 | <0.7 | 36 | no | 2.4 ± 0.24 | 2.6 ± 0.31 |
| 248/404/774 | 2.9* | <0.7 | <0.7 | <0.7 | <0.7 | <0.7 | <0.7 | ≦35 | yes | <2.0 | 1.8 ± 0.24 |
| 248/404/832 | 5.5** | <0.7 | <0.7 | <0.7 | <0.7 | <0.7 | <0.7 | ≦35 | yes | <2.0 | <1.7 |
| 248/404/886 | 5.0** | <0.7 | <0.7 | <0.7 | <0.7 | <0.7 | <0.7 | ≦35 | yes | <2.0 | <1.7 |
| 248/404/893 | 5.4** | <0.7 | <0.7 | <0.7 | <0.7 | <0.7 | <0.7 | ≦35 | yes | <2.0 | <1.7 |
| 248/404/1030 | 4.4* | 2.2** | <0.7 | <0.7 | <0.7 | <0.7 | <0.7 | 35 | yes | <2.0 | <1.7 |

[1]Shut-off temperature is defined as the lowest restrictive temperature at which at 100-fold or greater reduction of plaque titer is observed (bold figures in table).
[2]Mice were administered $10^{6.3}$ p.f.u. intranasally under light anesthesia on day 0, then sacrificed by $CO_2$ asphyxiation on day 4 when tissues were harvested for virus titer.
[3]Mean $\log_{10}$pfu/g tissue of six animals ± standard error.
*Small-plaque phenotype (<50% wild-type plaque size).
**Pinpoint-plaque phenotype (<10% wild-type plaque size).

TABLE 13

The efficiency of plaque formation and level of replication in mice of 14 mutants derived from RSV cpts530, compared with controls

| RSV | In vitro efficiency of plaque formation The titer of virus ($\log_{10}$pfu/ml) at the indicated temperature (° C.) | | | | | | | | Shut-off Temp. (° C.)[1] | Replication in mice[2] (mean $\log_{10}$pfu/g tissue of six animals ± SE) | |
|---|---|---|---|---|---|---|---|---|---|---|---|
| | 32 | 34 | 35 | 36 | 37 | 38 | 39 | 40 | | Nasal turbinates | Lungs |
| A2 | 6.3 | 6.3 | 6.1 | 6.2 | 6.3 | 6.3 | 6.1 | 5.6 | >40 | 5.0 ± 0.14 | 5.8 ± 0.05 |
| cpRSV | 6.5 | 6.2 | 6.2 | 6.2 | 6.1 | 6.0 | 6.1 | 5.6 | >40 | n.d. | n.d |
| cpts248 | 6.3 | 6.3 | 6.3 | 6.3 | 3.7** | <0.7 | <0.7 | <0.7 | 37/38 | 4.1 ± 0.08 | 5.1 ± 0.13 |
| 248/404 | 6.3 | 5.7* | 4.3** | <0.7 | <0.7 | <0.7 | <0.7 | <0.7 | 35/36 | 2.1 ± 0.19 | 3.6 ± 0.10 |
| cpts530 | 6.2 | 6.3 | 6.2 | 6.1 | 6.2* | 5.5** | <0.7 | <0.7 | 39 | 3.4 ± 0.09 | 4.3 ± 0.14 |
| 530/346 | 5.9 | 5.9 | 5.7 | 4.7 | 3.5 | <0.7 | <0.7 | <0.7 | 37 | 3.3 ± 0.11 | 4.7 ± 0.09 |
| 530/977 | 5.0 | 4.4 | 3.6 | 3.4 | 2.8* | <0.7 | <0.7 | <0.7 | 37 | 3.4 ± 0.11 | 2.7 ± 0.05 |

TABLE 13-continued

The efficiency of plaque formation and level of replication in mice of 14 mutants derived from RSV cpts530, compared with controls

| RSV | In vitro efficiency of plaque formation. The titer of virus ($log_{10}$pfu/ml) at the indicated temperature (° C.) | | | | | | | | Shut-off Temp. (° C.)[1] | Replication in mice[2] (mean $log_{10}$pfu/g tissue of six animals ± SE) | |
|---|---|---|---|---|---|---|---|---|---|---|---|
| | 32 | 34 | 35 | 36 | 37 | 38 | 39 | 40 | | Nasal turbinates | Lungs |
| 530/9 | 6.0 | 5.6 | 5.0 | 3.5* | 3.5* | <0.7 | <0.7 | <0.7 | 36 | 2.1 ± 0.06 | 3.5 ± 0.08 |
| 530/1009 | 4.8 | 4.0 | 3.7* | 2.0** | 1.5** | <0.7 | <0.7 | <0.7 | 36 | 2.2 ± 0.15 | 3.5 ± 0.13 |
| 530/667 | 5.5 | 4.9 | 4.5* | 2.0** | 0.7 | <0.7 | <0.7 | <0.7 | 36 | 2.4 ± 0.12 | 2.9 ± 0.15 |
| 530/1178 | 5.7 | 4.0 | 5.5 | 3.7** | 2.0** | <0.7 | <0.7 | <0.7 | 36 | 3.3 ± 0.06 | 42 ± 0.11 |
| 530/464 | 6.0 | 5.0* | 4.7* | 1.8** | <0.7 | <0.7 | <0.7 | <0.7 | 36 | <2.0 | 2.6 ± 0.10 |
| 530/403 | 5.7 | 5.1 | 4.3 | 2.9 | <0.7 | <0.7 | <0.7 | <0.7 | 36 | <2.0 | <1.7 |
| 530/1074 | 5.1 | 4.6 | 4.1* | <0.7 | <0.7 | <0.7 | <0.7 | <0.7 | 36 | 3.0 ± 0.13 | 3.8 ± 0.13 |
| 530/963 | 5.3 | 5.0 | 4.2* | 0.7 | <0.7 | <0.7 | <0.7 | <0.7 | 36 | 2.0 ± 0.05 | <1.7 |
| 530/653 | 5.4 | 5.1 | 4.5 | <0.7 | <0.7 | <0.7 | <0.7 | <0.7 | 36 | 2.2 ± 0.10 | 3.1 ± 0.16 |
| 530/1003 | 5.6 | 4.1 | 2.5 | 2.1** | <0.7 | <0.7 | <0.7 | <0.7 | 35 | <2.0 | <1.7 |
| 530/1030 | 4.3 | 3.7* | 1.7** | <0.7 | <0.7 | <0.7 | <0.7 | <0.7 | 35 | <2.0 | 1.8 ± 0.13 |
| 530/188 | 5.0* | 1.0* | 1.0 | <0.7 | <0.7 | <0.7 | <0.7 | <0.7 | ≧34 | <2.0 | <1.7 | n.d. = not done
*Small-plaque phenotype (<50% wild-type plaque size)
**Pinpoint-plaque phenotype (<10% wild-type plaque size)
[1]Shut-off temperature is defined as the lowest restrictive temperature at which a 100-fold or greater reduction of plaque titer is observed (bold figures in table).
[2]Mice were administered $10^{6.3}$ p.f.u. intranasally under light anesthesia on day 0, then sacrificed by $CO_2$ asphyxiation on day 4.

TABLE 14

Replication of cpts-530/1009, cp-RSV, or wild-type RSV A2 in the upper and lower respiratory tract of seronegative chimpanzees induces serum neutralizing antibodies.

| Animals infected with $10^4$ pfu of indicated virus | Route of inoculation | Chimpanzee Number | Virus Replication | | | | Rhinorrhea | | Day 28 reciprocal serum neutralizing antibody titer[g] |
|---|---|---|---|---|---|---|---|---|---|
| | | | Nasopharynx | | Trachea | | | | |
| | | | Duration[b] [days] | Peak Titer [$log_{10}$pfu/ml] | Duration[b] [days] | Peak Titer [$log_{10}$pfu/ml] | Scores Mean[c] | Peak | |
| cpts-530/1009 | IN + IT | 1 | 9 | 3.1 | 0 | <1.0 | 0.5 | 2 | 1,097 |
| | IN + IT | 2 | 10 | 4.0 | 10[a] | 1.8 | 0.5 | 2 | 416 |
| | IN + IT | 3 | 9 | 4.0 | 0 | <1.0 | 0.8 | 2 | 1,552 |
| | IN + IT | 4 | 9 | 3.3 | 0 | <1.0 | 0.4 | 1 | 1,176 |
| | | | mean 9.3 | mean 3.6 | mean 2.5 | mean 1.2 | mean 0.5 | mean 1.3 | mean 1,060 |
| cpts-530 | IN + IT | 5 | 9 | 3.5 | 4[e] | 2.6 | 0.3 | 1 | 10,085 |
| | IN + IT | 6 | 9 | 5.2 | 0 | <1.0 | 1.1 | 3 | 3,566 |
| | IN + IT | 7 | 8 | 3.3 | 0 | <1.0 | 0.6 | 2 | 588 |
| | IN + IT | 8 | 8 | 4.4 | 0 | <1.0 | 0.5 | 2 | 1,911 |
| | | | mean 8.5 | mean 4.1 | mean 1.0 | mean 1.4 | mean 0.6 | mean 2.0 | mean 4,038 |
| cp-RSV | IN | 9[d] | 20 | 5.3 | 8[e] | 2.9 | 1.0 | 3 | 416 |
| | IN | 10[d] | 16 | 5.8 | 6[e] | 3.0 | 1.8 | 3 | 2,048 |
| | IN + IT | 11[d] | 13 | 4.3 | 6[e] | 3.0 | 0.6 | 1 | 776 |
| | IN + IT | 12[d] | 16 | 5.0 | 10[e] | 2.8 | 0.5 | 1 | 891 |
| | | | mean 16 | mean 5.1 | mean 7.5 | mean 2.9 | mean 1.0 | mean 2.0 | mean 1,033 |
| A2 wild-type | IN | 13[f] | 9 | 5.1 | 13 | 5.4 | 1.0 | 1 | 1,351 |
| | IN | 14[f] | 9 | 6.0 | 8 | 6.0 | 1.7 | 4 | 676 |
| | IN + IT | 15[d] | 13 | 5.3 | 8 | 5.9 | 2.1 | 3 | 1,261 |
| | IN + IT | 16[d] | 9 | 5.4 | 8 | 5.6 | 1.0 | 3 | 20,171 |
| | | | mean 10 | mean 5.5 | mean 9.3 | mean 5.7 | mean 1.4 | mean 2.8 | mean 5,865 |

[a]IN = Intranasal only; IN + IT = Both intranasal and intratracheal administration.
[b]Indicates last day post-infection on which virus was recovered.
[c]Mean rhinorrhea score represents the sum of daily scores for a period of eight days surrounding the peak day of virus shedding, divided by eight. Four is the highest score; zero is the lowest score.
[d]Animals from Crowe, et al. Vaccine 12: 691-699 [1994].
[e]Virus isolated only on day indicated.
[f]Animals from Collins, et al. Vaccine 8: 164-168 [1990].
[g]Determined by complement-enhanced 60% plaque reduction of RSV A2 in HEp-2 cell monolayer cultures. All titers were determined simultaneously in a single assay. The reciprocal titer of each animal on day 0 was < 10.

TABLE 15

Immunization of chimpanzees with cpts-530/1009 or cpts-530 induces
resistance to wild-type RSV A2 virus challenge on day 28

| Virus used for immunization | Chimpanzee number | Virus replication | | | | Rhinorrhea scores | | Serum neutralizing antibody [reciprocal log$_2$] on day indicated[d] | |
|---|---|---|---|---|---|---|---|---|---|
| | | Nasopharynx | | Tracheal lavage | | | | | |
| | | Duration [days] | Peak titer [log$_{10}$pfu/ml] | Duration [days] | Peak titer [log$_{10}$pfu/ml] | Mean[a] | Peak | Day 28 | Day 49 or 56 |
| cpts-530/1009 | 3 | 7 | 2.1 | 0 | <0.7 | 0 | 0 | 1,552 | 3,823 |
| | 4 | 0 | <0.7 | 0 | <0.7 | 0 | 0 | 1,176 | 1,911 |
| cpts-530 | 5 | 0 | <0.7 | 0 | <0.7 | 0 | 0 | 10,085 | 6,654 |
| | 6 | 0 | <0.7 | 0 | <0.7 | 0.3 | 2 | 3,566 | 1,911 |
| cp-RSV | 11[b] | 5 | 1.0 | 0 | <0.7 | 0 | 0 | 776 | 2,048 |
| | 12[b] | 8 | 0.7 | 0 | <0.7 | 0 | 0 | 891 | 1,783 |
| None | 13[b] | 9 | 5.1 | 13 | 5.4 | 1.0 | 1 | <10 | 1,351 |
| | 14[b] | 9 | 6.0 | 8 | 6.0 | 1.7 | 4 | <10 | 676 |
| | 15[c] | 13 | 5.3 | 8 | 5.9 | 2.1 | 3 | <10 | 1,261 |
| | 16[c] | 9 | 5.4 | 8 | 5.6 | 1.0 | 3 | <10 | 20,171 |

[a]Mean rhinorrhea scores represent the sum of scores during the eight days of peak virus shedding divided by eight. Four is the highest score.
[b]Animals from Crowe et al. Vaccine 12:691-699 [1994].
[c]Animals from Collins et al. Vaccine 8:164-168 [1990].
[d]Serum neutralizing titers in this table, including those from animals previously described, were determined simultaneously in one assay.

Effect of Passively-Acquired Serum RSV Antibodies
on cpts Mutants in Chimpanzees In order to examine the effect of passively-acquired serum RSV antibodies on attenuation, immunogenicity and protective efficacy of various cpts mutants of the invention in chimpanzees, the in vivo replication of cpts248, cpts248/404, and cpts530/1009, was evaluated in seronegative chimpanzees which were infused with RSV immune globulin two days prior to immunization (Table 16). Antibody was passively transferred in order to simulate the conditions which obtain in young infants who possess maternally-derived RSV antibodies. In this way, it was possible to assess the immunogenicity of each indicated mutant in the presence of passive RSV antibodies to determine whether the replication of highly attenuated viruses might be so reduced in infants with a moderate to high titer of passive antibodies as to preclude the induction of a protective immune response. It would also be possible to define the nature of the antibody response to immunization in the presence of passively acquired antibodies, and to define the extent and functional activity of the antibody response to virus challenge. The level of virus replication in the nasopharynx and the associated clinical score for the attenuated mutants was either not altered or only moderately altered by the presence of serum RSV antibodies when the infection of those animals was compared to that of non-infused seronegative chimpanzees. In contrast, the presence of passively-acquired antibodies effectively prevented virus replication of cpts248 in the lower respiratory tract. Because the other two mutants were already highly restricted in the lungs, the similar effect of passive antibodies could not be evaluated against those mutants.

Infusion of human RSV immune globulin yielded moderately high serum levels of RSV F antibodies (titer 1:640 to 1:1600), and neutralizing antibodies (titer 1:199 to 1:252), but not appreciable amounts of serum RSV G antibody detectable above background (Table 17). Chimpanzees who were infused with human RSV antibodies prior to immunization with cpts248/404, cpts530/1009, or cpts248 developed only one-tenth the quantity of RSV F antibodies and about one-half the titer of neutralizing antibodies by day 42 post-immunization, compared to non-infused immunized animals tested 28 days post-immunization. Because the infused human IgG contained substantial amounts of RSV F and RSV neutralizing antibodies, the residual antibodies from the infusion present in the 42-day serum samples could not be distinguished from antibodies produced de novo in response to immunization. Given the half-life of human serum IgG antibodies in chimpanzees (Prince et al., *Proc. Natl. Acad. Sci. USA* 85:6944-6948), the observed levels of F and neutralizing antibodies on day 42 following immunization with cpts are higher than would be predicted for a residuum of the infusion. In addition, the RSV G antibody response following immunization of the infused animals confirms that these chimpanzees mounted an immune response to immunization.

Four to six weeks following immunization the chimpanzees were challenged with wild-type RSV. Each of the animals exhibited complete resistance in their lower respiratory tract, whether or not human IgG was infused two days before immunization (Table 18). Non-infused animals developed a modest neutralizing antibody response to challenge or none at all (Table 17). In contrast, the infused chimpanzees uniformly developed an unusually high titer of RSV neutralizing antibodies in response to wild-type virus challenge despite the fact that virus replication had been severely restricted (Tables 17 and 18). Moreover, following immunization in the presence of antibodies the most attenuated virus, cpts248/404, which exhibited the lowest level of virus replication and immunization, had the highest post-challenge neutralizing antibody titers (Table 17). In contrast, the least attenuated virus, cpts248, had the lowest post-challenge neutralizing antibody titer of the three groups of infused animals. In addition to an increase in the quantity of the antibodies induced by immunization in the presence of antibodies, the quality of the antibodies, as measured by the neutralizing to ELISA F antibody titer ratio, was significantly greater than that induced by immunization in seronegative animals (Table 17). The neutralizing/ELISA F ratio of the antibodies produced in the infused immunized animals post-challenge was about 10- to 20-fold higher than in the non-infused animals and was consistent in all groups, regardless of mutant used to immunize (Table 17).

The presence of passively-acquired antibodies at the time of immunization with a live virus vaccine might alter the immune response to vaccine in three distinct ways. First, a significant decrease in the level of replication of vaccine virus might occur that results in decreased immunogenicity. It is possible that the passively-transferred RSV antibodies could restrict the replication of the vaccine viruses, especially the most defective mutants, and greatly decrease their immunogenicity. The results presented herein indicate that replication of the least attenuated mutant (cpts248) in the lower respiratory tract was indeed abrogated by the presence of passively-acquired serum IgG RSV antibodies, whereas replication in the upper respiratory tract did not appear to be significantly affected. The replication of the least attenuated mutant tested, cpts248, was ≧200-fold more (i.e. completely) restricted in the lower respiratory tract in the presence of antibodies. The level of replication of the more attenuated mutants, cpts530/1009 and cpts248/404, in the lower respiratory tract was highly restricted even in the seronegative animals. Therefore, a significant effect of passive antibodies on virus replication could not be detected. Immunization with each of the three attenuated mutants induced a high degree of protection against wild-type challenge in both the upper and lower respiratory tracts, whether or not passively-acquired RSV antibodies were present at the time of immunization. Thus, the level of replication of the vaccine viruses in the upper respiratory tract of passively-immunized chimpanzees was sufficient to induce a high level of resistance to wild-virus challenge which was comparable to that induced in non-infused animals.

Second, passive antibodies can alter the immune response to infection by causing a decrease in the amount and functional activity of antibodies that are induced. For this reason the magnitude and the character of the antibody response to live virus immunization in the presence of passive antibodies was analyzed. Postimmunization serum ELISA IgG F antibody titers of immunized, infused animals were 10-fold lower than the postimmunization F titers of non-infused seronegative animals. The serum RSV neutralizing antibody response was also slightly decreased in those animals, on average being 2-fold lower than in non-infused animals. Because some of the ELISA F and neutralizing antibodies detected postimmunization represent residual antibodies from the infusion, the actual decrease of the neutralizing and F antibody response caused by preexisting antibodies is probably even more significant than is apparent. Moreover, the human immune globulin preparation used contained a low level of antibodies to the G glycoprotein of RSV (Table 17). This petted an examination of the IgG RSV G glycoprotein antibody response of the chimpanzees to infection with the candidate vaccine viruses. The G antibody responses demonstrated at least a 4-fold or greater increase, indicating that each of the passively-immunized animals was infected by vaccine virus, including chimpanzees immunized with cpts248/404 which did not shed virus. The magnitude of the G antibody response to immunization did not appear to be adversely influenced by the passively transferred antibodies.

Thirdly, the antibody response to RSV wild-type virus challenge of animals immunized in the presence of passively-acquired antibodies could be altered. Chimpanzees immunized in the absence of infused antibodies exhibited significant resistance to subsequent RSV challenge. In addition, these animals failed to develop an appreciable antibody response to challenge virus. Although each of the 6 infused, immunized animals also exhibited significant resistance to RSV, a greatly enhanced antibody response to challenge was observed. Post-challenge F or G antibody levels in the treated animals immunized with cpts530/1009 or cpts248/404 were increased at least 10-fold, while the neutralizing antibody response represented as much as an 800-fold increase. These results suggest that repeated immunization of infants possessing maternal antibodies with live attenuated mutants beginning very early in life might stimulate effective resistance and an associated enhanced secondary antibody response of high quality. The mechanism responsible for an enhanced immune response to second infection in the absence of appreciable replication of the challenge virus is not understood. The presence of serum antibodies at the time of immunization, while allowing a modest antibody response to immunization in infused animals, favors the development of a B cell repertoire that elaborates antibodies of highly functional activity following subsequent RSV challenge.

The results reported herein are highly significant in that for the first time live attenuated RSV virus vaccine has been shown to be efficacious in an animal model which mimics the target population for an RSV vaccine, i.e. the four to six week old infant having passively acquired RSV neutralizing antibodies as a result of transplacental transfer from the mother. The importance of this finding is clear from the fact that, as discussed, supra, the high expectation that the passively transferred RSV antibodies would have inhibited the replication of the cpts vaccine, rendering it non-immunogenic and non-protective has, surprisingly, not been borne out.

TABLE 16

Replication of RSV cpts-248/404, cpts-248, or cpts-530/1009 in the upper and lower respiratory tract of seronegative chimpanzees, some of which were infused with RSV neutralizing antibodies two days prior to immunization.

| Animal infected within $10^4$ pfu of indicated virus | Reciprocal serum RSV neutralizing antibody titer at time of immunization | Chimpanzee Number | Virus Replication | | | | Rhinorrhea Scores | |
|---|---|---|---|---|---|---|---|---|
| | | | Nasopharynx | | Trachea | | | |
| | | | Duration [days] | Peak Titer [$\log_{10}$pfu/ml] | Duration [days] | Peak Titer [$\log_{10}$pfu/ml] | Peak | Mean |
| cpts-248/404 | <10 | 17 | 0 | <0.7 | 0 | <0.7 | 0 | 0 |
| | <10 | 20 | 9 | <0.7 | 0 | <0.7 | 0 | 0 |
| | <10 | 19 | 8 | 1.9 | 0 | <0.7 | 2 | 0.3 |
| | <10 | 20 | 9 | 2.0 | 0 | <0.7 | 1 | 0.2 |
| | | | [mean 4.3] | [mean 1.3] | [mean 0] | [mean <0.7] | [mean 0.8] | [mean 0.1] |

TABLE 16-continued

Replication of RSV cpts-248/404, cpts-248, or cpts-530/1009 in the upper and lower respiratory tract of seronegative chimpanzees, some of which were infused with RSV neutralizing antibodies two days prior to immunization.

| Animal infected within $10^4$ pfu of indicated virus | Reciprocal serum RSV neutralizing antibody titer at time of immunization | Chimpanzee Number | Virus Replication Nasopharynx Duration [days] | Nasopharynx Peak Titer [$\log_{10}$pfu/ml] | Trachea Duration [days] | Trachea Peak Titer [$\log_{10}$pfu/ml] | Rhinorrhea Scores Peak | Mean |
|---|---|---|---|---|---|---|---|---|
|  | 142 | 21 | 0 | <0.7 | 0 | <0.7 | 2 | 0.6 |
|  | 156 | 22 | 0 | <0.7 | 0 | <0.7 | 1 | 0.1 |
|  |  |  | [mean 0] | [mean <0.7] | [mean 0] | [mean <0.7] | [mean 1.5] | [mean 0.4] |
| cpts-530/1009 | <10 | 1 | 9 | 3.1 | 0 | <1.0 | 1 | 0.3 |
|  | <10 | 2 | 10 | 4.0 | 10 | 1.8 | 1 | 1.1 |
|  | <10 | 3 | 9 | 4.0 | 0 | <1.0 | 1 | 0.6 |
|  | <10 | 4 | 9 | 3.3 | 0 | <1.0 | 1 | 0.5 |
|  |  |  | [mean 9.3] | [mean 3.6] | [mean 2.5] | [mean 1.2] | [mean 1.0] | [mean 0.6] |
|  | 259 | 23 | 8 | 3.0 | 0 | <0.7 | 1 | 0.1 |
|  | 190 | 24 | 7 | 1.2 | 0 | <0.7 | 1 | 0.2 |
|  |  |  | [mean 7.5] | [mean 2.1] | [mean 0] | [mean <0.7] | [mean 1.0] | [mean 0.2] |
| cpts-248 | <10 | 25 | 10 | 4.6 | 8 | 5.4 | 1 | 0.2 |
|  | <10 | 26 | 10 | 4.5 | 6 | 2.2 | 1 | 0.1 |
|  | <10 | 27 | 9 | 4.7 | 10 | 2.1 | 1 | 0.1 |
|  | <10 | 28 | 9 | 4.2 | 8 | 2.2 | 1 | 0.1 |
|  |  |  | [mean 9.5] | [mean 4.5] | [mean 8.0] | [mean 3.0] | [mean 1.0] | [mean 0.1] |
|  | 290 | 29 | 13 | 4.2 | 0 | <0.7 | 2 | 0.4 |
|  | 213 | 30 | 16 | 4.7 | 0 | <0.7 | 3 | 0.9 |
|  |  |  | [mean 14.5] | [mean 4.5] | [mean 0] | [mean <0.7] | [mean 2.5] | [mean 0.7] |

TABLE 17

Serum antibody response of chimpanzees immunized on day 0 with RSV cpts-248/404, cpts-248, or cpts-530/1009, in the presence or absence of passively-transferred antibodies, and challenged 4 to 6 weeks later with wild-type RSV A2.

| Animals infected with indicated virus | No. of animals | Infused with antibodies | RSV F Prior to study | RSV F Day 0 (48 hrs. after infusion of antibodies) | RSV F Post immunization[1] | RSV F 28 days post-challenge[2] | RSV G Prior to study | RSV G Day 0 (48 hrs. after infusion of antibodies) | RSV G Post immunization[1] | RSV G 28 days post-challenge[2] | Neutralizing[3] Prior to study | Neutralizing[3] Day 0 (48 hrs. after infusion of antibodies) | Neutralizing[3] Post immunization[1] | Neutralizing[3] 28 days post-challenge[2] | F | G |
|---|---|---|---|---|---|---|---|---|---|---|---|---|---|---|---|---|
| cpts-248/404 | 4 | no | <40 | <40 | 6,400 | 2,560 | 60 | 60 | 1,000 | 1,600 | <10 | <10 | 208 | 362 | 0.2 | 0.1 |
|  | 2 | yes | <40 | 1,600 | 640 | 25,600 | 100 | 100 | 1,600 | 21,760 | <10 | 199 | 111 | 92,681 | 4.3 | 3.6 |
| cpts-530/1009 | 4 | no | <40 | <40 | 6,400 | 10,240 | <40 | <40 | 10,240 | 2,560 | <10 | <10 | 256 | 2,521 | 1.0 | 0.3 |
|  | 2 | yes | <40 | 1,600 | 640 | 10,240 | 40 | 100 | 400 | 10,240 | <10 | 225 | 52 | 37,641 | 3.7 | 3.7 |
| cpts-248 | 4 | no | <40 | <40 | 7,840 | 6,400 | <40 | <40 | 250 | 2,560 | <10 | <10 | 147 | 338 | 0.1 | 0.1 |
|  | 2 | yes | <40 | 640 | 1,600 | 5,400 | 40 | 40 | 1,600 | 5,440 | <10 | 252 | 119 | 26,616 | 4.9 | 4.9 |

[1]The day on which postimmunization titer was determined was also the day on which challenge was performed, i.e., day 28 for animals not infused with antibody, day 42 for animals infused.
[2]Values determined from samples taken 28 days after challenge. Challenge performed on day 28 postimmunization for animals not infused with antibody, day 42 for animals infused.
[3]Determined by complement-enhanced 60% plaque reduction of RSV A2 in HEp-2 cell monolayer cultures. Neutralizing antibody titer represents the mean value from two tests.

TABLE 18

Immunization of chimpanzees with RSV cpts-248, cpts-248/404, or cpts-530/1009 cpts-530/1009 induces resistance to wild-type RSV A2 challenge 4-6 weeks later.

| Virus used for immunization | Passively-transferred RSV antibodies present | Chimpanzee Number | Replication of RSV A2 challenge virus[a] | | | | Rhinorrhea Scores | |
|---|---|---|---|---|---|---|---|---|
| | | | Nasopharynx | | Trachea | | | |
| | | | Duration [days] | Peak Titer [log₁₀pfu/ml] | Duration [days] | Peak Titer [log₁₀pfu/ml] | Mean[b] | Peak |
| cpts-248/404 | no | 17[c] | 0 | <0.7 | 0 | <0.7 | 0 | 0 |
| | no | 18[c] | 8 | 3.4 | 0 | <0.7 | 0 | 0 |
| | yes | 21 | 6 | 2.7 | 0 | <0.7 | 0.5 | 2 |
| | yes | 22 | 0 | <0.7 | 0 | <0.7 | 0 | 0 |
| cpts-530/1009 | no | 1 | 7 | 2.1 | 0 | <0.7 | 0 | 0 |
| | no | 2 | 0 | <0.7 | 0 | <0.7 | 0 | 0 |
| | yes | 23 | 6 | 2.5 | 0 | <0.7 | 0.5 | 1 |
| | yes | 24 | 7 | 2.0 | 0 | <0.7 | 0.2 | 1 |
| cpts-248 | no | 25[c] | 5 | 2.7 | 0 | <0.7 | 0 | 0 |
| | no | 26[c] | 9 | 1.8 | 0 | <0.7 | 0 | 0 |
| | yes | 29 | 0 | <0.7 | 0 | <0.7 | 0 | 0 |
| | yes | 30 | 6 | 2.4 | 0 | <0.7 | 1.2 | 3 |
| none | no | 13[d] | 9 | 5.1 | 13 | 5.4 | 1.0 | 1 |
| | no | 14[d] | 9 | 6.0 | 8 | 6.0 | 1.7 | 4 |
| | no | 15[c] | 13 | 5.3 | 8 | 5.9 | 2.1 | 3 |
| | no | 16[c] | 9 | 5.4 | 8 | 5.6 | 1.0 | 3 |

[a]Animals which were immunized with indicated virus 4 to 6 weeks prior were challenged with 10⁴ pfu of RSV A2 wild-type virus.
[b]Mean rhinorrhea scores represent the sum of scores during the eight days of peak virus shedding divided by eight
[c]Animals from Crowe, et al., Vaccine 12:691-699 [1994].
[d]Animals from Collins, et al., Vaccine 8:164-168 [1990].

EXAMPLE II

Use of Cold Adaptation to Attenuate cpRSV Mutants

This Example describes the introduction of growth restriction mutations into incompletely attenuated host range-restricted cpRSV strains by further passage of the strains at increasingly reduced temperatures to produce derivative strains which are more satisfactorily attenuated for use in human vaccines.

These cold-adaptation (ca) approaches were used to introduce further attenuation into the cpRSV 3131 virus, which is incompletely attenuated in seronegative children.

Under the first strategy, a parent stock of cold-passaged RSV A2 (cpRSV 3131) obtained from Flow Laboratories was prepared by passage in MRC-5 cells at 25° C. as described in Example 1. Briefly, cold-passaged virus was inoculated into MRC-5 or Vero cell monolayer culture at a multiplicity of infection of ≧0.01 and the infected cells were incubated for 3 to 14 days before subsequent passage. Virus was passaged over 20 times at 20-22° C. to derive more attenuated virus. The technique of rapid passage, as soon as the first evidence of virus replication is evident (i.e., 3 to 5 days), was preferable for selection of mutants able to replicate efficiently at low temperatures. Additionally, an RSV subgroup B strain, St. Louis/14617/85 clone 1A1, was isolated in primary African Green monkey kidney cells, passaged and cloned in MRC cells (1A1-MRC14), and cold-passaged 52 times in MRC-5 or Vero cells at 32 to 22° C.

A second strategy employed a biologically cloned derivative of the uncloned parental cpRSV 3131 virus. This virus was biologically cloned in bovine embryonic kidney (BEK) cells [the tissue used to originally derive the cpRSV 3131 virus—see Friedewald et al., *J. Amer. Med. Assoc.* 204:690-694 (1968)]. This cloned virus was then passaged at 10 day intervals in Vero cells at low temperature. Alternatively, the cpRSV 3131 virus was cloned by two serial terminal dilutions (TD2P4) in MRC-5 cells and passaged at 10-day intervals in MRC-5 or Vero cells.

The third strategy involved selection of mutants that produce large plaques at low temperature. An RSV 3131 derivative virus designated plaque D1 that produces large plaques at 25° C. has been identified. This virus was derived from the third passage (P3) level of the cp3131-1 (BEK) lineage cp3131-17 (BEK) lineage. The largest plaque produced by P3 virus was amplified at 32° C., then re-plaqued at 25° C. Once again the largest plaque was selected, amplified, and re-plaqued. After five such cycles, large placque mutant virus D1 was obtained. D1 was biologically cloned by two additional cycles of plaque-to-plaque purification at 25° C.

Biologically cloned virus D1 produces distinctly and uniformly larger plaques at 25° C. than cp3131 or wild-type virus A2. Thus D1 is cold adapted by the criterion of large plaque size at 25° C. Efficiency of plaque formation studies demonstrated that D1 is not temperature sensitive. At 37° C., D1 plaques are indistinguishable from those of wild-type RSV or cp3131, suggesting that D1 is not restricted in growth at this temperature. Consistent with this, D1 produces extensive cytopathic effects in Vero cell monolayers at 37° C. and 40° C. (i.e. the highest temperatures tested).

EXAMPLE III

Introduction of Further Attenuating Mutations Into ts-RSV

This Example describes the use of ts mutants as parental viruses to produce more completely attenuated strains. Two RSV A2 ts mutants were selected for this process, namely ts-4 and ts-1 NG1. Two distinct methods were chosen to introduce additional mutations into the RSV ts mutants. First, the incompletely attenuated RSV ts mutant was subjected to chemical mutagenesis, and mutagenized progeny that are more temperature-sensitive with regard to plaque formation were selected for further analysis. Second, the RSV ts mutants were passaged at low temperature to select RSV nts mutants with the ca phenotype, i.e., increased capacity to replicate at suboptimal temperature compared to wild-type parental virus.

A parent stock of ts-1 NG1 virus was prepared from Flow Laboratories Lot M4 of live Respiratory Syncytial Virus (A-2) ts-1 NG-1 mutant, MRC-5 grown virus. This mutant, derived from the ts-1 mutant by a second round of mutagenesis using nitrosoguanidine, possesses two or more independent ts mutations, but still induces substantial rhinorrhea in susceptible chimpanzees. This virus was passaged twice in Vero cells at 32° C. to create a ts-1 NG-1 suspension for mutagenesis. The virus was then grown in the presence of $4 \times 10^{-4}$M 5-fluorouracil to induce additional mutations during replication or was exposed to 5-azacytidine at 36° C. after 5—fluorouracil treatment. The mutagenized stock was then analyzed by plaque assay on Vero cells that were maintained under an agar overlay, and, after an appropriate interval of incubation, plaques were identified microscopically. 586 plaques were picked, and the progeny of each plaque were separately amplified by growth on fresh monolayers of Vero cells. The contents of each of the tissue cultures inoculated with the progeny of a single plaque of mutagenized ts-1 NG-1 virus were separately harvested when cytopathic effects on the Vero cells appeared maximal. Progeny virus that was more temperature-sensitive than ts-1 NG1 was sought by titering these plaque pools on HEp2 cells at 32° C. and 36° C. Any virus exhibiting greater temperature sensitivity than ts-1 NG1 (i.e., 100-fold or greater reduction in titer at restrictive temperature [36° C.] compared to 32° C.) was evaluated further. Six plaque progeny more ts than the tsRSV ts-1 NG-1 parent virus were identified and these strains were biologically cloned by serial plaque-purification on Vero cells three times, then amplified on Vero cells. The cloned strains were titered at 32° C., 35° C., 36° C., 37° C., and 38° C. (efficiency of plaque formation assay) to confirm their ts phenotype. Efficiency of plaque formation data generated by assay on HEp-2 cells further confirmed the phenotype of the six mutants (Table 19).

The two most ts viruses, A-20-4 and A-37-8, were highly attenuated in mice compared to their ts-1 NG1 parent virus, indicating that acquisition of increased level of temperature sensitivity was accompanied by augmented attenuation (Table 20). These viruses were infectious for mice because they induced an antibody response. The ts-1 NG1/A-20-4 virus is attenuated for chimpanzees (Table 21) and infection of chimpanzees with ts-1 NG1/A-20-4 induced resistance to wild-type virus challenge (Table 22). Significantly, rhinorrhea does not occur.

Mutagenesis of the ts-4 virus was also performed, using the same method as for mutagenesis of ts-1 NG1, virus. Mutations were also introduced into the ts-4 viruses by cold-passage. The ts-4 virus replicates to high titer at 22° C. after 43 cold-passages. Six plaque progeny that were more ts than the RSV ts-4 parent virus were identified (Table 23). The ts-4 cp-43 is even further restricted in replication in Balb/c mice (Table 24).

TABLE 19

Efficacy of plaque formation of ts-1NG1 derivatives

| Virus | Titer ($\log_{10}$pfu/ml) at indicated temperature | | | | |
|---|---|---|---|---|---|
| | 32° | 35° | 36° | 37° | 38° |
| A-204(4-1)[a] | 5.9* | <1 | <1 | <1 | <1 |
| A-37-8(1-2)[a] | 6.3 | 6.3 | <1 | <1 | <1 |
| A-15-7 | 3.5 | ND | 2.1 | 1.5 | <1 |
| A-25-8 | 5.3 | ND | 5.0* | 4.8* | <1 |
| A-21 | 5.1** | ND | 4.8** | 4.5** | <1 |
| Ts1NG1 | 6.6 | 6.6 | 6.5 | 6.6 | <1 |

[a] 3× plaque purified
*Small-plaque phenotype (<50% wild-type plaque size)
**Pinpoint-plaque phenotype (<10% wild-type plaque size)
ND = Not Done

TABLE 20

Replication of ts-1 NG1 parent and progency viruses in Balb/c mice

| Virus | Dose ($\log_{10}$pfu) | Day Post-Infection | Titer in Lung | | Titer in Lung | |
|---|---|---|---|---|---|---|
| | | | 32° | 38° | 32° | 38° |
| A2 wt | 6.1 | 4 | 4.66 ± 0.32[a] | 4.80 ± 0.16 | 3.18 ± 4.0 | 3.29 ± 0.33 |
| | | 5 | 5.18 ± 0.33 | 5.25 ± 0.23 | 3.40 ± 2.0 | 3.47 ± 0.17 |
| Ts1NG1 | 5.8 | 4 | 4.31 ± 0.17 | <2.0 | 2.82 ± 0.25 | <2.0 |
| | | 5 | 3.98 ± 0.12 | <2.0 | 2.74 ± 0.31 | <2.0 |
| Ts1NG1/A-20-4 | 6.1 | 4 | <2.0 | <2.0 | <2.0 | <2.0 |
| | | 5 | <2.0 | <2.0 | <2.0 | <2.0 |
| Ts1NG1/A-37-8 | 6.3 | 4 | <2.0 | <2.0 | <2.0 | <2.0 |
| | | 5 | <2.0 | <2.0 | <2.0 | <2.0 |

[a] Mean $\log_{10}$ pfu/g of indicated tissue ± standard error. 6 animals/group.

TABLE 21

Replication of ts-1 NG1/A-20-4, ts-1 NG1, ts-1 or wild-type RSV A2
in the upper and lower respiratory tract of seronegative chimpanzees

| Animal infected with indicated virus | Route of Inoculation[a] | Chimpanzee number | Virus Replication | | | | Rhinorrhea Scores | |
|---|---|---|---|---|---|---|---|---|
| | | | Nasopharynx | | Trachea | | | |
| | | | Duration[b] [Days] | Peak titer [log$_{10}$pfu/ml] | Duration[b] [Days] | Peak titer [log$_{10}$pfu/ml] | Mean[c] | Peak |
| ts-1NG1/A-20-4 | IN + IT | 15 | 0 | <0.7 | 0 | <0.7 | 0 | 0 |
| | IN + IT | 16 | 0 | <0.7 | 0 | <0.7 | 0 | 0 |
| | IN + IT | 17 | 0 | <0.7 | 0 | <0.7 | 0 | 0 |
| | IN + IT | 18 | 16[d] | 2.7 | 0 | <0.7 | 0 | 0 |
| | | | mean 4.0 | mean 1.2 | mean 0 | mean <0.7 | mean 0 | mean 0 |
| ts-1 NG1 | IN | 19[e] | 8 | 4.2 | 0 | <1.1 | 0.6 | 1 |
| | IN | 20[e] | 7 | 3.9 | 0 | <1.1 | 0.7 | 1 |
| | IN | 21[e] | 13 | 5.4 | 0 | <1.1 | 0.4 | 1 |
| | IN | 22[e] | 10 | 5.2 | 10d | 3.7[d] | 0.6 | 2 |
| | | | mean 9.5 | mean 4.7 | mean 2.5 | mean 1.8 | mean 0.6 | mean 1.3 |
| tS-1 | IN | 23[e] | 16 | 3.4 | 0 | <1.1 | 0.4 | 1 |
| | IN | 24[e] | 13 | 4.4 | 0 | <1.1 | 1.0 | 3 |
| | IN | 25[e] | 13 | 5.0 | 13d | 2.2 | 2.0 | 4 |
| | IN | 26[e] | 10 | 3.4 | 0 | <1.1 | 1.0 | 2 |
| | | | mean 13 | mean 4.1 | mean 3.3 | mean 1.4 | mean 1.1 | mean 2.5 |
| A2 wild-type | IN | 9[b] | 9 | 5.1 | 13 | 5.4 | 1.0 | 1 |
| | IN | 10[b] | 9 | 6.0 | 8 | 6.0 | 1.7 | 4 |
| | IN + IT | 11[a] | 13 | 5.3 | 8 | 5.9 | 2.1 | 3 |
| | IN + IT | 12[e] | 9 | 5.4 | 8 | 5.6 | 1.0 | 3 |
| | | | mean 10 | mean 5.5 | mean 9.3 | mean 5.7 | mean 1.4 | mean 2.8 |

[a]IN = intranasal only; IN + IT = Both intranasal and intratracheal administration.
[b]Indicates last day post-infection on which virus was recovered.
[c]Mean rhinorrhea score represents the sum of daily scores for a period of eight days surrounding the peak day of virus shedding, divided by eight. Four is the highest score; zero is the lowest score.
[d]Virus isolated only on day indicated.
[e]Animals from Crowe, et al., Vaccine 11: 1395-1404 [1993].

TABLE 22

Immunization of chimpanzees with $10^4$ pfu of RSV ts-1 NG1/A-20-4, ts-1 NG1, or
ts-1 induces resistance to $10^4$ pfu RSV A2 wild-type virus challenge on day 28.

| Virus used to immunize animal | Chimpanzee number | Virus Recovery | | | | Rhinorrhea scores | | Serum neutralizing antibody titer [reciprocal log$_2$] on day indicated[b]] | |
|---|---|---|---|---|---|---|---|---|---|
| | | Nasopharynx | | Trachea | | | | | |
| | | Duration [Days] | Peak titer [log$_{10}$pfu/ml] | Duration [Days] | Peak titer [log$_{10}$pfu/ml] | Mean[a] | Peak | Day 28 | Day 49 or 56 |
| ts-1 NG1/A-20-4 | 15 | 0 | <0.7 | 0 | <0.7 | 0 | 0 | <3.3 | 10.7 |
| | 16 | 0 | <0.7 | 0 | <0.7 | 0 | 0 | <3.3 | 11.9 |
| | 17 | 0 | <0.7 | 0 | <0.7 | 0 | 0 | 5.3 | 10.3 |
| | 18 | 3 | 2.0 | 0 | <0.7 | 0 | 0 | 8.2 | 11.8 |
| | | mean 0.8 | mean 1.0 | mean 0 | mean <0.7 | mean 0 | mean 0 | mean 5.0 | mean 11.2 |
| ts-1 NG1 | 19[b] | 0 | <0.7 | 0 | <1.1 | 0 | 0 | 11.1 | 9.8 |
| | 20[b] | 0 | <0.7 | 0 | <1.1 | 0 | 0 | 12.7 | 9.1 |
| | 21[b] | 0 | <0.7 | 0 | <1.1 | 0 | 0 | 10.8 | 11.0 |
| | 22[b] | 0 | <0.7 | 0 | <1.1 | 0 | 0 | 10.0 | 8.6 |
| | | mean 0 | mean <0.7 | mean 0 | mean <1.1 | mean 0 | mean 0 | mean 11.1 | mean 9.6 |
| ts-1 | 23[b] | 0 | <0.7 | 0 | <1.1 | 0 | 0 | 9.4 | 10.5 |
| | 29[b] | 0 | <0.7 | 0 | <1.1 | 0 | 0 | 12.4 | 12.8 |
| | 25[b] | 5 | 0.7 | 0 | <1.1 | 0 | 0 | 9.0 | 9.6 |
| | 26[b] | 5 | 0.7 | 0 | <1.1 | 0 | 0 | 13.4 | 12.0 |
| | | mean 2.5 | mean 0.7 | mean 0 | mean <1.1 | mean 0 | mean 0 | mean 11.0 | mean 11.2 |
| none | 9[c] | 9 | 5.1 | 13 | 5.4 | 1.0 | 1 | <3.3 | 11.0 |
| | 10[c] | 9 | 6.0 | 8 | 6.0 | 1.7 | 4 | <3.3 | 9.8 |
| | 11[b] | 13 | 5.3 | 8 | 5.9 | 2.1 | 3 | <3.3 | 9.4 |
| | 12[b] | 9 | 5.4 | 8 | 5.6 | 1.0 | 3 | <3.3 | 14.5 |
| | | mean 10 | mean 5.5 | mean 9.3 | mean 5.7 | mean 1.5 | mean 2.8 | mean <3.3 | mean 11.1 |

[a]Mean rhinorrhea score represents the sum of scores during the eight days of peak virus shedding divided by eight. Four is the highest score; zero is the lowest score.
[b]Animals from Crowe, et al., Vaccine 11: 1395-1404 [1993].
[c]Animals from Collins, et al., Vaccine 8: 164-168 [1990].
[d]Serum neutralizing titers in this table were determined in a new assay simultaneously with other specimens represented in the table.

TABLE 23

The efficiency of plaque formation of six mutants derived from RSV ts-4 and tested in HEp-2 cells at permissive and restrictive temperatures, compared with controls.

| Virus | The titer of virus [$\log_{10}$pfu/ml] at the indicated temperature [° C.] | | | | | | | | | Small-plaques at 32° C. | Shut-off temperature [° C.][1] |
|---|---|---|---|---|---|---|---|---|---|---|---|
| | 32 | 33 | 34 | 35 | 36 | 37 | 38 | 39 | 40 | | |
| A2 wild-type | 5.7 | 5.8 | 5.5 | 5.5 | 5.3 | 5.5 | 5.5 | 5.4 | 5.5 | no | >40 |
| ts-4 | 4.5 | 4.7 | 4.4 | 4.7 | 4.7 | 4.1 | 3.7 | 3.0 | 2.5 | no | 40 |
| ts-4 cp-43 | 6.2 | 6.1 | 6.1 | 6.0 | 4.4* | 4.2 | 1.7 | <0.7 | <0.7 | no | 37** |
| ts-4/20.7.1 | 6.0 | 5.9 | 5.7 | 5.7* | 4.5 | 1.8 | <0.7 | <0.7 | <0.7 | no | 37** |
| ts-4/19.1.2 | 5.8 | 5.7 | 5.5 | 5.6* | 4.4 | <0.7 | <0.7 | <0.7 | <0.7 | no | 37** |
| ts-4/15.8.2 | 5.3* | 5.4* | 4.8* | 4.9* | 2.8 | <0.7 | <0.7 | <0.7 | <0.7 | yes | 36** |
| ts-4/29.7.4 | 5.7 | 5.6 | 5.6 | 5.7* | <0.7 | <0.7 | <0.7 | <0.7 | <0.7 | no | 36 |
| ts-4/31.2.4 | 4.7 | 4.2 | 4.1 | 4.0* | <0.7 | <0.7 | <0.7 | <0.7 | <0.7 | no | 36 |

[1]Shut-off temperature is defined as the lowest restrictive temperature at which a 100-fold or greater reduction of plaque titer is observed [bold figures in table].
*Small-plaque phenotype [<50% wild-type plaque size]
**Pinpoint-plaque phenotype [<10% wild-type plaque size]

TABLE 24

Replication of RSV ts-4 and RSV ts-4 cp-43 in Balb/c mice[1]

| Virus used to infect animals: | Shutoff temperature of virus (C. °) | Virus titer (mean $\log_{10}$pfu/g tissue of six animals ± standard error) | |
|---|---|---|---|
| | | Nasal turbinates | Lungs |
| A2 wild-type | >40 | 5.0 ± 0.14 | 5.2 ± 0.05 |
| ts-4 | 39 | 4.3 ± 0.09 | 4.7 ± 0.11 |
| ts-4 cp-43 | 37 | 2.1 ± 0.09 | 2.7 ± 0.27 |

[1]Mice were administered $10^{6.3}$ p.f.u. intranasally under light anesthesia on day 0, then sacrificed by $CO_2$ asphyxiation on day 4.

EXAMPLE IV

RSV Subgroup B Vaccine Candidates

This Example describes the development of RSV subgroup B virus vaccine candidates. The same approach used for the development of the subgroup A mutants of the invention was utilized for the subgroup B viruses. A parent stock of wild-type B-1 RS virus was cold-passaged 52 times in Vero cells at low temperature (20-25° C.) and the virus was subjected to plaque purification at passages 19 and 52. Three of the clones derived from the passage 52 suspension were evaluated independently, and one clone, designated RSV B-1cp52/2B5, was selected for further evaluation because it was highly attenuated in the upper and lower respiratory tract of the cotton rat (Table 25). An evaluation of several clones at different passage levels of the cp RSV B-1 virus indicate that the RSV B-1cp52/2B5 mutant sustained multiple mutations that independently contribute to its attenuation phenotype. The RSV B-1cp52/2B5 mutant retained its attenuation phenotype following prolonged replication in immunosuppressed cotton rats (Table 26). This finding of a high level of genetic stability is consistent with the fact that it possesses three mutations contributing to the attenuation phenotype.

Further evaluation of the subgroup B mutants in order to characterize them in a similar manner as the subgroup A mutants, was carried out in Caribbean Green monkeys (Tables 27 and 28) and chimpanzees (Table 29). Monkeys immunized with either RSV B-1 cp-23 or cp52/2B5 were resistant to replication of RSV B-1 wild-type virus, indicating that infection with the highly attenuated derivatives of the RSV B-1 wild-type virus was sufficient to induce resistance to wild-type challenge (Table 27).

The results in the seronegative chimpanzee, like that in the Green monkeys, clearly evidence the attenuation of the RSV B-1cp52/2B5 in the upper and lower respiratory tracts.

The RSV B-152/2B5 mutant has been further mutagenized with 5-fluorouracil and the resulting plaques picked and screened at 32° vs. 38° C. for the ts phenotype. The selected cpts mutants were plaque-purified three times in Vero cells and then amplified twice in Vero cells. As a result, seven cpts mutants of RSV B-1cp52/2B5 have been identified (Table 30) and their level of replication in cotton rats has been studied (Table 31). One of these mutants, namely cpts176, was further mutagenized and a series of mutant derivatives were obtained that were more ts in vitro than the RSV B-1cpts 176 parent virus (Table 32).

As with the subgroup A mutants of the invention, the subgroup B mutants are infectious and exhibit a significant degree of attenuation for cotton rats, monkeys, and chimpanzees. Despite attenuation in vivo, the RSV B-1 cp mutant viruses induced resistance in monkeys against wild-type challenge. The ts mutants of the RSV B-1 cpts52/2B5 virus are attenuated and demonstrate a more restricted level of replication in the nasopharynx and lungs of the cotton rat than the RSV B-1 52/2B5 parent virus.

TABLE 25

Replication in cotton rats of RSV B-1 wild-type compared with five plaque-purified cold-passaged mutants derived from RSV B-1, in two separate experiments.

| Virus used to infect animals on day 0** | Virus recovery ($\log_{10}$pfu/g tissue) on day 4* | | | |
|---|---|---|---|---|
| | Nasal turbinates | | Lungs | |
| | Exp. 1 | Exp. 2 | Exp. 1 | Exp. 2 |
| RSV B-1 wild-type | 4.7 ± 0.14 | 5.1 ± 0.10 | 5.4 ± 0.15 | 5.8 ± 0.08 |
| RSV B-1 cp-12/B1A | nd | 3.3 ± 0.15 | nd | 4.4 ± 0.10 |
| RSV B-1 cp-23 | nd | 2.4 ± 0.36 | nd | 3.2 ± 0.31 |
| RSV B-1 cpsp-52/1A1 | 1.7 ± 0.11 | 2.1 ± 0.27 | 3.0 ± 0.13 | 2.3 ± 0.07 |
| RSV B-1 cp-52/2B5 | 1.8 ± 0.25 | 2.2 ± 0.3 | 1.8 ± 0.11 | 1.5 |
| RSV B-1 cp-52/3C1 | 1.8 ± 0.14 | nd | 1.8 ± 0.14 | nd |

TABLE 25-continued

Replication in cotton rats of RSV B-1 wild-type compared with five plaque-purified cold-passaged mutants derived from RSV B-1, in two separate experiments.

| Virus used to infect animals on day 0** | Virus recovery ($\log_{10}$pfu/g tissue) on day 4* | | | |
|---|---|---|---|---|
| | Nasal turbinates | | Lungs | |
| | Exp. 1 | Exp. 2 | Exp. 1 | Exp. 2 |
| RSV A2 | 5.9 ± 0.09 | 5.4 ± 0.07 | 6.6 ± 0.06 | 6.1 ± 0.06 |
| RSV A2 cpts530/1009 | 3.2 ± 0.11 | 2.1 ± 0.22 | 2.1 ± 0.19 | 1.7 ± 0.12 |

*Virus recovery determined by titration of tissue homogenates on Vero cell monolayer cultures at 32° C. with a 10-day incubation in Experiment 1, 7-day incubation in Experiment 2.
**Cotton rats infected intranasally with $10^{5.5}$ pfu of indicated virus.
nd = not done

TABLE 26

Growth in cotton rats of day 14 isolaes* from RSV B-1 cp52/2B5 infected immunosuppressed cotton rats compared with controls

| Virus infected animals[a] | Virus Recovery | | RSV B-1 wild-type $\log_{10}$pfu/g) | |
|---|---|---|---|---|
| | Virus titer on day 4 in indicated tissue (mean $\log_{10}$pfu/g tissue ± standard error of the mean) | | | |
| | Nasal turbinates[b] | Lungs[c] | Nasal turbinates | Lungs |
| RSV B-1 wild-type | 3.9 ± 0.03 (6/6) | 4.8 ± 0.12 (6/6) | — | — |
| RSV B-1 cp 52/2B5 | 2.0 ± 0.07 (8/8) | <1.5 (0/8) | 1.9 | >3.3 |
| isolate 1 | 1.5 ± 0.13 (5/8) | 1.5 ± 0.04 (1/8) | 2.5 | 3.3 |
| isolate 2 | 1.5 ± 0.13 (6/8) | <1.5 (0/8) | 2.4 | >3.3 |
| isolate 3 | 1.5 ± 0.16 (3/8) | <1.5 (0/8) | 2.5 | >3.3 |
| isolate 4 | 1.3 ± 0.09 (4/8) | <1.5 (0/8) | 2.6 | >3.3 |
| isolate 5 | 1.2 ± 0.00 (2/8) | <1.5 (0/8) | 2.7 | >3.3 |
| isolate 6 | 1.2 ± 0.00 (3/8) | <1.5 (0/8) | 2.7 | >3.3 |
| isolate 7 | 1.3 ± 0.06 (3/8) | <1.5 (0.8) | 2.7 | >3.3 |

*Isolates were virus suspensions obtained following amplification by one Vero cell tissue culture passage of virus present in the original nasal turbinate homogenate on day 14 of an immunosuppressed cotton rat.
[a]Groups of 8 cotton rats infected with $10^{5.5}$ pfu of indicated virus in a 0.1 ml inoculum on day 0.
[b]( ) indicates the numbers of animals from which virus was detected at 1.2 $\log_{10}$pfu/g or greater.
[c]( ) indicates the numbers of animals from which virus was detected at 1.5 $\log_{10}$pfu/g or greater.

TABLE 27

Replication in Caribbean Green monkeys of RSV A2 and RSV B-1 wild-types compared with that of two cold-passaged mutants derived from RSV B-1, followed by homologous or heterologous RSV A2 or B-1 wild-type challenge

| Virus used to infect animals on day 0[a] | Immunization | | | | | Challenge | |
|---|---|---|---|---|---|---|---|
| | NP swab | | Tracheal Lavage | | | NP swab | Tracheal Lavage |
| | Peak titer[b] | Days shed[b] | Peak titer | Days shed | Challenge virus | Peak titer[b] | Peak titer[b] |
| A2 | 3.4 | 9 | <0.7 | 0 | A2 | <0.7 | <0.7 |
| | 3.5 | 7 | <0.7 | 0 | A2 | <0.7 | <0.7 |
| | 3.5 | 9 | 4.8 | 10 | A2 | <0.7 | <0.7 |
| | 3.2 | 8 | 0.7 | 7 | A2 | <0.7 | <0.7 |
| | 1.7 | 6 | <0.7 | 0 | B-1 | <0.7 | <0.7 |
| | 3.5 | 10 | <0.7 | 0 | B-1 | <0.7 | <0.7 |
| | 2.4 | 8 | 0.7 | 0 | B-1 | <0.7 | <0.7 |
| | 4.2 | 9 | <0.7 | 0 | B-1 | <0.7 | <0.7 |
| | mean 3.2 | mean 8.3 | mean 1.2 | | | | |
| B-1 | 2.8 | 9 | 1.5 | 10* | B-1 | <0.7 | <0.7 |
| | 2.3 | 9 | 1.9 | 7 | B-1 | <0.7 | <0.7 |
| | 2.2 | 7 | 1.7 | 10* | B-1 | <0.7 | <0.7 |
| | 2.2 | 9 | 1.3 | 10* | B-1 | <0.7 | <0.7 |
| | 1.6 | 8* | 1.2 | 5* | A2 | <0.7 | <0.7 |
| | 2.1 | 10 | 1.7 | 7* | A2 | <0.7 | <0.7 |
| | mean 2.2 | mean 8.7 | mean 1.6 | | | mean <0.7 | mean <0.7 |
| B-1 cp-23 | 1.8 | 14 | <0.7 | 0 | B-1 | <0.7 | <0.7 |
| | 1.3 | 5 | <0.7 | 0 | B-1 | <0.7 | <0.7 |
| | 2.0 | 8 | 0.7 | 10 | B-1 | <0.7 | <0.7 |
| | 1.7 | 4 | <0.7 | 0 | B-1 | <0.7 | <0.7 |
| | mean 1.7 | mean 7.8 | mean <0.7 | | | mean <0.7 | mean <0.7 |
| B-1 cp-52 | 1.3 | 8 | <0.7 | 0 | B-1 | <0.7 | <0.7 |
| | 1.3 | 4 | <0.7 | 0 | B-1 | <0.7 | <0.7 |

TABLE 27-continued

Replication in Caribbean Green monkeys of RSV A2 and RSV B-1 wild-types
compared with that of two cold-passaged mutants derived from RSV B-1, followed
by homologous or heterologous RSV A2 or B-1 wild-type challenge

| Virus used to infect animals on day 0[a] | Immunization | | | | Challenge | | |
|---|---|---|---|---|---|---|---|
| | NP swab | | Tracheal Lavage | | | NP swab | Tracheal Lavage |
| | Peak titer[b] | Days shed[b] | Peak titer | Days shed | Challenge virus | Peak titer[b] | Peak titer[b] |
| | 1.3 | 7 | <0.7 | 0 | B-1 | <0.7 | <0.7 |
| | 0.7 | 3* | <0.7 | 0 | B-1 | <0.7 | <0.7 |
| | mean 1.2 | mean 5.5 | mean <0.7 | | | mean <0.7 | mean <0.7 |

[a]Animals infected intratracheally and intranasally with $10^{5.5}$ p.f.u. virus at each site in a 1.0 ml inoculum on day 0.
[b]$Log_{10}$pfu/ml titers determined by plaque assay on HEp-2 cell monolayer cultures for RSV A2, and Vero cell monolayer cultures for RSV B-1 and its derivatives.
*Virus detected only on day indicated.

TABLE 28

Neutralizing antibody response of Caribbean Green Monkeys infected with RSV A2, RSV B-1, or B-1
cpderivatives, then challenged with homologous or heterologous wild-type virus one month later.

| Animals infected on day 0 with indicated virus [number of animals] | Day 28 challenge virus [number of animals] | 60% Plaque reduction serum neutralizing titer against indicated virus [reciprocal mean] | | | | | |
|---|---|---|---|---|---|---|---|
| | | RSV A2 | | | RSV B-1 | | |
| | | Day 0 | Post-infection [day 28] | Post-challenge [day 56] | Day 0 | Post-infection [day 28] | Post-challenge [day 56] |
| A2 [8] | A2 [4] | <10 | 53,232 | 40,342 | <10 | 1,552 | 1,911 |
| | B-1 [4] | | | 23,170 | | | 1,911 |
| B-1 [6] | B-1 [4] | <10 | 3,327 | 3,822 | <10 | 2,048 | 2,521 |
| | A2 [2] | | | 30,574 | | | 35,120 |
| B-1 cp23[4] | B-1 [4] | <10 | 6,208 | 10,086 | <10 | 4,705 | 7,132 |
| B-1 cp-52/2B5 [4] | B-1 [4] | <10 | 194 | 16,384 | <10 | 239 | 3,822 |

TABLE 29

The replication of RSV B-1 or RSV B-1 cp-52 in seronegative chimpanzees
following simultaneous intratracheal and intranasal administration.[a]

| Animal infected with indicated virus on day 0 | Infection dose [pfu] | Exp. | Virus replication | | | | Rhinorrhea score | |
|---|---|---|---|---|---|---|---|---|
| | | | Nasopharynx | | Trachea | | | |
| | | | Duration[b] [days] | Peak titer [$log_{10}$pfu/ml] | Duration[b] [days] | Peak titer [$log_{10}$pfu/ml] | Peak | Mean[c] |
| RSV B-1 wild-type | $10^4$ | 1 | 9 | 3.7 | 8 | 3.2 | 1 | 0.5 |
| | | 1 | 10 | 3.5 | 0 | <0.7 | 2 | 0.9 |
| | | 1 | 10 | 2.8 | 0 | <0.7 | 3 | 1.1 |
| | | 1 | 10 | 2.7 | 8 | 3.4 | 3 | 0.9 |
| | | | avg. 9.8 | mean 3.2 | avg. 4.0 | mean 2.0 | mean 2.3 | mean 0.9 |
| | $10^5$ | 2 | 7 | 2.8 | 8 | 1.0 | 1 | 1.0 |
| | | 2 | 7 | 3.3 | 4 | 3.9 | 3 | 1.3 |
| | | | avg. 7.5 | mean 3.1 | avg. 6.0 | mean 2.5 | mean 2.0 | mean 1.1 |
| B-1 cp-52/2B5 | $10^4$ | 1 | 5 | 1.5 | 0 | <0.7 | 0 | 0 |
| | | 1 | 0 | <0.7 | 0 | <0.7 | 0 | 0 |
| | $10^5$ | 3 | 0 | <0.7 | 0 | <0.7 | 0 | 0 |
| | | 3 | 0 | <0.7 | 0 | <0.7 | 0 | 0 |
| | | | avg. 1.2 | mean 0.9 | mean 0 | mean <0.7 | mean 0 | mean 0 |

[a]These data were combined from three separate experiments, the infection dose of indicated virus in the first experiment was $10^4$, the second and third experiments were $10^5$.
[b]Indicates the last day post-infection on which virus was recovered.
[c]Mean rhinorrhea score represents the sum of daily scores for a period of eight days surrounding the peak day of virus shedding, divided by eight. Four is the highest score; zero is the lowest score.

TABLE 30

The efficiency of plaque formation of eight mutants derived from RSV B-1 cp52/2B5 Plaque titer ($\log_{10}$pfu/ml in Vero of HEp-2 Cells at indicated temperatures (° C.)

| RVS | Vero 32 | HEp-2 32 | 35 | 36 | 37 | 38 | 39 | HEp-2 Shutoff temp (° C.) |
|---|---|---|---|---|---|---|---|---|
| B-1 wild-type | 6.1 | 5.8 | 5.7 | 5.6 | 5.6 | 5.7 | 5.5 | >39 |
| B-1 cp52/2B5 | 5.9 | 5.4 | 5.2 | 5.1 | 5.0 | 5.0 | 4.7** | >39 |
| cpts452 | 6.1 | 5.6 | 5.2 | 5.2 | 3.3** | 3.1** | <0.7 | 37 |
| cpts1229 | 5.7 | 5.1 | 4.9 | 5.1 | 4.4** | <0.7 | <0.7 | 38 |
| cpts1091 | 5.7 | 5.1* | 4.7** | 5.2** | <0.7 | <0.7 | <0.7 | 37 |
| cpts784 | 5.1 | 4.3* | 4.0** | 4.1** | <0.7 | <0.7 | <0.7 | 37 |
| cpts176 | 6.1 | 5.4* | 4.8* | 5.0 | <0.7** | <0.7 | <0.7 | 37 |
| cptssp1415[a] | 5.8 | <0.7 | <0.7 | <0.7 | <0.7 | <0.7 | <0.7 | 38 |
| cpts1324 | 5.9 | 5.1 | 5.0* | 5.0 | <0.7 | <0.7 | <0.7 | 37 |
| cpts1313 | 5.7 | 3.9** | 3.0** | <0.7 | <0.7 | <0.7 | <0.7 | 36 |
| AS | 6.4 | 6.3 | 6.3 | 6.3 | 6.3 | 6.3 | 6.3 | >39 |
| A2/248 | 6.3 | 6.3 | 6.2 | 6.3 | 5.8 | <0.7 | <0.7 | 38 |
| A2/248/404 | 4.4 | 4.3 | 3.3 | 4.0 | <0.7 | <0.7 | <0.7 | 37 |
| A2/248/955 | 4.8 | 4.8 | 4.8 | 4.4 | <0.7 | <0.7 | <0.7 | 37 |

*Small-plaque phenotype (<50% wild-type plaque size).
**Pinpoint-plaque phenotype (<10% wild-type plaque size).
[a]At 32° C., no plaques were observed. Therefore, no shut-off temperature was determined by efficiency of plaque formation. The mutant was assigned a shutoff temperature of 38° C. in HEp-2 cell culture as determined by a 100-fold decrease in virus yield ($TCID_{50}$) in liquid medium overlay.
Bold figures denote shutoff temperatures (defined as the lowest restrictive temperature at which a 100-fold or greater reduction of plaque titer was observed).

TABLE 31

Level of replication in cotton rats of seven ts mutants derived from RSV B-1 cp-52/2B5

| | Replication in cotton rats[1] (mean $\log_{10}$pfu/g tissue of six animals ± s.e.) | |
|---|---|---|
| RSV | Nasal turbinates | Lungs |
| B-1 wild-type | 4.3 ± 0.05 (6/6)[2] | 4.4 ± 0.25 (6/6) |
| B-1 cp52/2B5 | 1.7 ± 0.11 (6/6) | <1.5 (0/6) |
| cpts452 | 1.4 ± 0.1 (3/6) | <1.5 (0/6) |
| cpts1091 | 1.7 ± 0.07 (4/6) | <1.5 (0/6) |
| cpts784 | 1.5 (1/6) | <1.5 (0/6) |
| cpts1229 | 1.4 ± 0.15 (3/6) | <1.5 (0/6) |
| cptsl76 | 1.5 ± 0.17 (3/6) | <1.5 (0/6) |
| cptssp1415 | <1.2 (0/6) | <1.5 (0/6) |
| cpts1324 | <1.2 (0/6) | <1.5 (0/6) |

[1]Cotton rats were inoculated intranasally with 4.5-5.8 $\log_{10}$pfu under light anesthesia on day 0, then sacrificed by $CO_2$ asphyxiation on day 4.
[2]Titer from samples containing virus only. Parenthesis indicate fraction of samples containing virus.

TABLE 32

The efficiency of plaque formation of 14 mutants derived from RSV B-1 cpts176, compared with controls
In vitro efficiency of plaque formation in HEp-2 cell monolayer culture

| | The titer of virus ($\log_{10}$pfu/ml) at the indicated temperature (° C.) | | | | Shut-off temperature |
|---|---|---|---|---|---|
| RSV | 32 | 35 | 36 | 37 | (° C.)[1] |
| B-1 wild-type | 5.6 | 5.5 | 5.4 | 5.3 | >39 |
| B-1 cp52/2B5 | 5.7 | 5.7 | 5.6 | 5.3 | >39 |
| B-1 cpts176 | 5.5 | 3.5 | 3.0 | 1.9 | 36/37 |
| 176/645 | 3.8 | 3.0 | 2.6 | <0.7** | 37 |
| 176/860 | 3.1 | 2.5 | 2.4 | <0.7 | 37 |
| 176/196 | 3.3 | 2.5 | 2.0 | <0.7** | 37 |
| 176/219 | 2.6 | 2.3 | 2.0 | <0.7** | 37 |
| 176/18 | 4.0 | 3.2 | <0.7 | <0.7 | 36 |
| 176/73 | 2.6 | 2.0 | <0.7 | <0.7 | 36 |
| 176/1072 | 3.2 | 2.3 | <0.7 | <0.7 | 36 |
| 176/1038 | 2.8 | 2.2 | <0.7 | <0.7 | 36 |
| 176/81 | 2.2 | 2.0 | <0.7 | <0.7 | 36 |
| 176/1040 | 3.2 | 2.0 | <0.7 | <0.7 | 36 |
| 176/1045 | 2.5 | 1.9 | <0.7 | <0.7 | 36 |
| 176/517 | 3.1 | 2.0 | <0.7 | <0.7** | 36 |
| 176/273 | 2.3 | <0.7 | <0.7 | <0.7 | 35 |
| 176/427 | 3.5 | <0.7 | <0.7 | <0.7 | 35 |

**Pinpoint-plaque phenotype (<10% wild-type plaque size)
[1]Shut-off temperature is defined as the lowest restrictive temperature at which a 100-fold or greater reduction of plaque titer is observed (bold figures in table).

To aid in the evaluation and manipulation of RSV B subgroup vaccine candidates, the complete nucleotide sequence of the wild-type B-1 virus has been determined [SEQ ID NO:2]. This sequence was compared with the sequence of the attenuated B-1 derivative, cp-52/2B5 (cp-52), described above. This sequence analysis revealed a large deletion in cp-52 spanning most of the SH and G genes, with no predicted ORF for either gene. More specifically, most of the region spanning the SH and G genes of the cp-52 virus was deleted, retaining only the SH gene-start signal and a portion of the 3' (downstream) end of the G gene and its gene-end signal. The remaining SH:G region could encode a chimeric transcript of ~91 nucleotides with no ORF. Northern blot analysis of cp-52 confirmed that multiple unique polytranscripts contained SH:G read-through mRNAs, consistent with a deletion mutation spanning the SH:G gene junction. Western blot and immunostain assays confirmed that intact G glycoprotein was not produced by the cp-52 virus. In addition to the long deletion, cp-52 virus contains seven nucleotide differences (Table 33), five of which are coding changes (one in the F gene and four in the L gene), one is silent (F gene), and one is in the noncoding G:F intergenic region. Importantly, this RSV mutant remains highly infectious in tissue culture despite the absence of SH and G proteins. These data identify a novel class of replication competent deletion mutants which provide for alternative or combinatorial approaches to developing recombinant RSV vaccine candidates.

TABLE 33

Sequence comparison of RSV B1 and cp-52

| Gene | Genomic position | Nucleotide* B1 | cp-52† | Amino acid change (#) B1→cp-52 | |
|---|---|---|---|---|---|
| G/F | 5626 | C | A** | non-coding | intergenic |
| F | 6318 | A | G | Glu→Gly | (218) |
|  | 6460 | U | C** | silent | (265) |
| L | 10973 | G | A | Arg→Lys | (822) |

TABLE 33-continued

Sequence comparison of RSV B1 and cp-52

| Gene | Genomic position | Nucleotide* B1 | cp-52† | Amino acid change (#) B1→cp-52 | |
|---|---|---|---|---|---|
|  | 13492 | A | C | Asn→His | (1662) |
|  | 14164 | U | A** | Leu→Ile | (1886) |
|  | 14596 | U | C** | Phe→Leu | (2030) |

*Positive (+) sense.
†Nucleotide position 4249-5540 spanning the SH and G genes is deleted in cp-52.
**Mutations present in cp-23

Other subgroup B mutants isolated at different passage levels in the cp-52 passage history incorporate various of the cp-52 mutations, depending on passage level (Table 34). Exemplary subgroup B mutants in this context include RSV B-1 cp-12, RSV B-1 cp-23, RSV B-1 cp-32, RSV B-1 cp-42. Table 34 depicts (as negative sense) the distribution of these specific mutations among exemplary B subgroup mutants. This varied distribution of mutations allows for more refined characterization of the attenuating effects of these mutations in the designated strains. For example, cp-23 incorporates the mutations at nucleotide positions 5626, 6460, 14164 and 14596 found in cp-52 (Table 34), but has no differences from the parental B-1 wild-type strain in the SH and G gene region that is deleted in cp-52. cp-42 incorporates the same SH and G deletion as cp-52, while cp32 presents a distinct deletion of sequences within the SH and G genes.

TABLE 34

Sequence comparison between RSVB1, RSVB1cp12, cp 23, cp32, cp 42, and cp 52
Nucleotide Changes
genome (−) sense

| Gene | Nucl. Pos. | RSVB1 | RSVB1 CP12 | RSVB1 **CP23 | RSVB1 CP32 | RSVB1 CP42 | RSVB1 •CP52 | Amino Acid Changes | |
|---|---|---|---|---|---|---|---|---|---|
| G/F | 5626 | G | G | T | T | *ND | T | non-coding | 1Gr |
| F | 6318 | T | ND | T | T | ND | C | Glu→Gly | (218) |
|  | 6460 | A | A | G | G | *ND | G | silent | (265) |
| L | 10973 | C | ND | C | C | T | T | Arg→Lys | (822) |
|  | 13492 | T | ND | T | T | T | G | Asn→His | (1662) |
|  | 14164 | A | A | T | T | T | T | Leu→Ile | (1886) |
|  | 14596 | A | G | G | G | G | G | Phe→**Leu | (2030) |

•Nucleotide region (position 4249-5540) spanning the SH and G genes is deleted in cp52.
**No nucleotide differences from B1 parent found in the SH and G gene region which is deleted in cp52.
*These nucleotides are most likely the same as in cp23 and cp 52.
**A Leucine at amino acid position 2030 in the L polymerase is also found in RSV2B.

EXAMPLE V

Bivalent RSV Subgroup A and B Vaccine

Studies with subgroup A and B viruses demonstrate that in vitro, no interference occurs between wild-type A2 and B-1 viruses, nor between cpts530/1009 and RSV B-1 cp52/2B5 derivatives in Vero cell monolayer cultures. The in vivo results of bivalent infection in cotton rats are presented in Table 34. These results confirm the in vitro results, which show no interference between A-2 and B-1 wild-type RSV, and cpts530/1009 and RSV B-1 cp52/2B5. It is expected, therefore, that each vaccine virus will induce homotypic immunity against wild-type virus, since each component of the bivalent vaccine replicates to a level in the dual infection comparable to that seen during single infection. Each virus alone is capable of inducing homotypic resistance against RSV wild-type challenge.

TABLE 35

Bivalent infection of cotton rats with RSV A2 and RSV B-1 viruses or mutant derivatives indicates no in vivo interference

| | Virus recovery from indicated tissue ($\log_{10}$pfu/g) | | | |
|---|---|---|---|---|
| | Nasal turbinates | | Lungs | |
| Viruses used to infect animals* | RSV A titer | RSV B titer | RSV A titer | RSV B titer |
| A2 | 5.4 ± 0.08 | — | 5.8 ± 0.07 | — |
| B-1 | — | 4.6 ± 0.03 | — | 5.4 ± 0.12 |
| A2 + B-1 | 5.2 ± 0.11 | 3.6 ± 0.07 | 5.7 ± 0.08 | 5.0 ± 0.05 |
| A2 cpts530/1009 | 3.2 ± 0.09 | — | 1.9 ± 0.15 | — |
| B-1 cp52 | — | 2.4 ± 0.08 | — | <1.5 |
| A2 cpts530/1009 + B1 cp-52 | 2.8 ± 0.13 | 2.0 ± 0.14 | 1.8 ± 0.08 | <1.5 |

*Groups of six animals infected with $10^5$ pfu intranasally on day 0 in a 0.1 ml inoculum.

EXAMPLE VI

A Single Mutation in Polymerase (L) Gene Elicits ts Phenotype

This Example describes the specific mutations in the polymerase gene (L) that were produced by chemical mutagenesis of incompletely attenuated host range-restricted cpRSV to produce ts strains, cpts248 and cpts530, which are more highly attenuated and suitable for use in RSV vaccine preparations. As described in the Examples above, cpts248 has been found to be attenuated, immunogenic, and fully protective against wild-type challenge in seronegative chimpanzees and is more stable genetically during in vivo replication than previously evaluated tsRSV mutants. As described above, the cpts248 strain was subjected to chemical mutagenesis to further reduce residual reactogenicity, yielding a series of mutants with increased temperature sensitivity or small plaque phenotype, including cpts248/404. In a like manner, cpts530/1009 was derived from cpts530.

The genetic bases for increased attenuation and ts phenotype of cpts248 and cpts530 were determined by comparing the complete genomic sequence of these viruses with that of the previously determined sequence of the cpRSV parental virus. The complete nucleotide sequence of cpRSV was determined and compared with that of RSV A2 wild-type virus (a laboratory strain which was not part of the direct passage lineage), as well as with the sequence of its low passaged wild-type parent virus (RSV A2/HEK7). The cpRSV differs from its RSV A2/HEK7 parent virus by five nucleotide changes, one in the nucleoprotein (N), two in the fusion protein (F) gene and two in the polymerase (L) gene. The complete 15,222 nucleotide sequence and amino acid sequence of cpts248, cpts248/404, cpts530, cpts530/1009, and cpts530/1030 were determined.

The derivation of the RSV mutants cpts248 and cpts530 from their cpRSV parent by random chemical mutagenesis was described in Example 1. The virus suspension used for infecting cells for production of virus to be used as a source of purified viral RNA was a clarified tissue culture supernatant containing virus that had been passaged four times in liquid medium in Vero cell monolayer culture following biological cloning (i.e., three plaque-to-plaque passages in Vero cell monolayers under agar).

Cell monolayers were infected at a multiplicity of infection (moi) of 0.1 with cpts248, cpts248/404, cpts530, cpts530/1009, or cpts530/1030 viruses. Total RNA was prepared from infected cell monolayers when moderate CPE was observed (average of 4-5 days postinfection). The supernatant fluid was removed by aspiration, and infected cell monolayers were harvested by lysis with guanidinium isothiocynanate, followed by phenol-chloroform extraction. RNA was reverse transcribed using Superscript II TM reverse transcriptase (Life Technologies) random hexamer primers, and reaction conditions as described in protocols supplied by the manufacturer.

The resulting cDNA was separated from primers using TE-100 spin columns (Clontech, Palo Alto, Calif.) and used as template in polymerase chain reactions (PCR) to generate a series of ten overlapping cDNA clones spanning the entire RSV genome. The oligonucleotide primers for PCR were designed from the nucleotide sequence of the prototype A2 virus (Mink et al., *Virology* 185:615-624 (1991); Stec et al., *Virology* 183:273-287 (1991); Collins et al., *Proc. Natl. Acad. Sci. U.S.A.* 88:9663-9667 (1991); Connors et al., *Virology* 208:478-484 (1995)), and had been demonstrated previously to amplify both the RSV A2 wild-type virus and its derivative, the cpRSV parental virus. Uracil-containing oligonucleotide primers were used for cloning RSV sequences into the pAMP1 vector using the CloneAmp uracil DNA glycosylase system (Life Technologies). PCR reactions were performed according to the manufacturer's protocols (Perkin-Elmer, Norwalk, Conn.) and carried out for 34 cycles of each 1 min. at 92.5° C., 1 min. at 55° C., and 3 min. at 72° C. Each fragment was electrophoresed in a 1% agarose/TAE gel, recovered by the Geneclean II System (Bio101, Vista, Calif.), and cloned into the pAMP1 vector. Two or more separate clones of each fragment were generated from separate PCR reactions. For analysis of the 3' leader region, viral RNA (vRNA) was polyadenylated as described in Mink et al., *Virology* 185:615-624 (1991) in a 50 μl reaction. Following incubation at 37° C. for 10 minutes, the reaction was stopped with 2 μl of 0.5 M EDTA. The polyadenylated RNA product was purified by extraction with phenol chloroform and ethanol precipitation, and then reverse transcribed into cDNA, amplified by PCR, and cloned using a rapid amplification by the 3' RACE system (Life Technologies). Similarly, for analysis of the 5' trailer region, vRNA was reverse transcribed into cDNA, tailed using terminal deoxynucleotidyl transferase and dCTP, column purified, made double-stranded and amplified by PCR, and cloned using a 5' RACE system (Life Technologies).

Cloned cDNAs for cpts248 were sequenced from double stranded plasmids by the dideoxynucleotide method using synthetic oligonucleotide primers (either plasmid primers or RSV specific primers), [$\alpha^{35}$S]DATP and Sequenase 2.0

(United States Biochemicals, Cleveland, Ohio). Differences between the observed sequences and those of the previously published parental virus cpRSV were confirmed by sequencing two or more clones in both forward and reverse directions, and by sequencing uncloned PCR products.

Nucleotide sequences of the cpts248/404, cptsS30, cpts530/1009, and cpts530/1030 were determined using a different technique. Three to ten overlapping cDNA clones representing the genome of cptsRSV mutant virus were generated by RT-PCR of total infected-cell RNA or vRNA. The complete nucleotide sequence of each clone was determined by automated DNA sequence at the NCI Frederick Cancer (Frederick, Md.) using Taq kit (ABI, Foster City, Calif.) on a M13 sonicated random library constructed in phage M13 for each plasmid insert. Both strands were sequenced and differences between the cpRSV and the cptsRSV mutant sequences were confirmed by manual sequencing (as above) of a second independently derived RT-PCR product using Sequenase 2.0 (USB, Cleveland, Ohio). The 3'- and 5'-end sequences were determined as described above.

The complete nucleotide sequence of the 15,222-nucleotide RNA genome of the cpts248, cpts248/404, cpts530, cpts530/1009, and cpts530/1030 strains were determined. Changes relative to the published sequences of the cpRSV and RSV A2/HEK7 (wild-type) parental viruses (Conners et al., *Virology* 208:478-484 (1995)) were confirmed on independently derived cDNA clones of these cptsRSV mutants, and were rechecked in the cpRSV virus by sequencing an additional clone of cpRSV. An ambiguity in the sequence of the cpRSV virus (compared with the A2/HEK7 wild-type virus) was identified. The ambiguity occurred at position 1,938 from the 3' end of the negative sense genome and consisted of nucleotide heterogeneity (G or A in positive sense) that would be predicted to encode an amino acid change (Val or Ile) at amino acid position 267 of the 391 amino acid-nucleocapsid (N) protein. Thus, the cpRSV actually consisted of a mixed population of viruses. This accounts for the initial failure to detect the change at position 1938 in Conners et al., supra. A virus with the A mutation at position 1,938 was the immediate parent of the cpts248 derivative as well as of the cpts530 sister clone. Thus, the cpRSV which was the immediate parent virus of the cpts derivative contains five amino acid differences from its A2/HEK parent.

A single nucleotide difference between the cpRSV and cpts248 mutants was found at nucleotide position 10,989 (an A to T change) (Table 36). This mutation occurred within the polymerase (L) translation open reading frame, encoding a predicted amino acid change of gin to leu at amino acid position 831 in the 2,165 amino acid L protein. The cpts248/404 mutant possesses two nucleotide differences from its cpts248 parent, one at nucleotide 12,046 (T to A) in the L gene, and one at nucleotide 7605 (T to C) in the transcription start signal sequence of the M2 gene. The nucleotide substitution in the L gene resulted in an amino acid change from asp to glu at position 1183 in the L protein. Thus after two independent rounds of mutagenesis of cpRSV, the cpts248/404 virus acquired two nucleotide changes in the L gene (corresponding to two amino acid substitutions) and one nucleotide change in the transcription start signal of the M2 gene. Compared to its wild-type progenitor, A2/HEK7, the cpts248/404 mutant differs in seven amino acids (four in L, two in F, and one in N) and in one nucleotide in the transcription start signal of the M2 gene.

TABLE 36

Nucleotide Sequence Differences among cp-RSV, cpts-248, cpts-248/404 mutant viruses

| | | | Nucleotide and Amino Acid Change | | | |
|---|---|---|---|---|---|---|
| Nucleotide[1] | Amino Acid | Gene | A2 wt (HEK-7) | cp-RSV | cpts-248 | cpts-248/404 |
| 1938 | 267 | N | G (val) | A (ile) | A (ile) | A (ile) |
| 3242 | | P | A | A | A | AA[2] |
| 6313 | 218 | F | A (glu) | C (ala) | C (ala) | C (ala) |
| 7228 | 523 | F | C (thr) | T (ile) | T (ile) | T (ile) |
| 7605 | | Gene Start (M2) | T | T | T | C |
| 9453 | 319 | L | G (cys) | A (tyr) | A (tyr) | A (tyr) |
| 10989 | 831 | L | A (gln) | A (gln) | T (leu) | T (leu) |
| 12046 | 1183 | L | T (asp) | T (asp) | T (asp) | A (glu) |
| 13565 | 1690 | L | C (his) | T (tyr) | T (tyr) | T (tyr) |

[1]Positive sense
[2]Increases genome length by 1 nucleotide.

The cpts530 differs from the parental strain cpRSV by the single additional nucleotide substitution of C to A at position 10,060 and results in a phe to leu amino acid change at position 521 of the L protein (Table 37). The cpts530/1009 mutant has a single nucleotide substitution at nucleotide 12,002 (A to G) resulting in a met to val substitution at amino acid 1169 of the L protein. Compared to its wild-type progenitor, A2/HEK7, the cpts530/1009 mutant differs in seven amino acids (four in L, two in F, and one in N).

The cpts530/1030 mutant has a single additional nucleotide substitution at nucleotide 12458 (T to A) resulting in a Tyr to Asn substitution at amino acid 1321 of the L protein. Compared to its wt progenitor, A2/HEK, the cpts530/1030 mutant differs in seven amino acids (four in L, two in F, and one in N).

TABLE 37

Nucleotide Sequence Differences among cp-RSV, cpts-530, cpts-530/1009 mutant viruses

| Nucleotide and Amino Acid Change | | | | | | |
|---|---|---|---|---|---|---|
| Nucleotide[1] | Amino Acid | Gene | A2 wt (HEK-7) | cp-RSV | cpts-530 | cpts-530/1009 |
| 1938 | 267 | N | G (val) | A (ile) | A (ile) | A (ile) |
| 6313 | 218 | F | A (glu) | C (ala) | C (ala) | C (ala) |
| 7228 | 523 | F | C (thr) | T (ile) | T (ile) | T (ile) |
| 9453 | 319 | L | G (cys) | A (tyr) | A (tyr) | A (tyr) |
| 10060 | 521 | L | C (phe) | C (phe) | A (leu) | A (leu) |
| 12002 | 1169 | L | A (met) | A (met) | A (met) | G (val) |
| 13565 | 1690 | L | C (his) | T (tyr) | T (tyr) | T (tyr) |

[1]Positive sense

Thus, the ts and attenuation phenotypes of the cpts248 and cpts530 each are associated with a single nucleotide change in the polymerase gene. The incremental increase in ts and attenuation phenotypes between the cpts530, and cpts530/1009 or cpts530/1030 was also each associated with a one amino change in L. In these four examples (i.e., cpts248, cpts530, cpts530/1009, and cpts530/1030) a single, but different, amino acid substitution in L conferred the ts and attenuation phenotypes on the progenitor strains. These amino acid substitutions are acting in cooperation with the five cpRSV mutations to enhance the stability of the ts phenotype following replication in animals. The incremental increase in attenuation and temperature sensitivity observed between the cpts248 and cpts248/404 was associated with two nucleotide changes, either or both of which could contribute to the ts and attenuation phenotypes. The four specific sites in L (i.e., those specific for the cpts530, cpts530/1009, cpts530/1030 and cpts248 viruses) that are singly associated with the ts and attenuation phenotypes and one or both sites in cpts248/404 are identified by the findings summarized herein as core regions of the RSV genome or L protein at which mutation can lead to attenuation. Although the specific mutations at the four sites in the L protein were specific amino acid substitutions, it is likely that other amino acid substitutions as well as in frame insertions or deletions at these sites and at contiguous amino acids within about five amino acids of a specific site can also result in attenuation.

The encoded amino acid changes in L do not appear to involve the regions of highest sequence conservation among the paramyxovirus polymerase proteins, the proposed ATP binding site (Stec et al., *Virology* 183:273-287 (1991)), nor the regions suggested to be homologous to motifs of RNA-dependent RNA and DNA polymerases (Poch et al., *EMBO J.* 8:3867-3874 (1989)). It is more likely that the effect of these mutations is at amino acid level rather than nucleotide level, given that the mutation does not lie within the 3' and 5' genome termini nor the short gene-start and gene-end sequences. These RNA regions are thought to contain all of the cis-acting RNA sequences required for efficient encapsidation, transcription, replication, and packaging into virions (Collins et al., *Proc. Natl. Acad. Sci. USA* 88:9663-9667 (1991); Collins et al., *Proc. Natl. Acad. Sci. USA* 93:81-85 (1996), each incorporated herein by reference).

These results provide the first full-length sequence of a tsRSV mutant. These results also indicate that pneumoviruses can be attenuated by the substitution of a single nucleotide that causes an amino acid change or change in, e.g, a GS sequence. Since the cpts248 and cpts530 viruses have a high degree of stability of the ts phenotype both in vitro and in vivo, it is remarkable indeed that this phenotype was found to be associated with a single, different amino acid change. Importantly, the cpts248/404, cpts530/1009, and cpts530/1030 contain at least three mutations that contribute to the attenuation phenotype, two ts and one non-ts (e.g., the five cp mutations), and this is a partial non-limiting explanation for the high level of stability of these viruses in vitro and in vivo.

Determination of the complete sequence of RSV vaccine virus strains and of their parental viruses permits analysis at the genetic level of the stability of vaccine viruses during vaccine virus production and during shedding by volunteers in clinical trials. The determination of the genetic basis for the attenuation and ts phenotypes of the cpts248, cpts530, cpts248/404 cpts530/1009 and cpts530/1030 viruses provides important new opportunities. According to the recombinant methods described hereinbelow, it is readily possible to generate novel vaccine candidates by site-directed mutagenesis of full-length RSV cDNA from which infectious viruses can be recovered. For example, it is possible to add to a cDNA clone of, e.g., the cpts248/404 virus, one or both of the ts mutations at amino acid position 521 (in the cpts530 mutant) or 1169 (in the cpts530/1009 mutant) or other attenuating or stabilizing mutations as desired. In this way, the level of attenuation of the cpts248/404 virus can be increased in an incremental fashion and a vaccine strain that has the specific level of attenuation desired for both safety and immunogenicity can be generated in a rational way. Similarly, the level of attenuation of the cpts530/1009 and cpts530/1030 mutants can be increased by the specific introduction of one or more of the attenuating mutations in the cpts248/404 virus. These examples of combinatorial recombinant viruses, incorporating multiple attenuating mutations from biologically derived mutant strains, overcome many of the difficulties which attend isolation and production of genetically stable, satisfactorily attenuated viruses using conventional approaches. Moreover, the phenotypic stability of these recombinant cptsRSV mutants can be enhanced by introducing, where possible, two or more nucleotide substitutions at codons that specify specific amino acids that are known to confer the attenuation phenotype. In this way the stability of the attenuation phenotype can be augmented by site-directed mutagenesis of full-length RSV cDNA.

EXAMPLE VII

Construction of cDNA Encoding RSV Antigenome

Figure 2:
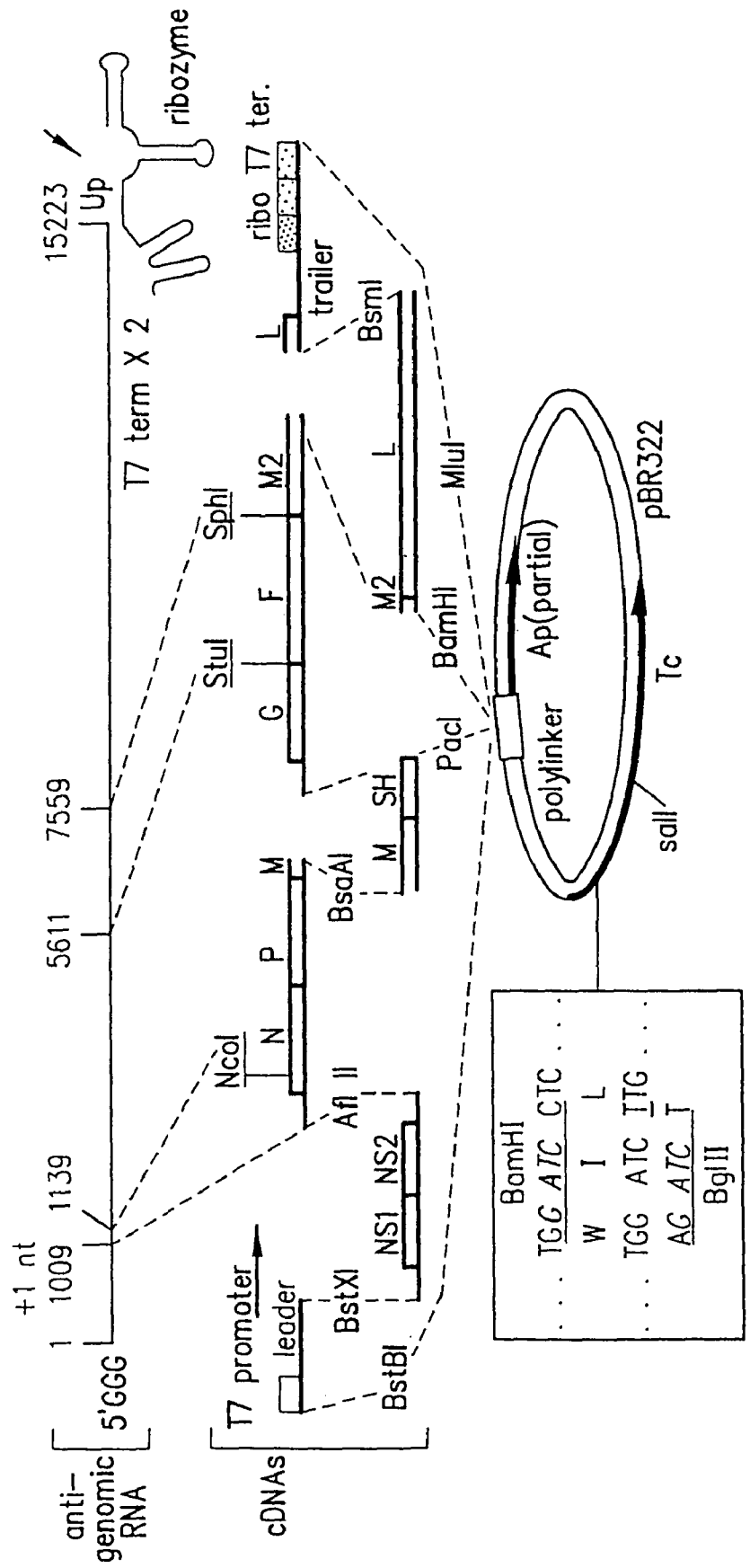
FIGS. 2 and 3 show the construction of cDNA encoding RSV antigenome RNA, where

A cDNA clone encoding the antigenome of RSV strain A2 was constructed, as illustrated in FIG. 2. The cDNA was synthesized in segments by reverse transcription (RT) and polymerase chain reaction (PCR) using synthetic oligonucleotides as primers and intracellular RSV mRNA or genome RNA isolated from purified virions as template. The final cDNA was flanked on the leader end by the promoter for T7 RNA polymerase, which included three transcribed G residues for optimal activity; transcription would result in the donation of these three nonviral G's to the 5' end of the antigenome. To generate a nearly-correct 3' end, the cDNA trailer end was constructed to be adjacent to a previously-described hammerhead ribozyme, which upon cleavage would donate a single 3'-phosphorylated U residue to the 3' end of the encoded RNA (Grosfeld et al., *J. Virol.* 69:5677-5686 (1995), incorporated herein by reference). The ribozyme sequence was followed by a tandem pair of terminators of T7 RNA polymerase. (The addition of three 5' G residues and one 31 U residue to a cDNA-encoded RSV minigenome containing the chloramphenicol acetyl transferase (CAT) reporter gene had no effect on the expression of CAT when complemented by RSV.)

FIG. 2 shows the structures of the cDNA and the encoded antigenome RNA. The diagram of the antigenome (at top) includes the following features: the 5'-terminal nonviral G triplet contributed by the T7 promoter, the four sequence markers at positions 1099 (which adds one nt to the length), 1139, 5611, and 7559, the ribozyme and tandem T7 terminators, and the single nonviral 3'-phosphorylated U residue contributed to the 3' end by ribozyme cleavage (the site of cleavage is indicated with an arrow).

Cloned cDNA segments (FIG. 2, middle) representing in aggregate the complete antigenome were constructed by RT-PCR of RSV mRNA or genome RNA. The complete antigenome cDNA is called D46 or D53; the different names referring to different preparations of the same plasmid. cDNAs containing the lefthand end of the antigenome, spanning from the T7 promoter and leader region complement to the SH gene and called D13, were assembled in a version of pBR322 (FIG. 2, bottom) in which the naturally-occurring BamHI site had been ablated by mutagenesis and the PstI-EcoRI fragment replaced with a synthetic polylinker containing unique restriction sites (including BstBI, BstXI, PacI, BamHI, MluI) designed to facilitate assembly. The box in FIG. 2 shows the removal of the BamHI site. The naturally occurring BamHI-SalI fragment (the BamHI site is shown in the top line in positive sense, underlined) was replaced with a PCR-generated BglII-SalI fragment (the BglII site is shown in the bottom line, underlined; its 4-nt sticky end [italics] is compatible with that of BamHI). This resulted in a single nt change (middle line, underlined) which was silent at the amino acid level.

These modifications to the vector facilitated construction of the cDNA by rendering unique a BamHI site in the antigenome cDNA.

The G, F and M2 genes were assembled in a separate plasmid, as were the L, trailer and flanking ribozyme and tandem T7 transcription terminators. The G-to-M2 piece was then inserted into the PacI-BamHI window of the leader-to-SH plasmid. This in turn was the recipient for the L-trailer-ribozyme-terminator piece inserted into the BamHI to MluI window, yielding the complete antigenome.

Four restriction site markers (FIG. 3) were introduced into the antigenome cDNA during the original construction by incorporating the changes into oligonucleotide primers used in RT-PCR. This was done to facilitate assembly, provide a means to identify recombinant virus, and illustrate the ability to introduce changes into infectious RSV. Three sites were in intergenic regions and the fourth in a nontranslated gene region, and they involved a total of five nt substitutions and a single nt insertion. This increased the length of the encoded antigenome by one nt from that of wild-type to a total of 15,223 nt (SEQ ID NO:1, which depicts the 5' to 3' positive-sense sequence of D46, whereas the genome itself is negative-sense; note that position four can be either G or C).

Figure 3:
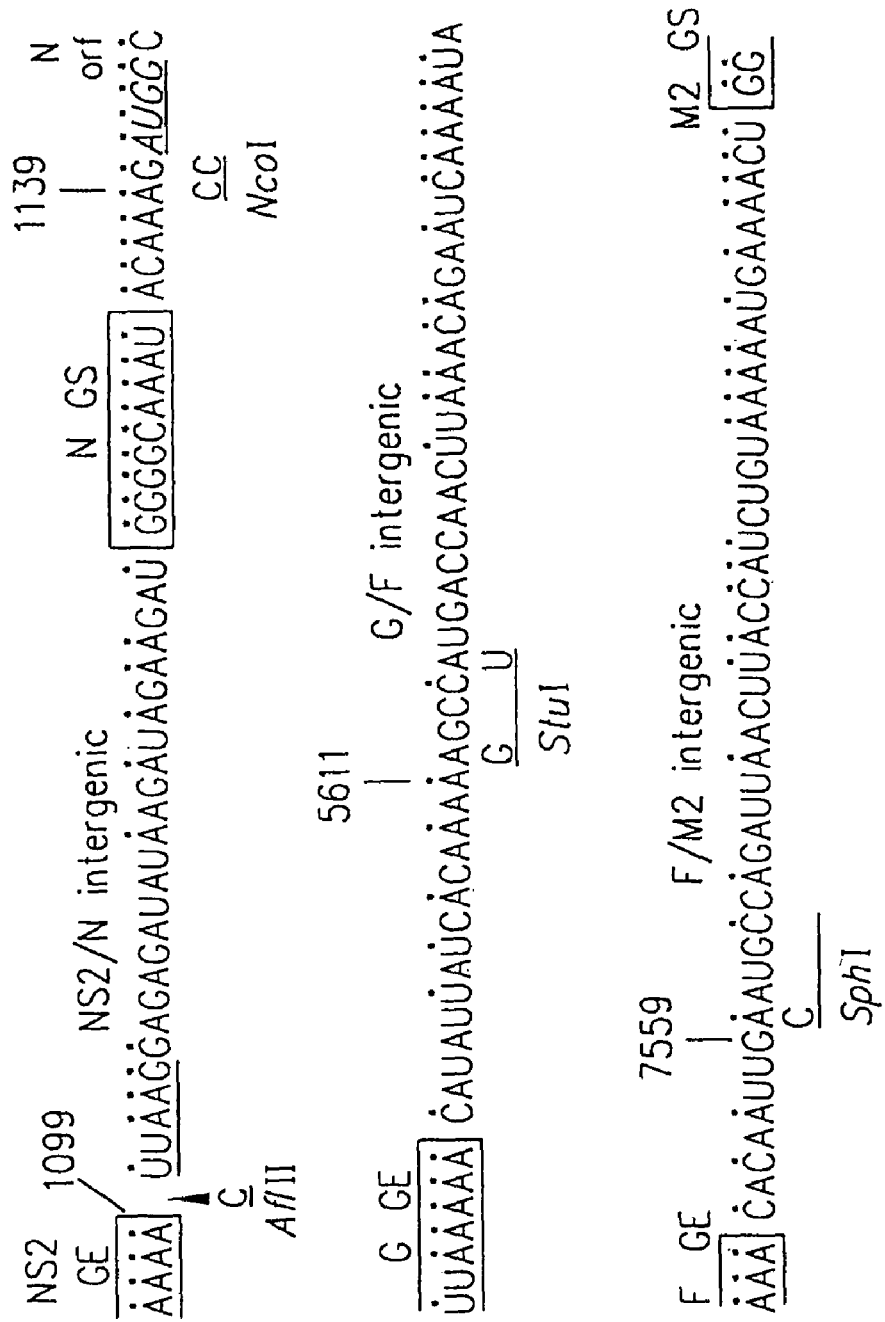

The sequence markers were inserted into the cDNA-encoded antigenome RNA as shown in FIG. 3. Sequences are positive sense and numbered relative to the first nt of the leader region complement as 1; identities between strains A2 and 18537 (Johnson and Collins, *J. Gen Virol.* 69:2901-2906 (1988), incorporated herein by reference), representing subgroups A and B, respectively, are indicated with dots; sequences representing restriction sites in the cDNA are underlined; GS and GE transcription signals are boxed; the initiation codon of the N translational open reading frame at position 1141 is italicized, and the sequence markers are shown underneath each sequence. In the top sequence, a single C residue was inserted at position 1099 to create an AflII site in the NS2-N intergenic region, and the AG at positions 1139 and 1140 immediately upstream of the N translational open reading frame were replaced with CC to create a new NcoI site. In the middle sequence, substitution of G and U at positions 5612 and 5616, respectively, created a new StuI site in the G-F intergenic region. And, in the bottom sequence of FIG. 3, a C replacement at position 7560 created a new SphI site in the F-M2 intergenic region.

All cDNAs were sequenced in their entirety, in most instances from several independent cDNAs, prior to assembly. The plasmids encoding individual RSV proteins are described in Grosfeld et al., *J. Virol.* 69:5677-5686 (1995) and Collins et al., supra, (1995), each of which is incorporated herein by reference. The complete cDNA was also sequenced in its entirety following assembly.

EXAMPLE VIII

Transfection and Recovery of Recombinant RSV

The method of the invention for producing infectious RSV from cDNA-expressed antigenome involves its coexpression with those RSV proteins which are sufficient to (i) produce an antigenome nucleocapsid capable of RNA replication, and (ii) render the progeny genome nucleocapsid competent for both RNA replication and transcription. Transcription by the genome nucleocapsid provides all of the other RSV proteins and initiates a productive infection.

Plasmid-borne cDNA encoding the antigenome was transfected, together with plasmids encoding proteins N, P, L and M2(ORF1), into HEp-2 cells which had been infected with a recently-described vaccinia virus MVA strain recombinant which expresses the T7 RNA polymerase (Wyatt et al., *Virol.* 210:202-205 (1995), incorporated herein by reference). The MVA strain is a host range mutant which grows permissively in avian cells whereas in mammalian cells there is a block at a late stage in virion maturation that greatly reduces the production of infectious virus. In HEp-2 cells, the MVA recombinant was similar to the more commonly-used WR-based recombinant (Fuerst et al., *Proc. Natl. Acad. Sci. USA* 83: 8122-8126 (1986)) with regard to the level of expression of T7 polymerase and cytopathogenicity, but the level of progeny produced was sufficiently low that supernatants could be passaged to fresh cells with minimal cytopathogenicity. This should facilitate the recovery of any recombinant RSV which might be produced in transfected, vaccinia virus-infected cells.

Transfection and recovery of recombinant RSV was performed as follows. Monolayer cultures of HEp-2 cells received, per single well of a six-well dish, one ml of infection-transfection medium prepared by mixing five plasmids in a final volume of 0.1 ml Opti-MEM (Life Technologies) medium, namely 0.4 μg each of antigenome, N and P plasmids, and 0.1 μg each of L and M2(ORF1) plasmids. This was combined with 0.1 ml of Opti-MEM containing 12 μl LipofectACE (Life Technologies). After 15 min incubation at room temperature, this was combined with 0.8 ml of Opti-MEM containing 2% heat-inactivated fetal bovine serum and $1.5 \times 10^6$ pfu of strain MVA vaccinia virus recombinant encoding T7 RNA polymerase (Wyatt et al., supra). This was added to the cells and replaced one day later by Opti-MEM containing 2% serum. Cultures were incubated at 32° C. and harvested on day three. Incubation at 32° C. was used because it was found that the MVA virus is slightly temperature sensitive and is much more efficient at this lower temperature.

Three days post-transfection clarified culture supernatants were passaged onto fresh HEp-2 cells and overlaid with methyl cellulose (for subsequent antibody staining) or agarose (for plaque isolation). After incubation for five days under methyl cellulose, the cells were fixed and stained by an indirect horseradish peroxidase method using a mixture of three murine monoclonal antibodies to the RSV F protein followed by an anti-mouse antibody linked to horseradish peroxidase, following the general procedure of Murphy et al., *Vaccine* 8:497-502 (1990).

Numerous RSV-like plaques were detected against a background of cytopathogenicity that presumably was due to a low level of MVA-T7 recombinant virus. The plaques contained an abundant amount of the RSV F protein, as indicated by brown-black coloration, and displayed cytopathic effects characteristic of RSV, notably syncytium formation.

The RSV-like plaques were picked from plates which were incubated under agarose and stained with neutral red. They were propagated and compared to a laboratory strain of RSV strain A2 by plaque assay and antibody staining. The plaques derived from the transfected cultures closely resembled those of the laboratory strain. One difference was that the plaques derived from the transfected cultures appeared to be slightly smaller than those from the laboratory strain, with centers which were less well cleared. The recombinant virus may differ phenotypically from this particular wild-type isolate, possibly being slightly more restricted in cell-to-cell spread and exhibiting a reduced rate of cell killing. With regard to the propagation of released virus, the yields of the recombinant versus laboratory virus in HEp-2 cells were essentially identical at 320 or 37° C. In preliminary studies, the recombinant and laboratory viruses were indistinguishable with regard to the accumulation of intracellular RSV mRNAs and proteins.

Plaque-purified, thrice-passaged recombinant RSV was analyzed in parallel with laboratory virus by RT-PCR using three primer pairs flanking the four inserted markers. Three independent plaque-purified recombinant RSV isolates were propagated in parallel with an uninfected control culture. Clarified medium supernatants were treated with polyethylene glycol and high salt (Zoller and Smith, *DNA* 3:479-488 (1984)) to precipitate virus and RNA was extracted from the pellets with Trizol™ (Life Technologies). These RNAs, in parallel with additional controls of no added RNA or 0.1 μg of RNA from a laboratory isolate of strain A2, were treated with DNAse, repurified, annealed each with 50 ng of random hexamers and incubated under standard RT conditions (40 μl reactions) with or without reverse transcriptase (Connors et al., *Virol.* 208:478-484 (1995), incorporated herein by reference). Aliquots of each reaction were subjected to PCR (35 cycles of 94° C. for 45s, 37° C. for 30s, 72° C. for 1 min) using three different pairs of synthetic deoxyoligonucleotide primers. Primer pair (A): positive-sense, positions 925-942 and negative-sense, positions 1421-1440, yielding a predicted product of 516 bp (517 bp in the case of the recombinant viruses) that included the AflII and NcoI sites inserted at, respectively, the junction of the NS2 and N genes and in the N gene. Primer pair (B): positive-sense, positions 5412-5429 and negative-sense, 5930-5949, yielding a predicted product of 538 bp spanning the StuI site inserted at the junction between the G and F genes. Primer pair (C): positive-sense, 7280-7297 and negative-sense, 7690-7707, yielding a 428 bp fragment spanning the SphI site inserted at the junction between the F and M2 genes. PCR products were analyzed by electrophoresis on neutral gels containing 1% agarose and 2% low-melting agarose in parallel with HaeIII-digested X174 DNA molecular length markers and visualized by staining with ethidium bromide. PCR products of the expected sizes were produced. The production of each was dependent on the RT step, indicating that each was derived from RNA rather than contaminating cDNA.

PCR products were analyzed by digestion with restriction enzymes. Digestion of products of primer pair A with AflII or NcoI yielded fragments corresponding to the predicted 177 and 340 bp (AflII) or 217 and 300 bp (NcoI). Digestion of products of primer pair B with StuI yielded fragments comparable to the predicted 201 and 337 bp. Digestion of products from reactions with primer pair C with SphI yielded products corresponding to the predicted 147 and 281 bp. The digests were analyzed by gel electrophoresis as above. The presence of residual undigested PCR product with AflII was due to incomplete digestion, as was confirmed by redigestion. Thus, the restriction enzyme digestion showed that the PCR products representing recombinant virus contained the expected restriction site markers while those representing the laboratory strain did not. Nucleotide sequence analysis of cloned PCR product confirmed the sequences spanning the restriction site markers.

As shown in Table 38, the efficiency of RSV production when complemented by N, P, L and M2(ORF1) was relatively high, ranging in three experiments from an average of 9.9 to 94.8 plaques per 0.4 μg of input antigenome cDNA and 1.5× $10^6$ cells. Since these plaques were derived from liquid overlay, the number of infected cells present in each well of the original transfection was not known. Nearly every transfected well (54 of 56 in Table 38) produced virus. Since the yield of released RSV per infected cell typically is very low (~10 pfu) even under ideal conditions, and since many wells yielded many times this amount (up to 169 plaques), it is likely that several RSV producing cells were present in many of the wells of transfected cells.

RSV was not recovered if any of the plasmids were omitted, as shown in Table 38. The requirement for M2(ORF1) also could be satisfied with the complete gene, M2(ORF1+2), provided the level of its input cDNA was low (0.016 μg per $1.5\times10^6$ cells (Table 38). At higher levels, the production of virus was greatly reduced, suggesting that an inhibition of minigenome RNA synthesis associated with M2(ORF2) also operates on the complete genome during productive infection.

These results showed that the production of infectious RSV was highly dependent on expression of the M2(ORF1) protein in addition to N, P and L. Furthermore, it showed that the optimal method of expression of M2(ORF1) was from an engineered cDNA in which ORF2 had been deleted, although the complete cDNA containing both ORFs also supported the production of RSV.

Thus, the present invention demonstrates that transcription by RSV differs from that of from previously-described non-segmented negative strand RNA viruses in requiring a fourth protein designated here as M2(ORF1), and previously called 22K or M2 (Collins et al., *J. Virol.* 54:65-71 (1985)). The M2(ORF1) protein was found to be an RNA polymerase elongation factor that is important for processive, sequential transcription, and therefore must be provided (e.g., endoded by the genome or antigenome or expressed in trans by a separate plasmid or sequence within a shared vector). (see, e.g., Collins et al., *Proc. Natl. Acad. Sci. USA* 93:81-85 (1996)). This requirement provides the capability, as part of this invention, for introducing specific, predetermined changes into infectious RSV.

TABLE 38

Production of infectious RSV was dependent on expression of M2 ORF 1.

| Complementing plasmids (μg cDNA per 1.5 × $10^6$ cells and antigenome cDNA) 0.4 μg | Production of infectious RSV #plaques × # wells* expt. 1 | expt. 2 | expt. 3 |
|---|---|---|---|
| N(0.4) | | | |
| P(0.4) | 0 × 24 | 0 × 12 | 0 × 12 |
| L(0.1) | | | |
| N(0.4) | 0 × 19[§] | 0 × 4 | 9 × 1 |
| P(0.4) | 1 × 2 | 3 × 1 | 10 × 1 |
| L(0.1) | 2 × 2 | 5 × 1 | 14 × 2 |
| M2 [ORF1 + 2] (0.016) | 3 × 1 | 6 × 1 | 22 × 1 |
| | | 9 × 1 | 28 × 1 |
| | av. 0.38 | 10 × 1 | 32 × 1 |
| | | 13 × 1 | 49 × 1 |
| | | 34 × 1 | 70 × 2 |
| | | 51 × 1 | 166 × 1 |
| | | | 169 × 1 |
| | | av. 10.9 | |
| | | | av. 48.6 |
| N(0.4) | 0 × 1  11 × 1 | 0 × 1 | 55 × 1 |
| P(0.4) | 1 × 1  12 × 1 | 2 × 1 | 59 × 1 |
| L(0.1) | 2 × 2  13 × 1 | 4 × 1 | 65 × 1 |
| M2 [ORF1] (0.1) | 3 × 2  21 × 1 | 5 × 1 | 71 × 1 |
| | 4 × 1  24 × 1 | 8 × 2 | 72 × 1 |
| | 5 × 2  26 × 1 | 10 × 3 | 87 × 1 |
| | 6 × 4  30 × 2 | 19 × 1 | 97 × 1 |
| | 7 × 2  33 × 2 | 20 × 1 | 100 × 1 |
| | 9 × 1  42 × 1 | 23 × 1 | 109 × 1 |
| | 10 × 2  73 × 1 | | 128 × 1 |
| | | av. 9.9 | 147 × 1 |
| | av. 13.7 | | 148 × 1 |
| | | | av. 94.8 |

*Supernatants from transfected cultures ($10^6$ cells per well) were passaged onto fresh HEp-2 cells, overlaid with methyl cellulose, and stained with F-specific monoclonal antibodies.
§Read as follows: 19 wells had 0 plaques, 2 wells had 1 plaque each, 2 wells had 2 plaques each, and 1 well had 3 plaques.

EXAMPLE IX

Construction of an Infectious Recombinant RSV Modified to Incorporate Phenotype-Specific Mutations of RSV Strain cpts530

This Example illustrates the introduction of specific predetermined mutations into infectious RSV using the recombinant methods described herein. As noted above, the complete nucleotide sequence of cpts530 RSV was determined and 5 mutations known to be present in the parent cpRSV were retained in cpts530, the further attenuated derivative. One additional nucleotide change was identified at nucleotide (nt) position 10060, which resulted in a phenylalanine to leucine change at amino acid position 521 in the large polymerase (L) protein (see Tables 37, 39). This single amino acid substitution was introduced alone or in combination with the cp mutations into the full-length cDNA clone of wild-type A2 RSV. Analysis of infectious viruses recovered from mutant cDNAs indicated that this single mutation specified complete restriction of plaque formation of recombinant cp530 in HEp-2 cell monolayer cultures at 40° C., and the level of temperature sensitivity was not influenced by the presence of the 5 cpRSV mutations. These findings identify the phenylalanine to leucine change at amino acid position 521 in the L protein as the mutation that specifies the ts phenotype of cpts530. Similarly, one additional nucleotide change was identified in the cpts530/1009 recombinant in comparison to its cpts530 parent virus (Table 37). This nucleotide substitution at position 12002 resulted in an amino acid change in L at position 1169 at which a methionine in the wild-type virus was replaced by a valine in the cpts530/1009 mutant. This mutation has also been introduced into recombinant RSV, and the recovered virus was temperature sensitive. These findings identify the methionine to valine change at position 1169 as the mutation that specifies the greater level of temperature sensitivity of cpts530/1009 over that of cpts530.

The levels of temperature sensitivity among the 530, 530/1009 and 530/1030 recombinant virus have been confirmed with RSV-CAT or RSV-Luciferase minigenome (see above) monitored by enzyme assay or Northern blot analysis. For example, at the elevated temperature of 37° C., the luciferase activity generated by selected mutants relative to wild-type L protein was 18.4%, 1.5% and 0.4% for 1009, 530, and the double mutant pTM1-L support plasmid. These exemplary mutations also decreased L function at 32° C. with 70% activity for 1009, 40% activity for 530, and 12.5% activity for 530/1009 L protein compared to wt L protein. The effects of these mutations on transcription and replication can also be determined using the minigenome system, alone or in combination with the recombinant viral methods disclosed herein.

TABLE 39

Mutations introduced into the RSV full-length cDNA clone.

| Mutation | Sequence of wt | Sequence of Mutation | Restriction Site | Amino Acid Change |
|---|---|---|---|---|
| site [L][1] | $_{9398}$CTTAAGA | $_{9398}$C C TAAGG | Bsu36I | — |
| site [L] | $_{11846}$TACATA | $_{11846}$TAC G TA | SnaBI | — |
| site [L] | $_{13339}$GTCTTAAT | $_{13339}$GT T T A AA C | PmeI | — |
| site [L] | $_{14082}$CGTACAG | $_{14082}$CG G AC C G | RsiII | — |
| site [L] | $_{14318}$TGTAACA | $_{14318}$G GTAAC C | BsiEI | — |
| site [L] | $_{14475}$TATGTA | $_{14475}$TA C GTA | SnaBI | — |
| HEX [F] | $_{5848}$AATATCAAGAAA | $_{5848}$AATAT T AAGG*AA | SspI | $_{65}$lys→glu |
| HEX [F] | $_{5958}$AGCAGAGAA | $_{5958}$AG T AC T GG*A | ScaI | $_{101}$gln→pro |
| cp [F] | $_{1935}$ATCAGTT | $_{1935}$ATC GA * TT | ClaI | $_{287}$val→ile |
| cp [F] | $_{6311}$TAGAAA | $_{6311}$T C G C G A | NruI | $_{213}$glu→ala |
| cp [F] | $_{7228}$ACAAAT | $_{7228}$A T T AAT | AseI | $_{522}$thr→ile |
| cp [L] | $_{9453}$T GT ATAC | $_{9453}$TAGATAC | lose AccI | $_{319}$cys→tyr |
| cp [L] | $_{13555}$TATTAACTAAAGAT | $_{13555}$T G TTAACTAAATAC | HpaI | $_{1690}$his→tyr |
| 248 [L] | $_{10982}$TCATGCTCAA | $_{10982}$G CATGCTGT*G | SphI | $_{851}$gln→leu |
| 404 [M2] | $_{7606}$TATGTCACGA | $_{7606}$C *ATG TC G CGA | NruI | — |
| 404 [L] | $_{12042}$TTGGAT | $_{12042}$C T C GA G | HhoI | $_{1153}$asp→glu |
| 530 [L] | $_{10059}$TTC | $_{10059}$TTA* | — | $_{521}$phe→leu |

TABLE 39-continued

Mutations introduced into the RSV full-length cDNA clone.

| Mutation | Sequence of wt | Sequence of Mutation | Restriction Site | Amino Acid Change |
|---|---|---|---|---|
| 1009 [L] | $_{11992}$CCACTGAGATG<u>ATG</u> | $_{11992}$*CCACTGAGATG<u>GTC</u>* | BsfXI | $_{1169}$met→val |
| 1030 [L] | $_{12452}$G <u>T</u> TAAC<u>T</u>AT | $_{12452}$*G<u>C</u>TAAC<u>AA</u>*AT | lose HpaI | $_{1321}$tyr→asn |

Note:
Nucleotide differences between wild-type and mutants [at the corresponding positions of are underlined. Recognition sites of restriction endonucleases are in italics. Codons in which the introduced nucteotide change[s] results in amino acid substitution are in bold. Asterisk identifies the single nucleotide change that was present in the biologically-derived mutant virus. Numbering system reflects the one nucleotide insertion in the full length cDNA.
[1]indicates the gene into which the mutation was introduced.

To incorporate the cpts530 and the cpts1009 specific mutations into a defined, attenuated recombinant RSV vaccine virus, the cDNA-based recovery system described herein was employed as follows. The previously-described RSV A2 wild-type full-length cDNA clone (Collins et al., supra., (1995)) was designed in the original construction to contain a single nucleotide insertion of C in the cDNA clone at nt position 1099 (which creates an AflII site) and a total of 6 additional nucleotide substitutions at 4 loci. Thus, the nucleotide numbering system for the naturally occurring virus and for the recombinant viruses derived from cDNA are out of register by one nt after position 1099. The nucleotide numbering in Tables 36 and 37, above, represents the positions for the naturally occurring viruses, while those for the cDNA clones (Table 39) and recombinant viruses derived from cDNA clones are one nucleotide more. One of the 6 nucleotide substitutions is a G to C change in genome sense at nt position 4 in the leader sequence. This nucleotide variation has been detected in non-recombinant RSV and was not found to have an effect on the temperature sensitivity of virus replication in tissue culture or in mice (Firestone, et al., *Virology,* 225:419-522 (1996), incorporated herein by reference). Table 39 lists the various mutations which were inserted into the RSV cDNA in this and subsequent Examples.

Intermediate clones (D50 and D39) were used to assemble the full-length RSV cDNA clone D53, which encodes positive-sense RSV antigenome (FIG. 4). The D50 plasmid contains the RSV genome from the leader to the M2-L overlap downstream of a T7 promoter, while the D39 plasmid encodes the full-length L gene and the trailer followed by the hammerhead ribozyme and two T7 terminators (approximately 7 kb in length) bordered by BamHI and MluI restriction sites. The full-length RSV cDNA clone (D53) used in transfections to rescue infectious virus was assembled by inserting the BamHI-MluI fragment of the D39 plasmid into the D50 plasmid (see U.S. patent application Ser. No. 08/720, 132; and published PCT Application No. PCT/US96/15524, each incorporated herein by reference). D50 was further separated into several pieces each placed in a phagemid plasmid for the purposes of facilitating mutagenesis: one piece was an XbaI-EcoRI fragment containing the N gene (cDNA pUC118.D50N), and one was a StuI-BamHI fragment containing the F and M2 genes (pUC118.F-M2). D39 was further separated into two pieces each placed in a separate phagemid plasmid: one piece (left hand half, cDNA pUC119.L1) runs from the BamHI site to the PmlI site at nucleotide 12255 (note that the sequence positions assigned to restriction site locations here and throughout are intended as a descriptive guide and do not alone precisely define all of the nucleotides involved), and the other (right hand half, cDNA pUC119.L2) from the Pm/I site to the end of the T7 terminator.

Mutations were placed into the pUC118- and pUC119-based constructs illustrated in the bottom row of FIG. 4 following standard procedures (see, e.g., Kunkel et al., Methods Enzymol, 54:367-382 (1987), incorporated herein by reference). The plasmids were propagated in a dut ung strain of *E. coli.*, in this case CJ236, and single stranded DNA was prepared by infection with a helper phage, in this case M13KO7. Phosphorylated synthetic oligonucleotides each containing one or more nucleotide changes of interest were prepared, annealed to the single stranded template singly or in combination, and used to direct DNA synthesis by T4 DNA polymerase. The products were ligated and transformed into a non-dut ung strain of *E. coli*, in this case DH5alpha or DH10B. Miniprep DNA of the transformant colonies was screened for the presence of the mutation by restriction enzyme digestion or by nucleotide sequence analysis of the mutagenized region. Fragments containing the appropriate mutations were transferred from the pUC constructs back into the D50 or D39 plasmids, which in turn were assembled into a full-length clone designated D53. Recombinant virus was recovered in HEp-2 cells by complementing the D53 plasmid with a mixture of the four support plasmids encoding the N, P, L and M2 (ORF1) proteins, as described above.

Four types of mutations are involved in this and subsequent examples describing specific recombinant RSV incorporating biologically derived mutations (see Tables 36, 37, 39):

(1) The first group of mutations involves six translationally silent new restriction site markers introduced into the L gene, collectively called the "sites" mutations. The six sites are Bsu36I, SnaBI, PmeI, RsrII, BstEII and a second, downstream SnaBI site, and are underlined in FIG. 4 above the D53 diagram. These six changes, collectively referred to as the "sites" mutations, were inserted for the purpose of facilitating cDNA construction. Also, it is known that recombination can occur during transfection between the D53 plasmid and the support plasmids, i.e., the N, P, M2(ORF1) and L plasmids (Garcin et al., EMBO J. 14:6087-6094 (1995), incorporated herein by reference). These restriction sites in L are present in the D53 construct but not in the L support plasmid, and thus provide a marker to confirm that recombination in L did not occur. This is particularly important since many of the attenuating mutations occur in L.

(2) The second group of mutations involves two amino acid changes in the F gene (FIG. 4, Table 39). The cpRSV, and hence all of its derivatives, is derived from a wild-type virus called HEK-7. The sequence of the original D53 cDNA differs from that of HEK-7 by single nucleotide substitutions at seven positions. One is at nucleotide 4, which is a C (in negative sense) in the original D53 and G in the HEK virus. However, biologically-derived viruses have been shown to contain either assignment, and can fluctuate between the two, and so this difference is considered incidental and not considered further here. Four other nucleotide substitutions were silent at the amino acid level; these were two changes in F, at positions 6222 and 6387, one in the F-M2 intergenic region at position 7560, and one in L at position 10515). These also are not considered significant and are not considered further. Finally, there were two nucleotide substitutions, each in the F gene, which each resulted in an amino acid substitution (Table 39). These two changes, collectively called the "HEK" assignments, were introduced into D53 such that the encoded recombinant wild-type virus would be identical at the amino acid level to the HEK-7 wild-type parent of the biologically-derived cpts mutants. Note that each of these changes was designed to also introduce a new restriction enzyme recognition site for the purpose of monitoring the presence of the introduced mutation in cDNA as well as in recovered virus.

(3) The third group of mutations involved the five amino acid substitutions found in the cpRSV virus, collectively called the "cp" mutations. These are present in all of the biologically-derived cpts viruses and contribute to the attenuation phenotype. In biologically-derived cpRSV, each of these amino acid changes is due to a single nucleotide change. As shown in Table 39, when the amino acid coding change was introduced into cDNA to make recombinant virus in four of the five cases each coding change was made to involve two nucleotide substitutions, which renders the recombinant RSV highly resistant to reversion to wild-type. Note that four of these changes were designed to introduce a new restriction enzyme site, whereas the fifth was designed to ablate an existing site, thus providing a method for monitoring the presence of the mutation by the presence or absence of the restriction site in cDNA or RT-PCR products generated from recombinant viruses.

(4) The fourth group of mutations involves point mutations specific to individual, biologically derived cpts viruses (Table 39, FIG. 4), which are named after the biological step at which they were acquired. For example, derivation of the cpts248/404 virus from cpRSV in the following Example involved two steps of mutagenesis. The first yielded the cpts248 virus, which sustained a single amino acid change that is therefore called the 248 mutation. The second mutagenesis step, applied to cpts248, yielded the cpts248/404 virus, which contains an amino acid change in L called the 404(L) mutation and a nucleotide change in the gene start (GS) signal of M2, called 404(M2) mutation. The remaining mutations, namely 530, 1009 and 1030, each involve a single (different) amino acid change. The 404(M2) mutation is noteworthy because it involves the GS transcription signal (and does not involve a protein-coding sequence) and because this mutation was shown in a minigenome system to be important for synthesis of the mRNA. Kuo et al., *J. Virol.* 71:4944-4953 (1977) (incorporated herein by reference). As outlined in Tables 36, 37, and 39, the amino acid coding changes of the 248, 404(L), and 1009 mutations were inserted into recombinant virus using two nucleotide substitutions for the purpose of improved genetic stability. Also, the 248, 404(M2), 404(L), and 1009 mutations for recombinant virus were each designed to introduce a new restriction site for monitoring purposes, while the 1030 mutation was designed to ablate an existing site.

In the present Example, several pUC118- and pUC119-based constructs were derived from the D50 and D39 plasmids and desired mutations were introduced into these constructs (FIGS. 4, 5). Fragments containing the appropriate mutations were transferred from the pUC constructs back into the D50 or D39 plasmids as indicated, which in turn were assembled into a full-length clone. In this way, six different types of D53 full-length derivative clones were generated (FIGS. 4, 5). In FIG. 5, the D53 constructs lacked the two HEK mutations in F (see FIG. 4).

Mutagenesis was performed using the Muta-Gene® Phagemid in vitro Mutagenesis kit (Bio-Rad, Hercules, Calif.) as recommended by the manufacturer. The mutagenized constructs were transformed into competent *E. coli* DH10B (Life Technologies). Miniprep DNA of the transformant colonies was screened for the presence of the mutation by restriction enzyme digestion (see below) or by nucleotide sequence analysis of the mutagenized region.

The six translationally silent restriction site markers, the 530 mutation ($_{521}$phe→leu), and the 5 cp mutations (Table 39) were introduced into the pUC-based constructs and subcloned into the D50 and D39 plasmids as indicated in FIGS. 4 and 5. The various full-length cDNA constructs were assembled using D50 and D39 constructs containing different combinations of the above mentioned mutations.

In the final cDNA constructs, the presence of the 530 and the cp mutations were confirmed by sequence analysis, while the presence of the silent restriction sites were determined by restriction endonuclease analysis. Each D53-based construct was analyzed using various restriction enzymes (e.g. HpaI, AccI, HindIII, PstI), and the restriction patterns of the newly generated full-length cDNA clones were compared with that of the previously rescued wild-type full-length cDNA clone. This restriction analysis was used to determine if an insertion or deletion of 100 nt or more had occurred during the bacterial amplification of the full-length plasmids.

Transfection was performed as described previously (Collins, et al., *Proc. Natl. Acad. Sci. USA*, 92:11563-11567 (1995), incorporated herein by reference). Briefly, monolayers of HEp-2 cells were infected at an MOI of 1 with recombinant vaccinia virus MVA strain expressing T7 RNA polymerase (MVA-T7) and were transfected using LipofectACE (Life Technologies) with a D53 antigenomic construct plus the N, P, L and M2 (ORF1) pTM1 support plasmids. On day three, supernatants (clarified medium) were passaged onto fresh HEp-2 cells for amplification of rescued virus. Virus suspensions from this first amplification were harvested 5 days after infection and, following inoculation at various dilutions onto monolayers of HEp-2 cells, were overlayed with methylcellulose for plaque enumeration or with agarose for plaque harvest and biological cloning. Plaque enumeration was performed using a monoclonal antibody-horseradish peroxidase staining procedure as previously described (Murphy et al., *Vaccine*, 8:497-502 (1990), incorporated herein by reference). The recovered recombinant viruses were biologically cloned by three successive plaque purifications, and then used to generate virus suspensions following two passages on HEp-2 cells. The biological cloning was important to ensure a homogeneous population of the recovered viruses, as recombination may arise during the first step of the rescue between the plasmid representing the full-length cDNA of RSV and the support plasmids containing RSV genes (Garcin et al., *EMBO J.*, 14:6087-6094 (1995), incorporated herein by reference). These biologically cloned and amplified virus suspensions were used in further molecular genetic or phenotypic characterization of the recombinant viruses. Two biologically cloned recombinant viruses were generated for each of the cDNA constructs (FIG. 5) except for $cp_L530$-sites and cp530-sites, for which only one biological clone was generated. In each case, when there were sister clones, they were indistinguishable on the basis of genetic and biological analyses described below. A representative example of the foregoing constructs corresponding to D53-530-sites (alternatively designated A2 ts530-s cl1cp, or ts530-sites) has been deposited under the terms of the Budapest Treaty with the ATCC and granted the accession number VR-2545.

The recombinant RSVs generated as described above were genetically characterized to determine if they indeed contained each of the introduced mutations. Monolayers of HEp-2 cells were infected with biologically cloned recombinant virus and total RNA was harvested 4 to 5 days post infection as described above. RT was performed using random hexamer primers and the generated cDNA was used as template in PCR using the Advantage™ cDNA PCR Kit (Clontech Lab. Inc., Palo Alto, Calif.) to generate three fragments representing almost the full-length of the recombinant RSV genomes. The PCR fragments corresponded to the RSV genome between nt positions 1-5131, 5949-10751 and 8501-15179. Also, a 544 bp fragment representing a portion of the L gene in the region of the 530 mutation between nt positions 9665 and 10209 was generated. This short PCR fragment was used in cycle sequencing (using 71001 delta TAQ™* Cycle Sequencing Kit, USB, Cleveland, Ohio) to confirm the presence or the absence of the 530 mutation in the recovered recombinant virus, whereas the large PCR products were used in restriction enzyme digestion to confirm the presence of the silent restriction site markers and the cp mutations which were marked with specific restriction sites.

To verify that the recombinant RSVs produced according to the above methods incorporated the desired phenotype, i.e., the phenotype specified by the incorporated sequence change(s), the efficiency of plaque formation (EOP) of the recombinant RSVs and the nonrecombinant control viruses was determined. Specifically, plaque titration at 32, 37, 38, 39 and 40° C. using HEp-2 monolayer cultures in temperature controlled water baths was conducted, as described previously (Crowe et al., Vaccine, 11:1395-1404 (1993); Firestone, et al., Virology 225:419-522 (1996), each incorporated herein by reference). Plaque identification and enumeration was performed using antibody staining as indicated above.

The level of temperature-sensitivity of the recombinant viruses and the wild-type and biologically derived mutant cpts530 viruses is presented in Table 40. These data show that the introduction of the silent restriction sites or the cp mutations does not confer a ts phenotype. This latter observation is consistent with our previous finding that the cpRSV is a $ts^+$ virus (Crowe, et al., Vaccine, 12:691-699 (1994)).

TABLE 40

Comparison of the Efficiency of Plaque Formation[a] of Recombinant and Biologically Derived Viruses in HEp-2 Cells at Various Temperatures.

| Virus | RSV Titer ($\log_{10}$pfu/ml at indicated temp.)[b] | | | | Reduction in Virus titer ($\log_{10}$) at indicated temperature compared to that at 32° C. | |
|---|---|---|---|---|---|---|
| | 32 | 38 | 39 | 40 | 39 | 40 |
| Wild-type[c] | 5.7 | 5.5 | 5.4 | 5.3 | 0.3 | 0.4 |
| r-sites | 5.4 | 5.1 | 5.2 | 5.2 | 0.2 | 0.2 |

TABLE 40-continued

Comparison of the Efficiency of Plaque Formation[a] of Recombinant and Biologically Derived Viruses in HEp-2 Cells at Various Temperatures.

| Virus | RSV Titer ($\log_{10}$pfu/ml at indicated temp.)[b] | | | | Reduction in Virus titer ($\log_{10}$) at indicated temperature compared to that at 32° C. | |
|---|---|---|---|---|---|---|
| | 32 | 38 | 39 | 40 | 39 | 40 |
| rcp-sites | 6.1 | 5.7 | 5.7 | 5.7 | 0.4 | 0.4 |
| r530 | 6.3 | 6.0 | 4.4 | <0.7 | 1.9 | >5.6 |
| r530-sites | 6.4 | 6.1 | 4.4 | <0.7 | 2.0 | >5.7 |
| rcp$_L$530-sites | 5.8 | 5.9 | 3.8 | <0.7 | 2.0 | >5.1 |
| rcp530-sites | 6.3 | 5.0 | 4.1 | <0.7 | 2.2 | >5.6 |
| cpts530[c] | 6.6 | 5.8 | 4.4 | <0.7 | 2.2 | >5.9 |

[a]Efficiency of plaque formation of the various RSV strains was determined by plaque titration on monolayers of HEp-2 cells under semisolid overlay for five days at the indicated temperatures (° C.).
[b]Virus titers are the average of two tests, except for r-sites and r cp-sites where data were derived from a single test.
[c]Biologically derived control viruses.

The above findings confirm that ts phenotype of the biologically derived cpts530 virus is specified by the single mutation identified above as being unique to this attenuated RSV strain. Genetic analysis of the cpts530 strain was confirmed in this context by the introduction of the 530 mutation into a full-length cDNA clone of the A2 wild-type $ts^+$ parent virus, followed by the recovery of a ts recombinant virus bearing the 530 mutation. Analysis of the level of temperature sensitivity of this and additional recombinant viruses containing the 530 and cp mutations revealed that the level of temperature sensitivity specified by the 530 mutation was not influenced by the five cp mutations. Thus, the methods and compositions of the invention identified the 530 mutation as the ts phenotype-specific mutation which is attributed with further attenuation of the cpts530 virus in model hosts over that of its cpRSV parent (Crowe et al., Vaccine, 12:783-90 (1994), Crowe et al., Vaccine, 13:847-855 (1995), each incorporated herein by reference).

In addition to the above findings, introduction of the 1009 mutation or 1030 mutation into recombinant RSV, in combination with the cpts530 mutation, generated recombinants whose levels of temperature sensitivity were the same as those of the respective, biologically derived cpts530/1009 and cpts530/1030 RSV mutants.

The above findings illustrate several important advantages of the recombinant methods and RSV clones of the invention for developing live attenuated RSV vaccines. The insertion of a selected mutation into recombinant RSV, as well as the recovery of mutations from the RSV A2 cDNA clone were relatively efficient. The antigenome cDNA clone used in this example had been modified in the original construction to contain changes at five different loci, involving 6 nucleotide substitutions and one nucleotide insertion. Mutagenized virus are also described containing mutations at an additional twelve loci involving 24 additional nucleotide substitutions. The fact that only the 530 mutation imparted a phenotype detectable in tissue culture indicates the relative ease of manipulation of this large RNA genome. Although recombination between the support plasmids and the full-length clone that is mediated by the vaccinia virus enzymes can occur (Garcin et al., EMBO J., 14:6087-6094 (1995)), its frequency is sufficiently low that each of the 10 viruses analyzed here possessed the mutations present in the cDNA clone from which it was derived. Thus, it is readily feasible to introduce further attenuating mutations in a sequential manner into RSV, to achieve a desired level of attenuation.

The demonstrated use of the present RSV recovery system for direct identification of attenuating mutations and the established success for manipulating recombinant RSV allow for identification and incorporation of other desired mutations into live infectious RSV clones. Previous findings from clinical studies and sequence analysis of the cpRSV virus suggest that the set of five non-ts mutations present in cpRSV are attenuating mutations for seropositive humans (Connors et al., *Virology*, 208:478-84 (1995), Firestone, et al., *Virology*, 225:419-522 (1996), Friedewald et al., *JAMA*, 203:690-694 (1968), Kim et al., *Pediatrics*, 48:745-755 (1971), each incorporated herein by reference). These and other mutations are selected for their confirmed specificity for attenuated and/or ts phenotypes using the methods described here, and can then be assembled into a menu of attenuating mutations. These and other attenuating mutations, both ts and non-ts, can then be introduced into the RSV A2 wild-type virus to produce a live attenuated virus selected for a proper balance between attenuation and immunogenicity. In this regard, it is advantageous that the 530 and other identified ts mutations are not in the G and F glycoproteins which induce the protective immune responses to RSV in humans. This permits the development of an attenuated RSV cDNA backbone with mutations outside of F and G that can serve as a cDNA substrate into which the F and G glycoproteins of RSV subgroup B or those of an epidemiologically divergent subgroup A strain can be substituted for the A2 F and G glycoproteins. In this way, a live attenuated RSV vaccine can be rapidly updated to accommodate antigenic drift within subgroup A strains, and a subgroup B vaccine component can also be rapidly produced.

EXAMPLE X

Construction of an Infectious Recombinant RSV Modified to Incorporate Phenotype-Specific Mutations of RSV Strain cpts248/404

This Example illustrates additional designs for introducing predetermined attenuating mutations into infectious RSV employing the recombinant procedures and materials described herein.

Previous sequence analysis of the RSV A2 cpts248 mutant also identified a single mutation in the L gene, a glutamine to leucine substitution at amino acid position 831 (Table 39; Crowe et al., *Virus Genes*, 13:269-273 (1996), incorporated herein by reference). This mutation was confirmed by the methods herein to be attenuating and ts. Sequence analysis of the further attenuated RSV mutant cpts248/404 revealed two additional mutations, a nt change in the M2 gene start sequence and an amino acid substitution, aspartic acid to glutamic acid at amino acid position 1183 in the L protein (Table 39; Firestone, et al., *Virology*, 225:419-522 (1996), incorporated herein by reference).

The biologically-derived attenuated RSV strain cpts248/404 was reconstructed as a recombinant virus (rA2 cp/248/404) according to the above described methods. cDNA D53 encoding rA2 cp/248/404 virus was constructed by insertion of the sites, HEK, cp, 248 and 404 changes (Table 39). Recombinant virus (rA2 cp/248/404) was recovered, plaque purified and amplified. The presence of the mutations in recombinant virus was analyzed by RT-PCR of viral RNA followed by restriction enzyme digestion or nucleotide sequencing or both. The rA2 cp/248/404 recombinant was recovered using either the pTMLwt or pTML248/404 support plasmid, the latter of which contains all of the mutations in L present in the biologically derived cpts248/404 mutant (Table 39, not including the mutations specific to the 530, 1009, or 1030 viruses). Using the pTML248/404 as a support plasmid precludes loss of 248/404 mutations present in a full length clone by homologous recombination with the support plasmid.

Recombinant viruses were recovered from D53 DNA in which only the sites and HEK mutations were present (rA2 in Table 41), to demonstrate that these changes were indeed phenotypically silent as expected. Recombinant virus containing the sites, HEK and cp mutations was recovered (called rA2 cp in Table 41), to evaluate the phenotypes specified by the cp mutations. Also, as shown in Table 41, separate viruses were constructed containing the sites, HEK and cp background together with (i) the 248 mutation (rA2 cp/248), (ii) the two 404 mutations (rA2 cp/404); and the 404(M2) mutation (rA2 cp/404(M2), and the 404(L) mutation (rA2 cp/404(L)).

These viruses were evaluated in parallel for the ability to form plaques in HEp-2 cells at 32° C., 36° C., 37° C., 38° C. and 39° C. This comparison showed that all viruses formed plaques at 32° C., and showed that the titers of the various virus preparations were within approximately three $\log_{10}$ units of each other, which is within the range of experimental variation typically seen among independent preparations of RSV. The introduction of the added "sites" and HEK mutations into wild-type recombinant virus (to yield virus rA2) did not alter the virus with regard to its ability to grow at the elevated temperatures, as compared with biologically-derived wild-type virus (virus A2 wt). The additional introduction of the cp mutations (to yield virus rA2 cp) also did not alter its ability to grow at elevated temperatures. This is the expected result, because the biologically derived cpRSV from which the mutations were derived does not have the ts phenotype; its mutations are of the host range variety. The 404 mutation in L does not appear to be a ts mutation since rA2 cp/404(L) was not ts. However, this mutation may otherwise prove to be attenuating, as will be determined by further analysis in accordance with the methods herein. Thus, of the two specific mutations in cpts 248/404 virus only the 404M2 mutation is ts. The further addition of the 248 and 404 mutations (to yield rA2 cp/248/404 virus) resulted in a ts phenotype that was essentially equivalent to its biologically-derived equivalent virus as evidenced by being greatly impaired in the ability to form plaques at 36° C.-37° C., with pinpoint plaques being formed at the former temperature. These recombinant viruses incorporated a variety of mutations predicted to have no effect on growth in tissue culture, and additional mutations expected to confer a ts phenotype. Each type of mutation yielded results consistent with these expectations, demonstrating that the RSV genome can be manipulated in a reasonably predictable way.

TABLE 41

Efficiency of Plaque Formation of Selected RSV Mutants

| Virus[1] | Trans-fectant | Virus titer ($\log_{10}$pfu/ml) at indicated temperature (° C.) | | | | | Shut-off temp. |
|---|---|---|---|---|---|---|---|
| | | 32 | 36 | 37 | 38 | 39 | |
| A2 wt[2] | | 5.0 | 4.8 | 5.1 | 4.6 | 4.7 | >39 |
| rA2 | 14-1B-1A2 | 4.9 | 4.2 | 4.4 | 4.5 | 3.9 | >39 |
| rA2cp | 12-2B-1B1 | 5.6 | 5.1 | 4.8 | 3.8 | 3.7 | >39 |
| rA2cp/248 | 12-6A-1A1 | 5.8 | 4.8* | 4.0* | <0.7 | <0.7 | 38 |
| rA2cp/404-L | 16-1A-1A1 | 5.4 | 5.2 | 5.1 | 4.9 | 5.0 | >39 |
| rA2cp/404-M2 | 15-1A-1A1 | 4.9 | <0.7 | <0.7 | <0.7 | <0.7 | 36 |
| rA2cp/404 | 16-4B-1B1 | 3.3 | 1.2* | <0.7 | <0.7 | <0.7 | 36 |
| rA2cp/248/404 | 32-6A-2 | 6.0 | <0.7 | <0.7 | <0.7 | <0.7 | 36 |

TABLE 41-continued

Efficiency of Plaque Formation of Selected RSV Mutants

| Virus[1] | Trans-fectant | Virus titer (log₁₀pfu/ml) at indicated temperature (° C.) | | | | | Shut-off temp. |
|---|---|---|---|---|---|---|---|
| | | 32 | 36 | 37 | 38 | 39 | |
| rA2cp/248/404/530 | 13-4B-3 | 5.7 | 4.7* | 2.5* | nd | <0.7 | 37 |
| cpts248/404 (WLVP)[2] | | 5.1 | <0.7 | <0.7 | <0.7 | <0.7 | 36 |

[1]Recombinant (r) viruses have been plaque purified and amplified in HEp-2 cells. Note that the stocks of recombinant and biologically-derived viruses had not been adjusted to contain equivalent amounts of pfu/ml: the level of variation seen here is typical for RSV isolates at an early stage of amplification from plaques. Each recombinant virus contains the L-gene sites and the F-gene HEK mutations. The code in the "Transfectant" column refers to the transfection and plaquing history.
[2]Biologically derived viruses: A2 wt and cpts248/404 (WLVP L16210B-150).
*Pin-point plaque size Table 41 shows further characterization of mutations specific to the 248 and 404 mutagenesis steps. Specifically, viruses were constructed using the sites, HEK and cp background with the addition of: (i) the 248 mutation (to yield virus rA2 cp/248), (ii) the two 404 mutations (virus rA2 cp/404); or the 404(M2) mutation (virus rA2 cp/404(M2)) (Table 39). Each of these three viruses exhibited the ts phenotype, providing direct identification of these mutations as being ts. The 248 mutation provided a lower level of temperature sensitivity, whereas the 404(M2) mutation was highly ts and was not augmented by the addition of the 404(L) mutation. It was remarkable that the 404(M2) mutation is ts, since it is a point mutation in a transcription initiation, or gene start (GS), signal, and this type of mutation has never been shown to be ts.

EXAMPLE XI

Construction of Recombinant RSV Combining Predetermined Attenuating Mutations From Multiple Attenuated Parent Viruses The present Example illustrates a combinatorial design for producing a multiply attenuated recombinant RSV (rA2 cp/248/404/530) which incorporates three attenuating mutations from one biologically derived RSV strain (specifically cpts248/404) and an additional attenuating mutation from another RSV strain (cpts530). This recombinant RSV exemplifies the methods of the invention for engineering stepwise attenuating mutations to fine tune the level of attenuation in RSV vaccines, wherein multiple mutations contribute to a further attenuated phenotype of the vaccine strain and provide for enhanced genetic stability.

The cDNAs and methods of Examples 1x and X above were used to construct a D53 cDNA containing the sites, HEK, cp, 248, 404 and 530 changes (Table 39). This involved a combination of attenuating mutations from four separate biologically-derived viruses, namely cpRSV, cpts248, cpts248/404 and cpts530. Recombinant virus (rA2 cp/248/404/530) was recovered, plaque purified and amplified. The presence of the mutations was analyzed by RT-PCR of viral RNA followed by restriction enzyme digestion or nucleotide sequencing or both. rA2 cp/248/404/530 lacked the 248 mutation in L, but possessed the 530 mutation and the other 248/404 mutation.

The rA2 cp/248/404 virus was evaluated for its ability to form plaques in HEp-2 cells at 32° C., 36° C., 37° C, 38° C. and 39° C. as described above (Table 41). All of viruses formed plaques at 32° C. and were similar to wild-type in the efficiency of growth at this temperature. The rA2 cp/248/404/530 virus was essentially equivalent to the biologically-derived cpts248/404 virus with regard to the ts phenotype, evidenced by being greatly impaired in the ability to form plaques at 37° C. Thus, the addition of the 530 mutation to the rA2 cp/248/404 background did not increase its ts phenotype, however, the recombinant lacked the 248 mutation in L.

Based on this and the foregoing Examples, the invention allows recovery of a wide variety of recombinant viruses containing two or more ts mutations from the set of mutations which have been identified and confirmed from biologically derived RSV mutants, for example the 248, 404, 530, 1009, or 1030 biological mutants. Examples of such recombinant viruses include RSV having a combination of 248/404/530 mutations, 248/404/1009 mutations, 248/404/1030 mutations, 248/404/530/1009 mutations, 248/404/530/1030 mutations, 248/404/530/1030 mutations, 248/404/1009/1030 mutations, or other combinations of attenuating mutations disclosed herein. In addition, recombinant RSV incorporating one or more ts mutations identified from biologically derived RSV mutants can be combined with other mutations disclosed herein, such as attenuating gene deletions or mutations that modulate RSV gene expression. One such example is to combine 248/404 mutations with an SH gene deletion in a recombinant clone, which yields a viable vaccine candidate. A host of other combinatorial mutants are provided as well, which can incorporate any one or more ts mutations from biologically derived RSV and any one or more other mutations disclosed herein, such as deletions, substitutions, additions and/or rearrangements of genes or gene segments. The cp mutations, which are attenuating host range rather than attenuating ts mutations, also can be included along with one or more other mutations within the invention. This provides a panel of viruses representing a broad spectrum in terms of individual and combined levels of attenuation, immunogenicity and genetic stability. These attenuating mutations from biologically derived RSV mutants can be further combined with the various other structural modifications identified herein, which also specify desired phenotypic changes in recombinant RSV, to yield yet additional RSV having superior vaccine characteristics.

EXAMPLE XII

Recovery of Infectious Respiratory Syncytial Virus Expressing An Additional, Foreign Gene The methods described above were used to construct recombinant RSV containing an additional gene, encoding chloramphenicol acetyl transferase (CAT). The CAT coding sequence was flanked by RSV-specific gene-start and gene-end motifs, the transcription signals for the viral RNA-dependent RNA polymerase. Kuo et al., J. Virol. 70:6892-6901 (1996) (incorporated herein by reference). The RSV/CAT chimeric transcription cassette was inserted into the intergenic region between the G and F genes of the complete cDNA-encoded positive-sense RSV antigenome, and infectious CAT-expressing recombinant RSV was recovered. The CAT mRNA was efficiently expressed and the levels of the G and F mRNAs were comparable to those expressed by wild-type recombinant RSV. The CAT-containing and wild-type viruses were similar with regard to the levels of synthesis of the major viral proteins.

Plasmid D46 was used for construction of cDNA encoding RSV antigenomic RNA containing the CAT gene. (Plasmids D46 and D53, the latter being described above, are different preparations of the same antigenome cDNA.) D46 which encodes the complete, 15,223-nucleotide RSV antigenome (one nucleotide longer than that of wild-type RSV) and was used to produce recombinant infectious RSV, as described above. During its construction, the antigenome cDNA had been modified to contain four new restriction sites as markers. One of these, a StuI site placed in the intergenic region between the G and F genes (positions 5611-5616 in the 3'-5' sequence of the wild-type genome), was chosen as an insertion site for the foreign CAT gene. A copy of the CAT ORF flanked on the upstream end by the RSV GS signal and on the downstream end by the RS GE signal was derived from a previously-described RSV-CAT minigenome (Collins et al., Proc. Natl. Acad. Sci. USA 88:9663-9667 (1991) and Kuo et al., J. Virol. 70:6892-6901 (1996), incorporated by reference herein). The insertion of this RSV/CAT transcription cassette into the StuI site yielded the D46/1024CAT cDNA (deposited under the terms of the Budapest Treaty with the ATCC and granted the accession number VR-2544), which increased the length of the encoded antigenome to a total of 15,984 nucleotides. And, whereas wild-type RSV encodes ten major subgenomic mRNAs, the recombinant virus predicted from the D46/1024CAT antigenome would encode the CAT gene as an eleventh mRNA. The strategy of construction is shown in FIG. 6.

Producing infectious RSV from cDNA-encoded antigenomic RNA, as described above, involved coexpression in HEp-2 cells of five cDNAs separately encoding the antigenomic RNA or the N, P, L or M2(ORF1) protein, which are necessary and sufficient for viral RNA replication and, transcription. cDNA expression was driven by T7 RNA polymerase supplied by a vaccinia-T7 recombinant virus based on the MVA strain. The MVA-T7 recombinant virus produced infectious progeny sufficient to cause extensive cytopathogenicity upon passage, and therefore, cytosine arabinoside, an inhibitor of vaccinia virus replication, was added 24 h following the transfection and maintained during the first six passages. The use of cytosine arabinoside was not required, however, and was not used in later examples herein.

Two antigenome cDNAs were tested for the recovery of RSV: the D46 cDNA, and the D46/1024CAT cDNA. Each one yielded infectious recombinant RSV. Cells infected with the D46/1024CAT recombinant virus expressed abundant levels of CAT enzyme. For each virus, transfection supernatants were passaged to fresh cells, and a total of eight serial passages were performed at intervals of five to six days and a multiplicity of infection of less than 0.1 PFU per cell.

The CAT sequence in the D46/1024CAT genome was flanked by RSV GS and GE signals, and thus should be expressed as an additional, separate, polyadenylated mRNA. The presence of this predicted mRNA was tested by Northern blot hybridization of RNA from cells infected with D46/1024CAT virus or D46 virus at the eighth passage. Hybridization with a negative-sense CAT-specific riboprobe detected a major band which was of the appropriate size to be the predicted CAT mRNA, which would contain 735 nucleotides not including poly(A). This species was efficiently retained by oligo(dT) latex particles, showing that it was polyadenylated. In some cases, a minor larger CAT-specific species was detected which was of the appropriate size to be a G-CAT readthrough mRNA. The D46/1024CAT virus had been subjected to eight passages at low multiplicity of infection prior to the infection used for preparing the intracellular RNA. There was no evidence of shorter forms of the CAT mRNA, as might have arisen if the CAT gene was subject to deletion.

Replicate blots were hybridized with negative-sense riboprobe specific to the CAT, SH, G or F gene, the latter two genes flanking the inserted CAT gene. The blots showed that the expression of the subgenomic SH, G and F mRNAs was similar for the two viruses. Phosphoimagery was used to compare the amount of hybridized radioactivity in each of the three RSV mRNA bands for D46/1024CAT and D46. The ratio of radioactivity between D46/1024CAT and D46 was determined for each mRNA: SH, 0.77; G, 0.87; and F, 0.78. The deviation from unity probably indicates that slightly less RNA was loaded for D46/1024CAT versus D46, although it is also possible that the overall level of mRNA accumulation was slightly less for D46/1024CAT RSV. The demonstration that the three ratios were similar confirms that the level of expression of each of these mRNAs was approximately the same for D46/1024CAT versus D46. Thus, the insertion of the CAT gene between the G and F genes did not drastically affect the level of transcription of either gene.

To characterize viral protein synthesis, infected HEp-2 cells were labeled with [$^{35}$S]methionine, and cell lysates were analyzed by PAGE either directly or following immunoprecipitation under conditions where recovery of labeled antigen was essentially complete. Precipitation with a rabbit antiserum raised against purified RSV showed that the D46/1024CAT and D46 viruses both expressed similar amounts of the major viral proteins Fl, N, P, M, and M2. That a similar level of M2 protein was recovered for each virus was noteworthy because its gene is downstream of the inserted CAT gene. Accumulation of the F protein, which is encoded by the gene located immediately downstream of the insertion, also was examined by immunoprecipitation with a mixture of three anti-F monoclonal antibodies. A similar level of the $F_1$ subunit was recovered for each virus. Phosphorimagery analysis of the major viral proteins mentioned above was performed for several independent experiments and showed some sample-to-sample variability, but overall the two viruses could not be distinguished on the basis of the level of recovered proteins. Precipitation with anti-CAT antibodies recovered a single species for the D46/1024CAT but not for the D46 virus. Analysis of the total labeled protein showed that the N, P and M proteins could be detected without immunoprecipitation (although detection of the latter was complicated by its comigration with a cellular species) and confirmed that the two viruses yielded similar patterns. The position corresponding to that of the CAT protein contained more radioactivity in the D46/1024CAT pattern compared to that of D46, as was confirmed by phosphorimagery of independent experiments. This suggested that the CAT protein could be detected among the total labeled proteins without precipitation, although this demonstration was complicated by the presence of a comigrating background band in the uninfected and D46-infected patterns.

RT-PCR was used to confirm the presence of the CAT gene in the predicted location of the genome of recombinant RSV. Total intracellular RNA was isolated from the cell pellet of passage eight of both D46/1024CAT and D46 RSV. Two primers were chosen that flank the site of insertion, the StuI restriction endonuclease site at RSV positions 5611-5616: the upstream positive-sense primer corresponded to positions 5412-5429, and the downstream negative-sense one to positions 5730-5711. The positive-sense primer was used for the RT step, and both primers were included in the PCR.

RT-PCR of the D46 virus yielded a single product that corresponded to the predicted fragment of 318 nucleotides, representing the G/F gene junction without additional foreign sequence. Analysis of D46/1024CAT viral RNA yielded a single product whose electrophoretic mobility corresponded well with the predicted 1079 nucleotide fragment, representing the G/F gene junction containing the inserted CAT transcription cassette. The latter PCR yielded a single major band; the absence of detectable smaller products indicated that the population of recombinant genomes did not contain a large number of molecules with a deletion in this region. When PCR analysis was performed on D46/1024CAT virus RNA without the RT step, no band was seen, confirming that the analysis was specific to RNA. Thus, the RT-PCR analysis confirmed the presence of an insert of the predicted length in the predicted location in the genomic RNA of the D46/1024CAT recombinant virus.

Enzyme expression was used to measure the stability of the CAT gene. Cell pellets from all of the passages beginning with the third were tested for CAT expression. For the virus D46/1024CAT, all these assays displayed conversion of [$^{14}$C] labeled chloramphenicol into acetylated forms. To investigate stability of expression, virus from 20 or 25 individual plaques from passage three or eight, respectively, was analyzed for CAT expression. All samples were positive, and the level of expression of CAT was similar for each of the 25 isolates from passage eight, as judged by assay of equivalent aliquots of cell lysate. This demonstrated that the activity of the CAT protein encoded by each isolate remained unimpaired by mutation.

To determine plaque morphology and size, beginning with the second passage, one-eighth of the medium supernatant (i.e., 0.5 ml) harvested from each passage stage was used to infect fresh HEp-2 cells in six-well plates that were incubated under methylcellulose overlay for five to seven days. The cells were then fixed and stained by incubation with monoclonal antibodies against RSV F protein followed by a second antibody linked to horseradish peroxidase. Earlier, it had been observed that recombinant RSV produced from cDNA D46 was indistinguishable from a naturally occurring wild-type RSV isolate with regard to efficiency of plaque formation over a range of temperatures in vitro, and the ability to replicate and cause disease when inoculated into the respiratory tract of previously uninfected chimpanzees. Thus, the D46 recombinant RSV was considered to be a virulent wild-type strain. The plaques produced by the D46 and D46/1024CAT recombinant viruses were compared by antibody staining. Plaque morphology was very similar for the two viruses, although the average diameter of the CAT-containing recombinant plaques was 90 percent of that of the D46 virus, based on measurement of thirty randomly-selected plaques for each virus.

The efficiency of replication in tissue culture of the D46 and D46/1024CAT viruses was compared in a single step growth cycle. Triplicate monolayers of cells were infected with either virus, and samples were taken at 12 h intervals and quantitated by plaque assay. The results showed that the production of D46/1024CAT virus relative to D46 was delayed and achieved a maximum titer which was 20-fold lower.

These results show that it is possible to construct recombinant, helper-independent RSV expressing a foreign gene, in this instance the CAT gene. The recombinant RSV directed expression of the predicted polyadenylated subgenomic mRNA that encoded CAT protein, the protein being detected both by enzyme assay and by radioimmunoprecipitation. Other examples have produced RSV recombinants with the luciferase gene inserted at the same CAT site, or with the CAT or luciferase genes inserted between the SH and G genes. These viruses also exhibit reduced growth, whereas the numerous wild-type recombinant viruses recovered exhibit undiminished growth. This indicates that the reduced growth indeed is associated with the inserted gene rather than being due to chance mutation elsewhere in the genome. The level of attenuation appears to increase with increasing length of the inserted gene. The finding that insertion of a foreign gene into recombinant RSV reduced its level of replication and was stable during passage in vitro suggests that this provides yet another means for effecting attenuation for vaccine use. Also, the insertion into recombinant RSV of a gene expressing a protein having antiviral activity, such as gamma interferon and IL-2, among others, will yield attenuation of the virus due to activity of the expressed antiviral protein.

In addition to demonstrating recovery of RSV having modified growth characteristics, the examples herein illustrate other important methods and advantages for gene expression of recombinant RSV and other nonsegmented, negative strand viruses. For example, the data provided herein show that foreign coding sequences can be introduced as a separate transcription cassette which is expressed as a separate mRNA. These results also show that RSV is tolerant of substantial increases in genome length, e.g., of 762 nucleotides in the case of the CAT gene to a total of 15,984 nucleotides (1.05 times that of wild-type RSV). The luciferase gene that was successfully recovered is almost three times longer.

The viral RNA-dependent RNA polymerases are known to have an error-prone nature due to the absence of proofreading and repair mechanisms. In RNA virus genomes, the frequency of mutation is estimated to be as high as $10^{-4}$-$10^{-5}$ per site on average (Holland et al., *Curr. Top. Microbiol. Immunol.* 176:1-20 (1992) and references therein). In the case of the recombinant D46/1024CAT RSV produced here, correct expression of the foreign gene would be irrelevant for virus replication and would be free to accumulate mutations. The passages described here involved a multiplicity of infection less than 0.1 PFU per cell, and the duration of each passage level indicated that multiple rounds of infection were involved. While yields of infectious virus from RSV-infected tissue culture cells typically are low, intracellular macromolecular synthesis is robust, and the poor yields of infectious virus seem to represent an inefficient step in packaging rather than low levels of RNA replication. Thus, the maintenance of CAT through eight serial passages involved many rounds of RNA replication. It was surprising that the nonessential CAT gene remained intact and capable of encoding fully functional protein in each of the 25 isolates tested at the eighth passage. Also, RT-PCR analysis of RNA isolated from passage eight did not detect deletions within the CAT gene.

A second infectious RSV-CAT recombinant was constructed in which the CAT transcription cassette was inserted into an XmaI site which had been engineered into the SH-G intergenic region (which is one position closer to the promoter than the F-G intergenic used above). The growth characteristics of this recombinant were similar to those of the D46/1024 CAT recombinant, whereas the level of CAT expression was approximately two to three-fold higher, consistent with its more promoter-proximal location. This illustrates that a foreign gene can be inserted at a second, different site within the genome and its level of expression altered accordingly. In principle, any portion of the genome should be able to accept the insertion of a transcription unit encoding a foreign protein as long as the insertion does not disrupt a mRNA-encoding unit and does not interfere with the cis-acting sequence elements found at both ends of the genome.

An infectious recombinant RSV was also recovered in which the CAT gene was replaced by that of the luciferase (LUC) marker enzyme. The LUC coding sequence is approximately 1,750 bp (three times the size of CAT), and is larger than any of the RSV genes except for F and L. It was inserted at either the SH-G or G-F intergenic regions and infectious recombinant virus was recovered. The LUC viruses were further attenuated relative to the CAT viruses with regard to growth in tissue culture, suggesting that increases in the size of the genome lead to decreases in growth efficiency. Characterization of these CAT and LUC viruses will determine the effect of foreign gene size on virus gene expression and growth, such as how much is due to the introduction of the additional set of transcription signals, and how much is due to increased genome length.

In the minireplicon system, an RSV-CAT minigenome was modified such that the transcriptional unit is in the "sense" orientation in the positive-sense antigenome rather than the minigenome. Thus, subgenomic mRNA can be made only if the polymerase is capable of transcription of the antigenome replicative intermediate. Interestingly, when complemented by plasmid-expressed N, P, L and M2 ORF1 protein, this inverse RSV-CAT minigenome was capable of synthesizing subgenomic, polyadenylated, translatable mRNA. Efficient mRNA synthesis was dependent on the M2 ORF1 protein, as is the case for minigenome transcription. The level of mRNA relative to its antigenome template was approximately the same as the ratio of mRNA to minigenome template made by a standard minireplicon. This indicates that the antigenome, as well as the genome, can be used to accept a foreign transcriptional unit. Thus, expression of a foreign gene can be achieved without placing it into the genome transcriptional order. This had the advantage that the foreign gene is not be part of the transcriptional program of the genome and thus will not perturb the relative levels of expression of these genes.

Because most of the antigenic difference between the two RSV antigenic subgroups resides in the G glycoprotein, recombinant RSV can be constructed to express the G protein of the heterologous subgroup as an additional gene to yield a divalent vaccine. Envelope protein genes of some other respiratory viruses, such as human parainfluenza 3 virus, also can be inserted for expression by recombinant RSV. Other uses include coexpression of immune modulators such as interleukin 6 to enhance the immunogenicity of infectious RSV. Other uses, such as employing modified RSV as described herein as a vector for gene therapy, are also provided.

EXAMPLE XIII

Recombinant RSV Having a Deletion of the SH Gene

This example describes production of a recombinant RSV in which expression of the SH gene has been ablated by removal of a polynucleotide sequence encoding the SH mRNA and protein. The SH protein is a small (64 amino acids in the case of strain A2) protein which contains a putative transmembrane domain at amino acid positions 14-41. It is oriented in the membrane with the C-terminus exposed and there is a potential glycosylation site in both the C-terminal and N-terminal domains (Collins et al., *J. Gen. Virol.* 71:3015-3020 (1990), incorporated herein by reference). In infected cells, the SH protein of strain A2 accumulates in four major forms; (i) SH0 (Mr 7500), the full-length, unglycosylated form that is the most abundant (Olmsted et al., *J. Virol.* 63:2019-2029 (1989), incorporated herein by reference); (ii) SHg (Mr 13,000-15,000), which is the full length form containing a single N-linked carbohydrate chain; (iii) SHp (Mr 21,000-40,000), which is a modified version of SHg in which the single N-linked carbohydrate chain is modified by the addition of polylactosaminoglycan (Anderson et al., *Virology* 191:417-430 (1992), incorporated herein by reference); (iv) SHt (Mr 4800), a truncated unglycosylated form which is initiated from the second methionyl codon (position 23) and which alone among the different forms does not appear to be transported to the cell surface. The SH0 and SHp forms have been detected in purified virions, suggesting that there is a selectivity at the level of virion morphogenesis (Collins et al., supra, (1993)).

Among the paramyxoviruses, ostensibly similar SH proteins have been found in simian virus 5 (Hiebert et al., *J. Virol.* 55:744-751 (1985), incorporated herein by reference), bovine RSV (Samal et al., *J. Gen. Virol.* 72:1715-1720 (1991), incorporated herein by reference), mumps virus (Elango et al., *J. Virol.* 63:1413-1415 (1989), incorporated herein by reference), and turkey rhinotracheitis virus (Ling et al., *J. Gen. Virol.* 73:1709-1715 (1992), incorporated herein by reference). The small hydrophobic VP24 protein of filoviruses is thought to be a surface protein (Bukreyev et al., *Biochem. Mol. Biol. Int.* 35:605-613 (1995), incorporated herein by reference) and is also a putative counterpart of the paramyxovirus SH protein.

The function of the SH protein has not been heretofore defined. In a fusion assay in cells expressing plasmid-encoded proteins, efficient fusion of CV-1 cells by RSV proteins required the coexpression of the F, G and SH proteins (Heminway et al., *Virology* 200:801-805 (1994), incorporated herein by reference). Without wishing to be bound by theory, several functions of the RSV SH protein may exist: (i) it may enhance viral attachment or penetration (Heminway et al., supra.); (ii) it may be involved in virion morphogenesis; or (iii) it may have a "luxury" function distinct from a direct role in virus growth, such as interaction with components of the host immune system as recently described for the V protein of Sendai virus (Kato et al., *EMBO J.* 16:178-587 (1997), incorporated herein by reference). Function (i) or (ii) above may involve an activity that modifies membrane permeability, as has been suggested by others for some hydrophobic proteins of various viruses (Maramorosh et al. (eds.), *Advances in Virus Research* 45:61-112 (1995); Schubert et al., *FEBS Lett.* (1996); Lamb et al., *Virology* 229:1-11 (1997), each incorporated herein by reference). All of these potential activities of the SH protein may be incorporated within the invention according to the methods and strategies described herein, to yield additional advantages in RSV recombinant vaccines.

To produce a recombinant RSV having a selected disruption of SH gene function, the SH gene was deleted in its entirety from a parental RSV clone. The above described plasmid D46 plasmid is one such clone which encodes a complete antigenomic RNA of strain A2 of RSV, which was used successfully to recover recombinant RSV (See U.S. patent application Ser. No. 08/720/132; U.S. Provisional Patent Application No. 60/007,083, each incorporated herein by reference). This antigenome is one nt longer than the naturally-occurring genome and contains several optional restriction site markers. The D46 plasmid was modified so that the complete SH gene was deleted, yielding plasmid D46/6368 (FIG. 7).

The construction of plasmid D46/6368 involved two parental subclones, D50, which contains a T7 promoter attached to the left-hand end of the genome encompassing the leader region to the beginning of the L gene, and D39, which contains the end of M2 and the L gene attached at the downstream end to a hammerhead ribozyme and tandem T7 transcription terminators. The D50 plasmid was digested with ScaI (position 4189 in the complete 15,223-nucleotide antigenome sequence) and PacI (position 4623) and the resulting 435 bp fragment was replaced with a short DNA fragment constructed from two complementary oligonucleotides. In this exemplary deletion, the 435-bp fragment located between the ScaI and PacI sites corresponds to the very downstream end of the M gene, its GE signal, and the complete SH gene except for the last six nucleotides of its GE sequence (FIG. 7). This was replaced with the two synthetic partially complementary oligonucleotides, 5'-ACT-CAAATAAGTTAATAAAAAATATCCCGGGAT-3' [SEQ ID NO: 3] (positive-sense strand, the M GE sequence is underlined, XmaI site is shown in italics, and the ScaI half-site and PacI sticky end at the left and right respectively are shown in bold italics) and 5'-CCCGGGATATTTTTTAT-TAACTTATTTGAGT-3' [SEQ ID NO: 4] (negative-sense strand). This cDNA, called D50/6368, was used to accept the BamHI-MluI fragment of D39 containing the remainder of the antigenome. This resulted in the plasmid D46/6368 which encoded the complete antigenome except for the deleted sequence, an antigenome that is 14,825 nt long, 398 nt shorter than the antigenome encoding by the wild-type plasmid D46. The sequence of the insert was confirmed by dideoxynucleotide sequence analysis. An XmaI site was optionally introduced so that inserts could easily be placed at this position in subsequent work.

Transfection, growth and passaging of virus, plaque purification, and antibody staining of viral plaques were generally performed according to the procedures described hereinabove, but with two modifications: (i) cytosine arabinoside, an inhibitor of vaccinia virus was not used; (ii) HEp-2 cells used for transfection were incubated at either 32° C. or 37° C., and all recovered viruses were propagated at 37° C.

To evaluate total RNA and poly(A)+ RNA, cells were scraped and resuspended in 100 µl of water, and total intracellular RNA was isolated using Trizol™ reagent (Life Technologies) according the manufacturer's recommendation (except that following isopropanol precipitation the RNA was extracted twice with phenol-chloroform followed by ethanol precipitation. Poly(A)+ RNA was isolated using the Oligotex mRNA kit (Qiagen, Chatsworth, Calif.).

To conduct reverse transcription and polymerase chain reaction (RT-PCR), the SH gene region was copied into cDNA and amplified. Total intracellular RNA was subjected to reverse transcription with Superscript II (Life Technologies) using as primer the positive sense synthetic oligonucleotide 5'-GAAAGTATATATTATGTT-3' [SEQ ID NO: 5]. This primer is complementary to nucleotides 3958-3975, which are upstream of the SH gene. An aliquot of the cDNA product was used as template in PCR using as primer the above-mentioned oligonucleotide together with the negative-sense oligonucleotide 5'-TATATAAGCACGATGATATG-3' [SEQ ID NO:6]. This latter primer corresponds to nucleotides 4763-4782 of the genome, which are downstream the SH gene. An initial 2 min. denaturation step was performed during which the Taq DNA polymerase was added, and then 33 cycles were performed (denaturation, 1 min. at 94° C.; annealing, 1 min. at 39° C.; elongation, 2 min. at 72° C.). The products were then analyzed on a 2.5% agarose gel.

For Northern blot hybridization, RNA was separated by electrophoresis on agarose gels in the presence of formaldehyde and blotted to nitrocellulose. The blots were hybridized with [$^{32}$P]-CTP-labeled DNA probes of the M, SH, G, F, M2 and L genes which were synthesized individually Ln vitro from cDNAs by Klenow polymerase with random priming using synthetic hexamers (Boehringer Mannheim, Indianapolis, Ind.). Hybridized radioactivity was quantitated using the Molecular Dynamics (Sunnyvale, Calif.) Phosphorlmager 445 SI.

$^{35}$S methionine labeling, immunoprecipitation, and polyacrylamide gel electrophoresis procedures were performed as described previously (Bukreyev et al., supra). Electrophoresis was conducted using pre-cast 4%-20% Tris-glycine gels (Novex).

For In vitro growth analysis, HEp-2, 293, CV-1, Vero, MRC-5, African green monkey kidney (AGMK), bovine turbinate (BT), and MDBK cell monolayers were used in a single-step growth cycle analysis. For each type of cells, three 25-cm$^2$ culture flasks were infected with 10$^7$ PFU of the D46/6368 (SH-minus) or D46 (wild-type recombinant) virus. Opti-MEM (Life Technologies) with 2% fetal bovine serum (FBS) (Summit) was used for HEp-2, Vero, 293, BT, MRC-5, and AGMK cells; E-MEM (Life Technologies) with 1%, or 2% FBS was used for MDBK or BT cells, respectively. After 3 hours adsorption at 37° C., cells were washed with 4 ml medium three times each, 4 ml medium was added, and the cells were incubated at 37° C. with 5% $CO_2$. Then, at various times after inoculation (see below), 200 µl aliquots of medium supernatant were removed, adjusted to contain 100 mM magnesium sulfate and 50 mM HEPES buffer (pH 7.5), flash-frozen and stored at −70° C. until titration; each aliquot taken was replaced with an equal amount of fresh medium. For titration, HEp-2 cells (24-well plates) were infected with 10-fold dilutions of aliquots, and overlaid with Opti-MEM containing 2% FBS and 0.9% methylcellulose (MCB Reagents). After incubation for 7 days, the medium was removed and the cell monolayer was fixed with 80% methanol at 4° C. The plaques were incubated with a mixture of three monoclonal antibodies specific to RSV F protein, followed by goat anti-mouse IgG conjugated with horseradish peroxidase (Murphy et al., Vaccine 8:497-502 (1990), incorporated herein by reference).

Recovery of infectious, recombinant RSV lacking SH gene function followed the above described procedures, wherein the D46/6368 plasmid was cotransfected into HEp-2 cells together with plasmids encoding the N, P, L and M2 ORF1 proteins, and the cells were simultaneously infected with a recombinant of the MVA strain of vaccinia virus that expresses T7 RNA polymerase. Parallel cultures were transfected with the D46 wild-type cDNA under the same conditions. Medium supernatants were harvested three days post-transfection and passaged once. After 6 days incubation at 37° C., an aliquot of medium supernatant representing each original transfection was plated onto fresh HEp-2 cells, incubated for six days under methylcellulose overlay, and stained by reaction with a mixture of three monoclonal antibodies specific to the RSV F protein followed by a second antibody conjugated with horseradish peroxidase. Morphology of plaques of wild-type recombinant virus versus the SH-minus virus were very similar, except that the latter plaques were larger. Notably, plaques formed by each of the control and SH minus viruses contained syncytia.

To confirm the absence of the SH gene in the genome of recovered D46/6368 virus, cells were infected with the first passage of wild-type or SH-minus recombinant virus, and total intracellular RNA was recovered and analyzed by RT-PCR. RT was performed with a positive-sense primer that annealed upstream of the SH gene, at genome positions 3958-3975. PCR was performed using the same primer together with a negative-sense primer representing nucleotides 4763-4782, downstream of the SH gene. As shown in FIG. 8, wild-type D46 virus yielded a single PCR product corresponding to the predicted 824 bp fragment between positions 3958 and 4782 (lane 3), In the case of the D46/6368 virus, the PCR product was shorter and corresponded to the predicted 426 bp fragment containing the deletion (lane 2). The generation of The PCR products was dependent on the RT step, showing that they were derived from RNA rather than DNA, as expected. Thus, RT-PCR analysis demonstrates that the genome of D46/6368 virus contains the expected 398-nucleotide deletion at the SH locus.

To examine the transcription of genes located upstream and downstream the SH gene, poly(A)+ mRNA was isolated from cells infected with the D46 or D46/6368 virus and analyzed by Northern blot hybridization (FIG. 9). The intracellular RNA purposefully was not denatured prior to poly(A)+ selection; thus, as shown below, the selected mRNA also contained genomic RNA due to sandwich hybridization to mRNA. This permitted simultaneous analysis of mRNA and genome, and the ability to relate the abundance of each mRNA to genomic RNA contained in the same gel lane made it possible to compare mRNA abundance between lanes. The blots were hybridized with [$^{32}$P]-labeled DNA probes which were synthesized from cDNA clones by random priming and thus contained probes of both polarities. Selected probes represented individually the M, SH, G, F, M2, and L genes (FIG. 9).

The SH probe hybridized to both subgenomic SH mRNA and genomic RNA in the case of the wild-type D46 virus but not for the D46/6368 virus (FIG. 9). The probes specific for other RSV genes hybridized in each case to the genome and to the expected major monocistronic mRNA for both viruses. In addition, a number of previously described dicistronic readthrough mRNAs also were detected with both viruses, such as the F-M2, G-F and P-M mRNAs.

The G-specific probe hybridized to an novel species specific to the D46/6368 virus, which appeared to be a readthrough of the M and G genes. This combination was possible due to the deletion of the intervening SH gene. The same species, specific to D46/6468 but not D46, appeared to hybridize in addition only with the M-specific probe.

Relative levels of synthesis were subsequently quantified for each mRNA of D46 versus D46/6368. For each pairwise comparison, the amount of mRNA in a given gel lane was normalized relative to the amount of genome. This comparison showed D46/6368 versus D46 expressed the following mRNAs in the indicated ratio (D46/6368 to D46): M (1.1), G (1.3), F (0.61), M2 (0.32), and L (0.17).

To compare viral proteins synthesized by D46 versus D46/6368 RSV clones, HEp-2 cells were infected at an input multiplicity of infection of 2 PFU per cell and labeled by incubation with [$^{35}$S]methionine from 16 to 20 h post-infection. Cell lysates were prepared and analyzed directly or following immunoprecipitation using a rabbit antiserum raised against purified RSV virions. Total and immunoprecipitated proteins were subjected to PAGE on 4-20% gradient gels (FIG. 10).

In the case of the D46 virus, the pattern of immunoprecipitated proteins included the unglycosylated form of SH protein, SH0, and the N-glycosylated form, SHg, whereas neither species was evident for the D46/6368 virus (FIG. 10). The SH0 protein also could be detected in the pattern of total infected-cell proteins in the case of D46, but not D46/6368. Otherwise, the patterns of proteins synthesized by D46 versus D46/6368 were essentially indistinguishable. Phosphorimager analysis of the N, P, M, F$_1$, and M2 proteins in the pattern of immunoprecipitated proteins showed that equivalent amounts were made by both viruses (FIG. 10).

As described above, preliminary comparison of the D46 and D46/6368 viruses by plaque assay indicated a difference in growth in vitro. Therefore, we further compared the two viruses with regard to plaque size in HEp-2 cells. Particular care was taken to ensure that the monolayers were young and not overgrown, since these variables can effect plaque size. After 7 days incubation at 37° C. under methylcellulose, the monolayers were fixed with methanol and photographed. This revealed a striking difference in plaque size. Measurement of 30 plaques of each virus viruses showed that the plaques of the D46/6368 virus were on average 70% larger than those of the D46 virus.

Further experiments were undertaken to render a growth curve analysis for eight different cell lines representing different species and different tissue origins, to compare efficiencies of replication of the D46 and D46/6368 viruses (Table 42). Triplicate monolayers of each type of cell were infected with either virus, and samples were taken at 12 or 24 hours intervals, and quantitated by plaque assay and antibody staining. Surprisingly, the D46/6368 virus grew to higher titers relative to the D46 wild-type in three cell lines, namely HEp-2, 293 and AGMK-21 cells. In HEp-2 cells (FIG. 11), the titer of progeny D46/6368 virus at 36 hours post infection was 2.6 fold greater than for the D46 virus. In 293 cells (FIG. 12), the yield of D46/6368 virus was two fold greater than that of the D46 virus at 36 hours post infection, and this difference increased to 4.8 and 12.6-fold at 60 and 84 h post infection, respectively. In AGMK-21 cells (FIG. 13), the yield of D46/6368 virus was 3.2 times at 36 hours post infection. In MRC-5, Vero, CV-1, MDBK and BT cells, a significant difference in replication among mutant and wild-type virus was not observed, indicating that the growth of SH-minus RSV was not substantially affected by host range effects.

TABLE 42

Replication of D46/6368 Virus as Compared to D46 Virus in Various Cell Lines

| Cell Type | Host | Tissue Type | D46/6368 Virus Replication As Compared to D46 |
|---|---|---|---|
| HEp-2 | human | larynx | increased |
| 293 | human | kidney | increased |
| MRC-5 | human | lung | similar |
| Vero | monkey | kidney | similar |
| AGMK-21 | monkey | kidney | increased |
| CV-1 | monkey | kidney | similar |
| BT | bovine | turbinate | similar |
| MDBK | bovine | kidney | similar |

These and other findings herein demonstrate that deletion of the SH gene yields not only recoverable, infectious RSV, but a recombinant RSV which exhibits substantially improved growth in tissue culture, based on both yield of infectious virus and on plaque size. This improved growth in tissue culture specified by the SH deletion provides useful tools for developing RSV vaccines, for example by overcoming problems of poor RSV yields in culture. Moreover, these deletions are highly stable against genetic reversion, rendering RSV clones derived therefrom particularly useful as vaccine agents.

To evaluate replication, immunogenicity and protective efficacy of the exemplary SH-deletion clone in mice, respiratory-pathogen-free 13-week old BALB/c mice in groups of 24 were inoculated intranasally under light methoxyflurane anesthesia on day 0 with 10$^6$ PFU per animal in a 0.1 ml inoculum of wild-type recombinant D46 virus, SH-minus recombinant D46/6368 virus, or biologically-derived cold-passaged (cp) temperature-sensitive (ts) virus cpts248/404 (Firestone et al., supra, (1996), incorporated herein by reference). This latter virus has been extensively characterized in rodents, chimpanzees and humans, and is highly restricted in replication in the upper and lower respiratory tract of the mouse. At each of days 4, 5, 6 and 8 post-inoculation, six mice from each group were sacrificed by $CO_2$ asphyxiation, and nasal turbinates and lung tissue were obtained separately, homogenized, and used in plaque assay for quantitation of virus using the antibody staining procedure described above.

In the upper respiratory tract, the SH minus D46/6368 virus exhibited an attenuation phenotype (FIG. 14). In the present example, its level of replication was 10-fold lower than that of the wild-type virus, and was comparable to that of the cpts248/404 virus. In contrast, in the lower respiratory tract (FIG. 15) the level of replication of the D46/6368 virus was very similar to that of the wild-type, whereas the cpts248/404 virus was highly restricted. In additional studies, it was shown that the SH-minus recombinant virus encoded by the parental D46 cDNA has a slightly attenuated phenotype in the upper respiratory tract and a moderately attenuated phenotype in the lower respiratory tract in naive chimpanzees, a fully permissive experimental animal. This mutant also elicited greatly reduced disease symptoms compared to wild-type RSV in naive chimps, while stimulating significant resistance to challenge by the wild-type virus. Whitehead et al., *J. Virol.* 73:(4) 3438-3442 (1999), incorporated herein by reference.

The foregoing data indicate that the parental recombinant virus, assembled as it was from a laboratory strain, contains a full complement of intact genes necessary for replication and virulence in a permissive host. These and other properties of exemplary gene deletion RSV strains render a host of methods and strains available for vaccine use.

To further evaluate immunogenicity and protective efficacy of recombinant RSV, four additional groups of mice were inoculated as described above with wild-type recombinant, its SH-minus derivative, or the cpts248/404 virus, or were mock infected. Four weeks later the mice were anesthetized, serum samples were taken, and a challenge inoculation of $10^6$ PFU of biologically-derived RSV strain A2 per animal was administered intranasally. Four days later the animals were sacrificed and nasal turbinates and lung tissues were harvested and assayed for infectious RSV as described above. Serum IgG antibodies which bind to the RSV F protein were quantitated in an ELISA using F glycoprotein which had been immunoaffinity-purified from RSV Long strain infected cells (Murphy et al., supra, 1990).

The immunogenicity assays for the D46 wild-type, D46/6368 SH-minus, and cpts248/404 viruses showed that mice which had been infected on day 0 with any of the three viruses developed high levels of F-specific serum antibodies (Table 43). All of these test hosts were highly resistant in both the upper and lower respiratory tracts to replication of RSV challenge virus. Thus, the SH-minus mutant could not be distinguished from its wild-type parent on the basis of its ability to induce RSV-specific serum antibodies and protection in the mouse.

TABLE 43

The RSV D46/6368 SH-minus virus is immunogenic and protects the upper and lower respiratory tract of mice against wild-type challenge

| Immunizing Virus[1] | No. of Mice | Serum antibody titer[2] (reciprocal mean $\log_2$) Day 0 | Day 28 | RSV A2 Replication after challenge[3] (mean $\log_{10}$pfu/g tissue) Nasal turbinates | Lungs |
|---|---|---|---|---|---|
| D46[4] | 6 | 7.3 | 15.0 | <2.0 | <1.7 |
| D46/6368[5] | 6 | 7.3 | 15.0 | 2.1 | <1.7 |
| cpts248/404 | 6 | 7.0 | 12.6 | 2.3 | <1.7 |
| none | 6 | 7.6 | 7.3 | 4.6 | 5.1 |

[1]Groups of BALB/c mice were immunized intranasally with $10^6$ pfu of the indicated virus on day 0.
[2]Serum IgG antibody response was quantitated in an ELISA using immunopurified F glycoprotein from RSV subgroup A.
[3]Mice were intranasally administered $10^6$ pfu of RSV A2 on day 28 and sacrificed 4 days later.
[4]Wild-type recombinant virus.
[5]SH-minus recombinant virus.

Comparisons of the SH genes of different RSVs and different pneumoviruses provide additional tools and methods for generating useful RSV recombinant vaccines. For example, the two RSV antigenic subgroups, A and B, exhibit a relatively high degree of conservation in certain SH domains. In two such domains, the N-terminal region and putative membrane-spanning domains of RSV A and B display 84% identity at the amino acid level, while the C-terminal putative ectodomains are more divergent (approx. 50% identity) (Collins et al., supra, 1990). Comparison of the SH genes of two human RSV subgroup B strains, 8/60 and 18537, identified only a single amino acid difference (Anderson et al., supra). The SH proteins of human versus bovine RSV are approximately 40% identical, and share major structural features including (i) an asymmetric distribution of conserved residues similar to that described above; (ii) very similar hydrophobicity profiles; (iii) the presence of two N-linked glycosylation sites with one site being on each side of the hydrophobic region; and (iv) a single cysteine residue on the carboxyterininal side of the central hydrophobic region of each SH protein. (Anderson et al., supra). By evaluating these and other sequence similarities and differences, selections can be made of heterologous sequence(s) that can be substituted or inserted within infectious RSV clones, for example to yield vaccines having multi-specific immunogenic effects.

Transcriptional analyses for D46 and D46/6368 yielded other important findings within the present example. Overall transcription levels were substantially the same for both viruses, whereas, Northern blot analysis revealed certain differences in accumulation of individual mRNA species. Notably, transcription of the M gene, located upstream of the SH gene, was substantially the same for the two viruses. However, deletion of the SH gene resulted in increased transcription for its downstream neighbor, the G gene (FIG. 16). Based on these results, transcriptional levels of selected RSV genes can be modulated simply by changing the respective polarities or proximity of genes on the RSV map. For example, the D46 virus G gene is seventh in the gene order, whereas deletion of the SH gene places it in the sixth position, resulting in increased levels of transcription. The observed increase in transcription associated with this change in gene order was less than the 2.5 to 3-fold increase which has been reported in other recombinant viral systems (see, e.g., Kuo et al., supra, (1996)).

Another important finding revealed in the foregoing studies was that each of the genes downstream of the G gene (F, M2 and L) was expressed less efficiently in the SH-minus mutant, and there was a steeper gradient of polarity for D46/6368 versus the wild-type D46 virus exhibited by these downstream genes (FIG. 16). Notably, the engineered M-G intergenic region of D46/6368 that was left following the SH deletion was 65 nt in length. In comparison, the longest naturally-occurring intergenic regions in strain A2 are the 44-nt M-SH, 46-nt F-M2, and 52-nt G-F intergenic regions, and strain 18537 has a F-M2 intergenic region of 56 nt (Johnson et al., *J. Gen. Virol.* 69:2901-2906 (1988), incorporated herein by reference). The naturally-occurring intergenic regions of strain A2, which range in size from one to 52 nt, did not substantially differ with regard to their effect on transcriptional readthrough and polarity in a dicistronic minigenome (Kuo et al, supra, (1996)). However, testing of regions longer than the 52-nt G-F region according to the methods of the invention may establish an upper limit after which the polymerase is affected more severely. Thus, the lower-than-expected increase in G gene transcription resulting from the change in gene order observed in the SH-minus deletion clones, as well as the reduced transcription of the downstream genes, may be attributable to the greater length of the intergenic region that was engineered between M and G. In this regard, adjustment in the selected length of intergenic regions of RSV clones within the invention is expected to provide yet additional tools and methods for generating useful RSV vaccines.

The above findings offer two additional methods for altering levels of RSV gene expression. First, the deletion of a nonessential gene can up-regulate the expression of downstream genes. Second, the insertion of longer than wild-type intergenic regions provide methods for decreasing the transcription of downstream genes. Decreased levels of expression of downstream genes are expected to specify attenuation phenotypes of the recombinant RSV in permissive hosts, e.g., chimpanzees and humans.

The finding that the SH-minus virus grows well in tissue culture and exhibits site-specific attenuation in the upper respiratory tract presents novel advantages for vaccine development. Current RSV strains under evaluation as live virus vaccines contain, e.g., cp mutations (acquired during extensive passage at progressively lower temperatures; to yield cpRSV strains). Exemplary cp mutations involve five amino acid substitutions in N, F and L, and do not confer temperature-sensitivity or cold-adaptation. These mutations further do not significantly affect growth in tissue culture. They are host range mutations, because they restrict replication in the respiratory tract of chimpanzees and humans approximately 100-fold in the lower respiratory tract. Another exemplary type of mutation, ts mutations, has been acquired by chemical mutagenesis of cpRSV. This type of mutation tends to preferentially restrict virus replication in the lower respiratory tract, due to the gradient of increasing body temperature from the upper to the lower respiratory tract. In contrast to these cp and ts mutants, the SH-minus mutants described herein have distinct phenotypes of greater restriction in the upper respiratory tract. This is particularly desirable for vaccine viruses for use in very young infants, because restriction of replication in the upper respiratory tract is required to ensure safe vaccine administration in this vulnerable age group whose members breath predominantly through the nose. Further, in any age group, reduced replication in the upper respiratory tract will reduce morbidity from otitis media. In addition to these advantages, the nature of SH deletion mutations, involving e.g., nearly 400 nt and ablation of an entire mRNA, represents a type of mutation which will be highly refractory to reversion.

EXAMPLE XIV

Recombinant RSV Having a Deletion of the SH Gene Without the Introduction of Heterologous Sequence This example describes the production of a recombinant RSV in which expression of the SH protein has been ablated by removing a polynucleotide sequence encoding the SH protein, without introducing heterologous sequence as was done in the preceding Example XIII. In that example, an RSV clone D46/6368 in which the SH coding sequence had been removed also featured an M-G intergenic region that was extended to 65 nucleotides in length compared to 52 nucleotides for the longest naturally occurring strain A2 intergenic region. Also, this engineered intergenic region contained heterologous sequence including a SmaI site. These changes yield certain advantageous results, such as reducing the efficiency of transcription of downstream genes. However, for other applications it is desirable to make deletions or changes which are not accompanied by the introduction of heterologous sequence, as illustrated in the present Example (FIG. 17).

The D13 plasmid, described hereinabove (see Example VII), contains the T7 promoter attached to the left-hand end of the genome encompassing the leader region, and the NS1, NS2, N, P, M, and SH genes (sequence positions 1 to 4623 in the complete 15,223 antigenome sequence). The ScaI (position 4189) to PacI (position 4623) fragment was replaced with the two partially-complementary synthetic oligonucleotides: ACTCAAATAAGTTAAT [SEQ ID NO:7] (positive-sense strand, the ScaI half site is italicized to the left and the PacI sticky end is italicized to the right, and part of the GE signal is underlined), and TAACTTATTTGAGT [SEQ ID NO:8] (negative sense, the ScaI half-site is italicized on the right, and part of the GE signal is underlined). This mutation resulted in the deletion of the M GE signal, the M-SH intergenic region and the complete SH gene, and had the effect of moving the SH GE signal up to replace that of the M gene. No heterologous nucleotides were introduced. The resulting cDNA, called D13/6340, was ligated with the G-F-M2 cDNA piece (see Example VII) to yield D50/6340, which spans from the leader region to the beginning of the L gene.

The StuI-BamHI fragment of D50/6340 (spanning positions 5613 to 8501, including the F and M2 genes) was excised and replaced with the equivalent fragment of D50-COR#1, which is isogenic except that it contains the two "HEK" changes to the F gene described hereinabove. The resulting D50/6340HEK was used to accept the BamHI-MluI fragment of D39sites#12, which contains the remainder of the antigenome cDNA and the flanking ribozyme and T7 transcription terminators (see Example IX). D39sites#12 is a version of D39 which contains the "sites" mutations (see Table 39). This resulted in plasmid D46/6340HEK, encoding an antigenome lacking the SH gene and containing the "HEK" and "sites" changes. The D46/6340 antigenome cDNA is 417 bp shorter than its parental D46 cDNA. The sequence of the ScaI PacI synthetic insert was confirmed by dideoxynucleotide sequencing. The cDNA was then used successfully to recover recombinant virus by the procedures described hereinabove. The recovered D46/6340 SH deletion virus resembled the D46/6368 SH deletion virus described in Example XIII on the basis of its plaque phenotype and growth characteristics.

EXAMPLE XV

Knock-out of NS2 Protein Expression

This example illustrates ablation of synthesis of an RSV protein, NS2. The selected method for ablation in this instance was introduction of stop codons into a translational open reading frame (ORF).

D13 is a cDNA representing the left hand end of the complete antigenome cDNA, including the T7 promoter, leader region, and the NS1, NS2, N, P, M and SH genes (sequence positions 1 to 4623) (FIG. 18). The AatII-AflIII fragment of this cDNA, containing the T7 promoter and NS1 and NS2 genes, was subcloned into a pGem vector and subjected to oligonucleotide-directed mutagenesis to introduce two translational stop codons into the NS2 ORF together with an XhoI site that was silent at the translational level and served as a marker (FIG. 18). The sequence of the mutation was confirmed, and the AatII-AflIII fragment was inserted into D13, which was then ligated with the PacI-BamHI fragment containing the G, F and M2 genes, to yield cDNA D50 containing the inserted mutations. This was then ligated with the insert of D39 to yield a complete antigenome cDNA which was used to recover recombinant virus. The presence of the mutation in the recombinant RSV was confirmed by sequencing of RT-PCR products and by XhoI digestion. In addition, the absence of synthesis of NS2 protein was confirmed by Western blot analysis using a rabbit antiserum raised against a synthetic peptide representing the C-terminus of NS2.

FIG. 19 shows growth curves comparing the NS2-knock-out virus with recombinant wild-type, using the methods described above for the SH-minus virus. These results demonstrate that the rate of release of infectious virus was reduced for the NS2-knock-out virus compared to wild-type. In addition, comparison of the plaques of the mutant and wild-type viruses showed that those of the NS2-knock-out were greatly reduced in size. This type of mutation can thus be incorporated within viable recombinant RSV to yield altered phenotypes, in this case reduced rate of virus growth and reduced plaque size in vitro. These and other knock-out methods and mutants will therefore provide for yet additional recombinant RSV vaccine agents, based on the known correlation between reduced plaque size in vitro and attenuation in vivo.

EXAMPLE XVI

Modulation of RSV Phenotype by Alteration of Cis-Acting Regulatory Sequence Elements This example illustrates modulation of growth properties of a recombinant RSV virus by altering cis-acting transcription signals of exemplary genes, NS1 and NS2.

The subcloned AatII-AflIII fragment of D13, representing the lefthand end of the genome, was subjected to oligonucleotide-directed mutagenesis to introduce changes at the GE signals of the NS1 and NS2 genes (FIG. 20). The NS1 GE signal sustained a single nucleotide substitution, whereas that of NS2 sustained three substitutions and one insertion. These changes had the effect of altering each signal to be identical to the naturally-occurring GE signal of the N gene.

These mutations were confirmed by dideoxynucleotide sequence analysis, and the AatII-flII fragment was replaced into D13, which in turn was taken through the above described steps to construct a complete D53 DNA containing the mutations. This clone was used to recover recombinant virus.

The GE-mutant virus was analyzed in HEp-2 cells and compared to wild-type virus with respect to plaque size and growth curve. This showed that the plaques were larger (on average 30% greater) than those of wild-type, and the rate of growth and yield of virus were increased. These results are consistent with modification of gene expression by altering cis-regulatory elements, for example to decrease levels of readthrough mRNAs and increase expression of proteins from downstream genes. The resulting recombinant viruses will preferably exhibit increased growth kinetics and increased plaque size, providing but one example of alteration of RSV phenotype by changing cis-acting regulatory elements in the genome or antigenome. These and other examples herein demonstrate a wide range of RSV mutations specific for phenotypic changes that are advantageous for providing effective vaccine agents.

EXAMPLE XVII

Recombinant RSV Having a Deletion of the NS1 Gene

This example describes the production of a recombinant RSV in which expression of the NS1 protein has been ablated by removal of the polynucleotide sequence encoding the protein. The NS1 protein is a small 139-amino acid species which is encoded by the first gene in the 3' to 5' RSV gene map (Collins and Wertz, *Proc. Natl. Acad. Sci. USA* 80:3208-3212 (1983), and Collins and Wertz, *Virol.* 243:442-451 (1985)). Its mRNA is the most abundant of the RSV mRNAs, consistent with the general finding that there is a gradient of transcription such that the efficiency of gene expression is reduced with increasing distance from the promoter at the 3' end. The NS1 protein is thought to be one of the most abundantly expressed RSV proteins, although a careful quantitative comparison remains to be done. Despite its abundance, the function of the NS1 protein has not yet been clearly identified. In the reconstituted RSV minigenome system (Grosfeld et al., *J. Virol.* 69:5677-5686 (1995), Collins et al., *Proc. Natl. Acad. Sci. USA* 93:81-85 (1996)), in which transcription and RNA replication of a minigenome is driven by viral proteins supplied by plasmids, the NS1 protein appeared to be a negative regulatory protein for both transcription and RNA replication. Thus, it might be a regulatory protein. It is very possible that other functions exist which remain to be identified. The NS1 protein does not have a known counterpart in other paramyxoviruses. Without wishing to be bound by theory, several functions of the NS1 protein may exist: (i) it may be a viral regulatory factor as suggested above, (ii) it may be involved in some other aspect of the viral growth cycle, (iii) it may interact with the host cell, such as to prevent apoptosis, and (iv) it may interact with the host immune system, such as to inhibit aspects of the host defense system such as interferon production, antigen processing or B or T cell functioning. All of these potential activities of the NS1 protein may yield additional advantages in RSV recombinant vaccines.

To produce a recombinant RSV having a selected disruption of NS1 gene function, the sequence encoding the NS1 protein was deleted in its entirety from a parental RSV cDNA. In this exemplary deletion, the substrate for the mutagenesis reaction was plasmid D13, which was described hereinabove and contains the left hand end of the complete antigenome cDNA including the T7 RNA promoter, the leader region, and the NS1, NS2, N, P, M, and SH genes (sequence positions 1 to 4623). The mutagenesis was done by the method of Byrappa et al. (Byrappa et al., *Genome Res.* 5:404-407 (1995)), in which synthetic primers which incorporate the desired change are made to face in opposite directions on the plasmid, which is then amplified by PCR, ligated, and transformed into bacteria. The forward PCR primer was GACACAACCCA-CAATGATAATACACCAC [SEQ ID NO:9] (the second codon of the NS2 ORF is italicized), and the reverse PCR primer was CATCTCTAACCAAGGGAGTTAAATT-TAAGTGG [SEQ ID NO:10] (the complement to the initiation codon of the NS2 ORF is italicized). D13 was used as the template for PCR with a high-fidelity polymerase. The deletion was made to span from immediately upstream of the AUG start site of the NS1 ORF to immediately upstream of the AUG start site of the NS2 ORF (FIG. 21). This resulted in the deletion of 529 bp including the NS1 coding sequence, the NS1 GE signal, the NS1-NS2 intergenic region, and the NS2 GS signal. It had the effect of fusing the upstream end of the NS1 gene, namely its GS and non-protein-coding region, to the NS2 ORF. This part of the NS1 gene was retained expressly because it is immediately adjacent to the leader region and thus might contain sequences important in transcription or RNA replication. The region containing the mutation was confirmed by sequence analysis. Then, the ~2230 bp segment between the Aat2 and Avr2 sites (FIG. 21) was excised and inserted into a fresh copy of D13, a step that would thereby preclude the possibility of PCR error elsewhere in the RSV cDNA. The D13 plasmid containing the deletion of NS1 (D13_NS1) was used to construct a complete antigenome (D53_NS1) which contained the "HEK" and "sites" changes.

The D53_NS1 plasmid was then used to recover virus. Interestingly, the recovered RSV_NS1 virus produced small plaques in tissue culture. The presence of the deletion was confirmed by RT-PCR. The fact that the RSV_NS1 virus can grow, albeit with reduced efficiency, identifies the NS1 protein as an accessory protein, one that is dispensable to virus growth. The plaque size of the RSV_NS1 virus was similar to that of the NS2-knock out virus described above in which expression of the NS2 protein was ablated by the introduction of translational stop codons into its coding sequence (Example XV). The small plaque phenotype is commonly associated with attenuating mutations. This type of mutation can thus be incorporated within viable recombinant RSV to yield altered phenotypes. These and other knock-out methods and mutants will therefore provide for yet additional recombinant RSV vaccine agents, based on the known correlation between plaque size in vitro and attenuation in vivo.

EXAMPLE XVIII

Recombinant RSV Having a Deletion of the NS2 Gene

This example describes the production of a recombinant RSV in which expression of the NS2 protein has been ablated by removal of a polynucleotide sequence encoding the protein. In Example XV, above, a recombinant virus (called NS2 knock-out or NS2-KO) was produced in which expression of the NS2 gene was ablated by the introduction of two translational stop codons into its coding sequence rather than by deletion of the coding sequence. Ablation of expression of the NS2 protein in the prototypic NS2-KO virus was associated with the small plaque phenotype and reduced kinetics of virus growth in vitro. Subsequent analysis showed that, upon passage of NS2 KO, it was possible to recover low levels of virus which had reverted to wild-type growth characteristics. Sequence analysis showed that the two introduced translational stop codons had mutated into sense codons, albeit with coding assignments different than in the parental wild-type virus. This was sufficient to restore synthesis of the NS2 protein as confirmed by Western blot analysis, which accounted for the wild-type phenotype. The present strategy offers an improvement because the complete NS2 gene is removed and thus same-site reversion cannot occur.

The NS2 protein is a small 124-amino acid protein which is encoded by the second gene in the gene order (Collins and Wertz, *Proc. Natl. Acad. Sci. USA* 80:3208-3212 (1983), and Collins and Wertz, *Virol.* 243:442 451 (1985). Its mRNA is the second most abundant of the RSV mRNAs, and the NS2 protein is thought to be one of the most abundantly-expressed RSV proteins, although a careful quantitative comparison remains to be done. Despite its abundance, the function of the NS2 protein remains to be identified. In the reconstituted RSV minigenome system (Grosfeld et al., *J. Virol.* 69:5677-5686 (1995), Collins et al., *Proc. Natl. Acad. Sci. USA* 93:81-85 (1996)), in which transcription and RNA replication of a minigenome is driven by viral proteins supplied by plasmids, the NS2 protein had a modest negative regulatory effect against both transcription and RNA replication. Relatively high levels of NS2 protein expression were required to observe this effect, and so its significance is unclear. Thus, as suggested for the NS1 protein, NS2 might: (i) be a viral regulatory factor, (ii) be involved in some other aspect of the viral growth cycle, (iii) interact with the host cell, such as to prevent apoptosis, and (iv) interact with the host defense system, such as to inhibit aspects of the host immune system such as interferon production or aspects of antigen processing or B or T cell functioning. All of these potential activities of the NS2 protein may be incorporated within the invention according to the methods and strategies described herein, to yield additional advantages in RSV recombinant vaccines.

To produce a recombinant RSV having a selected disruption of NS2 gene function, the sequence encoding its mRNA was deleted from a parental RSV cDNA. In this exemplary deletion, the substrate for the mutagenesis reaction was plasmid D13, which was mentioned previously and contains the left hand end of the complete antigenome cDNA including the T7 RNA promoter, the leader region, and the NS1, NS2, N, P, M, and SH genes (sequence positions 1 to 4623). The mutagenesis was done by the method of Byrappa et al. (Byrappa et al., *Genome Res.* 5:404-407 (1995)), in which synthetic primers which incorporate the desired change are made to face in opposite directions on the plasmid, which is then amplified by PCR, ligated, and transformed into bacteria. The forward PCR primer was TTAAGGAGAGATATAAGATA-GAAGATG [SEQ ID NO:11] (sequence from the NS2 N intergenic region is underlined, and the first nucleotide of the N GS signal is italicized), and the reverse PCR primer was GTTTTATATTAACTAATGGTGTTAGTG [SEQ ID NO:12] (the complement to the NS1 GE signal is underlined). D13 was used as the template for PCR with a high-fidelity polymerase. The deletion was made to span from immediately downstream of the NS1 GE signal to immediately downstream of the NS2 GS signal (FIG. 22). Thus, the mutation deleted 522 nucleotides including the NS1—NS2 intergenic region and the complete NS2 gene (FIG. 22).

In the D13 plasmid containing the deletion, the region of the mutation was confirmed by sequence analysis. Then, the ~2230 bp segment between the Aat2 and Avr2 sites (FIG. 22) was excised and inserted into a fresh copy of D13, a step that would thereby preclude the possibility of PCR error elsewhere in the RSV cDNA. The D13 plasmid containing the deletion of NS2 (D13_NS2) was used to construct a complete antigenome (D53_NS2) which contained all of the "sites" and "HEK" changes.

The D53_NS2 plasmid was then used to recover virus. As is described above for the NS2-KO virus (see Example XV), the RSV_NS2 produced small plaques. The presence of the deletion was confirmed by RT-PCR. The fact that the RSV_NS2 virus can grow, albeit with reduced efficiency, identified the NS2 protein as an accessory protein, one that is dispensable to virus growth. The small plaque phenotype is commonly associated with attenuating mutations and can thus be incorporated within viable recombinant RSV to yield altered phenotypes. In accordance with these findings, the NS2-minus mutant exhibited a moderately attenuated phenotype in the upper respiratory tract and a highly attenuated phenotype in the lower respiratory tract in naive chimpanzees. This mutant also elicited greatly reduced disease symptoms in chimps while stimulating significant resistance to challenge by the wild-type virus. Whitehead et al., *J. Virol.* 73:(4)3438-3442 (1999), incorporated herein by reference. Therefore, these and other knock-out methods and mutants will provide for yet additional recombinant RSV vaccine agents, based on the known correlation between plaque size in vitro and attenuation in vivo.

EXAMPLE XIX

Ablation of the Translational Start Site for the Secreted Form of the G Glycoprotein This example describes the production of a recombinant RSV in which the translational start site for the secreted form of the G glycoprotein has been ablated. The RSV G protein is synthesized in two forms: as an anchored type II integral membrane protein and as a N terminally resected form which lacks essentially all of the membrane anchor and is secreted (Hendricks et al., *J. Virol.* 62:2228-2233 (1988)). The two forms have been shown to be derived by translational initiation at two different start sites: the longer form initiates at the first AUG of the G ORF, and the second initiates at the second AUG of the ORF at codon 48 and is further processed by proteolysis (Roberts et al., *J. Virol.* 68: 4538-4546 (1994)). The presence of this second start site is highly conserved, being present in all strains of human, bovine and ovine RSV sequenced to date. It has been suggested that the soluble form of the G protein might mitigate host immunity by acting as a decoy to trap neutralizing antibodies. Also, soluble G has been implicated in preferential stimulation of a Th2-biased response, which in turn appears to be associated with enhanced immunopathology upon subsequent exposure to RSV. With regard to an RSV vaccine virus, it would be highly desirable to minimize antibody trapping or imbalanced stimulation of the immune system, and so it would be desirable to ablate expression of the secreted form of the G protein. This would represent a type of mutation whose action would be to qualitatively and/or quantitatively alter the host immune response, rather than to directly attenuate the virus.

Plasmid pUC19 bearing the G, F and M2 genes (see Example VII) was used as template in PCR mutagenesis by the procedure of Byrappa et al. (Byrappa et al., *Genome Res.* 5:404-407 (1995). The forward PCR primer was: TTATAAT-TGCAGCCATCATATTCATAGCCTCGG [SEQ ID NO:13], and the reverse primer was: GTGAAGTTGAGATTACAAT-TGCCAGAATGG [SEQ ID NO: 14] (the complement of the two nucleotide changes is underlined). This resulted in two amino acid coding changes (see FIG. 23), namely AUG-48 to AUU-48, which ablates the translational start site, and AUA-49 to GUA-49, which contributes to the insertion of an MfeI site for the purpose of monitoring the mutation.

The sequence surrounding the site of mutation was confirmed by dideoxynucleotide sequencing. Then, the PacI-StuI fragment, which contains the G gene, was substituted into plasmid D50, which is described hereinabove and contains the first nine genes from the leader to the beginning of the L gene. This was then used to construct a complete antigenome cDNA, D53/GM48I, which was used to recover virus. These mutations have previously been shown to ablate the expression of the secreted form of G under conditions where the G cDNA was expressed in isolation from the other RSV genes by a recombinant vaccinia virus (Roberts et al., *J. Virol.* 68:4538-4546 (1994)).

Two isolates of the recovered D53/M48I virus were evaluated for growth kinetics in vitro in parallel with wild-type recombinant RSV (FIG. 24). This showed that both viruses grew somewhat more slowly, and to somewhat lower titers, than did the wild-type. This difference in growth might be due to the reduced expression of the G protein, which would be expected to occur since the AUG-48 of the secreted form was eliminated whereas in this Example the AUG-1 of the membrane-bound form was not modified to increase its expression. In nature, the expression of AUG-1 of the G ORF is thought to be suboptimal because it is preceded in the G sequence by another AUG in another reading frame which opens a short ORF that overlaps AUG-1 of the G ORF and thus would reduce its expression. It might be anticipated that additional modification of the antigenome cDNA to eliminate this ORF might restore full growth properties. Alternatively, the mutations at position 48 and 49, acting alone or in concert, might be deleterious to the function of the G protein. The amino acid at position 49 could be restored to its natural coding assignment, and a different amino acid substitution could be chosen at position 48, which might restore full growth properties. These possibilities can be readily evaluated with the methods and materials described here. Nonetheless, the recovery of the D53/GM48I virus shows that the translational start site for the secreted form can be ablated, and this virus is now available for evaluation in experimental animals and humans.

EXAMPLE XX

Production of An Attenuated Chimeric RSV Vaccine Virus For RSV Subgroup B

The present example describes the production of live-attenuated chimeric vaccines specific to subgroup B RSV. The preceeding examples demonstrate production of various, RSV subgroup A live-attenuated vaccines having a range of selectable attenuating mutations, including mutations adopted from biologically derived mutants as well as a series of other defined nucleotide changes within the RSV A genome. Each of these changes are amenable to introduction, individually or in a full array of combinations, into the full-length cDNA clone, and the phenotype of each recovered recombinant virus can be readily characterized and confirmed to confer a desired level of attenuation for vaccine use.

A live-attenuated RSV vaccine ideally should be effective against multiple RSV strains and/or subgroups. In this regard, RSV is considered to be serologically monotypic, since convalescent serum against any one strain will neutralize other strains. However, it has long been recognized that the efficiency of cross-neutralization varies among different strains (Coates, Alling, and Chanock, 1966). More recently, studies with monoclonal antibodies and by sequence analysis showed that RSV strains can be segregated into two antigenic subgroups, A and B (Anderson et al., *J. Infect. Dis.* 151(4): 626-33 (1985); Collins et al., *J. Gen. Virol.* 71(Pt 7):1571-6. (1990); Johnson et al., *Proc. Natl. Acad. Sci. USA* 84(16): 5625-9 (1987b); Mufson et al., *J. Gen. Virol.* 66(Pt 10):2111-24 (1985).

Sequence divergence between the RSV A and B subgroups exists across the entire genome, but the extent of divergence is not uniform. The two most divergent regions are the extracellular domains of the G and SH proteins which, at the amino acid level, are 56 and 50% divergent, respectively (Collins et al., *J. Gen. Virol.* 71(Pt 7):1571-6. (1990); Johnson et al., *J. Gen. Virol.* 69(Pt 10):2623-8 (1988); Johnson et al., *Proc. Natl. Acad. Sci. USA* 84(16): 5625-9 (1987b), each incorporated herein by reference. The F glycoprotein, the third RSV transmembrane surface protein, is 11% different between subgroups at the amino acid level (Johnson et al., *J. Gen. Virol.* 69(Pt 10):2623-8 (1988)). The percent antigenic relatedness between the two subgroups for the G and F proteins, which are the two major protective antigens, was measured to be 5% and 50%, respectively (Johnson et al., *J. Virol.* 61(10): 3163-6 (1987a)). This amount of difference is such that both antigenic subgroups should be represented in an RSV vaccine, especially the G glycoprotein.

For subgroup B, a comparable panel of attenuated vaccine candidates or a collection of cDNA reagents from which to produce virus is not yet available. However, an initial group of live-attenuated subgroup B vaccine candidates has been prepared (Crowe et al., *J. Infect. Dis.* 173(4), 829-39 (1996a)). While these candidates may be unsatisfactory for vaccine use due to spontaneous deletion of the SH and G genes (Karron et al., *Proc. Natl. Acad. Sci. USA* 94(25):13961-6 (1997a)), they will provided useful mutations for use within chimeric RSV of the invention.

The present example provides a RSV subgroup B-specific vaccine virus in which an attenuated subgroup A virus is used to express the F and G glycoproteins of a subgroup B RSV. Because the F and G proteins are the major protective antigens and confer most of the RSV subgroup specificity, this chimeric virus will stimulate a strong immune response against subgroup B. This strategy may be implemented using two alternative approaches. One is to insert the G glycoprotein gene of a subgroup B virus into the subgroup A background as an additional gene. This virus would therefore encode two G proteins, one of subgroup A and one of subgroup B. In this context, Jin et al., *Virology* 251(1):206-14 (1998) described a subgroup A virus which expresses the G protein of subgroup B as an additional gene (Jin et al., *Virology* 251(1):206-14 (1998)). However, since the F protein also exhibits significant subgroup-specificity, it would be preferable to express both subgroup B glycoproteins in a subgroup B-specific vaccine. Moreover, it is desireable to further modify a subgroup B virus to achieve proper attenuation and immunogenicity in accordance with the teachings herein.

The second, more desirable strategy to achieve an RSV subgroup B vaccine is disclosed in the present example, which documents removal of the G and F genes from a subgroup A recombinant cDNA backbone, and replaces them with the G and F genes of a subgroup B RSV. Thus, a chimeric RSV is provided which contains the internal proteins of subgroup A and the external protective antigens of subgroup B. This virus can then be attenuated to a desired level according to the methods of the invention by systematic incorporation of attenuating mutations from those identified above into a subgroup A background. This attenuated virus bearing the subgroup B protective antigens can then be combined with a biologically-derived or recombinant attenuated subgroup A virus to yield a two-component RSV vaccine which would cover both antigenic subgroups.

According to the general methods disclosed herein, a genomic or antigenomic cDNA of a viral strain representing one subgroup, for example RSV subgroup A, is modified so that the F and G surface glycoprotein genes are replaced by their counterparts from a virus of the heterologous subgroup, in this example RSV subgroup B. This cDNA is then used to produce an infectious chimeric virus by the above described methods involving transfection of cultured cells with the antigenome or genome cDNA supported by plasmids expressing RSV nucleocapsid and polymerase proteins (see also, Collins et al., *Proc. Natl. Acad. Sci. USA* 92:11563-11567 (1995); U.S. Provisional Patent Application No. 60/007,083, each incorporated herein by reference). Since the resulting virus bears the heterologous subgroup F and G glycoproteins, which are the major protective antigens, it will induce immunity that is highly effective against subsequent infection by a virus of the heterologous subgroup.

Within the present example, any RSV glycoprotein or other relevant gene or gene segment can be substituted singly. However, in the case of protective antigens, the protective effect against a heterologous subgroup virus is far more desirable if two or more immunogenic proteins or epitopes are represented (either by introduction of entire proteins or immunogenic regions thereof). Other genes can also be substituted or included as additional genes. For example, the gene encoding the third RSV surface glycoprotein, SH, can also be substituted by its heterologous subgroup counterpart, or added as a supernumary glycoprotein within a chimeric RSV (see, e.g., Bukreyev et al., *J. Virol.* 71(12):8973-82 (1997), incorporated herein by reference). The sequence replacements can involve any of the RSV genes or genetic elements singly or in combination. For example, they can involve substitution of part of a translational open reading frame (ORF), a complete ORF, a complete gene including transcription signals, cis-acting elements, or any combination or functional segments thereof. In the present example, the transferred genes are placed in the same genome locations which were occupied by their recipient counterparts, but this need not be the case. For example, the donor genes can be moved closer to or more distant from the viral promoter in order to increase or decrease expression.

In practicing the current aspect of the invention, either subgroup A or B RSV can be used as the recipient, with the other group serving as the donor. In the examples described here, a subgroup A backbone is the recipient for subgroup B glycoprotein genes. Also, any subgroup A or B strain can be used, although the specific examples described here involve the A2 and B1 strains. Additional subgroups or significant antigenic variants might emerge in the future, and could also readily provide useful recipient and/or donor sequences for gene or gene segment exchanges and transfers.

In conjunction with the present example, modification of the RSV cDNA is further undertaken to render the cDNA capable of being manipulated and propagated with maximum stability, if this is found to be necessary. Instability in RSV sequences is common, and is thought to be manifest during propagation in bacteria. However, instability of RSV sequence also has been observed during passage of the virus in cell culture. Specifically, the G gene of a biologically-derived cpRSV of subgroup B was deleted during passage in vero cells. In this example, the gene-end signal of the strain B1 G gene was determined by routine methods to be unstable. Altering the sequence in ways which did not alter amino acid coding or greatly perturb cis-acting signals resulted in cDNA which could be successfully propagated without unplanned changes.

A third aspect of the strategy described and validated in the present example is that the backbone of a chimeric RSV can be modified as necessary by introducing attenuating mutations in selected combinations. For example, a strain A2 backbone can be modified by the introduction of the cp mutations, ts mutations, and various other mutations which have been characterized above to yield desired functional or phenotypic characteristics, e.g., to improve attenuation of the virus. These mutations can involve any substitution, insertion, deletion or rearrangement which confers the desirable property in this context. For example, deletion of the SH gene has the additional property of larger plaque size and improved growth in some cell lines. Other desirable properties include, but are not limited to, improved antigen expression, reduced reactogenicity, and improved or altered immunogenicity. Importantly, the ability to introduce these mutations in stepwise fashion and in various combinations renders it possible to achieve a finely tuned balance between attenuation and immunogenicity, as well as other desirable properties.

As the present example indicates, recombinant chimeric A/B virus exhibits growth characteristics in cell culture and chimpanzees which are wild-type-like and are intermediate between those observed for parent strains A2 and B1. This shows that a fully viable chimeric virus can readily be produced and further manipulated to achieve desired changes. The property of unrestricted growth in cell culture is crucial for the production of vaccine virus. Also, a fully viable, wild-type-like virus is the most appropriate substrate for subsequent attenuation in a directed manner. Furthermore, since the growth properties of a chimeric A/B virus are not very different than those of the A2 parent, the introduction of desirable mutations which have been identified for strain A2 are predicted to have similar effects in the AB chimera.

As further described below, a panel of six A/B chimeric viruses were developed in accordance with the methods of the invention, which were modified by insertion of various combinations of known attenuating mutations into the A2 RSV background. These examples evince that many other modifications to the chimeric A/B virus disclosed herein can be readily achieved to develop additional vaccine strains. As expected, the A/B chimeric virus derivatives showed phenotypes in cell culture which were consistent with those of the corresponding recombinant attenuated strain A2 vaccine candidates, indicating that the attenuation phenotypes are reasonably predictable when transferred from a parent strain to a chimeric derivative. For example, deletion of the SH gene in three of the viruses resulted in an increase in plaque size, whereas the addition of the 1030 mutation to two of the viruses resulted in decreased plaque size which is consistent with attenuation. It might be anticipated that some combinations of changes might yield results that are not in complete accord with predictions. Nonetheless, this invention provides the means for incremental adjustments.

In the present example, RSV strain A2 is used as a donor in view of the wide range of vaccine candidates and known phenotype-specific mutations identified above. In this context, the description below details the importation of representative attenuating mutations which are placed into a chimeric recipient background, although in practice they also can also be introduced into the donor gene(s). The specific attenuating mutations described include: (i) three of the five cp mutations, namely the mutation in N (V267I) and the two in L (C319Y and H1690Y), but not the two in F since these are removed by substitution with the B1 F gene; (ii) the 248 (Q831L), 1030 (Y1321N) and, optionally, 404-L (D1183E) mutations which have been identified in attenuated strain A2 viruses; (iii) the single nucleotide substitution at position 9 in the gene-start signal of the M2 gene, and (iv) deletion of the SH gene. Other immediately available mutations can include, but are not limited to, the NS1 or NS2 gene deletions, or the 530 or 1009 mutations, alone or in combination.

It is not uncommon for RSV cDNAs to sustain unwanted sequence changes during manipulation or propagation in bacteria. For example, the first strain A2 antigenome cDNA which was successfully used to produce recombinant RSV exhibited separate instability problems in the M and SH genes which were ameliorated by using a lower-copy-number plasmid, growth at 30° C. rather than 37° C., and different bacterial strains (Collins et al., 1995)). The G gene is also frequently associated with instability. Furthermore, the RSV G gene has been shown to be unstable under certain conditions of RSV growth in cell culture (Kerran et al., 1992). To resolve this problem, stabilization of the sequence of the strain B1 G gene was achieved by altering the nucleotide sequence in a way designed to leave amino acid coding unchanged. Although the changes altered cis-acting signals, this alteration should not significantly alter function. These modifications rendered the cDNA capable of being manipulated and propagated without unplanned changes.

Construction and Recovery of a "Wild-Type" Chimeric AB Virus

As noted above, one of the available strategies for developing an effective RSV subgroup B vaccine based on an attenuated RSV subgroup A virus is to replace the G and F genes in the strain A2 antigenomic cDNA with a restriction fragment bearing the G and F genes of subgroup B (FIG. 25A-C). The A2 antigenomic cDNA has a naturally-occurring PacI site within the SH gene-end signal, and during the construction of the antigenomic cDNA we had inserted an SphI site in the F-M2 intergenic region (Collins et al., 1995). Therefore, the cDNA fragment bearing the G and F genes of strain A2 could be replaced with a cDNA bearing the G and F genes of a subgroup B donor strain, such strain as B1. If appropriate PacI and SphI sites did not occur in the subgroup B strain, as was the case with strain B1, they could be generated during PCR using mutagenic oligonucleotides following standard procedures.

The B1 virus has been sequenced in its entirety by analysis of RT-PCR products, which thus provides a consensus sequence, and was shown to be a wt virus based on studies with human volunteers (Karron et al., 1997a, incorporated herein by reference). The B1 virus was grown in HEp-2 cell culture and concentrated from the clarified medium by precipitation with polyethylene glycol. The virion RNA was extracted and purified (Collins et al., 1995) and used as template for reverse transcription (RT) using random hexamer primers by conventional procedures (Collins et al., 1995) The resulting cDNA was subjected to the polymerase chain reaction (PCR) to amplify the two genes in a single cDNA. The PCR was performed with a positive-sense oligonucleotide designed to prime at the beginning of the intergenic region preceding the G gene (GCATGGATCCTTAATTAAAAAT-TAACATAATGATGAATTATTAGTATG [SEQ ID NO: 15]; annotated so that the PacI site is in bold italics, a BamHI site used for cloning the initial PCR product is in italics, and the subgroup B-specific sequence is underlined) and a negative-sense primer which hybridized midway through the intergenic region on the downstream side of the F gene (GTGT-TGGATCCTGATTGCATGCTTGAGGTTTTTATGTAAC-TATGAGTTAAG [SEQ ID NO: 16]; annotated as above, except that the SphI site is in bold italics). The primers were designed to introduce a PacI site at the upstream end of the intergenic region preceeding G and an SphI site into the intergenic region that follows the F gene. The PacI and SphI sites were flanked in turn each by BamHI sites for the purposes of cloning the initial PCR product into the BamHI site of pBR322.

Four cloned G-F cDNAs were analyzed completely by nucleotide sequencing. Each of the cDNA clones was found to contain a similar error in the G gene-end signal. This signal (AGTTATTCAAAAA [SEQ ID NO: 17]) ends with a run of five A residues, but in each clone this had been elongated to 30 or more. In addition, each cDNA contained at least one additional mutation elsewhere in the G or F gene. These errors might have been introduced by the RSV polymerase, RT, the DNA polymerase used in PCR, or propagation in bacteria. By the exchange of restriction fragments it was possible to eliminate all of these differences except for the gene-end mutation. Additional cloned DNAs were examined in this region, and each was found to contain an elongated GE signal. A single cDNA clone was identified which contained a GE signal of the correct sequence, but upon further propagation in bacteria this too became elongated. This suggested that the elongation occurred during propagation in bacteria. Growth at a lower temperature and using other bacterial strains failed to provide clones with the correct sequence at this signal.

It is not uncommon for certain sequences to be difficult to propagate stably in bacteria, for reasons which often are not apparent from examination of the DNA sequence. For example, two specific regions of the strain A2 antigenome cDNA are unstable unless specific bacteria strains and growth conditions are used. Because changes in bacterial strain and growth conditions failed to stabilize the B1 cDNA, its sequence was modified to make it more stable. To achieve this objective, a number of nucleotides at the downstream end of the G gene and in the downstream intergenic region were changed as follows: (i) for the last eleven codons of the G ORF, the nucleotide assignment of the third nucleotide in each codon was changed without altering the amino acid coding assignment; (ii) the termination codon of the G ORF was changed to an alternative termination codon assignment, (iii) four nucleotides were introduced into the downstream nontranslated region of the G gene between the ORF and the gene-end signal, (iv) the G gene-end signal was changed by two nucleotide substitutions and the A tract was reduced in length by one nucleotide, so that the signal became identical to that of the F gene of strain A2, and (v) the G-F intergenic region was shortened by 47 nucleotides and an MfeI site was introduced (see FIG. 26).

Mutagenesis was conducted using a PCR-based procedure in which two abutting oligonucleotides which contain the desired changes are used to prime DNA synthesis in opposite directions on the plasmid template, after which the resulting linear DNA is circularized by ligation (Byrappa, Gavin, and Gupta, 1995). The positive-sense oligonucleotide was as follows (broken into triplets at coding nucleotides, with nucleotide assignments which differ from the wt B1 sequence underlined, the introduced MfeI site in bold, and the G gene end and F gene-start signals in italics):

C CAC GCC TAATGAGTTATATAAAACAATT GGGGCAAATAACC ATG GAG [SEQ ID NO: 18]

The negative-sense oligonucleotide was as follows (annotated as described above):

GA CTG AGT GTT CTG AGT AGA GTT GGA TGT AGA GGG CTC GGA TGC TG [SEQ ID NO: 19]

The G-F cDNA described above was used as template in a PCR using the two oligonucleotide primers indicated above. The PCR product was gel-purified, circularized by ligation, and cloned in *E. coli* strain DH10B (Life Technologies). Six cloned cDNAs were identified which were the appropriate size to contain the full-length insert, and sequence analysis of the region containing the gene-end signal showed that each of the six contained the correct sequence. One cDNA, MH5-7, was sequenced in full and contained the correct sequence. Its PacI-SphI fragment containing the subgroup B G and F genes was then excised in preparation for the construction of a chimeric antigenomic cDNA.

The antigenomic strain A2 cDNA D53 contained the following features. First, it contained a G to C (negative-sense) substitution at leader position 4, called the 4C mutation, as described previously (Collins et al., 1995). This change has been described in certain biologically-derived attenuated strains of RSV but is not associated with an attenuation phenotype. However, it has been described as an up-regulator of RNA replication (Grosfeld, Hill, and Collins, 1995), and also improves the efficiency of recovery of infectious virus from cDNA although it does not appear to affect viral yield in cell culture (Collins et al., 1995). Second, D53 contains five nucleotide substitutions and a single nucleotide insertion which place restriction site markers in four locations: immediately downsteam of the NS2 gene, upstream of the N ORF, in between the G and F genes, and in between the F and M2 genes (Collins et al., 1995). The antigenomic cDNA also was then further modified by the insertion of a set of six translationally silent restriction site markers into the L gene, which are collectively called the "sites" mutations (Whitehead et al., 1998b).

It was undesirable to directly replace the PacI-SphI fragment of the D53 cDNA with that bearing the B1 G and F genes because the PacI and SphI sites are not unique in the D53 plasmid. Therefore, this replacement was done on the subclone D50, which contains the left-hand end of the antigenome cDNA from the 3' extragenic leader region, through the first nine genes, and to the start of the L gene (Collins et al., 1995; Whitehead et al., 1998b). In this D50 plasmid, the PacI and SphI sites are unique, and a direct restriction fragment exchange was made. The remainder of the antigenomic cDNA, namely the L gene and the trailer region and adjoining T7 promoter, was contained in the plasmid D39sites, and this cDNA was then inserted as a BamHI-MluI fragment into the BamHI-MluI window of B/D50.

The resulting complete chimeric antigenomic cDNA was then used to produce virus by the above described method of complementation with N, P, M2-1 and L proteins expressed from cotransfected plasmids. This resulted in the recovery of the recombinant chimeric virus rAB, containing the B1 G and F genes in the wt A2 background. This novel virus was readily propagated in cell culture and formed plaques which were similar in size to those of wt rA2. The level of virus produced in cell culture were essentially identical to that of the wild-type parents. Expression of the B1 G and F glycoproteins, and the lack of expression of the A2 G and F glycoproteins, was demonstrated by immunoperoxidase staining using monoclonal antibodies which are specific to the G proteins of subgroup B and A, respectively. The presence of the B1 genes in the A2 backbone was confirmed by RT-PCR of RNA purified from rAB virions using oligonucleotide primers specific for the B1 sequence. In summary, a chimeric AB cDNA was constructed and successfully used to recover an infectious AB chimeric virus which has properties consistent with it being very similar to its parents in viability.

Although direct replacement of the strain A2 G and F genes by their strain B1 counterparts introduces B1-specific gene-start and gene-end transcription signals into the A2 background, this is not considered to be an important factor in light of the close similarity between the two viruses in these signals. For example, the gene-start signals of the G and F genes are exactly conserved between the subgroups, and the gene-end signal of the F gene has a single change (AGTTA TATAAAA [SEQ ID NO: 20] for strain A2, with the underlined position being C in strain B1). The gene-end signal of the G gene has three changes (AGTTACTTAAAAA [SEQ ID NO: 21] in positive sense for strain A2, with the three underlined positions being TTC for strain B1), but as noted above it was modified to be identical to that of the F gene of strain A2 and thus would be fully compatible with the strain A2 polymerase. The junctions between the B1 cDNA and the A2 backbone involved the SH-G and F-M2 intergenic regions. The length of the former did not change from 44 nucleotides: this is the same for both the A2 and B1 viruses, and the PacI site was designed to maintain this spacing. The length of the F-M2 intergenic region is 46 and 45 nucleotides for strains A2 and B1, respectively, and the AB chimera was designed to have the latter length. The G-F intergenic region was reduced in length to 5 nucleotides as described above, which is much shorter than its counterpart in the A2 and B1 viruses, which is 52 nucleotides in each case. Moreover, even though the naturally-occurring intergenic regions of RSV show considerable diversity in sequence and length between gene junctions and between viruses, those of strain A2 are equivalent with regard to their effect on minigenome replication and transcription, and thus the changes introduced here into the intergenic region likely will be silent (Kuo et al., 1996, incorporated herein by reference).

Construction and Recovery of AB chimeric RSV Having Attenuating Mutations in the A2 Backbone In accordance with the general teachings of the invention, the strain B1 G-F cDNA was substituted into a series of A2 backbones which contained various combinations of attenuating mutations for the purpose of generating attenuated AB viruses as vaccine candidates for subgroup B. These attenuating mutations included: (i) three of the five amino acid substitutions of cpRSV, namely the mutation in N (V267I) and the two in L (C319Y and H1690Y), but not the two in F since these are removed by substitution with the B1 F gene; (ii) the 248 (Q831L), 1030 (Y1321N) and, optionally, 404-L (D1183E) amino acid substitutions which were identified in the L protein of the attenuated strain A2 viruses cpts248, cpts248/404, and cpts530/1030; (iii) the nucleotide substitution at position 9 of the gene-start signal of the M2 gene of cpts248/404, and (iv) deletion of the SH gene. In the case of mutations in the L gene, these were inserted into the D39 plasmid containing the L gene as described above, and then combined with B/D50 plasmid as described above to make complete antigenomic cDNA. In the case of mutations that lie within D50, restriction fragment substitution was used to replace the relevant regions either within B/D50, which was then joined with D39, or within B/D53. Each mutation was marked by the introduction of a new restriction site, or ablation of a naturally-occurring one, which was silent at the amino acid level, as previously described (Juhasz et al., 1998; Juhasz et al., 1997; Whitehead et al., 1998a; Whitehead et al., 1998b, each incorporated herein by reference). In all cases, the structure of regions of antigenomic cDNA which were modified by mutagenesis was confirmed by nucleotide sequence analysis. A total of six modified AB antigenomic cDNAs were made. Each antigenomic cDNA was then used to recover infectious virus as described above, and in each case the chimeric virus was successfully recovered. The presence of each planned mutation in each recombinant virus was confirmed by reverse transcription (RT)-polymerase chain reaction (PCR) followed by restriction analysis or nucleotide sequencing. The six different recombinant AB chimeras containing attenuating mutations which have were recovered are listed in Table 44. Specifically, these attenuated chimeras include rAB, which is a wild-type chimera constructed with a wild-type strain A2 backbone and wild-type B1 G and F genes. The remaining viruses contain a variety of attenuating mutations in the strain A2 backbone and represent candidate vaccines against subgroup B. Each virus can be propagated in cell culture. This illustrates the feasibility of generating AB chimeras containing a number of different combinations of mutations.

TABLE 44

RSV Subgroup B Vaccine Candidates Based on Recombinant AB Chimeric Viruses

| Virus[1] | Description[2] |
|---|---|
| rAB | Wild type |
| rABcp | Cold passage (cp) mutations[3] |
| rABΔSH | Deletion of SH gene |
| rABcp248/404ΔSH | plus deletion of the SH gene |

TABLE 44-continued

RSV Subgroup B Vaccine Candidates Based
on Recombinant AB Chimeric Viruses

| Virus[1] | Description[2] |
|---|---|
| rABcp248/404/1030 | (cp, 248[4] and 404[5] mutations) plus the 1030[6] mutation |
| rABcp248/404/1030ΔSH | rABcp248/404/1030 plus deletion of the SH gene |

[1] All viruses are strain A2 in which the F and G glycoprotein genes have been replaced with those of strain B1.
[2] Phenotypes in cell culture which are consistent with expected properties conferred by mutations are as follows: each virus containing the ΔSH mutation made larger plaques than its counterpart containing the SH gene, and each virus containing the 1030 mutation made smaller plaques than its counterpart lacking the mutation.
[3] The cp mutations are the three amino acid substitutions in the N and L proteins: the two substitutions in F are not involved due to the gene replacement.
[4] The 248 mutation is Gln-831-Leu in the L protein.
[5] The 404 mutations are Asp-1183-Glu in the L protein and a point mutation in the M2 gene-start signal.
[6] The 1030 mutation is Tyr-1321-Asn in the L protein.

Two of the introduced mutations would be expected to confer phenotypes discernable in cell culture, based on their effect on strain A2. For example, the introduction of the _SH mutant confers larger plaque size, and the 1030 mutant confers reduced plaque size. Each of the AB chimeras which contained these mutations behaved appropriately. For example, the three chimeras lacking the SH gene made plaques which were larger than those of the corresponding virus which contained the SH gene. This suggests that these chimeras will also possess the mild attenuation phenotype which is associated with the deletion. Also, the addition of the 1030 mutation to rABcp248/404 and rABcp248/404_SH resulted in a decrease in plaque size compared to counterparts which lacked the 1030 mutation. This indicates that whenever a mutation was introduced which was predicted to alter the cell culture phenotype, the expected change was observed in the chimeric virus. It may be that some combinations will not conform to predictions. Nonetheless, this provides a method for incremental changes in phenotype. It is likely that other phenotypes associated with these mutations, such as attenuation in vivo, also will be conferred to the AB chimeras.

In addition, as shown in Table 45, the following viruses were analyzed for the temperature sensitive phenotype by measuring the efficiency of plaquing at various temperatures: the biologically-derived A2 and B1 wt viruses, the wt chimeric rAB virus, and the following derivatives of rAB containing attenuating mutations: rABcp, containing the cp mutations in N (V267I) and L (C319Y and H1690Y); rABΔSH, which is rAB from which the SH gene had been deleted; rABcpΔSH, which contains the aforementioned cp changes and SH deletion; rABcp248/404ΔSH, which is a version of rABcpΔSH which also contains the 248 (Q831L in the L protein) and 404 (D1183E in the L protein and a point mutation in the M2 gene start signal) mutations; and rABcp248/404/1030, which is a version of rABcp which contains the 248 and 404 mutations together with the 1030 mutation (Y1321N in the L protein). As shown in Table 45, the biologically-derived A2 and B1 viruses were not temperature sensitive. Viruses containing the B glycoprotein replacements showed a slight sensitivity, with a shut off temperature of 40 C. Inclusion of the cp and ΔSH mutations had no effect, which was expected since these do not confer the ts phenotype in strain A2. Inclusion of the 248 and 404 mutations together, or the 248, 404 and 1030 mutations together, yielded viruses with shut off temperatures of 37 C and 36 C, respectively, with small plaques formed at the next lower temperature in each case. These results are essentially indistinguishable from those obtained with these same two constellations of mutations placed in the wt A2 recombinant background. Thus, it has been possible to faithfully reconstruct these ts phenotypes in the rAB chimeras.

TABLE 45

Temperature sensitivity of AB chimeric RSV derivatives

| Virus | Virus titer ($\log_{10}$pfu/ml) on HEp-2 cells at indicated temperature (° C.) | | | | | | | Shut-off temp.[a] |
|---|---|---|---|---|---|---|---|---|
|  | 32 | 35 | 36 | 37 | 38 | 39 | 40 |  |
| rABcp248/404/1030 | 3.6 | 2.4* | <0.7 | <0.7 | <0.7 | <0.7 | <0.7 | 36 |
| rABcp248/404ΔSH | 5.2 | 3.9 | 3.8* | <0.7 | <0.7 | <0.7 | <0.7 | 37 |
| rABcpΔSH | 4.6 | 4.6 | 4.8 | 4.8 | 4.4 | 3.6* | <0.7 | 40 |
| rABΔSH | 4.9 | 4.1 | 4.4 | 4.1 | 4.1 | 3.2* | <0.7 | 40 |
| rABcp | 4.8 | 4.0 | 4.4 | 3.8 | 3.2 | 3.2* | <0.7 | 40 |
| rAB | 4.5 | 4.3 | 4.1 | 4.2 | 3.1 | 3.7* | 2.2 | 40 |
| wt RSV A2 | 5.3 | 5.2 | 5.3 | 5.0 | 5.1 | 5.1 | 4.8 | >40 |
| wt RSV B1 | 4.9 | 4.9 | 5.0 | 4.6 | 4.4 | 3.8 | 3.2 | >40 |

[a] Shut-off temperature is defined as the lowest restrictive temperature at which a 100-fold or greater reduction of titer is observed. Virus titers at the shut-off temperature are bolded.
*Pin-point plaque size Growth of rAB Viruses in the Respiratory Tract of Cotton Rats and Chimpanzees The chimeric recombinant rAB virus was evaluated for its ability to grow in the respiratory tract of cotton rats, a widely accepted model in which RSV A2 and B1 replicate comparably. Animals in groups of 5-6 were inoculated intranasally with $10^6$ pfu per animal of wt rAB virus or its _SH, cp or cp_SH derivatives. Since the attenuation phenotype associated with the _SH mutation is marginal in rodents, and that associated with the cp mutation set is essentially undetectable in rodents due to its host range nature, the purpose of this initial study was simply to demonstrate viability in vivo. On day 4 post infection, nasal turbinates and lungs were harvested and virus titers were determined by plaque assay. The parental A2 and B1 viruses replicated to $10^{6.0}$-$10^{6.5}$ pfu per g tissue. The wild type chimeric rAB virus and its derivatives containing attenuating mutations replicated to between $10^2$ and $10^4$ pfu g. This showed that the wild type and mutant AB viruses were viable in an experimental animal. also, it raises the possibility that the exchange of glycoproteins in the chimera was itself an attenuating change, although as shown below this appears to be a rodent-specific effect.

The chimpanzee is the experimental animal which most closely resembles the human with regard to RSV growth and disease. Therefore the wt rAB chimeric virus was administered to four seronegative juvenile chimpanzees, with each animal inoculated intranasally and intratracheally with $10^5$ pfu in a one ml inoculum at each site. An additional three animals were inoculated in the same way with the putative attenuated derivative rAPcp248/404/1030. Nasopharyngeal swabs were taken daily from day 1 to day 10 and on day 12, and tracheal lavages were taken on days 2, 5, 6, 8 and 12 mean peak titer of 2.0 $\log_{10}$ pfu/ml, which was 200-fold lower than that of the rAB wt. There were no disease symptoms associated with the rABcp248/404/1030 virus. These findings illustrate that the introduction of attenuating mutations into the A2 background restricts replication and eliminates disease symptoms.

TABLE 46

Replication of recombinant chimeric virus rAB in the upper and lower respiratory tract of chimpanzees

| Chimp | Virus ($\log_{10}$ pfu/site)[a] | Nasopharyngeal swab titer ($\log_{10}$ pfu/ml) Day post-inoculation | | | | | | | | | | | | Tracheal lavage titer ($\log_{10}$ pfu/ml) Day post-inoculation | | | | | | Peak rhinorrhea score |
|---|---|---|---|---|---|---|---|---|---|---|---|---|---|---|---|---|---|---|---|---|
| | | 1 | 2 | 3 | 4 | 5 | 6 | 7 | 8 | 9 | 10 | 12 | Peak | 2 | 5 | 6 | 8 | 12 | Peak | |
| 1622 | rAB (5.0) | <0.7 | 0.7 | 3.0 | 3.6 | 3.7 | 3.9 | 4.1 | 2.2 | 0.7 | <0.7 | <0.7 | 4.1 | <0.7 | 3.7 | 4.1 | 2.0 | <0.7 | 4.1 | 2 |
| 1625 | rAB (5.0) | <0.7 | 1.2 | 3.0 | 2.7 | 3.7 | 4.2 | 4.6 | 2.5 | 1.7 | <0.7 | <0.7 | 4.6 | <0.7 | 3.7 | 3.4 | 2.6 | <0.7 | 3.7 | 3 |
| 1627 | rAB (5.0) | <0.7 | 1.7 | 2.9 | 2.9 | 4.1 | 3.7 | 4.3 | 2.3 | 1.7 | <0.7 | <0.7 | 4.3 | <0.7 | 4.5 | 3.8 | 2.5 | <0.7 | 4.5 | 2 |
| 1628 | rAB (5.0) | <0.7 | 1.5 | 3.6 | 2.9 | 3.4 | 3.5 | 4.1 | 1.5 | 0.7 | <0.7 | <0.7 | 4.1 | <0.7 | 3.2 | 3.9 | 2.5 | <0.7 | 3.9 | 3 |
| | mean | | | | | | | | | | | | 4.3 | | | | | | 4.1 | 2.5 |
| 5835 | wtB1 (5.0) | <0.7 | <0.7 | 2.7 | 1.7 | 3.0 | 2.1 | 2.2 | <0.7 | <0.7 | <0.7 | <0.7 | 3.0 | <0.7 | <0.7 | <0.7 | <0.7 | <0.7 | 1.0 | 1 |
| 5867 | wtB1 (5.0) | <0.7 | <0.7 | 2.3 | 2.5 | 1.8 | 2.4 | 1.9 | 2.2 | <0.7 | <0.7 | <0.7 | 2.5 | <0.7 | 3.9 | <0.7 | <0.7 | <0.7 | 3.9 | 2 |
| | mean | | | | | | | | | | | | 2.8 | | | | | | 2.5 | 1.5 |
| 337 | wtB1 (4.0) | <0.7 | <0.7 | 2.4 | 2.9 | 2.9 | 2.9 | 3.7 | 1.0 | 2.5 | <0.7 | <0.7 | 3.7 | <0.7 | <0.7 | <0.7 | <0.7 | <0.7 | <0.7 | 3 |
| 346 | wtB1 (4.0) | <0.7 | <0.7 | <0.7 | <0.7 | <0.7 | 2.7 | 3.0 | 2.2 | 2.7 | 2.9 | <0.7 | 3.0 | <0.7 | <0.7 | <0.7 | <0.7 | <0.7 | <0.7 | 2 |
| 362 | wtB1 (4.0) | <0.7 | <0.7 | <0.7 | <0.7 | <0.7 | <0.7 | 2.5 | 2.3 | <0.7 | 1.7 | <0.7 | 2.5 | <0.7 | <0.7 | <0.7 | <0.7 | <0.7 | <0.7 | 3 |
| 365 | wtB1 (4.0) | <0.7 | <0.7 | <0.7 | 1.0 | 1.4 | 2.2 | 2.2 | 2.7 | <0.7 | 0.7 | <0.7 | 2.7 | <0.7 | <0.7 | <0.7 | 3.4 | <0.7 | 3.4 | 2 |
| | mean | | | | | | | | | | | | 3.0 | | | | | | 1.4 | 2.5 |
| 96A001 | 1030 (5.0)[b] | <0.7 | <0.7 | <0.7 | 1.0 | 1.2 | 2.4 | 1.3 | 1.6 | 2.0 | <0.7 | <0.7 | 2.4 | <0.7 | <0.7 | <0.7 | <0.7 | <0.7 | <0.7 | 0 |
| 95A013 | 1030 (5.0)[b] | <0.7 | <0.7 | <0.7 | 1.0 | 0.7 | 1.9 | 1.3 | 1.8 | 1.5 | <0.7 | <0.7 | 1.9 | <0.7 | <0.7 | <0.7 | <0.7 | <0.7 | <0.7 | 0 |
| 95a014 | 1030 (5.0)[b] | <0.7 | <0.7 | 1.0 | 1.0 | 1.0 | 1.6 | 1.8 | 1.8 | 1.0 | 1.0 | <0.7 | 1.8 | <0.7 | <0.7 | <0.7 | <0.7 | <0.7 | <0.7 | 0 |
| | mean | | | | | | | | | | | | 2.0 | | | | | | <0.7 | 0 |

[a]Each virus was administered in a 1.0 ml inoculum intranasally and intratracheally.
[b]Virus administered was rABcp248/404/1030

(Table 46). For comparison, other animals received at a dose of $10^4$ or $10^5$ plaque forming units (PFU)/site, as indicated. The table gives data for each animal with regard to shedding in the upper (nasopharyngeal swab) and lower (tracheal lavage) respiratory tract from days 1 to 12, and the peak rhinorrhea score on an increasing scale of 0 to 4. This also is illustrated in FIG. 27. The rAB chimera replicated to average peak titers of 4.3 $\log_{10}$ and 4.1 $\log_{10}$ pfu/ml in the nasopharynx and trachea, respectively. This exceeded the levels of replication of the biologically-derived wt B1 virus. Furthermore, the rAB virus caused disease symptoms (rhinorrhea) which equalled or exceeded the severity of those of the wt B1 virus. In contrast, replication of the rABcp248/404/1030 virus was highly restricted. This virus was not recovered from any of the tracheal lavages, representing a reduction in replication of greater than 2,500-fold whereas in the upper respiratory tract the rABcp248/404/1030 virus replicated to a To further evince successful practice of the invention, replication of the wt rAB chimera was compared with that of the wt A2 virus. Table 47 shows a summary of the data for the wt viruses from Table 46, together with historic controls involving two versions of strain A2: (i) four animals which had received rA2 at a dose of $10^4$ pfu per site, and (ii) four which had received biologically-derived A2 at a dose of $10^4$ pfu per site. This comparison showed that the wt B1 virus replicated less efficiently than did the wt A2 virus, whether biologically-derived or recombinant. Furthermore, growth of the chimeric AB virus was intermediate between that of the parental A2 and B1 viruses. The intermediate nature of the growth of rAB compared to its parents suggests that both the A2 backbone and the B1 glycoproteins contribute to growth fitness. The poor growth of the rAB viruses in cotton rats is likely attributed to a host range effect which reduces fitness in rodents but not primates. The level of replication in rodents can generally be used to predict the level in chimpanzees and humans. However, some dissociation between rodents and primates is occasionally observed, as in the present case.

TABLE 47 rAB Chimpanzee Study Summary

| No. | Virus (log$_{10}$pfu/site) | No. of chimps | Mean peak virus titer (log$_{10}$pfu/ml) Nasopharyngeal Swab | Mean peak virus titer (log$_{10}$pfu/ml) Tracheal Lavage | Mean Peak Rhinorrhea Score (Range = 0-4) |
|---|---|---|---|---|---|
| 1 | rAB (5.0) | 4 | 4.3 ± 0.12 | 4.1 ± 0.17 | 2.5 |
| 2 | wtB1 (5.0) | 2 | 2.8 ± 0.25 | 2.5 ± 1.45 | 1.5 |
| 3 | wtB1 (4.0) | 4 | 3.0 ± 0.26 | 1.4 ± 0.68 | 2.5 |
| 4 | rA2sites (4.0) | 4 | 5.0 ± 0.14 | 4.7 ± 0.43 | 2.5 |
| 5 | wtA2 (4.0) | 4 | 5.0 ± 0.35 | 5.5 ± 0.40 | 3.0 |

These foregoing results show that the G and F glycoproteins of a subgroup A virus, in this example strain A2, can be replaced by those of a subgroup B virus, in this example strain B1, without compromising viability. The chimera was fully competent for replication in the chimpanzee, the experimental animal which is the most permissive and is the most reliable model for infection in humans. Furthermore, the chimeric AB virus could be attenuated by the introduction of known attenuating mutations into the strain A2 backbone.

Although the foregoing invention has been described in some detail by way of illustration and example for purposes of clarity of understanding, it will be obvious that certain changes and modifications may be practiced within the scope of the appended claims.

What is claimed is:

1. An infectious chimeric respiratory syncytial virus (RSV) comprising a major nucleocapsid (N) protein, a nucleocapsid phosphoprotein (P), a large polymerase protein (L), a RSV M2 ORF1 RNA polymerase elongation factor (M2(ORF1)), and a partial or complete genome or antigenome of RSV A comprising genome segments encoding antigenic determinants of RSV B F and G glycoproteins, wherein the RSV A genome or antigenome contains the following attenuating mutations:
   i) a mutation encoding V267I in the N gene;
   ii) a mutation encoding C319Y in the L gene;
   iii) a mutation encoding H1690Y in the L gene;
   iv) a mutation encoding Q831L in the L gene;
   v) a mutation encoding D1183E in the L gene;
   vi) a point mutation T to C at nucleotide 7605 of the gene start of the M2 gene;
   and wherein the RSV A genome or antigenome further contains at least one of the following:
   a mutation encoding Y1321N in the L gene; or
   a deletion of the SH open reading frame.

2. The chimeric RSV of claim 1, wherein the chimeric genome or antigenome includes at least one attenuating mutation stabilized by multiple nucleotide changes in a codon specifying the mutation.

3. The chimeric RSV of claim 1 further comprising a nucleotide modification specifying a phenotypic change selected from a change in growth characteristics, attenuation, temperature-sensitivity, cold-adaptation, plaque size, host-range restriction, or a change in immunogenicity.

4. The chimeric RSV of claim 3, wherein a SH, NS1, NS2, M2ORF2, or G gene is modified.

5. The chimeric RSV of claim 4, wherein the SH, NS1, NS2, M2ORF2, or G gene is deleted in whole or in part or expression of the gene is ablated by introduction of one or more stop codons in an open reading frame of the gene.

6. The chimeric RSV of claim 3, wherein the nucleotide modification comprises an insertion, deletion, substitution, or rearrangement of a translational start site within the chimeric genome or antigenome.

7. The chimeric RSV of claim 1 which is a virus.

8. The chimeric RSV of claim 1 which is a subviral particle.

9. An immunogenic composition to elicit an immune response against RSV comprising an immunologically sufficient amount of the chimeric RSV of claim 1 in a physiologically acceptable carrier.

10. The immunogenic composition of claim 9, formulated in a dose of $10^3$ to $10^6$ PFU.

11. The immunogenic composition of claim 9, formulated for administration to the upper respiratory tract by spray, droplet or aerosol.

* * * * *

```
                        SEQUENCE LISTING

<160> NUMBER OF SEQ ID NOS: 38

<210> SEQ ID NO 1
<211> LENGTH: 15223
<212> TYPE: DNA
<213> ORGANISM: Respiratory Syncytial Virus

<400> SEQUENCE: 1
acgcgaaaaa atgcgtacaa caaacttgca taaaccaaaa aaatggggca aataagaatt      60
tgataagtac cacttaaatt taactcccct ggttagagat gggcagcaat tcattgagta     120
tgataaaagt tagattacaa aatttgtttg acaatgatga agtagcattg ttaaaaataa     180
catgctatac tgataaatta atacatttaa ctaatgcttt ggctaaggca gtgatacata     240
caatcaaatt gaatggcatt gtgtttgtgc atgttattac aagtagtgat atttgcccta     300
ataataatat tgtagtaaaa tccaatttca caacaatgcc agtactacaa aatggaggtt     360
atatatggga aatgatggaa ttaacacatt gctctcaacc taatggtcta ctagatgaca     420
attgtgaaat taaattctcc aaaaaactaa gtgattcaac aatgaccaat tatatgaatc     480
aattatctga attacttgga tttgatctta atccataaat tataattaat atcaactagc     540
aaatcaatgt cactaacacc attagttaat ataaaactta acagaagaca aaaatggggc     600
aaataaatca attcagccaa cccaaccatg gacacaaccc acaatgataa tacaccacaa     660
agactgatga tcacagacat gagaccgttg tcacttgaga ccataataac atcactaacc     720
agagacatca taacacacaa atttatatac ttgataaatc atgaatgcat agtgagaaaa     780
cttgatgaaa agcaggccac atttacattc ctggtcaact atgaaatgaa actattacac     840
aaagtaggaa gcactaaata taaaaaatat actgaataca acacaaaata tggcactttc     900
cctatgccaa tattcatcaa tcatgatggg ttcttagaat gcattggcat taagcctaca     960
aagcatactc ccataatata caagtatgat ctcaatccat aaatttcaac acaatattca    1020
cacaatctaa aacaacaact ctatgcataa ctatactcca tagtccagat ggagcctgaa    1080
aattatagta atttaaaact taaggagaga tataagatag aagatgggc aaatacaacc    1140 atggctctta gcaaagtcaa gttgaatgat acactcaaca agatcaact tctgtcatcc    1200 agcaaataca ccatccaacg gagcacagga gatagtattg atactcctaa ttatgatgtg    1260
cagaaacaca tcaataagtt atgtggcatg ttattaatca cagaagatgc taatcataaa    1320
ttcactgggt taataggtat gttatatgcg atgtctaggt taggaagaga agacaccata    1380
```

```
aaaatactca gagatgcggg atatcatgta aaagcaaatg gagtagatgt aacaacacat    1440
cgtcaagaca ttaatggaaa agaaatgaaa tttgaagtgt aacattggc aagcttaaca    1500 actgaaattc aaatcaacat tgagatagaa tctagaaaat cctacaaaaa aatgctaaaa    1560
gaaatgggag aggtagctcc agaatacagg catgactctc ctgattgtgg gatgataata    1620
ttatgtatag cagcattagt aataactaaa ttagcagcag gggacagatc tggtcttaca    1680
gccgtgatta ggagagctaa taatgtccta aaaaatgaaa tgaaacgtta caaaggctta    1740
ctacccaagg acatagccaa cagcttctat gaagtgtttg aaaaacatcc ccactttata    1800 gatgttttg ttcattttgg tatagcacaa tcttctacca gaggtggcag tagagttgaa    1860 gggattttg caggattgtt tatgaatgcc tatggtgcag gcaagtgat gttacggtgg    1920 ggagtcttag caaaatcagt taaaaatatt atgttaggac atgctagtgt gcaagcagaa    1980
atggaacaag ttgttgaggt ttatgaatat gcccaaaaat tgggtggtga agcaggattc    2040
taccatatat tgaacaaccc aaaagcatca ttattatctt tgactcaatt tcctcacttc    2100
tccagtgtag tattaggcaa tgctgctggc ctaggcataa tgggagagta cagaggtaca    2160
ccgaggaatc aagatctata tgatgcagca aaggcatatg ctgaacaact caaagaaaat    2220
ggtgtgatta actacagtgt actagacttg acagcagaag aactagaggc tatcaaacat    2280
cagcttaatc caaaagataa tgatgtagag ctttgagtta ataaaaatg gggcaaataa    2340 atcatcatgg aaaagtttgc tcctgaattc catggagaag atgcaaacaa cagggctact    2400
aaattcctag aatcaataaa gggcaaattc acatcaccca aagatcccaa gaaaaaagat    2460
agtatcatat ctgtcaactc aatagatata gaagtaacca agaaagccc tataacatca    2520 aattcaacta ttatcaaccc aacaaatgag acagatgata ctgcagggaa caagcccaat    2580
tatcaaagaa aacctctagt aagtttcaaa gaagaccta caccaagtga taatccttt    2640 tctaaactat acaaagaaac catagaaaca tttgataaca atgaagaaga atccagctat    2700
tcatacgaag aaataaatga tcagacaaac gataatataa cagcaagatt agataggatt    2760
gatgaaaaat taagtgaaat actaggaatg cttcacacat tagtagtggc aagtgcagga    2820
cctacatctg ctcgggatgg tataagagat gccatggttg gtttaagaga agaaatgata    2880
gaaaaaatca gaactgaagc attaatgacc aatgacagat tagaagctat ggcaagactc    2940
aggaatgagg aaagtgaaaa gatggcaaaa gacacatcag atgaagtgtc tctcaatcca    3000
acatcagaga aattgaacaa cctattggaa gggaatgata gtgacaatga tctatcactt    3060
gaagatttct gattagttac caatcttcac atcaacacac aataccaaca gaagaccaac    3120
aaactaacca acccaatcat ccaaccaaac atccatccgc caatcagcca acagccaac    3180 aaacaaccca gccaatccaa aactaaccac ccggaaaaaa tctataatat agttacaaaa    3240
aaaggaaagg gtggggcaaa tatggaaaca tacgtgaaca agcttcacga aggctccaca    3300
tacacagctg ctgttcaata caatgtctta gaaaaagacg atgaccctgc atcacttaca    3360
atatgggtgc ccatgttcca atcatctatg ccagcagatt tacttataaa agaactagct    3420
aatgtcaaca tactagtgaa acaaatatcc acacccaagg gaccttcact aagagtcatg    3480
ataaactcaa gaagtgcagt gctagcacaa atgcccagca aatttaccat atgcgctaat    3540
gtgtccttgg atgaaagaag caaactagca tatgatgtaa ccacaccctg tgaaatcaag    3600
gcatgtagtc taacatgcct aaaatcaaaa aatatgttga ctacagttaa agatctcact    3660
atgaagacac tcaaccctac acatgatatt attgctttat gtgaatttga aaacatagta    3720
```

```
acatcaaaaa aagtcataat accaacatac ctaagatcca tcagtgtcag aaataaagat    3780
ctgaacacac ttgaaaatat aacaaccact gaattcaaaa atgctatcac aaatgcaaaa    3840
atcatcccatt actcaggatt actattagtc atcacagtga ctacaacaa aggagcattc    3900
```

```
acatcaaaaa aagtcataat accaacatac ctaagatcca tcagtgtcag aaataaagat    3780
ctgaacacac ttgaaaatat aacaaccact gaattcaaaa atgctatcac aaatgcaaaa    3840
atcatcccatt actcaggatt actattagtc atcacagtga ctacaacaa aggagcattc    3900
aaatacataa agccacaaag tcaattcata gtagatcttg gagcttacct agaaaaagaa    3960
agtatatatt atgttaccac aaattggaag cacacagcta cacgatttgc aatcaaaccc    4020
atggaagatt aaccttttc ctctacatca gtgtgttaat tcatacaaac tttctaccta    4080
cattcttcac ttcaccatca caatcacaaa cactctgtgg ttcaaccaat caaacaaaac    4140
ttatctgaag tcccagatca tcccaagtca ttgtttatca gatctagtac tcaaataagt    4200
taataaaaaa tatacacatg gggcaaataa tcattggagg aaatccaact aatcacaata    4260
tctgttaaca tagacaagtc cacacaccat acagaatcaa ccaatggaaa atacatccat    4320
aacaatagaa ttctcaagca aattctggcc ttactttaca ctaatacaca tgatcacaac    4380
aataatctct ttgctaatca taatctccat catgattgca atactaaaca aactttgtga    4440
atataacgta ttccataaca aaacctttga gttaccaaga gctcgagtca acacatagca    4500
ttcatcaatc caacagccca aaacagtaac cttgcattta aaaatgaaca cccctacct     4560
ctttacaaca cctcattaac atcccaccat gcaaaccact atccatacta taagtagtt    4620
aattaaaaat agtcataaca atgaactagg atatcaagac taacaataac attggggcaa    4680
atgcaaacat gtccaaaaac aaggaccaac gcaccgctaa gacattagaa aggacctggg    4740
acactctcaa tcatttatta ttcatatcat cgtgcttata taagttaaat cttaaatctg    4800
tagcacaaat cacattatcc attctggcaa tgataatctc aacttcactt ataattgcag    4860
ccatcatatt catagcctcg gcaaaccaca aagtcacacc aacaactgca atcatacaag    4920
atgcaacaag ccagatcaag aacacaaccc caacatacct cacccagaat cctcagcttg    4980
gaatcagtcc ctctaatccg tctgaaatta catcacaaat caccaccata ctagcttcaa    5040
caacaccagg agtcaagtca accctgcaat ccacaacagt caagaccaaa aacacaacaa    5100
caactcaaac acaacccagc aagcccacca caaaacaacg ccaaaacaaa ccaccaagca    5160
aacccaataa tgatttttcac tttgaagtgt tcaactttgt accctgcagc atatgcagca    5220
acaatccaac ctgctgggct atctgcaaaa gaataccaaa caaaaaacca ggaaagaaaa    5280
ccactaccaa gcccacaaaa aaaccaaccc tcaagacaac caaaaaagat cccaaacctc    5340
aaaccactaa atcaaaggaa gtacccacca ccaagcccac agaagagcca accatcaaca    5400
ccaccaaaac aaacatcata actacactac tcacctccaa caccacagga aatccagaac    5460
tcacaagtca aatggaaacc ttccactcaa cttcctccga aggcaatcca agcccttctc    5520
aagtctctac aacatccgag tacccatcac aaccttcatc tccacccaac acaccacgcc    5580
agtagttact taaaaacata ttatcacaaa aggccttgac caacttaaac agaatcaaaa    5640
taaactctgg ggcaaataac aatggagttg ctaatcctca aagcaaatgc aattaccaca    5700
atcctcactg cagtcacatt ttgttttgct tctggtcaaa acatcactga agaattttat    5760
caatcaacat gcagtgcagt tagcaaaggc tatcttagtg ctctgagaac tggttggtat    5820
accagtgtta taactataga attaagtaat atcaagaaaa ataagtgtaa tggaacagat    5880
gctaaggtaa aattgataaa acaagaatta gataaatata aaaatgctgt aacagaattg    5940
cagttgctca tgcaaagcac acaagcaaca acaatcgag ccagaagaga actaccaagg    6000
tttatgaatt atacactcaa caatgccaaa aaaccaatg taacattaag caagaaaagg    6060
aaaagaagat ttcttggttt tttgttaggt gttggatctg caatcgccag tggcgttgct    6120
```

```
gtatctaagg tcctgcacct agaaggggaa gtgaacaaga tcaaaagtgc tctactatcc    6180
acaaacaagg ctgtagtcag cttatcaaat ggagttagtg ttttaaccag caaagtgtta    6240
gacctcaaaa actatataga taaacaattg ttacctattg tgaacaagca aagctgcagc    6300
atatcaaata tagaaactgt gatagagttc aacaaaaga acaacagact actagagatt     6360
accagggaat ttagtgttaa tgcaggcgta actacacctg taagcactta catgttaact    6420
aatagtgaat tattgtcatt aatcaatgat atgcctataa caaatgatca gaaaaagtta    6480
atgtccaaca atgttcaaat agttagacag caaagttact ctatcatgtc cataataaaa    6540
gaggaagtct tagcatatgt agtacaatta ccactatatg gtgttataga tacaccctgt    6600
tggaaactac acacatcccc tctatgtaca accaacacaa agaagggtc caacatctgt      6660 ttaacaagaa ctgacagagg atggtactgt gacaatgcag gatcagtatc tttcttccca     6720
caagctgaaa catgtaaagt tcaatcaaat cgagtatttt gtgacacaat gaacagttta    6780
acattaccaa gtgaagtaaa tctctgcaat gttgacatat tcaaccccaa atatgattgt    6840
aaaattatga cttcaaaaac agatgtaagc agctccgtta tcacatctct aggagccatt    6900
gtgtcatgct atggcaaaac taaatgtaca gcatccaata aaaatcgtgg aatcataaag    6960
acattttcta acgggtgcga ttatgtatca aataaagggg tggacactgt gtctgtaggt    7020
aacacattat attatgtaaa taagcaagaa ggtaaaagtc tctatgtaaa aggtgaacca    7080
ataataaatt tctatgaccc attagtattc ccctctgatg aatttgatgc atcaatatct    7140
caagtcaacg agaagattaa ccagagccta gcatttattc gtaaatccga tgaattatta    7200
cataatgtaa atgctggtaa atccaccaca aatatcatga taactactat aattatagtg    7260
attatagtaa tattgttatc attaattgct gttggactgc tcttatactg taaggccaga    7320
agcacaccag tcacactaag caaagatcaa ctgagtggta taaataatat tgcatttagt    7380
aactaaataa aaatagcacc taatcatgtt cttacaatgg tttactatct gctcatagac    7440
aacccatctg tcattggatt ttcttaaaat ctgaacttca tcgaaactct catctataaa    7500
ccatctcact tacactattt aagtagattc ctagtttata gttatataaa acacaattgc    7560
atgccagatt aacttaccat ctgtaaaaat gaaaactggg gcaaatatgt cacgaaggaa    7620
tccttgcaaa tttgaaattc gaggtcattg cttaaatggt aagaggtgtc attttagtca    7680
taattatttt gaatggccac cccatgcact gcttgtaaga caaaacttta tgttaaacag    7740
aatacttaag tctatggata aaagtataga taccttatca gaaataagtg gagctgcaga    7800
gttggacaga acagaagagt atgctcttgg tgtagttgga gtgctagaga gttatatagg    7860
atcaataaac aatataacta aacaatcagc atgtgttgcc atgagcaaac tcctcactga    7920
actcaatagt gatgatatca aaaagctgag ggacaatgaa gagctaaatt cacccaagat    7980
aagagtgtac aatactgtca tatcatatat tgaaagcaac aggaaaaaca ataaacaaac    8040
tatccatctg ttaaaaagat tgccagcaga cgtattgaag aaaaccatca aaaacacatt    8100
ggatatccat aagagcataa ccatcaacaa cccaaaagaa tcaactgtta gtgatacaaa    8160
tgaccatgcc aaaaataatg atactacctg acaaatatcc ttgtagtata acttccatac    8220
taataacaag tagatgtaga gttactatgt ataatcaaaa gaacacacta tatttcaatc    8280
aaaacaaccc aaataaccat atgtactcac cgaatcaaac attcaatgaa atccattgga    8340
cctctcaaga attgattgac acaattcaaa attttctaca acatctaggt attattgagg    8400
atatatatac aatatatata ttagtgtcat aacactcaat tctaacactc accacatcgt    8460
```

```
tacattatta attcaaacaa ttcaagttgt gggacaaaat ggatcccatt attaatggaa    8520
attctgctaa tgtttatcta accgatagtt atttaaaagg tgttatctct ttctcagagt    8580
gtaatgcttt aggaagttac atattcaatg gtccttatct caaaaatgat tataccaact    8640
taattagtag acaaatcca ttaatagaac acatgaatct aaagaaacta aatataacac    8700
agtccttaat atctaagtat cataaaggtg aaataaaatt agaagaacct acttattttc    8760
agtcattact tatgacatac aagagtatga cctcgtcaga acagattgct accactaatt    8820
tacttaaaaa gataataaga agagctatag aaataagtga tgtcaaagtc tatgctatat    8880
tgaataaact agggcttaaa gaaaaggaca agattaaatc caacaatgga caagatgaag    8940
acaactcagt tattacgacc ataatcaaag atgatatact ttcagctgtt aaagataatc    9000
aatctcatct taaagcagac aaaaatcact ctacaaaaca aaaagacaca atcaaaacaa    9060
cactcttgaa gaaattgatg tgttcaatgc aacatcctcc atcatggtta atacattggt    9120
ttaacttata cacaaaatta aacaacatat taacacagta tcgatcaaat gaggtaaaaa    9180
accatgggtt tacattgata gataatcaaa ctcttagtgg atttcaattt attttgaacc    9240
aatatggttg tatagtttat cataaggaac tcaaaagaat tactgtgaca acctataatc    9300
aattcttgac atggaaagat attagcctta gtagattaaa tgtttgttta attacatgga    9360
ttagtaactg cttgaacaca ttaaataaaa gcttaggctt aagatgcgga ttcaataatg    9420
ttatcttgac acaactattc ctttatggag attgtatact aaagctattt cacaatgagg    9480
ggttctacat aataaaagag gtagagggat ttattatgtc tctaatttta aatataacag    9540
aagaagatca attcagaaaa cgattttata atagtatgct caacaacatc acagatgctg    9600
ctaataaagc tcagaaaaat ctgctatcaa gagtatgtca tacattatta gataagacag    9660
tgtccgataa tataataaat ggcagatgga taattctatt aagtaagttc cttaaattaa    9720
ttaagcttgc aggtgacaat aaccttaaca atctgagtga actatatttt ttgttcagaa    9780
tatttggaca cccaatggta gatgaaagac aagccatgga tgctgttaaa attaattgca    9840
atgagaccaa attttacttg ttaagcagtc tgagtatgtt aagaggtgcc tttatatata    9900
gaattataaa agggtttgta aataattaca acagatggcc tactttaaga aatgctattg    9960
ttttacccct aagatggtta acttactata aactaaacac ttatcctttct ttgttggaac   10020
ttacagaaag agatttgatt gtgttatcag gactacgttt ctatcgtgag tttcggttgc   10080
ctaaaaaagt ggatcttgaa atgattataa atgataaagc tatatcacct cctaaaaatt   10140
tgatatggac tagtttccct agaaattaca tgccatcaca catacaaaac tatatagaac   10200
atgaaaaatt aaaattttcc gagagtgata aatcaagaag agtattagag tattatttaa   10260
gagataacaa attcaatgaa tgtgatttat acaactgtgt agttaatcaa agttatctca   10320
acaaccctaa tcatgtggta tcattgacag gcaaagaaag agaactcagt gtaggtagaa   10380
tgtttgcaat gcaaccggga atgttcagac aggttcaaat attggcagag aaaatgatag   10440
ctgaaaacat tttacaattc tttcctgaaa gtcttacaag atatggtgat ctagaactac   10500
aaaaaatatt agaactgaaa gcaggaataa gtaacaaatc aaatcgctac aatgataatt   10560
acaacaatta cattagtaag tgctctatca tcacagatct cagcaaattc aatcaagcat   10620
ttcgatatga aacgtcatgt atttgtagtg atgtgctgga tgaactgcat ggtgtacaat   10680
ctctattttc ctggttacat ttaactattc ctcatgtcac aataatatgc acatataggc   10740
atgcacccccc ctatatagga gatcatattg tagatcttaa caatgtagat gaacaaagtg   10800
gattatatag atatcacatg ggtggcatcg aagggtggtg tcaaaaacta tggaccatag   10860
```

```
aagctatatc actattggat ctaatatctc tcaaagggaa attctcaatt actgctttaa    10920
ttaatggtga caatcaatca atagatataa gcaaaccaat cagactcatg gaaggtcaaa    10980
ctcatgctca agcagattat ttgctagcat taaatagcct taaattactg tataaagagt    11040
atgcaggcat aggccacaaa ttaaaaggaa ctgagactta tatatcacga gatatgcaat    11100
ttatgagtaa aacaattcaa cataacggtg tatattaccc agctagtata aagaaagtcc    11160
taagagtggg accgtggata aacactatac ttgatgattt caaagtgagt ctagaatcta    11220
taggtagttt gacacaagaa ttagaatata gaggtgaaag tctattatgc agtttaatat    11280
ttagaaatgt atggttatat aatcagattg ctctacaatt aaaaaatcat gcattatgta    11340
acaataaact atatttggac atattaaagg ttctgaaaca cttaaaaacc ttttttaatc    11400
ttgataatat tgatacagca ttaacattgt atatgaattt acccatgtta tttggtggtg    11460
gtgatcccaa cttgttatat cgaagtttct atagaagaac tcctgacttc ctcacagagg    11520
ctatagttca ctctgtgttc atacttagtt attatacaaa ccatgactta aaagataaac    11580
ttcaagatct gtcagatgat agattgaata agttcttaac atgcataatc acgtttgaca    11640 aaaccctaa tgctgaattc gtaacattga tgagagatcc tcaagcttta gggtctgaga    11700
gacaagctaa aattactagc gaaatcaata gactggcagt tacagaggtt ttgagtacag    11760
ctccaaacaa aatattctcc aaaagtgcac aacattatac tactacagag atagatctaa    11820
atgatattat gcaaaatata gaacctacat atcctcatgg gctaagagtt gtttatgaaa    11880
gtttaccctt ttataaagca gagaaaatag taaatcttat atcaggtaca aaatctataa    11940
ctaacatact ggaaaaaact tctgccatag acttaacaga tattgataga gccactgaga    12000
tgatgaggaa aaacataact ttgcttataa ggatacttcc attggattgt aacagagata    12060
aaagagagat attgagtatg gaaaacctaa gtattactga attaagcaaa tatgttaggg    12120
aaagatcttg gtctttatcc aatatagttg gtgttacatc acccagtatc atgtatacaa    12180
tggacatcaa atatactaca agcactatat ctagtggcat aattatagag aaatataatg    12240
ttaacagttt aacacgtggt gagagaggac ccactaaacc atgggttggt tcatctacac    12300
aagagaaaaa aacaatgcca gtttataata gacaagtctt aaccaaaaaa cagagagatc    12360
aaatagatct attagcaaaa ttggattggg tgtatgcatc tatagataac aaggatgaat    12420
tcatggaaga actcagcata ggaaccctug ggttaacata tgaaaaggcc aagaaattat    12480
ttccacaata tttaagtgtc aattatttgc atcgccttac agtcagtagt agaccatgtg    12540
aattccctgc atcaatacca gcttatagaa caacaaatta tcactttgac actagcccta    12600
ttaatcgcat attaacagaa aagtatggtg atgaagatat tgacatagta ttccaaaact    12660
gtataagctt tggccttagt ttaatgtcag tagtagaaca atttactaat gtatgtccta    12720
acagaattat tctcataccct aagcttaatg agatacattt gatgaaacct cccatattca    12780
caggtgatgt tgatattcac aagttaaaac aagtgataca aaaacagcat atgttttac    12840 cagacaaaat aagtttgact caatatgtgg aattattctt aagtaataaa acactcaaat    12900
ctggatctca tgttaattct aatttaatat tggcacataa aatatctgac tattttcata    12960
atacttacat tttaagtact aatttagctg acattggat tctgattata caacttatga    13020
aagattctaa aggtattttt gaaaaagatt ggggagaggg atatataact gatcatatgt    13080
ttattaattt gaaagttttc ttcaatgctt ataagaccta tctcttgtgt tttcataaag    13140
gttatggcaa agcaaagctg gagtgtgata tgaacacttc agatcttcta tgtgtattgg    13200
```

```
aattaataga cagtagttat tggaagtcta tgtctaaggt atttttagaa caaaaagtta   13260
tcaaatacat tcttagccaa gatgcaagtt tacatagagt aaaaggatgt catagcttca   13320
aattatggtt tcttaaacgt cttaatgtag cagaattcac agtttgccct tgggttgtta   13380
acatagatta tcatccaaca catatgaaag caatattaac ttatatagat cttgttagaa   13440
tgggattgat aaatatagat agaatacaca ttaaaaataa acacaaattc aatgatgaat   13500
tttatacttc taatctcttc tacattaatt ataacttctc agataatact catctattaa   13560
ctaaacatat aaggattgct aattctgaat tagaaaataa ttacaacaaa ttatatcatc   13620
ctacaccaga aaccctagag aatatactag ccaatccgat taaaagtaat gacaaaaaga   13680
cactgaatga ctattgtata ggtaaaaatg ttgactcaat aatgttacca ttgttatcta   13740
ataagaagct tattaaatcg tctgcaatga ttagaaccaa ttacagcaaa caagatttgt   13800
ataatttatt ccctatggtt gtgattgata gaattataga tcattcaggc aatacagcca   13860
aatccaacca actttacact actacttccc accaaatatc cttagtgcac aatagcacat   13920
cactttactg catgcttcct tggcatcata ttaatagatt caattttgta tttagttcta   13980
caggttgtaa aattagtata gagtatattt taaaagatct taaaattaaa gatcccaatt   14040
gtatagcatt cataggtgaa ggagcaggga atttattatt gcgtacagta gtggaacttc   14100
atcctgacat aagatatatt tacagaagtc tgaaagattg caatgatcat agtttaccta   14160
ttgagttttt aaggctgtac aatggacata tcaacattga ttatggtgaa aatttgacca   14220
ttcctgctac agatgcaacc aacaacattc attggtctta tttacatata aagtttgctg   14280
aacctatcag tctttttgtc tgtgatgccg aattgtctgt aacagtcaac tggagtaaaa   14340 ttataatega atggagcaag catgtaagaa agtgcaagta ctgttcctca gttaataaat   14400
gtatgttaat agtaaaatat catgctcaag atgatattga tttcaaatta gacaatataa   14460
ctatattaaa aacttatgta tgcttaggca gtaagtaaa gggatcggag gtttacttag   14520
tccttacaat aggtcctgcg aatatattcc cagtatttaa tgtagtacaa aatgctaaat   14580
tgatactatc aagaaccaaa aatttcatca tgcctaagaa agctgataaa gagtctattg   14640
atgcaaatat taaaagtttg ataccctttc tttgttaccc tataacaaaa aaggaatta   14700 atactgcatt gtcaaaacta agagtgttg ttagtggaga tatactatca tattctatag   14760
ctggacgtaa tgaagttttc agcaataaac ttataaatca taagcatatg aacatcttaa   14820
aatggttcaa tcatgtttta aatttcagat caacagaact aaactataac catttatata   14880
tggtagaatc tacatatcct tacctaagtg aattgttaaa cagcttgaca accaatgaac   14940
ttaaaaaact gattaaaatc acaggtagtc tgttatacaa ctttcataat gaataatgaa   15000
taaagatctt ataataaaaa ttcccatagc tatacactaa cactgtattc aatttatagtt   15060 attaaaaatt aaaaatcata taattttta aataactttt agtgaactaa tcctaaagtt   15120
atcattttaa tcttggagga ataaattta accctaatct aattggttta tatgtgtatt   15180
aactaaatta cgagatatta gttttgaca cttttttct cgt                      15223
```

<210> SEQ ID NO 2
<211> LENGTH: 15225
<212> TYPE: DNA
<213> ORGANISM: Respiratory Syncytial Virus

<400> SEQUENCE: 2

```
acgcgaaaaa atgcgtacta caaacttgca cattcggaaa aaatgggca aataagaatt    60 tgataagtgc tatttaagtc taacctttc aatcagaaat ggggtgcaat tcactgagca   120
```

-continued

```
tgataaaggt tagattacaa aatttatttg acaatgacga agtagcattg ttaaaaataa    180
catgttatac tgacaaatta attcttctga ccaatgcatt agccaaagca gcaatacata    240
caattaaatt aaacggtata gttttttatac atgttataac aagcagtgaa gtgtgccctg   300
ataacaacat tgtagtaaaa tctaacttta caacaatgcc aatattacaa aacggaggat    360
acatatggga attgattgag ttgacacact gctctcaatt aaacggtcta atggatgata    420
attgtgaaat caaattttct aaaagactaa gtgactcagt aatgactaat tatatgaatc    480
aaatatctga tttacttggg cttgatctca attcatgaat tatgtttagt ctaactcaat    540
agacatgtgt ttattaccat tttagttaat ataaaaactc atcaaaggga aatggggcaa    600
ataaactcac ctaatcaatc aaactatgag cactacaaat gacaacacta ctatgcaaag    660
attaatgatc acggacatga gacccctgtc gatggattca ataataacat ctctcaccaa    720
agaaatcatc acacacaaat tcatatactt gataaacaat gaatgtattg taagaaaact    780
tgatgaaaga caagctacat ttacattctt agtcaattat gagatgaagc tactgcacaa    840
agtagggagt accaaataca agaaatacac tgaatataat acaaaatatg cactttccc    900 catgcctata tttatcaatc atggcgggtt tctagaatgt attggcatta agcctacaaa    960
acacactcct ataatataca aatatgacct caacccgtaa attccaacaa aaaaaaccaa   1020
cccaaccaaa ccaagctatt cctcaaacaa caatgctcaa tagttaagaa ggagctaatc   1080
cgttttagta attaaaaata aaagtaaagc caataacata aattggggca atacaaaga    1140 tggctcttag caaagtcaag ttaaatgata cattaaataa ggatcagctg ctgtcatcca   1200
gcaaatacac tattcaacgt agtacaggag ataatattga cactcccaat tatgatgtgc   1260
aaaaacacct aaacaaacta tgtggtatgc tattaatcac tgaagatgca aatcataaat   1320
tcacaggatt aataggtatg ttatatgcta tgtccaggtt aggaagggaa gacactataa   1380
agatacttaa agatgctgga tatcatgtta aagctaatgg agtagatata acaacatatc   1440
gtcaagatat aaatggaaag gaaatgaaat tcgaagtatt aacattatca agcttgacat   1500
cagaaataca agtcaatatt gagatagaat ctagaaaatc ctacaaaaaa atgctaaaag   1560
agatgggaga agtggctcca gaatataggc atgattctcc agactgtggg atgataatac   1620
tgtgtatagc agcacttgta ataaccaaat tagcagcagg agacagatca ggtcttacag   1680
cagtaattag gagggcaaac aatgtcttaa aaaatgaaat aaaacgctac aagggtctca   1740
taccaaagga tatagctaac agtttttatg aagtgtttga aaaacaccct catcttatag   1800 atgttttgt gcactttggc attgcacaat catcaacaag agggggtagt agagttgaag    1860
gaatctttgc aggattgttt atgaatgcct atggttcagg gcaagtaatg ctaagatggg   1920
gagttttagc caaatctgta aaaaatatca tgctaggtca tgctagtgtc caggcagaaa   1980
tggagcaagt tgtggaagtc tatgagtatg cacagaagtt gggaggagaa gctggattct   2040
accatatatt gaacaatcca aaagcatcat tgctgtcatt aactcaattt cctaacttct   2100
caagtgtggt cctaggcaat gcagcaggtc taggcataat gggagagtat agaggtacgc   2160
caagaaacca ggatctttat gatgcagcca aagcatatgc agagcaactc aaagaaaatg   2220
gagtaataaa ctacagtgta ttagacttaa cagcagaaga attggaagcc ataaagaatc   2280
aactcaaccc taaagaagat gatgtagagc tttaagttaa caaaaatac ggggcaaata   2340 agtcaacatg gagaagtttg cacctgaatt tcatggagaa gatgcaaata acaaagctac   2400
caaattccta gaatcaataa agggcaagtt cgcatcatcc aaagatccta agaagaaaga   2460
```

```
tagcataata tctgttaact caatagatat agaagtaacc aaagagagcc cgataacatc   2520
tggcaccaac atcatcaatc caacaagtga agccgacagt accccagaaa ccaaagccaa   2580
ctacccaaga aaacccctag taagcttcaa agaagatctc accccaagtg acaacccttt   2640
ttctaagttg tacaaagaaa caatagaaac atttgataac aatgaagaag aatctagcta   2700
ctcatatgaa gagataaatg atcaaacaaa tgacaacatt acagcaagac tagatagaat   2760
tgatgaaaaa ttaagtgaaa tattaggaat gctccataca ttagtagttg caagtgcagg   2820
acccacttca gctcgcgatg gaataagaga tgctatggtt ggtctgagag aagaaatgat   2880
agaaaaaata agagcggaag cattaatgac caatgatagg ttagaggcta tggcaagact   2940
taggaatgag gaaagcgaaa aaatggcaaa agacacctca gatgaagtgc ctcttaatcc   3000
aacttccaaa aaattgagtg acttgttgga agacaacgat agtgacaatg atctgtcact   3060
tgatgatttt tgatcagtga tcaactcact cagcaatcaa caacatcaat aaaacagaca   3120
tcaatccatt gaatcaactg ccagaccgaa caaacaaatg tccgtcagcg gaaccaccaa   3180
ccaatcaatc aaccaactga tccatcagca acctgacgaa attaacaata tagtaacaaa   3240 aaagaacaa gatggggcaa atatggaaac atacgtgaac aagcttcacg aaggctccac   3300
atacacagca gctgttcagt acaatgttct agaaaaagat gatgatcctg catcactaac   3360
aatatgggtg cctatgttcc agtcatctgt accagcagac ttgctcataa agaacttgc    3420 aagcatcaac atactagtga agcagatctc tacgcccaaa ggaccttcac tacgagtcac   3480
gattaactca agaagtgctg tgctggctca aatgcctagt aatttcatca taagcgcaaa   3540
tgtatcatta gatgaaagaa gcaaattagc atatgatgta actacacctt gtgaaatcaa   3600
agcatgcagt ctaacatgct taaaagtgaa aagtatgtta actacagtca aagatcttac   3660
catgaagaca ttcaacccca ctcatgagat cattgctcta tgtgaatttg aaaatattat   3720
gacatcaaaa agagtaataa taccaaccta tctaagacca attagtgtca aaacaagga    3780 tctgaactca ctagaaaaca tagcaaccac cgaattcaaa aatgctatca ccaatgcgaa   3840
aattattccc tatgctggat tagtattagt tatcacagtt actgacaata aaggagcatt   3900
caaatatatc aagccacaga gtcaatttat agtagatctt ggtgcctacc tagaaaaaga   3960
gagcatatat tatgtgacta ctaattggaa gcatacagct acacgttttt caatcaaacc   4020
actagaggat taaatttaat tatcaacact gaatgacagg tccacatata tcctcaaact   4080
acacactata tccaaacatc atgaacatct acactacaca cttcatcaca caaaccaatc   4140
ccactcaaaa tccaaaatca ctaccagcca ctatctgcta gacctagagt gcgaataggt   4200
aaataaaacc aaaatatggg gtaaatagac attagttaga gttcaatcaa tctcaacaac   4260
catttatacc gccaattcaa tacatatact ataaatctta aatgggaaa tacatccatc    4320 acaatagaat tcacaagcaa attttggccc tatttacac taatacatat gatcttaact    4380
ctaatctctt tactaattat aatcactatt atgattgcaa tactaaataa gctaagtgaa   4440
cataaaacat tctgtaacaa tactcttgaa ctaggacaga tgcatcaaat caacacatag   4500
tgctctacca tcatgctgtg tcaaattata tcctgtata tataaacaaa caaatccaat    4560
cttctcacag agtcatggtg tcgcaaaacc acgccaacta tcatggtagc atagagtagt   4620
tatttaaaaa ttaacataat gatgaattat tagtatggga tcaaaacaa cattgggca    4680 aatgcaacca tgtccaaaca caagaatcaa cgcactgcca ggactctaga aaagacctgg   4740
gatactctca atcatctaat tgtaatatcc tcttgtttat acagattaaa tttaaaatct   4800
atagcacaaa tagcactatc agttctggca atgataatct caacctctct cataattgca   4860
```

```
gccataatat tcatcatctc tgccaatcac aaagttacac taacaacggt cacagttcaa    4920
acaataaaaa accacactga aaaaaacatc accacctacc ttactcaagt cccaccagaa    4980
agggttagct catccaaaca acctacaacc acatcaccaa tccacacaaa ttcagccaca    5040
acatcaccca acacaaagtc agaaacacac cacacaacag cacaaaccaa aggcagaacc    5100
accacctcaa cacagaccaa caagccgagc acaaaaccac gcctaaaaaa tccaccaaaa    5160
aaaccaaaag atgattacca ttttgaagtg ttcaacttcg ttccctgtag tatatgtggc    5220
aacaatcaac tttgcaaatc catctgtaaa acaataccaa gcaacaaacc aaagaagaaa    5280
ccaaccatca aacccacaaa caaaccaacc accaaaacca caaacaaaag agacccaaaa    5340
acaccagcca aaacgacgaa aaaagaaact accaccaacc caacaaaaaa accaaccctc    5400
acgaccacag aaagagacac cagcacctca caatccactg tgctcgacac aaccacatta    5460
gaacacacaa tccaacagca atccctccac tcaaccaccc ccgaaaacac acccaactcc    5520
acacaaacac ccacagcatc cgagccctct acatcaaatt ccacccaaaa tacccaatca    5580
catgcttagt tattcaaaaa ctacatctta gcagaaaacc gtgacctatc aagcaagaac    5640
gaaattaaac ctggggcaaa taaccatgga gctgctgatc cacaggttaa gtgcaatctt    5700
cctaactctt gctattaatg cattgtacct cacctcaagt cagaacataa ctgaggagtt    5760
ttaccaatcg acatgtagtg cagttagcag aggttatttt agtgctttaa gaacaggttg    5820
gtataccagt gtcataacaa tagaattaag taatataaaa gaaaccaaat gcaatggaac    5880
tgacactaaa gtaaaactta taaaacaaga attagataag tataagaatg cagtgacaga    5940
attacagcta cttatgcaaa acacaccagc tgccaacaac cgggccagaa gagaagcacc    6000
acagtatatg aactatacaa tcaataccac taaaaaccta atgtatcaa taagcaagaa    6060 gaggaaacga agatttctgg gcttcttgtt aggtgtagga tctgcaatag caagtggtat    6120
agctgtatcc aaagttctac accttgaagg agaagtgaac aagatcaaaa atgctttgtt    6180
atctacaaac aaagctgtag tcagtctatc aaatggggtc agtgttttaa ccagcaaagt    6240
gttagatctc aagaattaca taaataacca attattaccc atagtaaatc aacagagctg    6300
tcgcatctcc aacattgaaa cagttataga attccagcag aagaacagca gattgttgga    6360
aatcaacaga gaattcagtg tcaatgcagg tgtaacaaca cctttaagca cttacatgtt    6420
aacaaacagt gagttactat cattgatcaa tgatatgcct ataacaaatg atcagaaaaa    6480
attaatgtca agcaatgttc agatagtaag gcaacaaagt tattctatca tgtctataat    6540
aaaggaagaa gtccttgcat atgttgtaca gctacctatc tatggtgtaa tagatacacc    6600
ttgctggaaa ttacacacat cacctctatg caccaccaac atcaaagaag gatcaaatat    6660
ttgtttaaca aggactgata gaggatggta ttgtgataat gcaggatcag tatccttctt    6720
tccacaggct gacacttgta aagtacagtc caatcgagta ttttgtgaca ctatgaacag    6780
tttgacatta ccaagtgaag tcagcctttg taacactgac atattcaatt ccaagtatga    6840
ctgcaaaatt atgacatcaa aaacagacat aagcagctca gtaattactt ctcttggagc    6900
tatagtgtca tgctatggta aaactaaatg cactgcatcc aacaaaaatc gtgggattat    6960
aaagacattt tctaatggtt gtgactatgt gtcaaacaaa ggagtagata ctgtgtcagt    7020
gggcaacact ttatactatg taaacaagct ggaaggcaag aacctttatg taaaagggga    7080
acctataata aattactatg accctctagt gtttccttct gatgagtttg atgcatcaat    7140
atctcaagtc aatgaaaaaa tcaatcaaag tttagctttt attcgtagat ctgatgaatt    7200
```

```
actacataat gtaaatactg gcaaatctac tacaaatatt atgataacta caattattat    7260
agtaatcatt gtagtattgt tatcattaat agctattggt ttgctgttgt attgcaaagc    7320
caaaaacaca ccagttacac taagcaaaga ccaactaagt ggaatcaata atattgcatt    7380
cagcaaatag acaaaaaacc acctgatcat gtttcaacaa cagtctgctg atcaccaatc    7440
ccaaatcaac ccataacaaa cacttcaaca tcacagtaca ggctgaatca tttcttcaca    7500
tcatgctacc cacacaacta agctagatcc ttaactcata gttacataaa aacctcaagt    7560
atcacaatca aacactaaat caacacatca ttcacaaaat taacagctgg ggcaaatatg    7620
tcgcgaagaa atccttgtaa atttgagatt agaggtcatt gcttgaatgg tagaagatgt    7680
cactacagtc ataattactt tgaatggcct cctcatgcct tactagtgag gcaaaacttc    7740
atgttaaaca agatactcaa gtcaatggac aaaagcatag acactttgtc tgaaataagt    7800
ggagctgctg aactggacag aacagaagaa tatgctcttg gtatagttgg agtgctagag    7860
agttacatag gatctataaa caacataaca aaacaatcag catgtgttgc tatgagtaaa    7920
cttcttattg agatcaatag tgatgacatt aaaaagctga gagataatga agaacccaat    7980
tcacctaaga taagagtgta caatactgtt atatcataca ttgagagcaa tagaaaaaac    8040
aacaagcaaa caatccatct gctcaaaaga ctaccagcag acgtgctgaa gaagacaata    8100
aaaaacacat tagatatcca caaaagcata atcataagca acccaaaaga gtcaaccgtg    8160
aatgatcaaa atgaccaaac caaaaataat gatattaccg gataaatatc cttgtagtat    8220
atcatccata ttgatttcaa gtgaaagcat gattgctaca ttcaatcata aaaacatatt    8280
acaatttaac cataaccatt tggataacca ccagcgttta ttaaataata tatttgatga    8340
aattcattgg acacctaaaa acttattaga tgccactcaa caatttctcc aacatcttaa    8400
catccctgaa gatatatata caatatatat attagtgtca taatgcttgg ccataacgat    8460
tctatatcat ccaaccataa aactatctta ataaggttat gggacaaaat ggatcccatt    8520
attaatggaa actctgctaa tgtgtatcta actgatagtt atttaaaagg tgttatctct    8580
ttttcagaat gtaatgcttt agggagttac ctttttaacg gcccttatct caaaaatgat    8640
tacaccaact taattagtag acaaagtcca ctactagagc atatgaatct taaaaaacta    8700
actataacac agtcattaat atctagatat cataaaggtg aactgaaatt agaagaacca    8760
acttatttcc agtcattact tatgacatat aaaagcatgt cctcgtctga acaaattgct    8820
acaactaact tacttaaaaa aataatacga gagctatag aaataagtga tgtaaaggtg    8880
tacgccatct tgaataaact aggactaaag gaaaaggaca gagttaagcc caacaataat    8940
tcaggtgatg aaaactcagt acttacaact ataattaaag atgatatact ttcggctgtg    9000
gaaagcaatc aatcatatac aaattcagac aaaaatcact cagtaaatca aaatatcact    9060
atcaaaacaa cactcttgaa aaattgatg tgttcaatgc aacatcctcc atcatggtta    9120
atacactggt tcaatttata tacaaaatta ataacatat taacacaata tcgatcaaat    9180
gaggtaaaaa gtcatgggtt tatattaata gataatcaaa ctttaagtgg ttttcagttt    9240
attttaaatc aatatggttg tatcgtttat cataaaggac tcaaaaaaat cacaactact    9300
acttacaatc aattttttaac atggaaagac atcagcctta gcagattaaa tgtttgctta    9360
attacttgga taagtaattg tttgaataca ttaaataaaa gcttagggct gagatgtgga    9420
ttcaataatg ttgtgttatc acaattattt ctttatggag attgtatact gaaattattt    9480
cataatgaag gcttctacat aataaaagaa gtagagggat ttattatgtc tttaattcta    9540
aacataacag aagaagatca atttaggaaa cgattttata atagcatgct aaataacatc    9600
```

```
acagatgcag ctattaaggc tcaaaagaac ctactatcaa gggtatgtca cactttatta    9660
gacaagacag tgtctgataa tatcataaat ggtaaatgga taatcctatt aagtaaattt    9720
cttaaattga ttaagcttgc aggtgataat aatctcaata atttgagtga gctatatttt    9780
ctcttcagaa tctttggaca tccaatggtt gatgaaagac aagcaatgga tgctgtaaga    9840
attaactgta atgaaactaa gttctactta ttaagtagtc taagtacgtt aagaggtgct    9900
ttcatttata gaatcataaa agggtttgta aatacctaca acagatggcc cactttaagg    9960
aatgctattg tcctacctct aagatggtta aactattata aacttaatac ttatccatct   10020
ctacttgaaa tcacagaaaa tgatttgatt attttatcag gattgcggtt ctatcgtgaa   10080
tttcatctgc ctaaaaaagt ggatcttgaa atgataataa atgacaaagc catttcacct   10140
ccaaaagatc taatatggac tagttttcct agaaattaca tgccatcaca tatacaaaat   10200
tatatagaac atgaaaagtt gaagttctct gaaagcgaca gatcaagaag agtactagag   10260
tattacttga gagataataa attcaatgaa tgcgatctat acaattgtgt agtcaatcaa   10320
agctatctca acaactctaa tcacgtggta tcactaactg gtaaagaaag agagctcagt   10380
gtaggtagaa tgtttgctat gcaaccaggt atgtttaggc aaatccaaat cttagcagag   10440
aaaatgatag ccgaaaatat tttacaattc ttccctgaga gtttgacaag atatggtgat   10500
ctagagcttc aaaagatatt agaattaaaa gcaggaataa gcaacaagtc aaatcgttat   10560
aatgataact acaacaatta tatcagtaaa tgttctatca ttacagatct tagcaaattc   10620
aatcaagcat ttagatatga acatcatgt atctgcagtg atgtattaga tgaactgcat   10680
ggagtacaat ctctgttctc ttggttgcat ttaacaatac ctcttgtcac aataatatgt   10740
acatatagac atgcacctcc tttcataaag gatcatgttg ttaatcttaa tgaagttgat   10800
gaacaaagtg gattatacag atatcatatg ggtggtattg agggctggtg tcaaaaactg   10860
tggaccattg aagctatatc attattagat ctaatatctc tcaaagggaa attctctatc   10920
acagctctga taaatggtga taatcagtca attgatataa gtaaaccagt tagacttata   10980
gagggtcaga cccatgctca agcagattat ttgttagcat taaatagcct taaattgcta   11040
tataaagagt atgcaggtat aggccataag cttaagggaa cagagaccta tatatcccga   11100
gatatgcagt tcatgagcaa aacaatccag cacaatggag tgtactatcc agccagtatc   11160
aaaaaagtcc tgagagtagg tccatggata aatacaatac ttgatgattt taagttagt   11220
ttagaatcta taggtagctt aacacaggag ttagaataca gaggggaaag cttattatgc   11280
agtttaatat ttaggaacat ttggttatac aatcaaattg ctttgcaact ccgaaatcat   11340
gcattatgta acaataagct atatttagat atattgaaag tattaaaaca cttaaaaact   11400
tttttaatc ttgatagtat cgatatggcg ttatcattgt atatgaattt gcctatgctg   11460
tttggtggtg gtgatcctaa tttgttatat cgaagctttt ataggagaac tccagacttc   11520
cttacagaag ctatagtaca ttcagtgttt gtgttgagct attatactgg tcacgattta   11580
caagataagc tccaggatct tccagatgat agactgaaca aattcttgac atgtgtcatc   11640
acattcgata aaaatcccaa tgccgagttt gtaacattga tgagggatcc acaggcgtta   11700
gggtctgaaa ggcaagctaa aattactagt gagattaata gattagcagt aacagaagtc   11760
ttaagtatag ctccaaacaa atatttttct aaaagtgcac aacattatac taccactgag   11820
attgatctaa atgacattat gcaaaatata gaaccaactt accctcatgg attaagagtt   11880
gtttatgaaa gtctacccct ttataaagca gaaaaaatag ttaatcttat atcaggaaca   11940
```

-continued

```
aaatccataa ctaatatact tgaaaaaaca tcagcaatag atacaactga tattaatagg    12000
gctactgata tgatgaggaa aaatataact ttacttataa ggatacttcc actagattgt    12060
aacaaagaca aaagagagtt attaagttta gaaaatctta gtataactga attaagcaag    12120
tatgtaagag aaagatcttg gtcattatcc aatatagtag gagtaacatc gccaagtatt    12180
atgttcacaa tggacattaa atatacaact agcactatag ccagtggtat aattatagaa    12240
aaatataatg ttaatagttt aactcgtggt gaaagaggac ctactaagcc atgggtaggt    12300
tcatctacgc aggagaaaaa aacaatgcca gtgtacaata gacaagtttt aaccaaaaag    12360
caaagagacc aaatagattt attagcaaaa ttagactggg tatatgcatc catagacaac    12420
aaagatgaat tcatggaaga actgagtact ggaacacttg gactgtcata tgaaaaagcc    12480
aaaaagttgt ttccacaata tctaagtgtc aattatttac accgtttaac agtcagtagt    12540
agaccatgtg aattccctgc atcaatacca gcttatagaa caacaaatta tcatttcgat    12600
actagtccta tcaatcatgt attaacgaaa agtatggag atgaagatat cgacattgtg    12660
tttcaaaatt gcataagttt tggtcttagc ctgatgtcgg ttgtggaaca attcacaaac    12720
atatgtccta atagaattat tctcataccg aagctgaatg agatacattt gatgaaacct    12780
cctatattta caggagatgt tgatatcatc aagttgaagc aagtgataca aaaacagcat    12840
atgttcctac cagataaaat aagtttaacc caatatgtag aattattcct aagtaacaaa    12900
gcacttaaat ctggatctaa catcaattct aatttaatat tagtacataa aatgtctgat    12960
tattttcata atgcttatat tttaagtact aatttagctg acattggat tctaattatt    13020 caacttatga aagattcaaa aggtattttt gaaaaagatt ggggagaggg gtacataact    13080
gatcatatgt tcattaattt gaatgttttc tttaatgctt ataagactta tttgctatgt    13140
tttcataaag gttatggtaa agcaaaatta gaatgtgata tgaacacttc agatcttctt    13200
tgtgttttgg agttaataga cagtagctac tggaaatcta tgtctaaagt tttcctagaa    13260
caaaaagtca taaaatacat agtcaatcaa gacacaagtt tgcatagaat aaaaggctgt    13320
cacagtttta agttgtggtt tttaaaacgc cttaataatg ctaaatttac cgtatgccct    13380
tgggttgtta acatagatta tcacccaaca catatgaaag ctatattatc ttacatagat    13440
ttagttagaa tggggttaat aaatgtagat aaattaacca ttaaaaataa aaacaaattc    13500
aatgatgaat tttacacatc aaatctcttt tacattagtt ataacttttc agacaacact    13560
catttgctaa caaacaaat aagaattgct aattcagaat tagaagataa tttataacaaa    13620 ctatatcacc caaccccaga aactttagaa aatatatcat taattcctgt taaaagtaat    13680
aatagtaaca aacctaaatt ttgtataagt ggaaataccg aatctataat gatgtcaaca    13740
ttctctaata aaatgcatat taaatcttcc actgttacca caagattcaa ttatagcaaa    13800
caagacttgt acaatttatt tccaaatgtt gtgatagaca ggattataga tcattcaggt    13860
aatacagcaa aatctaacca actttacatc accacttcac atcagacatc tttagtaagg    13920
aatagtgcat cactttattg catgcttcct ggcatcatg tcaatagatt aactttgta    13980 tttagttcca caggatgcaa gatcagtata gagtatattt taaagatct taagattaag    14040 gaccccagtt gtatagcatt cataggtgaa ggagctggta acttattatt acgtacggta    14100
gtagaacttc atccagacat aagatacatt tacagaagtt taaagattg caatgatcat    14160 agtttaccta ttgaatttct aagattatac aacgggcata taaacataga ttatggtgag    14220
aatttaacca ttcctgctac agatgcaact aataacattc attggtctta tttacatata    14280
aaatttgcag aacctattag catctttgtc tgcgatgctg aattacctgt tacagccaat    14340
```

-continued

```
tggagtaaaa ttataattga atggagtaag catgtaagaa agtgcaagta ctgttcttct    14400
gtaaatagat gcattttaat cgcaaaatat catgctcaag atgatattga tttcaaatta    14460
gataacatta ctatattaaa aacttacgtg tgcctaggta gcaagttaaa aggatctgaa    14520
gtttacttag tccttacaat aggccctgca aatatacttc ctgtttttga tgttgtgcaa    14580
aatgctaaat tgatttttc aagaactaaa aatttcatta tgcctaaaaa aactgacaag     14640
gaatctatcg atgcaaatat taaaagctta ataccttcc tttgttaccc tataacaaaa    14700
aaaggaatta agacttcatt gtcaaaattg aagagtgtag ttaatgggga tatattatca    14760
tattctatag ctggacgtaa tgaagtattc agcaacaagc ttataaacca caagcatatg    14820
aatatcctaa aatggctaga tcatgtttta aattttagat cagctgaact taattacaat    14880
catttataca tgatagagtc cacatatcct tacttaagtg aattgttaaa tagtttaaca    14940
accaatgagc tcaagaaact gattaaaata acaggtagtg tactatacaa ccttcccaac    15000
gaacagtaac ttaaaatatc attaacaagt ttggtcaaat ttagatgcta acacatcatt    15060
atattatagt tattaaaaaa tatgcaaact tttcaataat ttagcttact gattccaaaa    15120 ttatcattt attttaagg ggttgaataa aagtctaaaa ctaacaatga tacatgtgca     15180
tttacaacac aacgagacat tagtttttga cactttttt ctcgt                    15225
```

<210> SEQ ID NO 3
<211> LENGTH: 33
<212> TYPE: DNA
<213> ORGANISM: Artificial Sequence
<220> FEATURE:
<223> OTHER INFORMATION: Positive-sense M gene fragment

<400> SEQUENCE: 3
actcaaataa gttaataaaa aatatcccgg gat                                 33

<210> SEQ ID NO 4
<211> LENGTH: 31
<212> TYPE: DNA
<213> ORGANISM: Artificial Sequence
<220> FEATURE:
<223> OTHER INFORMATION: Negative-sense M gene fragment

<400> SEQUENCE: 4
cccgggatat tttttattaa cttatttgag t 31

<210> SEQ ID NO 5
<211> LENGTH: 18
<212> TYPE: DNA
<213> ORGANISM: Artificial Sequence
<220> FEATURE:
<223> OTHER INFORMATION: Positive-sense primer uptream of SH gene

<400> SEQUENCE: 5
gaaagtatat attatgtt 18

<210> SEQ ID NO 6
<211> LENGTH: 20
<212> TYPE: DNA
<213> ORGANISM: Artificial Sequence
<220> FEATURE:
<223> OTHER INFORMATION: Negative-sense primer downstream of SH gene

<400> SEQUENCE: 6
tatataagca cgatgatatg 20

<210> SEQ ID NO 7
<211> LENGTH: 16
<212> TYPE: DNA
<213> ORGANISM: Artificial Sequence
<220> FEATURE:
<223> OTHER INFORMATION: Positive-sense M gene fragment

<400> SEQUENCE: 7
actcaaataa gttaat                                                    16

<210> SEQ ID NO 8
<211> LENGTH: 14
<212> TYPE: DNA
<213> ORGANISM: Artificial Sequence
<220> FEATURE:
<223> OTHER INFORMATION: Negative-sense M gene fragment

<400> SEQUENCE: 8
taacttattt gagt                                                      14

<210> SEQ ID NO 9
<211> LENGTH: 28
<212> TYPE: DNA
<213> ORGANISM: Artificial Sequence
<220> FEATURE:
<223> OTHER INFORMATION: Forward PCR primer for NS1 gene deletion

<400> SEQUENCE: 9
gacacaaccc acaatgataa tacaccac                                       28

<210> SEQ ID NO 10
<211> LENGTH: 32
<212> TYPE: DNA
<213> ORGANISM: Artificial Sequence
<220> FEATURE:
<223> OTHER INFORMATION: Reverse PCR primer for NS1 gene deletion

<400> SEQUENCE: 10
catctctaac caagggagtt aaatttaagt gg                                  32

<210> SEQ ID NO 11
<211> LENGTH: 27
<212> TYPE: DNA
<213> ORGANISM: Artificial Sequence
<220> FEATURE:
<223> OTHER INFORMATION: Forward PCR primer for NS2 gene deletion

<400> SEQUENCE: 11
ttaaggagag atataagata gaagatg                                        27

<210> SEQ ID NO 12
<211> LENGTH: 27
<212> TYPE: DNA
<213> ORGANISM: Artificial Sequence
<220> FEATURE:
<223> OTHER INFORMATION: Reverse PCR primer for NS2 gene deletion

<400> SEQUENCE: 12
gttttatatt aactaatggt gttagtg                                        27

<210> SEQ ID NO 13
<211> LENGTH: 33
<212> TYPE: DNA
<213> ORGANISM: Artificial Sequence
<220> FEATURE:
<223> OTHER INFORMATION: Forward PCR primer for ablation of G gene -continued start site

<400> SEQUENCE: 13
ttataattgc agccatcata ttcatagcct cgg 33

<210> SEQ ID NO 14
<211> LENGTH: 30
<212> TYPE: DNA
<213> ORGANISM: Artificial Sequence
<220> FEATURE:
<223> OTHER INFORMATION: Reverse PCR primer for ablation of G gene
start site

<400> SEQUENCE: 14
gtgaagttga gattacaatt gccagaatgg 30

<210> SEQ ID NO 15
<211> LENGTH: 48
<212> TYPE: DNA
<213> ORGANISM: Artificial Sequence
<220> FEATURE:
<223> OTHER INFORMATION: Positive-sense primer for intergenic region
preceding the G gene

<400> SEQUENCE: 15
gcatggatcc ttaattaaaa attaacataa tgatgaatta ttagtatg 48

<210> SEQ ID NO 16
<211> LENGTH: 51
<212> TYPE: DNA
<213> ORGANISM: Artificial Sequence
<220> FEATURE:
<223> OTHER INFORMATION: Negative-sense primer for intergenic region
downstream of F gene

<400> SEQUENCE: 16
gtgttggatc ctgattgcat gcttgaggtt tttatgtaac tatgagttaa g 51

<210> SEQ ID NO 17
<211> LENGTH: 13
<212> TYPE: DNA
<213> ORGANISM: Artificial Sequence
<220> FEATURE:
<223> OTHER INFORMATION: Description of Artificial Sequence: G
gene-end signal

<400> SEQUENCE: 17
agttattcaa aaa 13

<210> SEQ ID NO 18
<211> LENGTH: 48
<212> TYPE: DNA
<213> ORGANISM: Artificial Sequence
<220> FEATURE:
<223> OTHER INFORMATION: Positve-sense primer with G gene-end and F
gene-start signals

<400> SEQUENCE: 18
ccacgcctaa tgagttatat aaaacaattg gggcaaataa ccatggag 48

<210> SEQ ID NO 19
<211> LENGTH: 46
<212> TYPE: DNA
<213> ORGANISM: Artificial Sequence
<220> FEATURE:
<223> OTHER INFORMATION: Negative-sense primer with G gene-end and F
gene-start signals

<400> SEQUENCE: 19
gactgagtgt tctgagtaga gttggatgta gagggctcgg atgctg                46

<210> SEQ ID NO 20
<211> LENGTH: 12
<212> TYPE: DNA
<213> ORGANISM: Artificial Sequence
<220> FEATURE:
<223> OTHER INFORMATION: Description of Artificial Sequence: F
      gene-end signal of RSV A2

<400> SEQUENCE: 20
agttatataa aa                                                     12

<210> SEQ ID NO 21
<211> LENGTH: 13
<212> TYPE: DNA
<213> ORGANISM: Artificial Sequence
<220> FEATURE:
<223> OTHER INFORMATION: G gene-end signal of RSV A2

<400> SEQUENCE: 21
agttacttaa aaa                                                    13

<210> SEQ ID NO 22
<211> LENGTH: 51
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n, if present, is c

<400> SEQUENCE: 22
aaaanuuaag gagagauaua agauagaaga uggggcaaau acaamsaugg c           51

<210> SEQ ID NO 23
<211> LENGTH: 53
<212> TYPE: RNA
<213> ORGANISM: Artificial Sequence
<220> FEATURE:
<223> OTHER INFORMATION: Synthetic oligonucleotide

<400> SEQUENCE: 23
uuaaaaacau auuaucacaa aargccwuga ccaacuuaaa cagaaucaaa aua         53

<210> SEQ ID NO 24
<211> LENGTH: 51
<212> TYPE: RNA
<213> ORGANISM: Artificial Sequence
<220> FEATURE:
<223> OTHER INFORMATION: Synthetic oligonucleotide

<400> SEQUENCE: 24
aaacacaauu gmaugccaga uuaacuuacc aucuguaaaa augaaaacug g           51

<210> SEQ ID NO 25
<211> LENGTH: 73
<212> TYPE: DNA
<213> ORGANISM: Artificial Sequence
<220> FEATURE:
<223> OTHER INFORMATION: Synthetic oligonucleotide

<400> SEQUENCE: 25

```
ccaaaaaagt cccgggtcaa aaatggggca aataagaatt tgataagtac cacttaaatt      60
taactctaga atg                                                        73

<210> SEQ ID NO 26
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 26
taactgcagt attcaattat agttattaaa aattaacccg ggaaatcat                 49

<210> SEQ ID NO 27
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 27
atgagaccgt wgtmacytga gaccata                                         27

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide

<400> SEQUENCE: 28

Met Arg Pro Leu Ser Leu Glu Thr Ile
1               5

<210> SEQ ID NO 29
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 29
agttaatata aaa                                                        13

<210> SEQ ID NO 30
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 30
agttaataaa aaa                                                        13

<210> SEQ ID NO 31
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 31
agtaatttaa aa                                                         12
```

```
<210> SEQ ID NO 32
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 32
agttaataaa aaa                                                          13

<210> SEQ ID NO 33
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is Met or Ile
<220> FEATURE:
<221> NAME/KEY: misc_feature
<222> LOCATION: (5)..(5)
<223> OTHER INFORMATION: Xaa is Ile or Val

<400> SEQUENCE: 33

Ile Leu Ala Xaa Xaa Ile Ser Thr Ser
 1               5

<210> SEQ ID NO 34
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 34
auucuggcaa ukruaaucuc aacuuca                                           27

<210> SEQ ID NO 35
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 35
actataaagt agttaattaa aaattaacat aatgatgaat tat                         43

<210> SEQ ID NO 36
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 36
cttaactcat agttacataa aaacctcaag catgccagat taacttacca tctg             54

<210> SEQ ID NO 37
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 37
tccaactcta ctcagaacac tcagtcccac gcctaatgag ttatataaaa caattggggc       60
```

```
aaataa                                                              66

<210> SEQ ID NO 38
<211> LENGTH: 11
<212> TYPE: PRT
<213> ORGANISM: Artificial Sequence
<220> FEATURE:
<223> OTHER INFORMATION: Synthetic peptide

<400> SEQUENCE: 38

Ser Asn Ser Thr Gln Asn Thr Gln Ser His Ala
1               5                   10
```